US007947480B2

(12) United States Patent
Hosted et al.

(10) Patent No.: US 7,947,480 B2
(45) Date of Patent: May 24, 2011

(54) EVERNINOMICIN BIOSYNTHETIC GENES

(75) Inventors: Thomas J. Hosted, Summit, NJ (US);
Tim X. Wang, Roselle Park, NJ (US);
Ann C. Horan, Summit, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/875,342

(22) Filed: Sep. 3, 2010

(65) Prior Publication Data

US 2011/0027865 A1 Feb. 3, 2011

Related U.S. Application Data

(60) Continuation of application No. 11/739,945, filed on Apr. 25, 2007, now Pat. No. 7,790,411, which is a continuation of application No. 11/021,825, filed on Dec. 23, 2004, now Pat. No. 7,229,813, which is a division of application No. 09/758,759, filed on Jan. 11, 2001, now Pat. No. 6,861,513.

(60) Provisional application No. 60/175,751, filed on Jan. 12, 2000.

(51) Int. Cl.
| C12N 9/02 | (2006.01) |
| C12N 9/00 | (2006.01) |
| C12N 15/00 | (2006.01) |
| C12N 1/20 | (2006.01) |
| C12P 21/06 | (2006.01) |
| C12P 19/34 | (2006.01) |
| A61K 39/395 | (2006.01) |
| C07H 21/02 | (2006.01) |
| C07H 21/04 | (2006.01) |

(52) U.S. Cl. ...... 435/189; 435/183; 435/69.1; 435/91.1; 435/320.1; 435/252.3; 424/130.1; 424/146.1; 536/23.1; 536/23.2

(58) Field of Classification Search .................. 435/189, 435/183, 69.1, 91.1, 320.1, 252.3; 424/130.1, 424/146.1; 536/23.1, 23.2
See application file for complete search history.

(56) References Cited

U.S. PATENT DOCUMENTS

| 5,190,870 A | 3/1993 | Lipscomb et al. |
| 5,190,871 A | 3/1993 | Cox et al. |
| 5,741,675 A | 4/1998 | Friedmann et al. |
| 6,833,135 B1 | 12/2004 | Frazao Moniz Pereira et al. |
| 7,229,813 B2 | 6/2007 | Hosted et al. |

FOREIGN PATENT DOCUMENTS

| EP | 350341 B1 | 5/1995 |
| JP | 3139284 | 6/1991 |
| WO | WO 93/07904 | 4/1993 |
| WO | WO 93/13663 | 7/1993 |
| WO | WO 95/16046 | 6/1995 |
| WO | WO 97/13777 | 4/1997 |

OTHER PUBLICATIONS

Altreuter and Clark, 1999, Curr. Op. Biotech. 10:130.
Baltz and Hosted, 1996, TIBTECH 14:245.
Baltz et al., 1998, Trends Microbiol. 2:76-83.
Baltz, 1990, Curr. Op. Biotech. 1:12-20.
Bao et al., 1999, J. Bacteriol 181:4690-5.
Bao W, et al,, 1999, *Biochemistry*. 38: 9752-9757.
Beck et al., 1990, European Journal of Biochemistry 192:487-498.
Becker A, etal., 1993, *Mol Gen Genet*. 241: 367-379.
Brautaset T, et al., 2000, *Chem Biol*. 7: 395-403.
Buttner et al., 1990, J. Bacteriol. 172:3367-78.
Cheng-Cai, 1996, Molecular Microbiology 20:9-15.
Cundliffe, 1989, Annual Review of Microbiology 43:207-33.
Distler J, et al., 1987, *Nucleic Acids Res*. 15: 8041-8056.
Donadio et al., 1993, Proc. Natl. Acad. Sci. U.S.A. 90:7119-23.
Fath et al., 1993, Microbial Reviews 57:995-1017.
Faust B, D Hoffmeister, et al., 2000, *Microbiology*. 146: 147-154.
Fernandez et al., 1996, Molecular and General Genetics 251:692-698.
Fernandez et al., 1998, Journal of Bacteriology 18:4929-4937.
Flett F, et al., 1997, *FEMS Microbiol Lett*. 155: 223-229.
Foster DR, 1999, *Pharmacotherapy*. 19: 1111-1117.
Gaisser et al., 1997, Journal of Bacteriology 179:6271-6278.
Ganguly AK, et al., 1975, *J Am Chem Soc*. 97: 1982-1985.
Ganguly AK, et al., 1979, *J Antibiot* (Tokyo). 32: 1213-1216.
Garbe TR, et al., 1994, *Microbiology*. 140: 133-138.
Guilfoile et al., 1991, Proc. Natl. Acad. Sci. USA 88:8553-8557.
Hanlon et at., 1997, Molecular Microbiology 23:459-71.
Hopwood, at al., 1990, Annual Review of Microbiology 24:37-66.
Hosted and Baltz, 1997, J. Bacteriol. 179:180-6.
Hung-wen et al., 1994, Annual Review of Microbiology 48:223-56.
Hutchinson CR, et al., 1993, *Antonie Van Leeuwenhoek*. 64: 165-176.
Hutchinson at al., 1995, Annual Review of Microbiology 49:201-238.
Ikeda H, 1999, et al., *Proc Natl Acad Sci U S A*. 96: 9509-9514.
Johnson et al., 1998, Current Opinion Chem. Biol. 5:642-9.
Kim et al, 1995, J. Bacteriol. 77:1202.
Lichenstein HS, et al., 1990, *Gene*. 88: 81-86.
Liu and Thorson, 1994, Annu. Rev. Microbiol. 48:223.
Liu W, et al., 2000., *Antimicrob Agents Chemother*. 44: 382-392.

(Continued)

Primary Examiner — Ganapathirama Raghu

(57) ABSTRACT

This invention is directed to nucleic acids which encode the proteins that direct the synthesis of the orthosomycin everninomicin and to use of the nucleic acids and proteins to produce compounds exhibiting antibiotic activity based on the everninomycin structure. The DNA sequence for the gene clusters responsible for encoding everninomicin biosynthetic genes, which provide the machinery for producing everninomicin, are provided. Thus, this invention provides the nucleic acid sequences needed to synthesize novel everninomicin-related compounds based on everninomicin, arising from modifications of the DNA sequence designed to change glycosyl and modified orsellinic acid groups contained in everninomicin. A *Micromonospora* site-specific integrase gene is also provided, which can be incorporated in a vector for integration into any actinomycete, and, particularly into *Monospora*. Thus, the invention further provides methods for introducing heterologous genes into an actinomycete chromosome using this particular vector.

10 Claims, 128 Drawing Sheets

OTHER PUBLICATIONS

Figure 1:
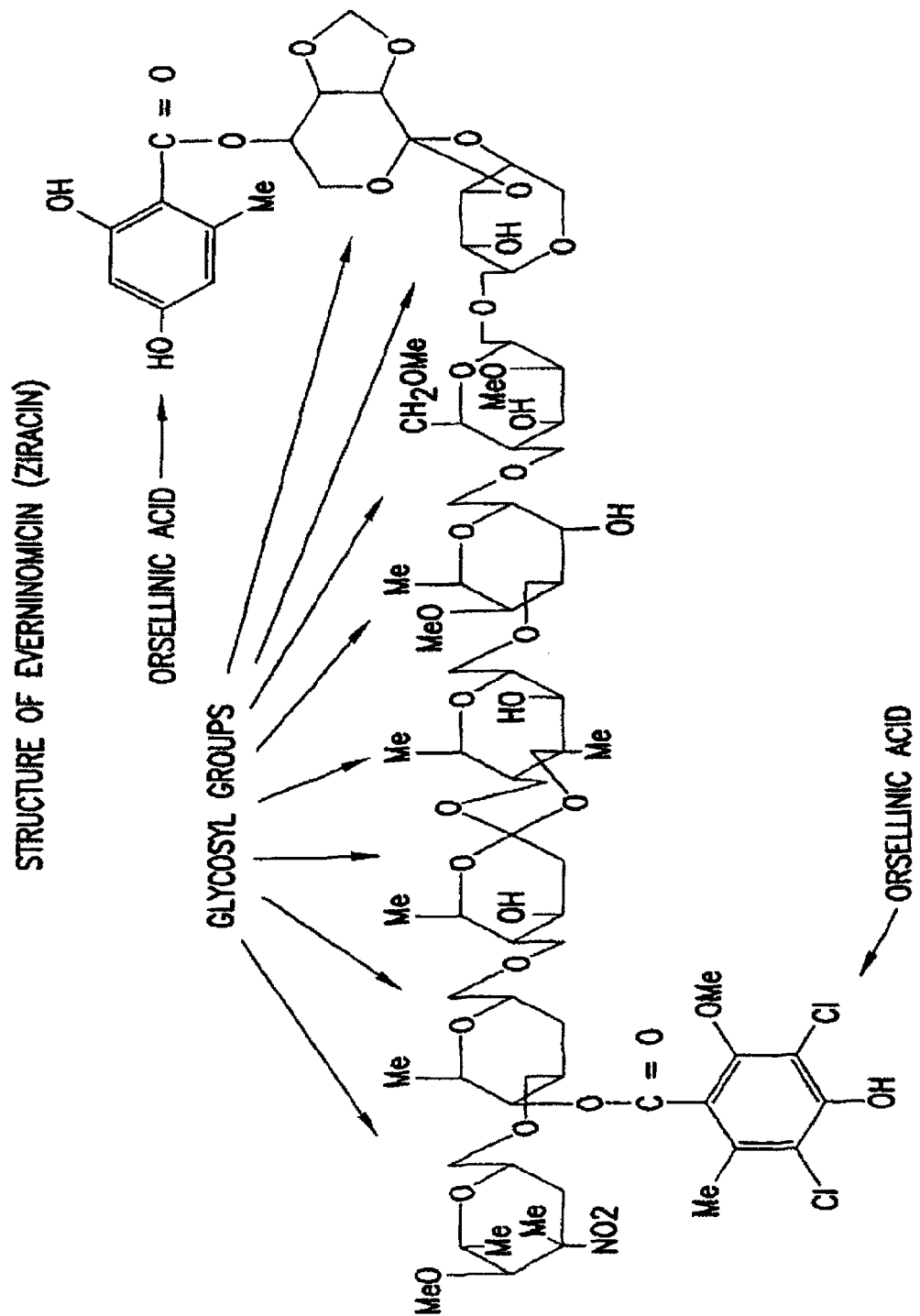

Madduri et al., 1998, Nature Biotechnology, 16:69-74.
McNicholas et al., Abstract C-846, ICAAC, San Francisco, CA, 1999.
McNicholas PM, 2000, *Antimicrob Agents Chemother.* 44: 1121-1126.
Merson-Davies LA, et al., 1994, *Mol Microbiol.* 13: 349-355.
Mertz JL, et al., 1986, *J Antibiot* (Tokyo). 39: 877-887.
Ninet L, F Benazet, et al., 1974, *Experientia*, 30: 1270-1272.
Oh and Chater, 1997, J. Bacteriol. 179:122-7.
Olano et al., 1998, Molecular Gen. Genetics 3:299-308.
Paget E, et al., 1996, *J Bacteriol.* 178: 6357-6360.
Piepersberg W., et al., 1994, *Crit Rev Biotechnol.* 14: 251-285.
Pissowotzki K, et al., 1991, *Mol Gen Genet.* 231: 113-123.
Puar MS, et al., 1998, *J Antibiot* (Tokyo). 51: 221-224.
Rao et al., 1987, Methods in Enzymology 153:166-198.
Reynolds, Proc. Natl. Acad. Sci. USA, 1998, 95:112744.
Rodriguez E, et al., 1999, *Microbiology.* 145: 3109-3119.
Saitou N, et al., 1987, *Mol Biol Evol.* 4: 406-425.
Smith et al., 1997, FEMS Microbiol. Lett. 155:223-9.
Solenberg et al., Chem Biol, 1997, 4:195-202.
Strohl et al., 1991, J. Industr. Microbiol. 7:163.
Stutzman-Engwall KJ, et al., 1992, *J Bacteriol.* 174: 144-154.
Summers et al., 1997, Microbiology 143:3251-3262).
Tang L, et al., 1994, Ann. N Y Acad. Sci. 721:105-16.
Trefzer A,, et al., 1999, *Nat Prod Rep.* 16: 283-299.
Ueda et al., 1996, Gene 169:91-95.
van Wageningen AM, et al., 1998, *Chem Biol.* 5: 155-162.
Weinstein MJ, 1965, *Antimicrob Agents Chemother.* 5: 821-827.
Wilson et al., 1998, Gene 214:95-100.
Wohlleben et al., 1994, Acta Microbiol. Immunol. Hung 41:381-9.
Wolk CP, 1991, *Proc. Natl. Acad. Sci.* 88: 5355-5359.
Wright F, et al., 1992, *Gene.* 113: 55-65.
Ylihonko et al., 1996, Microbiology 142:1965.
Zhang et al., 1998, Molecular and General Genetics 258:26-33.
Adrian PV, et al., 2000, *Antimicrob Agents Chemother.* 44: 732-738.
Decker, H., (1996), FEMS Microbiology Letters 141:195-201.
Bechthold, A., (1999), Biorganic Chemistry, Diederichsen U. et al. Wiley-VCH Verlag GMBH, Weinheim, Germany, p. 313-321.
Malpartida, F., (1987), Nature, 325:818-821.
Koch, C., (1996), International Journal of Systematic Bacteriology, 46(2):383-387.
International Search Report for International Patent Application No. PCT/US01/01187; Date of Completion: Aug. 7, 2001.
Freitas-Vieira et al. (1998) Microbiology 144:3397-3406.

COSMID pSPRX256

REGIONS SEQUENCED INDICATED BY CROSSHATCHES.

FRAGMENTS CLONED INDICATED BY CLONE DESIGNATION BENIGTH FRAGMENT.

COSMID pSPRX256 pSPR256 MAP.PATENT (429 bp)

| Kpnl | Kpnl | Kpnl Kpnl | Kpnl | Kpnl | Kpnl | Kpnl | Kpnl | Kpnl |
| 2.15kb | 8.0kb | 1.6kb | 4.3kb | 5.0kb | 5.5kb | 5.0kb | 4.3kb | 4.6kb | pSPRX369 pSPRX367 pSPRX361 pSPRX365 pSPRX501 pSPRX502 pSPRX363 pSPRX369

LEFT EDGE                                                                 RIGHT EDGE

FIG.2C

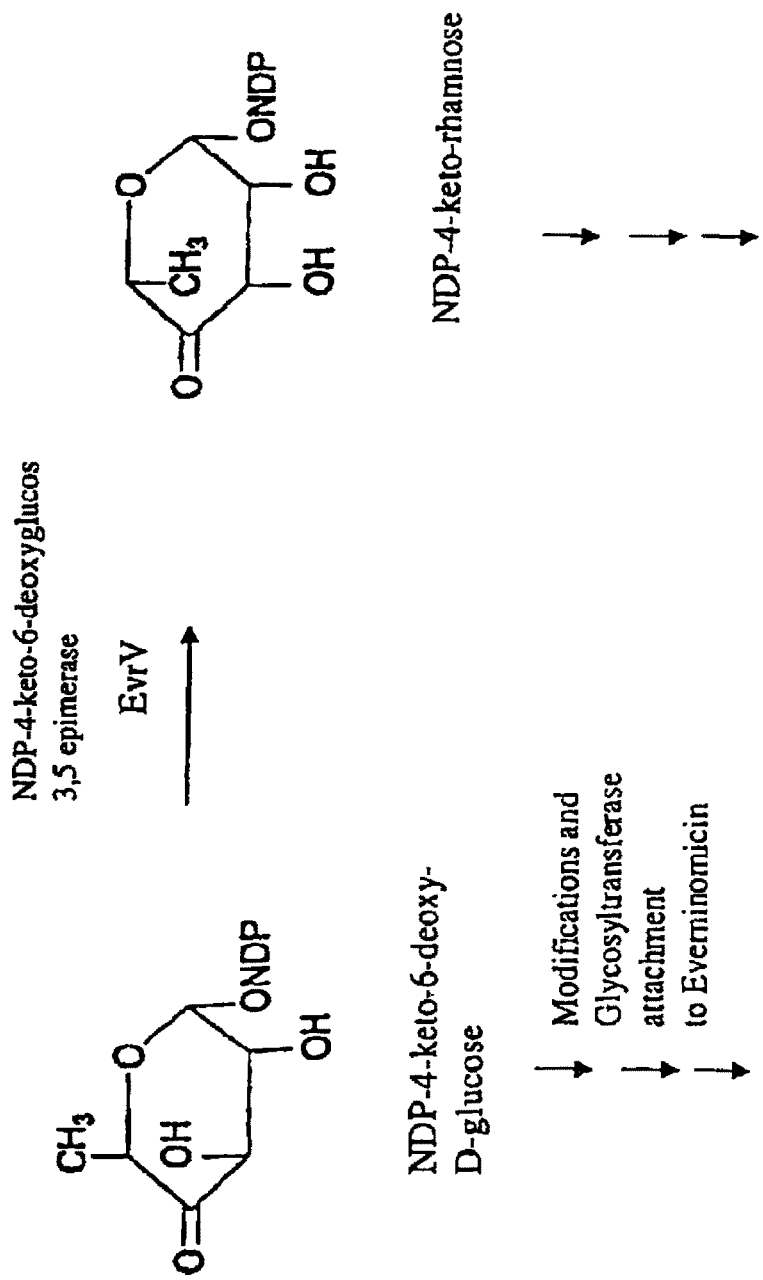

pSPRH830b *E.coli*–MICROMONOSPORA SHUTTLE VECTOR pSPRH830b — pSPRH826b BACKBONE

| FUNCTION | SOURCE |
|---|---|
| – AMPICILLIN RESISTANCE | (pUC18) |
| – MULTIPLE CLONING SITE | (pUC18) |
| – pUC18 ORIGIN | (pUC18) |
| – HYGROMYCIN RESISTANCE | (p16R1) |
| oriT (ORIGIN OF TRANSFER) | (pRL1058) |
| pIJ702 ORIGIN OF REPLICATION | (pIJ702) |

```
  1 GTACCTCGGCCTTGATCGTGCCGGGGTGGCCTCGGCCCGGCTTGCTTGCGGTAGGGTGGGACATCTGGACTCCTTGCTTGCGGTAGGC?????CGGGTGGGAGCCTC
117 GGCCCGGTGGTGCGGGGCTCGTCTGGCGTCAGGCCGGCCAGCCGGCCGGCTGGGCTTGATCGGTTGGGCTTGGGCTTGATCGGTTGCGGCCGGGGGGCTTCGGCGCCCTCGGCGGGGTTG
233 GTGGGGCGCGCGAGGGGGAGAGCTGGGCTTTTTCGGGCCCGAAGATCGGGCCACGCACGCAGCGGGCGGGGTGTCGGGTCGGTCTTCTTGCTCTCAAGCCAGCCAGCAGGGATGGTCCTCGTCGAA
349 GCGCGCGGTGCCGGCCGGACCCCAGGGTGATCGGCCAGGGTCCGGCGCGGTGATGCGGTCGGCCAGGTCACCTCGGACGCGCCAGCGGGGCGGGCGAGCGTGCTCCTTGTTCATCAGCGGCT
465 TCATGCGGCGGCCCTCGGCCAACAGGTCCTCGAACAGGTCCTCGAACGGCTCAAGGCTCGGGGGGGGTCCTGCCCCTTTGCGGATGCCGCAGCAGATTGACCCGAT
581 CCATGCCGCACAGTCGCGCCCCGAGCGGGGGCGTTGGGTCGTGCGGGCCAGCTTCCGCGGGCGCAGGTCGTGCGTGAAGACGGTCAGTGCGTAGCCGATGCGGACACGGTGCCGGATTG
697 ATCTCGGAGGTGCTGCACTGTCATGTCGAAGGTCGTGCAAGCCTAGGGTCGTCGTGCCACCTGTGTGCAGCCGATTCTGACCCGGCCCTCCAGACCCTACTGTTGCATGTGACAGTGCA
813 ACACCTTATGAAGGGAAGCAAGATGCCCGGCACGACCAGAGAGGGAGGTTAGGCAGCAAGCAGAGAGGGCCCATAGTCCTCACCGCCGCCGCGAGCGCCGAGCGCGACTGACCAAG
929 GGTCCGACCTCGCGTTAGGACCTTAGGCGGTGCACATGCGCAACACACCGGCTCGGGCGCGGCACATGTCCTCACCGCCGCCGGCGACTGACCGCCGCCCGAGCGCGACTGACCAAG
                 1▶ M R N T P G L G R G T W A A Y V L T A R E R A G L T K
1044 AGGGAGTTGGCCAGGCGGCATCCAGAAGGACCGGCACGTCGGCCAGGAGGACCCGGAGGACCAAGACCGGCGACCTCGTTGCCCGGCGTCGCCAGGTGCTCGGCCT
  28▶ S E L A R R I Q K D R A T V G R W E D G K N R P D D A D L V A R V A Q V L G L
1160 CGACCTGGACGAAGCCCTGGCGGCCGCAAGCCCTGCGGCCGCCCAGGTCTACCGGCAGGGTGTTACCCCGGCCGCCACGCCCACCATGGACCTGGACGAGGAAATCGAGCTGGTCCGCACCGACCCCAAGCTGG
  66▶ D L D E A L A A A G L R P G V T P P A T P T M D L D E E I E L V R T D P K L
1276 AGGAGGACATGAAGCGACGGATCATCGCCCTAATCCTGGAGCGCCGCGACCAAGCGGCTTCATCGACCTGTTCCGGCCGAGCTGACA.
 105▶ E D M K R R I I A L I L E R R E R D K A A A I E E T K R L I D L F R R S *

```
3812  CGAGTCCCTCAGCGCGCAGCTCGGCGACCGCCCGTCGCCAGCGGTGCCCTGCCACGGGTGCCCACCCGTACTCTCTGCCTCAGCCGGAGTCTCCTGGGCAGCAGCCCGCGCCCCAGCGGTAGGTGCCG

3928  TCCTGGATGCGGCGCGCAGCAGCGGCGCAGCTGGAGGGCGGGGCCAGCTGAGCGGCCTGAGCTGGTGGGGCTGATCACAGGCGGACGCGTAGGGATGCCCGGGGGCGGACGGTTCGCCCGGCGCGCAA

4044  CGTTCGAAGGTTCGGTGCGCTCTATGCCTCGGCCACGTATACCCCTGCTCCGGGGCGCGGCCAGGGTAAGCCCGGCGGTGAGCTCCAGGGCGCGCTGGATGGTCGACACGC

4160  TGACGGAGTACAGATCGCCCAGCTCTCGCAGCGACGGGAGCTTCGACCCCGGCGGGGTACTCGCTGCTGCCGATCGGGGCGGTCAGGTCGTCGGCGATCTGCGCGACGACATGGGG

4276  ATGGGCATGGGCGGATCTCCCTGGTTGGCCCGCCGATGACATCACGCCCGCCACGCTGCCTCAAGCAGCAGCAGTCATTGACCAGTAGTCACACAGTGACCTAGGTTGGCCGATGGGTAC
```

FIG.7B(4)

Analysis of M. Carbonacea and M. Halophytica pSPRH840 insertion site AttB/AttP region Alignment of pMLP1 attP region with religation clone edge sequence

```
M. Halophytica PstI relig-9    TGATCAACTCTAGGGGAGGGGTAGGGGAATCCACTCCGGAGACGCCCGGAGCAATCCGGA 60
M. Carb PstI relig-1           TGATCAACTCTAGGGGAGGGGTAGGGGAAT-CNCTCCGGAGACGCCCGGAGCAATCCGGA 59
M. carb PstI relig-4           TGATCAACTCTAGGGGAGGGGTAGGGGAATCCACTCCGGAGACGCCCGGAGCAATCCGGA 60
pMLP1.intTGA.att region        TGATCAACTCTAGGGGAGGGGTAGGGGAATCCACTCCGGAGACGCCCGGAGCAATCCGGA 60

Consensus                      TGATCAACTCTAGGGGAGGGGTAGGGGAATCCNCTCCGGAGACGCCCGGAGCAATCCGGA 60

M. Halophytica PstI relig-9    GCATGACGGAGCAACCAGCAGGTCAGGTGGCCTGTTGACCCCCTGACCAGGGCCCCGGTA 120
M. Carb PstI relig-1           GCATGACGGAGCAACCAGCAGGTCAGGTGGCCTGTTGACCCCCTGACCAGGGCCCCGGTA 119
M. carb PstI relig-4           GCATGACGGAGCAACCAGCAGGTCAGGTGGCCTGTTGACCCCCTGACCAGGGCCCCGGTA 120
pMLP1.intTGA.att region        GCATGACGGAGCAACCAGCAGGTCAGGTGGCCTGTTGACCCCCTGACCAGGGCCCCGGTA 120

Consensus                      GCATGACGGAGCAACCAGCAGGTCAGGTGGCCTGTTGACCCCCTGACCAGGGCCCCGGTA 120
```

FIG.9A(1)

```
M. Halophytica PstI relig-9   CGGGTTCAATTCCCATCAGTCACCCCAGGTAAGACCCAGGTCAGGGCCGGTTCTCACC-G   179
M. Carb PstI relig-1          CGGGTTCAATTCCCATCATCAGTCACCC---GT-ACACGAAGGCCCCTCCAC-TCGGAGGGG   174
M. carb PstI relig-4          CGGGTTCAATTCCCATCAGTCACCC---GT-ACACGAAGGCCCCTCCAC-TCGGAGGGG   175
pMLP1.intTGA.att region       CGGGTTCAATTCCCATCAGTCACCC---G--GCAAGTGGATCTACTCCACAGCAGATCAG   175

Consensus                     CGGGTTCAATTCCCATCAGTCACCCaaGgTARSAMSHRGRYCHVSKCCRSWKCDSABSRG   180

M. Halophytica PstI relig-9   GCCCT-GACGCATTTTCAGGGG------                                   200
M. Carb PstI relig-1          GCCTTCGGCGT-TCCTGAGGGTTCGCG-                                   200
M. carb PstI relig-4          GCCTTCGGGCGT-TCCTGAGGGTTCGC-                                   200
pMLP1.intTGA.att region       GCCCCCTCCG----AAGAGGGGGCCTGAT                                   200

Consensus                     GCCYCYKVCGYATYHMSAGGGKKCSYGAT                                   209
```

FIG. 9A(2)

Insertion juncture pMLP1 attP region

```
  1 TGATCAACTCTAGGGGAGGGGGTAGGGAATCACTCCGGAGACGCCCGAGCAATCcGGAGCATGCGGAGCAACCAGCAGGTCAGGTGGCCT

94 GTTGACCCCCTGACAGGAGCCCCGGTACGGGTTCAATTCCCATCAGTCACCcGgCAAGTGGATCTACTCCACAGCAGATC

174 AGGCCCCCTCCGGAAGAGAGGGGGCTGATGCGTCATAGGGGACAGGTAGGGAACTCAA
```

FIG. 9B

```
   1 GGTACCCGACCGTGTCCCGGAACAACGAGTCGAGATACGGGGAGAGGAACACCCCGGGTAGTCCGGGTAGACGGGTGGGCGCGAAGGCGTAC
  93 GCGCCTTCGACGGTCAGCGGGGCGGACACCGGCGGGTCAGCTGTCACGTGTACGCGGGGACGTACAGGATCCACTGTCCGCCAGCC
                 < .  S  T  V  H  V  R  P  V  Y  L  I  W  Q  G  G  A
 184 CGGCGGAACTCCTGCTCCTTGCCATGATCGTCGTCGTCGTTCCAGGCGAAGAGCAGCGCGTAGTCCACCGCGTCGGGCGTGAACGCGTC
     <R  R  F  E  Q  E  K  A  M  I  E  D  A  H  N  W  A  F  L  L  A  Y  D  V  A  D  P  T  F  A  D
 276 CGGGGTGCGCACCGGGATGCGTGCCGGGGTGAGCGGCCGGCCCTGCTTGGCCGGGTCGTGTCGCACACCAGGAGACCAGGTCCGACCGA
     <P  T  R  V  P  I  H  T  G  P  T  L  R  G  Q  K  A  P  T  T  D  C  V  W  S  V  L  D  P  G  I
 368 TGCCCAGAAGTTCGTCACGAGTTGCCCTCTTCGCCGTCGCGCTCACGGCCGTACGCCCTTGCCCTGGCCTTGAGCGAGTTCAGCAGGGCG
     <  G  C  F  N  T  V  T  A  S  K  A  T  A  G  Y  A  V  V  R  K  G  E  A  K  L  S  N  L  L  A
 460 AGCAGGTCGGTGCGGATGCCCTGACGTCGGCGGCGAACCTGTCGAGCCGGTCGGCAGCTGCGGTCGGGCGTCCTCGCGATCAG
     <L  L  D  T  R  I  G  E  V  D  A  A  F  R  D  L  R  S  R  D  A  V  G  R  A  D  E  E  G  I  L
 552 CGGGGCCACCGCTCGGCCGGCTGCCGCCGGCCGGCACGCGGCGATGGTGTAGCGGCGACCTCCCACCGTGCACCGGAAGGCGTTCCACGTCGA
     <A  A  V  R  E  A  P  Q  R  A  G  A  R  A  I  T  Y  R  V  E  G  G  H  V  P  L  R  E  V  D  V
 664 CGAGCGCGAAGCGGGCGCAGCGCTGCGACCGCGAGAAGAAGAAAATGCTGCTGTAGATCGTGGTCGAAGGACGTC
     <L  A  F  G  F  R  A  A  L  A  Q  V  S  R  A  S  F  F  F  H  E  D  Y  I  Q  D  F  S  T
 736 TTGTCCAGGATGTCCCCGAGGTACGGCAGGTCGCTCAACGCCGTCGGCGCGGGGCGTCCGGCGGGCGGGCGGGTGGACTCCTCGAAGA
     <K  D  L  I  D  G  L  Y  P  D  E  F  V  F  V  G  D  P  A  L  L  A  D  V  G  R  L  I  S  D  L
 828 GTAGGGGATGTGGCAGAGTGTGTTGGCGCAGAAGATCACATCGGCGGCGTGCCGGGGGCTCGAAGCCGGCTGCCGACTCCCGCCTGTGG
     <Y  P  I  H  C  I  T  N  A  A  F  I  V  D  A  P  G  D  T  E  R  V  R  R  A  T  S  E  E  F  F
 920 ACTCGGTGACCACCGCACCCGTGCCACCGGCCACATGCGGATCCGGCACGACGGCTCGAAGCCCAGGTGCCGCACTCCCGGCCTCGTGG
     <  E  T  V  V  R  V  G  H  G  R  A  V  D  A  V  G  G  S  P  E  F  G  L  H  R  V  G  A  E  H
1012 ACGGTACGCAGCAGATCACCCGCGTTGCAGCCGATCTCCACCACGAACGGGTCCGGGCCGGTGCCTCGTGCTCCAGCAGGTGCCGCCGGGT
     <V  T  R  L  M  V  G  D  N  C  G  I  E  V  V  F  P  D  P  G  T  A  E  H  E  L  L  H  R  A  T
```

FIG.11A(1)

FIG.11A(2)

```
2204 CTGGCCGTAGAGGTGCACCGGCAGCAGCGCCTTGCGTCCGGGGGGTGACCGGCCTCGGCCAGCAGCTCGGTGTCATCAGGTAGTCGTCGGGCGC
     < Q   G   Y   L   H   V   P   L   L   A   K   T   R   P   T   V   A   E   A   L   L   E   T   D   M   L   Y   D   D   A   R
2296 GGACGTCCACGAAGACCGGCGTCGCCGACCGCGTCGATGCCGCAGCACCGTCGGCGCGACGGTGGAGACGGTGATGACCTCGTCGCC
     < V   D   V   F   V   P   T   A   G   V   A   D   I   A   L   V   T   P   A   A   T   N   S   V   T   I   V   E   D   G
2388 GGCCCGACGTCGAGGCCTGAGCTGCAGCTTGGTGCCGAGTCGTTGATGCCGAGCCAGTGCGGCATGTCGTGACATGGCGGCGAA
     < P   G   V   D   L   A   Q   L   A   L   K   I   A   N   T   G   N   D   V   T   V   C   H   P   M   D   H   Y   A   A   F
2480 CTCCTGCTCGAAGCCGCGCAGCCCGCGGTTCCCGAGGATGAGGTTCCGGACTCGAAGACGTCTGCACGGCGTCGAGGAGGTGTCGCCGTTCCT
     < E   Q   E   F   G   R   V   S   A   G   L   I   L   N   G   S   E   F   V   T   Q   V   A   D   L   L   D   D   R   E   K
2572 TCTCGTACTCCGGCAGGTAGCCCACACTCGGATGGTCATCTTCGCCATGCACGCTCAT    <   *   A   S   T   R   S   R   L   A   R   V   S   H
     < E   Y   E   P   L   Y   G   W   V   R   I   T   M
2661 GTAGTCGTTGTCCCGGCTCGAGTCGCAAGTGCCTGACCGCGTAGGGCTGCATGAACCCGGCCC
     < Y   D   N   D   R   D   L   G   L   A   Q   G   S   L   Y   D   V   A   D   V   Y   S   Y   P   Q   M   F   G   G   A   R
2753 GCACGTCGGCGATAGAGCTCGGCAGGAGAGTGGCCGCCTGTGAGGCGAGGCTGAGGCAGTCGAGGACCTCGTCCACCGCCGGGGCC
     < V   D   R   Y   L   R   S   L   P   H   G   A   T   Y   A   L   G   G   V   L   S   L   C   D   D   V   V   A   P   A
2845 AGCTCGTTGACGGTCATCTTCGCCGTACTGGAACGGGTCATCATCCGTGCGGCGGTCAGGAAGGTCGACAGGTCGACGCCGC
     < L   E   N   V   T   M   K   A   Y   Q   F   P   T   M   M   R   R   G   R   E   D   P   D   G   S   L   D   V   S   A   A
2937 GTCGGGCGTTGGTCAACGCCGGCGACCGTGTCAACGCCGTAGAGCGCGGTAGGCCGCCGACCAGCGCCGACCAGGCCACCGGCCGTG
     < D   A   N   T   L   A   A   G   V   T   T   R   L   A   Y   L   R   T   D   L   G   A   V   L   A   R   A   G   A   R   P
3029 GCTCGCCGCCGCCGCAGCCGAGAAAACGACGCGATGTCCCTGGGCGATGCCGAGCATGGTAGATCGAGCTG
     < E   G   G   R   G   A   C   F   G   V   A   I   D   R   A   A   Q   A   I   G   A   V   I   G   L   M   T   I   S   S
3121 ACCGGTCTGCCCGGCAGCAGCCCTGCCCGACCGCCCAGCCGCTCGGCCCGAGCTGGAGGATGCCCGGGTACCGGGTCGAAGAC
     < V   T   Q   G   A   L   V   A   D   R   R   A   G   V   P   G   R   E   L   L   E   D   A   R   V   P   C   R   D   F   V
```

FIG.11A(3)

```
3213 CACCTCCAGCGTCCCGAGGCACGCATTCCCAGGCCGTGTCCAGTTGTGTCCAGCACCGGTGAGCCGTGCGGGGGCGTCGGCGGTGTGCACGACCGGCAGG
      < V E L T G S A R M G L G D W N D L V T L G P A D R H V V P V A
3305 CGAGGAACACCGAGCCGTCGTCGGCCGCTGGGCGTGCACGAAGAGTGGGTCGCGCATGGGCGCATGTGCGACCTTGCGGCCC
      < L F V S G D D D R R Q A H V F F H T A I P A M S V L V K R G
3397 GACAGCAGCGCGCGGCCGCGCCGGAATGCAGCTCGGTGACGCCGGTCGTCTTGAGCGCCGAGACGGGCGGCCTCGCCCTC
      < S L L W G G A G D S H L E T V V G P A D K L A G C V A A E G E
3489 CGCCATCGCCGCAGCAGCCGCGCGCGGCGGTGCCGTGCTGCCACTCGTAGGTGAGGTGAGGCCCCGGCTGAGCT
      < A M A R L L R E A M A R V P P T G H Q W E Y T L T L G R S L Q
3581 GCACGTGCCAGGCCAGCGCGTGGACGCGCTCGGCCTCGAACTGCTTCAGCAAGGCCAGGATCAGCCGGTCTACAGCCCGGGTCAACCCAGGCCG
      < V H W A L A T S A D A E A L R M L A T A V D Y L R T L G L G
3673 CCCAGCTCGGCGGGGAACGGTGGCGCCCATCAACCCGAGCTTCGCGAACTTCGCGAACCCCTCGAACGCTCCACCGGGAAGGTGCCGGTGCCGGTGCCGGTG
      < G L E A P V T A G M L G L K A F Q E F A E V P F F T G T R D R D
3765 GGCGGGCCTCCCGCACTGATTCTCGGGATCACGCGGCAAGCAGGTCGACGTCCTGCTGCGCGTGAGCGGGCGCGAAGATCCGCCG
      < A E A S I R P I V G A L L D V V T R G A P T L P A R L D A A
3857 CCACCCATCTCTCGGTCAGATTAGACATCGTTCGGCGTGCCAGAACCTGTGCTATCAGGGTGCCGGGCGATCACC
      < V
3947 AATTGCTGGCTGATTGTCACCGACGATGCTCGACAGGATACCCAGGATCGCTCGGCGAAACCCTGTGTGCGGAGT
     > V K I L F I A G P T K S S L F G L A P L A I A A R M
4039 TCGCCAAGTCTAGTTGGAACTCAGTAGTGAACCATGGGCGCGGTTGACGTCGCGCTATATATTCGGCCGACACG
      > S G H E V V M A S T Q E V V P A T M S V G L P A F P L A A L T
4131 TGCGAGGACTCGTGAAGATACTGTTCATCGCAGGACCGACGAAGTCCAGCGCCTATTCGGCTGCCTGGGCCCCACTGGCAATGCGCCCGGATG
      > V K I L F I A G P T K S S L F G L A P L A I A A R M
4221 AGCGGGCACGAGGTCGTGATGGCTTCCACGCAGGAGGTCGTACCGGCGACGATGTCCGGCGACCTTCCGGCTGCCGGGCCTTCCCGCTGCGCGCTGAC
      > S G H E V V M A S T Q E V V P A T M S V G L P A F P L A A L T
4313 CCTCGCCGAGCTCATGACCACCGACCGGGCCGGATCCGGCGAGGACCCGCTCCGCCTTCGTCCCCTTCGTGGGCCGGATGT
      > L A E L M T T D R A G D P L R I P A E D A A F V P F F V G R M
```

FIG. 11A(4)

```
4405 TCGGCCCGGCTGGCGGGCGATCAGCCTGGATCCGCTGCGCGACCTGGTCGGCGGGGTGGCGGCCCGACCTGATCGTCGGCGGCCCGCACGCCTAC
    >F  G  R  L  A  A  I  S  L  D  P  L  R  D  L  V  G  G  W  R  P  D  L  I  V  G  G  P  H  A  Y
4497 GCCGCGCCGATCCTGGCCACCGAACTTGGCGTGCCCTGCGTGCGGCACCTGCTCACCGGCAACCGGTGGACCGGGAGGGCACCATCCGGG
    >A  A  P  I  L  A  T  E  L  G  V  P  C  V  R  H  L  L  T  G  N  P  V  D  R  E  G  T  H  P  G
4589 GGTCACGACGAGGTCGCCGGCCCGGCAGCTGGCCCAGGTGCCGCCGTTCCACCTGGCCCTGGACATCTTCCCGGCCAGCA
    >V  D  E  E  L  R  P  E  L  A  A  L  G  L  A  Q  V  P  P  F  H  L  A  L  D  I  F  P  A  S
4681 CCCGGATCGACGACGTCCCGGCGCAGCCGGTGCCAGTCCGGATCCTGCGCTGGATCCCGACCAACCAGCAGCCGGTGGCGCCGTGGATGCTC
    >T  R  I  D  D  V  P  P  A  Q  P  V  R  P  L  R  W  I  P  T  N  Q  Q  P  V  A  P  W  M  L
4773 TCGCGCGGGCCGCGTCCTGGTCCTGGTCACCGCCGGCAGTCGGCCGCCGCCGAGGTGGGTCGGGCCCTGCACGACGTCCTCACGGACTGGCCGGCAC
    >S  R  G  P  R  R  R  L  V  T  A  G  S  L  V  T  T  T  H  N  F  D  F  L  H  G  L  A  G  T
4865 CCTGGCCGAGCAGGACGTCGAGGTCGTGGTCGCCGCCACTGTGACCTGATCGTGCACCACTCCGGCACGATGACCGCGCTTGAACGCGGGGGTG
    >L  A  E  Q  D  V  E  V  V  V  A  A  P  P  E  V  G  R  A  L  H  D  V  P  G  V  R  H  A  G
4957 GGCTCCCCGCTGATCGTGTGCCGCAGAGAGCCGGTTCATCGAGTGGGCGCGCAACCTGTCGACCCTGGGCGTGGCGCAGACCCTCGCGCGGCGA
    >W  L  P  L  D  V  V  L  P  H  C  D  L  I  V  H  H  S  G  T  M  T  A  L  T  A  L  N  A  G  V
5049 CCCCAGCTGATCGTGCCGCAGAGCCGGTTCATCGAGTGGGCGCGCAACCTGTCGACCCTGGGCGTGGCGCAGACCCTCGCGCCGGGCGA
    >P  Q  L  I  V  P  Q  E  S  R  F  I  E  W  A  R  N  L  S  T  L  G  V  A  Q  T  L  A  P  G  E
5141 GGACACCCCGGAAGCGGTCGGCAAGGTCGTGGCCCGACTGCTCCTGGAGGATCCGGTCCACGCCACCAGCGCCGCCGCGATCGCCCGGGAGATCG
    >D  T  P  E  A  V  G  K  V  A  R  L  L  L  E  D  P  V  H  A  T  S  A  A  A  I  A  R  E  I
5233 CCGAGATGCCCGGCCCCACGGAGGTCGTGGGCCAGTTCGCGCACCGAGTTCGCCACCCGAGGGCTGACCCGCGGCTTGACCACCGGGAGCC
    >A  E  M  P  G  P  T  E  V  V  G  Q  L  T  E  F  A  T  R  G  L  T  C  A  S  S  .
5324 GGGTTCATCGGCTCCCACCTGACCGACGCGCTGCTCGAACGCGGCGACAGCGTCACCGTCCTCGACGACCTGTCCACCGGCCGCCCGAGCC
    >G  F  I  G  S  H  L  T  D  A  L  L  E  R  G  D  S  V  T  V  L  D  D  L  S  T  G  R  P  E  R
5416 GCTGCCCGCCGGCGTGCCGCTGCACCACGGGTCGATCACCGACCGGGCCGGGCTGACCCGGGCGCTGACCCGGCTCGCCGAGCAGTGTCGCCCGGAGGTCATCT
    >L  P  A  G  V  P  L  H  H  G  S  I  T  D  R  A  G  L  T  R  L  A  E  Q  C  R  P  E  V  I
```

FIG.11A(5)

```
5508 GCCACCTGGCCGCCCAGGCCGACGTGCGCAACTCGGTGGCCGACGCCACCTCGGACACCGGGGTCAACGTGGTCGGCACCGTCAACGTCCTG
     >C  H  L  A  A  Q  A  D  V  R  N  S  V  A  D  A  T  S  D  T  G  V  N  V  V  G  T  V  N  V  L

5600 GAGGCCGCCCGGGCCATCGACGCCCGGGTGGTCTTCGCCTCCAGCGGCGGCGCCCTCTACGGGGAGGTCGACGAGCTGCCCTCCCCGAGGA
     >E  A  A  R  A  I  D  A  R  V  V  F  A  S  S  G  G  A  L  Y  G  E  V  D  E  L  P  S  P  E  D

5692 CGTCCGGCCGGCCGCCGTGGGGCGCCAAGTACTGCGCGGAGCAGTACCTGGCGCTCTACAACCGGCTCTACGGCTCGACCC
     >  V  R  P  A  P  W  A  P  Y  G  A  A  K  Y  C  A  E  Q  Y  L  A  L  Y  N  R  L  Y  G  S  T

5784 ACGCGGCGCTGCGGCTCGGCAACGTGTACGGGCCACGCCAGGACCCGACCGGCGAGGCCGGGGTCGTCTCGATCTTCTGCGGCCTGCTGGTG
     >H  A  A  L  R  L  G  N  V  Y  G  P  R  Q  D  P  T  G  E  A  G  V  V  S  I  F  C  G  L  L  V

5876 GCCGGGCGCGACGGTGTTCGGCGACGGCGAGAACATCTGGAACATCGGCACCTCGACCATCCGCAAACTACTGGACGTCCTCGTCGGCCGCACCGCGGGC
     >A  G  R  R  P  T  V  F  G  D  G  E  Q  T  R  D  Y  I  Y  V  A  D  V  V  E  A  F  L  L  A  V

5968 CGGGGCACGGTGGCCCCGGCCGCTTCGAGCCCACCCGCCTGGGGCAGCTGAAGCACTCCGCGCTGAAGGTGACCCGGCGGCCCGGAGCTGCGCTGG
     >  G  H  G  G  P  G  L  W  N  I  G  T  S  T  S  I  R  K  L  L  D  L  V  G  R  T  A  G

6060 GCGTCCCGGACCCCGCTCGAGCCGCCGCGCCTGGGCGAGCTGAAGCACTCCGCGCTGAAGGTGACCCGGCGGCCCGGAGCTGCGCTGG
     >R  V  P  D  P  R  F  E  P  P  R  L  G  E  L  K  H  S  A  L  E  V  T  R  A  A  R  E  L  R  W

6152 GCGGGCCCGAACGAGGCTCGCCGGCATCCGCGAAGGTCTACAAGTGGGTCGAGGCCGACGAACCGGTCCGCGGGGGAGCGATGACCCGCG
     >  A  A  R  T  R  L  A  D  G  I  A  K  V  V  Y  K  W  V  E  A  D  E  P  V  R  G  E  R  .
                                                                                       >M  T  R

6242 AGGGGTCAACGCCGGTTAGGGTCGGCCACCATCACGGTCGGCACCAACGAGATCCGTTGGCTGGACCGCGCGCTCGGCTCGCTGCTCGCC
     >E  G  S  T  P  P  V  R  V  A  T  I  T  V  G  T  N  E  I  R  W  L  D  R  A  L  G  S  L  L  A

6334 AGCGACACGACCGGCTTCGAGCTGACGGTCTTCTACGTGGACAACGCGTCCGGCGACGGCTCGGCGCACGTCATGTCGGCGTTCCCGGG
     >S  D  T  T  G  F  E  L  T  V  F  Y  V  V  D  N  A  S  A  D  G  S  V  A  H  V  M  S  A  F  P  G

6426 CGTCCGGGTCATCCGCAACCCCGGAATCTCGGCTTCACCGGCGAACAACGTCGGCATGCGGGCGGCCCTGGCGGGAGGCTTCGACCACA
     >  V  R  I  R  N  P  R  N  L  G  F  T  G  A  N  N  V  G  M  R  A  A  L  A  R  G  F  D  H

6518 TCTTCCTGGTCAACCCCGGAACACCTGGACACCTGGACACCTGGTCCGCGGCTGGTCCGCGAGTTCGCGCAGCGGTGGCCGCAGTACGGCGTCATC
     >I  F  L  V  N  P  D  T  W  T  P  P  G  L  V  R  G  L  V  E  F  A  Q  R  W  P  Q  Y  G  V  I
```

FIG.11A(6)

FIG.11A(7)

```
7713  TGCTTCGGGCCTGGCAGCGCCGGTGCGGCACCCGCTGGAACTGGGCACCGGCGCCCAGTCGCGCCCGTACGACCTCCAGTACATCGGCAGCAA
      >C F G L A A P V R H P L E L G T G A Q S R P Y D L Q Y I G S N
7805  CTGGTGCGGGTGGGAGCCGATGACCGAGATGGTCGAGGCCGCGGCGGCCGGGCCCGGCCTGCGCCGGCTGCGGGTGTGCGGACGCTGGT
      >W W R W E P M T E M V E A A A A R P L R R L R V C G R W
7897  GGGACGGCGGCAGTTGCGCGGGCAGTCTTGCCGGGCGACGCTCAGCGAGCTCAGCGAGGAGGCAGGCTTCGAGGAGGCGGCGAGCACCAGCACGGGCCTGTTGACCCC
      >W D G G S C A G F E E A T L S E P G W L R A R G V E V H P P V
7989  CCGTTCGGCCACGTGGTCGAGCAGATGGGCCGGTCGCTCATCTCACCGGTGCTCGTTCGGCCGCTGGTCACCAGCACCGGCCTGTTGACCCC
      >P F G H V V E Q M G R S L I S P V L V R P L V T S T G L L T P
8081  CCGGATGTTCGAGACGCTGGCCTCGGGCAGCCTGGGCGAACGTGAAGTTCCTCGCCGTCGTCTACGGCGACGAGGCGGAAC
      >R M F E T L A S G S L P V L P V A A K F L A P V Y G D E A E
8173  ACCTGATGCTCGGCGACGACCCGGCCGGAACGGTACGGCTACCCTCGCGTCCTCGGGGACCTGCTCGATCTGCTGGCC
      >H L M L G D D P A G T L S R L S A E H E R Y G R L V G E I Q D
8265  CGGCTCCGGCGTCGAGTACGGCTACCCCTCGCGTCCTCGCCGTACGGCTGAGGAGCAGATGACCCCCCTG
      >R L R V E Y G Y P R V L R D L L D L L A .
                                          >M T P L
8354  CGGATCGCGATGGTCAACATACCGTTCCGAGCGACCGGGCCAGTGGATCACGGCGGGATCCAGTG
      >R I A M V N I P F R L P S D E R Q W I T V P P Q G Y G G I Q W
8446  GATCGTGGCCAACAAGATCAAGGGCCTGCTCGAACTGGGCACGAGGTGTTCCTGCTGGGCAGTCCGGCGTACGCATCCACGCC
      >I V A N K I K G L L E L G H E V F L L G A P G S P R T H P R
8538  TGACCGTGGTGCCGGGGGAGCCGGAGGACATCGGAGACTGTTGAAGTCCGCTCCGGTGGACGTCTCAACGACGTATACAGCTGCGGCAAG
      >L T V V P A G E P E D I R A W L K S A P V D V V N D Y S C G K
8630  GTGGATCCGATCGAGCTGCCCCCGGGCGTGCTGCGGCCTGGTGGCCTCGCCACCATGACCACCCGCCGTCATCCCGATCGGGGTGTACGC
      >V D P I E L P P G V G L V A S H H M T T R P S Y P A G C V Y A
8722  CTCGAAGGCGCAGCGGGAGCAGTGCGGCGGCGCCGACGCCCCGGTCATCCCGATCGGGGTGGATCCGTCGCTCTACCGGCCGGACC
      >S K A Q R E Q C G G G A D A P V I P I G V D P S L Y R P G D
```

FIG.11A(8)

FIG.11A(9)

```
10008  GGAGACGGGCAGGCGGCGGCTCGTCCGGATGTCCCGGTAGTCGCCGGTGTCGGGCGACGCGTGATCGGCGAAGAGCCGGTCG
       < L R A P A A D D G R G A I D R Y D G T D P S A H D A F L R D
10100  TAGGCGGCCCGGACCAGGCGACCTCGGCGTCGTCCCGGAGAGTCACGAAGCCATCGCGCCGGTAAGCCTCCAGCCGACGGTC
       < Y A A R L W A V E A D D A L Q P L T V F G D R R Y A E L R R D
10192  GACGACCTCCGCACCAACAGTCCCCACGGCCATTTGACCACCTCTGTCCGGAATAAACCATACGGTAGGAACAGCGCG
       < V V E A G V T G V A M
10282  GCGATACCGCTCCCGAGCGGGAAATAGGGATTCGACTAGTATTCGGTCGCCGCCTGCCAGAACGGCAGCGCTCTCGATTGTCCATTCAT
       > M T G H S A V A L D V G G V
10374  CCCCGTGCGAGACTCGCCTCGATGTCCTCGATGTCGGTGGGGGGTTTGGAGATGACCGGCACAGCCGTCGCGCTGGACGTCGGGCGGGGT
       > V Y Y D E P F E L A W L Q D T F D R L Q A T D P T L D L R A
10465  CGTCTACTACGACGAGCCGTTCGAGCTGGCTTGGCTCCAGGACACCTTCGACCGCCTCCAGGCAACCGACGCTCCACTCGACCTGCGCGCTGAGCTGG
       > F L E H V E R F Y H Y G E G D P T G R T W L H S E A A L S W
10557  TTCTGGAGCACGTCGAGCGGTTCTACCACTACGGCGAGGGCGACCCGACCGGCCGCACCTGGCTCCACTCGGAGGCCGCGCTGAGCTGG
       > F L E H V E R F Y H Y G E G D P T G R T W L H S E A A L S W
10649  TCGCGGGTCCGGCAGTCCTGGGCGAGCTCGCCCAGGAGATTCCCGGTGCCGGTCGCGGACTGGCCAGGAACTACCGTCGT
       > S R V R Q S W G E L A Q E I P G A V R A V T R L A R E L P V V
10741  GATCGTCGCCAACCAGCCCCCGAGTGCGCAGGACGTACTGGCCCGGAATGGCAGTCAGCGCTGGGCGGATCGGGCGGATCCCCGGCGATCCCGGCGACTCCTCG
       > I V A N Q P P E C A D V L A R N Q V S Q V C R E V L L D S L
10833  TCGGGGTGGCCAAGCCGGACCCGGCACTGCTCGGGCTCGGGCTGCCGTTGCGTGCCGGGTCGTTCGTGCCGGACCCGGCGTACCGGCGGGGCGTCCA
       > V G V A K P D P A L L G L A L R R L A I P P A E L L V G N R
10925  ACGGATCACGACGTCCTGCCGGGTCCTGCACGGAGCTGACACGGAGCCGTTCGTGCCGGACCCGGCGTACCGGCGGGGCGTCCA
       > T B H D V L P A L G L G C P V A F V L P D P A Y R R P P G V H
11017  TCCGGACCTGGTCCGGGTCTACACGGAGCTGCGGGCGTTCCGCACCGGCTCCCCGCCGGACGCCCGGGTCACCGTGGCGTCCCTGG
       > P D L V R V Y T E L R A F R T G S P P A D A R V T V A S L
11109  CGGCCCTGGCCGACTCTCCCCCGCTGACCAGTGCCGCCACCCCGCGTTCGAACGCCGGACTTTGACGAAGGAGTGCAGTTGCGACGCC
       > A A L A D S P L T S A T P R S N A G T G G L .
```

FIG.11A(10)

FIG.11A(11)

```
12451 CCTGACTGGAGGTTGCCCCGGTACGGCTGAGGGCCAGGTCGAAATCAACCCGTGGGGTGCGCGAAC
       >P.
      <G S Q L N G G T R S L A L D F D L G H A H A F
12520 GCGGAGTCCACCCCCATGACGCGCCCCAGATCTTGATGTTTCCCTGGTCACGGGTGCCAGGTGGAACTGGCCGGA
                                      junction marker
      <A S D V G M C A G W I K I N G Q D R H W G V L H F Q G S
12603 GGTGACGTACCACGGCAGACGGCAGCCAGGCGGGGCGGGTGCCGACGTGCGCGGTCGCGCAGGCTCTTGCGGACGGGCGTCGA
      <T V Y W P L R L A P R A L R T G V V H A G D R L S K R V A D V
12695 CGGCAGGCGGGTCGAGCCGGTCGAGCCGCACGTCGTCGACGAACATCAGATCTTGTGCGGCCAGCGAGCATCGCGTTGCGGGAAGGCCGACAGG
      < A A D L R V D D D V F M L H H H P W R A L M A N R S A S L
12787 CCATTGGTGGCACCGAGGATGCGCCAGGATGCCGTCCTCGGGCGTGCCCTCGGGCGTGACGGGCCGGTCCAG
      <G N T A G L I R M T G G A A R V E E A V E E A T V P R D L
12879 CAGGACGTAGTACTCGTCGCCGAGAGCTCGCGGCTGACCGCTGACGAGGCGTTGTTCGGACATCTTGTTCCTGACGTCCCTGACATGAGCGTTGTGGGGCCGGCGGGGAGA
      < L V Y Y E D G S L Q A M N H A L H K R V N E V R F A C I A V V
12971 CCATCGGGTGGTCGAGCGGATCGCGTCCCTGGGACGGAGCGTTGTTCGGCATGTTGTCCGAGCATGCCCCTGACGTCCCTGACATGAGCGTT
      < M P H D S P D R S V V S A N N P M
13061 GGCGGCCCCACCGGATCGCGCTCCGCGGGCCAGGCGGTGCCGCGGCGCCGCCGGCCGGCCGCCGCAGCGCGGGCGGGCGTCCGG
13153 TGAGCGCGCGGAGGCGCGAGCTCAGGGCGCTCCGAGCTCCTGCGGTCCGGAGGGTGCGGGCAGGTGCCGCGGCGGATGCCATGCGCGTACGGCTT
13245 CGGGATCAGGGGCCGGCCGTTGGGCACTGCGGTTCTGCAACAGCTTGCTGACGCAGTGTGGTACGGCTGACCGCGTCGACGCTAGAGACCTTGT
13337 TGGCGATATGCAGGTCGTCGTGGATCTGTTGGCTCGGCTGCGACGCGTCGATGGCCCGGAACACCCCCTGCCGAGGTGCCGGTGGACGAGTGTGCTCCGCT
13429 CCTTGATTGTCCAGCCGTCAGCGCGGCCGAGCGGCCGGAAAGGCCTGCTCGGCTTGCGGGCCGGTGCCGGAGCTGTGTCAGTGTGCCACAGGAACCAGGTGCGGTGATGCCGATGTCCGCT
13521 GGAAGACCGTCAGCGCGGCGGCGGAAGGCCTCGGCCTGTCCGGCCTTGGGCCTCCAACCCATCGGTTCGGCGCTGCCACAGGAACCAGGGAGGAAGTGACGAACATTGAGTTTC
13613 TAGCCCGGCTTCGACGGCTACGTGCTACTGTCGATCGACATCACTGGCGAAATGAAACGACCGGATAGTTACGGAAAGTGACCAATCGGCTTGGCC
13705 GAAGCCCTTCGGCTTCGACGGCTACTGCTGCTACTGCTCGATCGACATCACTGGCGAAATGAAACGACCGGATAGTTACGGAAAGTGACCAATCGGCTTGGCC
13797 CTGTCGCCTCGCGCTGAACTGACCACCAATACACGCGGCCCCACCTGCGACGTCCACCCCCCGAGGATATCGCCAGGCTTCCATG
```

FIG.11A(12)

```
13889  CAGAACTGGCAGGATCTTTCATCTCAGCGGCACCTGGGCGACAAACCCTGCTCAAGACCATGAGTAAGCAGGCGCGGAAATCCATGCAGT
13981  GACATGTGTCACTTAGACAACCAGCTCCAGCCAGCCCACACCGCACCCTGACAAAAGGGGCGGAATCGCGACCAGAGCGACACCAGCATTC
14073  CTAGGGGATTCCTTAGTCTGGGAGCGTCGATCCCCACCCGTCAATCAATTGCCGAACAAATTGCCACCCGTCAAGATCAACACTCCG
14165  CACCGTGAGCAGGCCGACGTCCGGCAATGCGACGTCGCGCGTCCGGTAGCCTCACCGCCGCGCGCGGGGACCGGCACGGAAGATCTCCG
14257  CACCGTCGGCGTCGTGATCAGCGGGTCGCTGTGTCCGGGGCATCGCGCGCGGAACCGCGTTCAGCGCCGGAGGACCGATCGGGAAGCCGACT
14349  GCGAACCTGTCAGCCCTGCAAGCGGACCGGCATCGCGCGCGGAACCACCGACGATCGTCGGGCCGAGCAGGTCACGGCGGGCCCGGGTCGACGC
                                          < -   R  R  S  R  D  P  L  R  S
14440  CGCGGGCCTCGTCCCAGAGCCGCCATCCCCGCCATCGTCGGGCGATCGTCGGGCGATCGTCGGGCGATCGGGAAGCAGGTCACGGCGGGCCCGGGTCGACGC
         <A  A  E  D  W  L  G  G  V  A  D  R  L  S  R  R  P  R  W  G  L  L  D  R  A  P  G  P  D  V  R
14532  GGGCCCAGTCGACGACGTCCACCGAGCCGGGCCGAATCTCGGTCGGCAACCTCACCTCGATCAACATCTCCACG
         <A  W  D  V  V  E  V  S  G  P  R  D  P  L  E  V  V  E  T  P  V  G  S  V  E  I  L  M  E  V
14624  AGGGAGCGGAACGGAACCTCCCCCGCCCTCCCCGTCGGTGACGACTCACCGCCGTGGCCGACACCACCGCCTCGGCGAC
         <L  S  R  V  P  V  A  E  G  R  G  V  G  I  V  R  G  T  V  S  E  R  T  A  S  V  V  A  E  A  V
14716  GTCCCGCACGTCAGTCGACGTCTACGACCGCCACGCCCGGGTCTGCGGTCGACGGTCTCGCGGCCGTCGCGAGCCGGCCGC
         <D  R  V  D  V  Y  D  R  H  A  R  L  P  S  L  E  V  R  A  S  R  D  R  G  A  A  D  V  L  R  V
14808  CGACGACCCGCACGACCGGCTGTCGATGGCACGCAGCTTCGCAGAGCTCGCGGAGCACCGTCGCCGAGCCGGCCGC
         <V  V  R  G  L  L  S  D  P  P  V  G  P  G  V  V  N  A  L  R  L  V  T  A  D  V  S  G  A  R
14900  GTCCGCGAGCACGGCCTGCCGAGCTTCGCCTGCACCAGCTTCCAGGAGCGGGCCAGCGTTGGGCACCGGCACCGTGGGCACGGGCGCCCGAGCCCC
         <T  A  A  L  V  A  Q  T  A  A  L  K  A  R  G  Y  M  S  E  P  Q  T  P  V  T  A  G  A  P  A  G
14992  GGGTGGCTCCTGGACGTCCTGGACGCGCGAGGTGCAACGGCTGCACCAGCGCAACGGGTGCCGTCCAGCGCCGGTGACACTCCACG
         <P  P  E  Q  V  R  E  L  V  S  G  L  H  V  L  R  P  R  C  R  T  R  E  L  A  A  T  V  S  W  T
15084  TCGGGATCGTGCAGCTCCGACGGCCAGCTCCAGGTTCCACTTGCCGGCGGTGGCGCCACCGCGTTGGGCGTCGGCGTCG
         <P  I  T  C  S  S  P  L  E  A  D  T  L  N  W  K  G  G  T  A  N  V  V  A  D  P  Q  E  A  D
```

FIG.11A(13)

```
15176 AACACGGGCGGCCAGCGCGGGGCTCCAGGGTGGCGACGTCCAGCGCCGGGGCCCGGTACGGCAGCCCCGACGGGCAGCGGGGCCAA
       <F  V  A  A  L  A  A  P  E  L  T  A  V  D  L  A  R  A  R  Y  P  L  G  A  S  P  V  R  R  A  L
15268 CACGAGGACGTCGTCGCCCCGGGGCGGCCAAGCGCGGGCGCTCACGTGACGCGAAGCCCGTACCACCGACGAGACGACAGGCCGCGCGC
       <V  L  V  D  D  G  R  A  A  L  A  A  S  V  H  R  G  V  F  G  T  G  G  V  V  V  R  R  A  G
15360 CCATCCGGTACCTCCTGGGGATCAGTCTGTGCGCGGCGGACGACCTCAGGGGACGCCCTGACAGGTCACGGGGGCGCGCAACAC
       <M                <*  D  R  A  G  A  A  D  L  R  G  G  P  G  Q  C  T  V  P  A  R  L  V
15449 CCTGGCCCGGTCGCGGAACCTCGTCCACGAGCCGGGGCCCGTCACCTCTCCGGCGCTGACCGGTGACGCGGTGACGCGGGA
       <R  A  R  D  R  V  E  D  L  L  R  A  R  I  A  T  V  E  E  A  P  Q  G  A  T  V  A  R  V
15541 CGAACTCTGCATCGTGTTGACGAACTGGTCCTCGGCGCGGAGAAGGTCAGTCTCCCGCGTCTCGTCCTGCGCTCCACCGGTGC
       <F  E  R  M  T  N  V  F  Q  D  E  A  P  F  T  L  E  R  T  E  D  Q  R  E  V  R  V  V  P  H
15633 CAGGCCGGCGGTGGGGTGTACGCCGGTCGCGGCTGTCCGGCGTACACAACAGCGGGCACCCGAAACGTCCACGGGATCGGGGGTCGG
       <W  A  P  P  P  T  Y  A  R  D  V  V  I  R  G  A  S  G  W  L  Q  Y  E  C  R  Y  S  H  E  F  G
15725 GAAGGCGATCTGTGCCGGTCCTCCGGCAGGAAGAACCGGCGGCGGGAAACCGGAAGCGTCCAGATCCAGCAGCGCTCCGCCACCCGCCTCG
       <F  A  I  Q  A  T  R  G  D  P  T  C  L  L  A  A  G  S  V  D  V  G  R  D  P  D  E  R  L  T  A
15817 CCGGCCACCTCCGGCTCTCCGGCCAGCCAGCAGCCGGGATCTCGCCGGATCGCCAGTCGGCGCGGCCAGTCGCGGCGGCCGATCTCGCCGGCGGCCTCG
       <A  V  V  E  P  E  E  P  L  F  F  R  A  A  G  L  P  Y  V  G  L  D  L  L  A  G  G  L  E
15909 GGTCGGTAACGGAATGTCGCCCGACAAGTGTGCACCCCATGTGCCGGAGGAAGGTGAGGTTGTCATCAACACGCTGACGCGGGGCCTCAGTCAGCACCGCCG
       <P  R  Y  R  I  D  G  A  P  L  P  P  F  G  F  V  G  S  V  M  R  L  E  G  I  E  G  A  A  V  M
16001 CCGGCGCACGAAGTGGTGCACCCCATGTGCCGGAGGAAGGTGAGGTTGTCATCAACACGCTGACGCGGGGCCTCAGTCAGCACCGCCG
       <R  R  V  F  H  H  V  G  H  R  L  F  T  L  N  D  M  L  V  L  G  R  S  R  A  Q  T  L  V  A  A
16093 CGGTGTCGACCAGCGGCGGTGTCAGGCGGTCTCCCACCAGACGTGTTGCCCGGGCCAGGACGCGTTCGATCCAGTTGTGGTGCAGCCCG
       <T  D  V  L  R  T  T  L  P  K  E  V  L  V  H  K  G  A  A  L  A  R  E  I  W  T  H  H  L  G
16185 GTCGGCAGCGGAATGTCAGACGGCATCGATGTCCGGGCGGTCAGCCCTCAGTGGACTGTTGCCGGAGCGAGCGCCACCCGGGGGTCGCCCTGAGCCGGCGGCGAAGCCCTCAGCCGGCGGCGAAGCCCTCAGCCGGCGGCGAAGCCCTCAG
       <T  P  L  P  I  Y  V  A  D  I  D  P  R  D  L  V  S  Q  Y  G  E  A  A  A  C  G  F  E  A  A  F
```

FIG. 11A(14)

```
16277 GGCGCGGCGCCTTGGCCAGTTCCCGCGCCGCCGACCACCGAGGTCTCCGGGACCCGCCTGATCGCCGGCAGGGCACGCAGGGCACGCAGGGCGGCGA
       < A R A K A L E R A A V V L E A E P V R R I A P L A R R R A I
16369 TGTCGGCGACCCGAGAACCCGATGCGAGGACTGCGTCATCTCCGGCAGCTGCAGGCAGGCCAGCAAGCTGCGGGCC
       < D A C G K V G I R V T M E A M • W L S R L C A L L S R A
16459 TCGGATGTTGAGGTAGTAGCCCTGGAGAGCCTCCAGTGGCACCGTGGCCAGCAGAACTCGTCGGCACCTCGGTCGGGAAGTC
       < E I N L Y Y G H R L L A E L Q R V T V W C F E D P V E T P F D
16551 GTCGGCGGCCGGTCGACCAGGAGGTAACGGTTCTCCGACCGGTAGAATCGCCGCCCTCCGGTGAGCACGGTGTCGTAGAGGACACGCTCGG
       < D G A D V L L Y R N E S R Y F R G G E E T L V T D Y L V R E P
16643 GGGCGGCTTCCAGCACCTCGGCGTGCTAGCGCGGCAGGTGCGCCACTCCGGTGGGATGCATGCCAGGTTGGGCCATCTCCATCGGCG
       < A A E L V E A L F L P R P G P Q N D P I C Q V T P G M E M A
16735 TCGAGCAGCCCGCTAGCGGCGCTGACTCCACCCGGTCAGCCTGGTTGTCGGCGATCGATTTCCTTGACCAAGGCGACCACGCCGGTGCCG
       < D L L G A Q Y R A H V L L H A V G D I E K V L G A V V G R H R
16827 CGGATACAACAGCGGGCTGACTCCACCCGGTCAGCCTGGTCAGCAGGTTGTCGGCGCACCGTGAGCCACGAGGAGTGCCGGCCGTCGTCCC
       < P Y L L P Q S W G T V E R N D I R V T V G V V S F H R G D D R
16919 GCGCGATCCCGTGTGCCGCACCAGGTCTGCGCGGCAGCGTGCTGCAGCGATCGCCGAGCGACGATCGCCGGCGACGACGGCGCCTC
       < A I G D A T H R W D P L G R L P V R R V T M E H R G K A G T
17011 AACCAGCTCAACGCTGGGCGCGGCGGAGTCTGCGGCAGGCAGACATGCGTGTCCATGTTGACCAGGCCGTCACCGCGTCAGCG
       < F W S L V S V L D H R G P A G A A S R V I A A V A P S S P A E
17103 GGTCTCCTGGGCGGCGGCGACTCCAGAAGGCCGTAGTGGTGAGCCCACGGGAAGTCGCGGTAGTCCGACTTGACCAGGCCGTCACCGCGTCAGCG
       < T E Q A A A Y F A S P L C S L V T R T D M N V L G D V R L L A
17195 CGAGCAGTTCGCGGCAGCCTCGCCCAGCGGACGGGAAGCCACCGTGGTAGTCGCCGGACCATGTTCCGGTTGGCGTTGCGC
       < L L E R L P L W R H Y D G A P V D E D V Q V V M N R K R
17287 AGGAACCAGGAGCCCTGCTCCGACTGCAGGACGTCAACGACGTCGAGGACTGAAGTAGTGCAGGGGGTGAAGTAGTGCAGGGCTACTTCGTGCCGCC
       < L F W S G Q E S Q L V D V L V R G A G P R T F Y D L Y K T G G
```

FIG.11A(15)

```
17379  GCCACGGTGTGACCCGGGTGTAGTTGCTCTCCGGGTGGCCTGCATGACGTTGATGTTGCCGGGCTCCACCTTGGCCT
       <G  R  H  V  R  T  Y  N  S  R  T  A  Q  V  T  P  S  L  Q  M  V  N  I  N  G  P  E  V  K  A  Q
17471  GGAGCAGGCAGTACGGTGTCCGTCGACGACCTTGACGCAGTGCCGAGATGCCGGATCTCCGGTTGATGATCGGCTGGTGCCATTCG
       <L  L  C  Y  P  T  G  D  V  V  K  V  L  M  G  L  I  G  I  E  P  Q  N  I  I  P  Q  H  W  E
17563  CGCACCGGGCCGTAGGTGGTCTGGAAGTTCAGCAGGTGCACGGGTCACCCGGCTCTCGTCGTCGGAGAACCTGGCGGTCACCGGGTCGAA
       <R  V  A  G  Y  T  T  Q  V  H  L  G  E  I  V  F  F  R  G  S  E  H  L  N  G  T  V  P  D  F
17655  CGCCCACCCGGGCCAGGCGGTCCAGGTCCACGCGGTCCAGCGGTAGGGTCGACCGGATCCGCTCGGCGAACCAGGAGAAGTCCGGCC
       <A  W  G  P  L  R  D  L  P  V  R  D  V  E  C  Y  T  S  R  T  R  E  A  F  W  S  L  F  D  P  R
17747  GGACCCCCCTCGCAACGCCGACCACGAGCGCTCACCAAGAATCGCTCACCACAGAGCGTGGGAAGACCCGTGTCCGGCCAA
       <V  G  E  A  H  L  A  S  W  S  G  G  D  V  P  G  P  R  H  P  G  A  D  R  T  L  L  P  G  D
17839  GCGCGGACCTTCGGGCGTCGGGTCGACGAATGCTCACCACAGAGCTCGGCCAGTTCGGCGAAGACCCGTGTCCGTCG
       <A  R  V  K  P  D  P  S  S  D  S  V
17930  CAGGCGCAGATCGCTGTCGACAGATCGCTGTCGACATCATGGCGACCATCATGGCCGACGAAGGAGACGGAGGGTTTCCAGCCGAGCCGCTGGGCGGCCCTTCGTCGGAT
       <*  W  L  E  A  L  E  A  S  F  A  H  S  S  G  D  T  D  A  L
       <L  R  L  D  S  D  V  M  M  A  V  M  E  E  F  S  V  S  P  K  W  G  L  R  Q  R  A  K  T  P  D
18022  CCGCGCAGAGCAGCTCGACCTCGGCGGGCCAGGATCTGTCGCCGGAGACTCGTCCACCACCGACTGGGCGAAGCC
       <A  C  L  L  E  V  E  A  P  R  I  L  S  E  D  V  V  H  D  R  W  N  L  G  V  H  A  F  A
18114  GCCTGACCAGTCGCCGAAGCTGCGGTCGCCGAGCCGTGACCCCGTCGAGGCGTAGTCCTCCGGCCAGCATCAGGACCATGCCCCG
       <A  E  V  L  E  R  V  S  H  T  V  G  T  G  L  V  Y  D  E  P  E  D  Q  A  L  M  L  V  M  G  R
18206  CACGTAGTCGCCGAAGCTGCCCAGTCCCGTCGGGCAGTTGCCGAAGCGAGTGAATGCCAGCTTCACCGAGCTTCACCGAGCTTCACCCACGC
       <V  Y  D  G  A  F  G  W  D  R  E  A  S  L  N  G  L  R  L  S  S  R  I  G  L  K  V  A  A  V  G
18298  CCAGGCGACACCTTGCGGGTGACAACTCGGGACTCGGTTGAACAGAATGCCGGAGAACATGCCGTACGAC
       <L  S  V  K  R  T  V  F  E  P  G  R  V  P  S  E  H  N  F  L  I  G  S  V  A  Y  M  G  Y  S
18390  TCACGTAGTTCTGCACCATGTAATGCCGCGCCTTGGCCCGCGTACGCCTCAGTGAACGGGGTCATTCTGGACGGG
       <E  R  Y  N  Q  V  M  Y  H  G  F  A  K  A  A  G  Y  P  S  R  P  H  F  P  T  L  E  N  Q  V  P
```

FIG.11A(16)

```
18482  CTCCCGGCACCTTGCCGAACATCTCCGACGAAGAGACGCCTGATAAAAGCGCGGCTGCGGGACTGCGGGAATCCGACAGGCCCCCA
       < E   R   V   K   G   F   M   E   S   S   S   A   Q   Y   F   R   P   Q   G   A   A   P   S   R   S   D   S   L   G   G   V

18574  CGATCCGCAAGGCTTCGAGCATGCGGAGCACACCCATGCCGGTGACTCCGCGTCGGACTGCCGCCACGACACCGGCACGGTACGAC
       < I   R   L   A   E   L   M   R   L   V   G   M   H   G   T   V   E   A   T   T   T   S   Q   R   W   S   V   P   V   Y   S

18666  AGCGCGCCGAGGTTGTAGACCTCGTCCGGCGCCGTTGATGCCGCCGCGCTTGCCGACGCGGCTCGTGATCTCAGAAGGTCGCGATCAGCTT
       < L   A   G   L   N   Y   V   E   D   P   A   A   R   E   I   A   A   V   L   S   T   Q   D   L   L   D   G   S   I   L   K

18758  GACCGCTGGATCAGGTTGCCGACGGTTGCGGACCGAGGGCGGTCTGCCGGCGACCAATCCAAATACTCGTATCCGGACTGAAGCAGGT
       < V   A   P   D   P   Q   R   L   S   R   V   S   P   A   T   Q   G   R   V   L   G   F   V   E   Y   G   S   Q   L   L   H

18850  GCTCCGGAGATACGTGCCGTCCTGGCCGGTAATTCCAGTGATCAGCGCGCCGTGTCAGGGTAGTCTCAGCCGTGAAGCCACCTGGCC
       < E   A   L   Y   T   G   D   Q   G   T   I   G   T   I   L   A   R   R   T   L   T   T   E   L   R   S   A   V

18941  GAGGCGTGACCTCGCGCGATGGCGGACCCAAAGATCCGCCGTTCGAAATGGGGTCGGATCTCCGCTACGCGCTCACGGTACGCGAATCT

19033  CCAAGCGGATTCAGGCGACCCGGACGCCGGAAAGCAATATAGGGAGGTTACTAGTACTTTCGGGCGGCCCAGCGCCGGACGACCGGCA

19125  GGATCGCCCCGTTCGGCCGGGACGACCACCATCCCGGGACACCTTCGTCGGGATCGTCGCCGAGATCGTCGCCGATGCGAACTGCTTGACTCC

19217  ACCGTTTTGTCCCCTAACGTCGGCCGGCCCGCCGCCGGCCCAGCGCACCCCAGCGCTGCCAGCGCCGGGTTCACGAAGGCGCCAACTTCCGGTGAGAGAGCAG
                                                                                                > M   V   A   L   V   A   V   M   I

19309  GGCTCATGTCGCAGAGCGGCCTGATGGTCTGCGCGTTCGCCATCATGGTGGAGGTTCTGGCCGGCCCTGACCTGCCGAAGTACCAGGGCATCATGTCGG
                                                                                                > M   V   A   L   V   A   V   M   I

19400  CCCGATGGTGCTGGCCACCCTCGACAACACCATCATCGGTACGCTGCCCACTGCCCAGGTGGTCGGCGGCCTTGGGCGGGCCTTCAGCACGCTCTCCT
       > P   M   V   L   A   T   L   D   N   T   I   I   G   T   A   L   P   T   V   V   G   E   L   G   G   L   S   T   L   L   S

19492  GGGTGATCACCTCGTACACGCTGGCCACGGCCGCCAGCACGCCGGTCTGGGGCATGGCTGGCCGACATGTACGGCGGCAAGGTGGTCTTCGTG
       > W   V   I   T   S   Y   T   L   A   T   A   A   S   T   P   V   W   G   K   L   A   D   M   Y   G   G   K   V   V   F   V

19584  GCCACGCTGGTCGTGTTCCTGGCGGGCTCGCTGCTGTCCGGGATGGCGCAGAGCATCACCCAGCTGACCGTCTTCCGCGCCGTGCACGGGCT
       > A   T   L   V   V   F   L   A   G   S   L   L   S   G   M   A   Q   S   I   T   Q   L   T   V   F   R   A   V   H   G   L

19676  CGGCGGCGGCCTGATGGTCTGCGCGTTCGCCATCATGGTGGAGGTTCTGGCCGGCCCTGACCTGCCGAAGTACCAGGGCATCATGTCGG
       > G   A   G   G   L   M   V   C   A   F   A   I   M   V   E   V   L   A   G   P   D   L   P   K   Y   Q   G   I   M   S
```

FIG.11A(17)

```
19768  CGACCATGGGCCTGACCATGGTGGCGGGCCCGCTCGTCGGGGGCCTGATCACCGATGAGCTGGGCTGGCGGTGCTTCTACATCAACCTG
      >A T M G L T M V A G P L V G G L I T D E L G W R W C F Y I N L
19860  CCGATCGGGGCGGTCGCGCTGCTCATCGTGGTGCTGATGCATCTGCCGCGCCACACCAAGGCCCGGATCGATTACGCGGGTGCTGC
      >P I G A V A L L I V V L M H L P R R H T K A R I D Y A G A A
19952  CCTGCTCACCGTGGTCAGTTCGTGCGTCGTGCTGGTGACCACTTGGGGCATCACCTACCCCGTCGCGTCTCCGATGATCCTGGGGCTGG
      >L L T V V S S C V V L V T T W G I T Y P W A S P M I L G L
20044  TCGCGCTCGGGGTGCTGACCTGCGCGCTCTTCGTGGTGGTCGAGCGACGGGTTGCCGAGCCGTTGGTGCCCCTGGCCATGTTCCGCAGCCTG
      >V A L G V L T C A L F V V E R R V A E P L V P L A M F R S L
20136  AACTTCACCCTGAGCACCCTGATCGCCTTCCTGGTCGGCTTCGCCCTGATCGCGGGGCTGACCTTCCTGGCCCTGTTCCAGCAGGCGGTGCA
      >N F T L S T L I A F L V G F A L I A G L T F L A L F Q Q A V Q
20228  GGGTGCCTCCGCGTCCGACTCGGGCCTGCTGCTGCCGCTGCTGTCCATGGCGGCGGTCAACGTGGTCGGGGGTCGCCTGATGAGCG
      >G A S A S D S G L L L P L L L S M A A V N V V G G R L M S
20320  GCGGGGGGTTCCTACCGGCGTCTGCTGATGCTCGCCGGGGCGGCGCTGATGACCCTGAGCCTGCTGCTCTTCGCCCTGATGGACGTGGGCACCAGC
      >G G R S Y R L L M L A G A A L M T L S L L L F A L M D V G T S
20412  CGGACGTGCTGGGCTCACCGGGATCCCCATGGTCGGCTTCGGCGCGGGGCTGGGGCTCATGCAGACGAGCCTGATGGTGGCGCTGAGCAGCGTGGAA
      >R T V T A I P M V G F G A G L G L L M Q T S L M V A L S S V E
20504  GATGAGGAACTTCGGGGTGGCGGTGGCCTCGACGCTCTTCCGCACCATCGGTGGGGGCGGTGCGGTCGCGAGCGTCTCGCTGTTCT
      >M R N L G V A A S T L F R T I G G A V G A S A T V S L F
20596  CCGTGCGCCAGTCGGCGCTGGCCGATCGGGGCGTGGCCGACGTGGCGGACCTGCTGGGCCACTCCGCGCGGCTGGACGCCGGCGGGCTG
      >S V R V Q S A L A D R G V A D V A D L L G H S A R L D A A G L
20688  GCCCAACTCCCCGCGGCCGTCCGTGTCCACTTCATGCACGCGGTCGCGTCGGGCACCCGGTGGGCCTTCCTGATGACCGTGCTGGCGGGCT
      >A Q L P R A V R V H F M H A V A S G T R W A F L M T V L A G L
20780  GATCTGCGTCGCGGCGGCCTGGTTCCTGCGCCGGGTCACCCCGTTGACGTCGGCACCGGTGGCACCGGAACCGGCCGCGGACGTCGCCGCCGC
      >I C V A A W F L R R V T P L T S A P V A P E P A R D V A A
```

FIG.11A(18)

```
20872 CCGCCGCCAGCAGCGGGGCGCGCCGAACTACTAGCGGATTTCCTGTCGACGGTAGAGCTGAATTCACCGGCGACCTAACA
     >P  A  A  S  S  G  R  A  P  N  Y  .

20963 TTCTTTTCGCGATCCGGAATCCGTCCATTCCCGTGTCTGTGGCGATGGTCGACGGGCCGGCCGGTGCCGAGCGGACAGACAGATTCTCGGAT

21055 TGGAGCTCGATGTCCAGCAAGATCCTAGTCATCGGAGGTCCGGCCGGGATCGCCGCCGCTGCTCGCCGATCGGGGCTGTCG
     >M  S  S  K  I  L  V  I  G  G  P  A  G  S  T  A  A  L  L  A  R  S  G  L  S

21145 GTGACGCTCCTGGAAAAGGAGACGTTCCCGCGATACCACATCGGCGAGTGCGAGTCGTCGTCGCCACCATCGTCGATTTCGTGGGCGC
     >V  T  L  L  E  K  E  T  F  P  R  Y  H  I  G  E  S  I  A  S  S  C  R  T  I  V  D  F  V  G  A

21237 TCTCGACGAGGTCGACTCGCGGGGCTACCCGCAGAAGAACGGGGTCCTGCTGCGGTGGGGCAACGAGGACTGGGCCATCGACTGGGCCAAGA
     >L  D  E  V  D  S  R  G  Y  P  Q  K  N  G  V  L  L  R  W  G  N  E  D  W  A  I  D  W  A  K

21329 TCTTCGGGCCGGTGCGGTCCTGGCAGGTCGACCGGGACGACTTCGACCACGTCCTGCTCAACAACGCCGGCAAGCAGGGCGCCAAGATC
     >I  F  G  P  V  R  S  W  Q  V  D  R  D  D  F  D  H  V  L  L  N  N  A  G  K  Q  G  A  K  I

21421 ATCCAGGGCGCGGTGAAGCGGGTGCTGTTCGACGGGGAGCGGGCCACGGCCGCGGAGTGGTTCGACCCCGAGTCGGGTGAGGTCCGGCAC
     >I  Q  G  A  A  V  K  R  V  L  F  D  G  E  R  A  T  A  A  E  W  F  D  P  E  S  G  E  V  R  T

21513 CATCGATTTCGACTACGTGGTCGATGGCGCATCTGGGCGTACTGGCAGGGTCGGCGCTCCGCCGCCGGATCAAACGTCATCTCCGGCCGACGGC
     >F  I  D  F  D  Y  V  V  D  A  S  G  R  A  G  L  I  P  S  Q  H  F  K  H  R  R  P  T  E  T  F

21605 AGAACGTGGCCATCTGGGGCTACTGGCAGGGGCAGGGGCAGGGATCGCTGCTGCCGAACTCTCCGGGCGATCAACGTCATCTCCGGCCGACGGC
     >K  N  V  A  I  W  G  Y  W  Q  G  G  S  L  L  P  N  S  P  S  G  G  I  N  V  I  S  A  P  D  G

21697 TGGTACGTGCTGCTCATCCCGCTGCGGGGCGACCGGTACAGCATCGGCTTCGTCTGCCACCAGAGCCGCTTCCTGGAGCGGCGCAAGGAGCACGC
     >W  Y  V  I  P  L  R  G  D  R  Y  S  I  G  F  V  C  H  Q  S  R  F  L  E  R  R  K  E  H  A

21789 CTCGCTGGAGGACATGCTGGCGCTGGTGCAGGAGAGTCCCACCGTGGTCGGGCGCCTGACCGCGAACGGTACCTACCAGCCGGGTGTGCGGG
     >S  L  E  D  M  L  A  A  L  V  Q  E  S  P  T  V  R  G  L  T  A  N  G  T  Y  Q  P  G  V  R

21881 TGGAGCAGGACTTCTCGTACATCTCCGACAGCTTCTGCGGGCCCGGCTACTTCGCGGCGGGCGACTCCGCCTGCTTCCTGGACCCACTGCTG
     >V  E  Q  D  F  S  Y  I  S  D  S  F  C  G  P  G  Y  F  A  A  G  D  S  A  C  F  L  D  P  L  L
```

FIG. 11A(19)

```
21973 TCCACCGGGGTGCACCTCGCCCTCTACAGCGGGCATGCTCGCCTCGGCGTCCATCCTGGCCACCATCCAGGGTGACGTCACCGAGGAGGAGGC
      > S  T  G  V  H  L  A  L  Y  S  G  M  L  A  S  A  S  I  L  A  T  I  H  G  D  V  T  E  E  E  A
22065 GCGGGCGTTCTACGAGTCCCTCTACCGCAACGCCTACCAGCGCCTGTTCACCCTCGTCGCGGGCGTCTACCAGCAGCAGGCCGGCAAGAGGG
      > R  A  F  Y  E  S  L  Y  R  N  A  Y  Q  R  L  F  T  L  V  A  G  V  Y  Q  Q  Q  A  G  K  R
22157 CATACTTCGGCCTGGCCGACGCGCTGGTGCACGACAGCGGCGAACCGAGTACGAGAAGGTAGACGGGGCCCGCGCCTTCGCCCAGCTCGTC
      > A  Y  F  G  L  A  D  A  L  V  H  D  S  G  E  P  E  Y  E  K  V  D  G  A  R  A  F  A  Q  L  V
22249 GCCGGCCTCGCCGACCTGGACGACGCGGCAGAGGGACGGCACGACAGCACGGCGGAGCGGCATGACAGCACGGCGCGCACGCCGTCCGCA
      > A  G  L  A  D  L  D  D  A  A  E  G  R  H  D  S  T  A  A  A  P  A  E  Q  D  N  S  V  R  Q
22341 GCTCTTCTGGCCGACTGGGCAACCGGCCTCTACCTGGTCACCACCCCGCGGCTCGGGATCGCGCGCAAGCCCGACAGCAGGCGGGCG
      > L  F  L  A  E  E  A  R  R  M  A  D  A  R  T  P  S  A  P  V  S  E  A  P  G  K  L  D  S
22433 ACGACCTCTTCGACTCGGCCACCGGTCTGTACCTGGTCACCACCCCGCGGCTCGGGATCGCGCGCAAGCCCGACGCAGGCGCGGCG
      > H  D  L  F  D  S  A  T  G  L  Y  L  V  T  T  P  R  L  G  I  R  R  A  K  P  A  D  T  Q  A  A
22525 GCAGAGCAGTCTGCCTGGGCAGGGGCAGGCAGGGCAGGGGCAGGCAGGCAGGGGCAGGCAGGGCAGGCAGGCAGGCAGGCAGGCAGCG
      > A  E  Q  S  A  .
22616 GCATCCGGGTGCCGGCGGCTGAGCAGGGGCACGCCCCGCGCCCGGGGCAGGGCAGGCAGGCAGGCAGGCAGGCAGGGGCACCGGC
22708 GTTGCTCGCCCTCGGCAGCCCTGGCCGCGGCCGGAGGCACCGTCATGTCACGCCTCCGAGACGCGCAGGCGCAGGCGGCACCGGC
      > M  S  R  S  L  R  R  D  A  Q  A  A  Q  A  A  P  A
22798 GTCGCCGGCCAACCCGCACGCGGGCCACGCGGCACCGGTCCCCGCGCGGCGTCTCCGCGACATCGACGTCTACGAGATCCCCATCCGGCCCGCCCAGGTGCAGATCCTG
      > S  P  A  N  P  H  A  G  H  A  A  P  V  P  S  R  V  S  T  T  T  V  A  V  T  P  F  T  E  P
22890 TGCCCGGTCCCGCCGCCGCGGCTGACCCCGGTCTCCCGCGACGGCATCGACGTCTACGAGATCCCCATCCGGCCCGCCCAGGTGCAGATCCTG
      > M  P  V  P  P  R  L  T  P  V  S  R  R  D  G  I  D  V  Y  E  I  P  I  R  P  A  Q  V  Q  I  L
22982 CCCGGCCTGCTCACGCCCGCCTACACCTACGCGGGTTCCTTCGTCGGCAGCGCGGCACGGGCCGGTGCCGGGATCACCTA
      < P  G  L  L  T  P  A  Y  T  Y  A  G  S  F  V  G  P  T  I  R  A  R  T  G  R  P  V  R  I  T  Y
23074 CACCAACGGGCTGACACGGCACCGCAACGTGCACCTGCACGGCGGGCACGTGCCGGCCACCAGCGACGGTCACCCGATGGACCTGATCCCGC
      > T  N  G  L  D  T  H  A  N  V  H  L  H  G  G  H  V  P  A  T  S  D  G  H  P  M  D  L  I  P
```

FIG. 11A(20)

```
23166 CGGGCGGGCTCGAAGGTCTACGACTACCCGAACCTTCAGCGCGGGCGGCGCGAGCGCTCTGGTACCACACCCACGCTCTACGAGGCCGACCAC
      > P  G  G  S  K  V  Y  D  Y  P  N  L  Q  R  G  A  T  L  W  Y  H  D  H  T  H  A  Y  E  A  D  H

23258 GTCTACGGCGACTGCACGGTCTTCTATCTGATCGACGACCCGGCCGAGCATCACCTGCGCTGCCTGCGCAAGTACGACGTGCCGATCAT
      > V  Y  R  G  L  H  G  F  Y  L  I  D  D  P  A  E  H  H  L  R  L  P  A  G  K  Y  D  V  P  I  M

23350 GCTGCGCAACGCCCAGTTCGACGACTCCGGCGCCCTCGTCTTCGGCCACCCGGTCACCATCCTGGCGAACGGCAAGGCCCAGC
      > L  R  N  A  Q  F  D  D  S  G  A  L  V  F  G  H  P  D  D  R  V  T  I  L  A  N  G  K  A  Q

23442 CCTACTTCGAGGTGGCCCCGCGGTACCGGTTCCGCCTGCTCAACGCGCTGAAGCACGTCTTCCGGCTCAACCTGGGCGGCGAACCG
      > P  Y  F  E  V  A  P  R  R  Y  R  F  R  L  L  N  A  A  L  K  H  V  F  R  L  N  L  G  G  E  P

23534 CTCACCCGCATCGCCACGGACGGCGGCCTGCTGCCCGCCGGGCCGGTCTACCTCTACGACGGGGACAACCCGATCCTGCGCTTCGACGTGTCCTCCCGGGCAGCGGGTCTCCGGGCGG
      > L  T  R  I  A  T  D  G  G  L  L  P  A  P  T  S  H  T  E  L  A  L  S  S  G  E  R  V  E  I  V

23626 GATCGACTTCGCCGAGCACGCAGGCGGGCCAGGCGGCGGTCACCCTGCCGGTCACCCTGCCGGTGCCCTCGCCGTCGATGAGCTTCGAC
      > I  D  F  A  E  H  A  G  G  P  V  Y  L  Y  D  G  D  N  P  I  L  R  F  D  V  S  S  R  A

23718 TCACCGACCCCAGCCGGTGCCGGTCACCCTGCGCGCCCTGCCGGGGACGGCAACCCGTTCGACCCTCTCCGGGTGACGTACAGGTCAAGCGGGGACGTACAGCAGCAGGACACCGAGAT
      > V  T  D  P  S  R  V  P  V  T  L  R  A  L  P  P  M  G  T  P  T  V  E  R  T  V  S  M  S  F  D

23810 ATGTCGGCCCGGCCCCCGATCGCGCTCATGGACGGCAAGCCGTTCGACGACCATCCCCTTCGACGACATCCGTTCCACCTGACCTGGTCACGTCCTGGTGACGTTCCGGGTGCTCGGCCGCGACG
      > M  S  A  R  P  P  I  A  L  M  D  G  K  P  F  D  P  L  R  V  D  V  Q  V  K  R  G  S  T  E  I

23902 CTGGAACGTGGTCAACGGGATACCGGACCCGGAGGACGGCCTCAAGGACACCGTCTGTCGTCTCAAGATCCAGGTGTCTGTCAAGATCCAGGTGACCTTCGCCACG
      > W  N  V  V  N  A  D  T  D  P  F  P  F  D  H  P  F  F  H  L  H  L  V  T  F  R  V  L  G  R  D

23994 GCGGGCCCGGCCCCGGCCCCGGAGGACGCGGGCCTCAAGGACACCGTCTACGTCTACGTCTCGCCCAAGGGGTCTGTCAAGATCCAGGTGACCTTCGCCACG
      > G  G  P  P  A  P  E  D  A  G  L  K  D  T  V  Y  V  S  P  K  G  S  V  K  I  Q  V  T  F  A  T

24086 CCGGTACCTCGGGCAGTACGTCGTCTACCACTGCCACTACCTGGAGCACTCCTCGCTCGGCATGATGGCCCAGCTGGAGGTTGTGCCCTGAGGGC
      > P  Y  L  G  Q  Y  V  V  H  C  H  Y  L  E  H  S  S  L  G  M  M  A  Q  L  E  V  V  P  •

24177 TCAGCCGTGCAGGTCGACGATCGAGGGGTGGGCGCCGGAACCGGCGCACCCGGCGCGGGGGCCAGG
      < •  G  H  L  D  V  I  S  P  H  A  G  F  L  S  V  P  R  V  D  G  V  G  F  G  A  A  R  A  L
```

FIG.11A(21)

```
24268 TCGGCCTGGTCGGCGAACTCGTGCAGCAGTACGCCCGGCCCGCCGTGACCGGCGCAGTCCGCGGAAGAGGCGGCCGGAATC
       <D  A  Q  D  A  F  E  H  L  L  L  V  A  R  G  G  D  V  T  V  R  R  L  E  A  F  L  R  G  S  D
24360 ACCGGCGAGCACGCCCCGCGCCTGCACCTGCGGGTCCCAGGGCGGATTGCTGACCACCGGGTTCCGACCGGTTCCGCAGCGGCAATCGTC
       <G  A  L  V  G  R  A  Q  V  Q  R  D  W  P  P  N  S  V  V  R  D  V  R  G  T  R  L  P  L  R  G
24452 CGGCGTCGGCGACGTCGCCCAGGTGACCGTTGGCCGCCGAGTTGGCGACGGCCGCGAGTCTCCGGGTCGTGTCCGAGCCG
       <A  D  A  V  A  W  T  V  R  A  G  S  A  A  S  N  A  V  A  A  G  V  T  E  P  D  H  D  S  G
24544 AACAGCACCGCCCCCGGTGCCAGCCCGGTGCCTCCACGGGATCGTGCCGGTGCCAGCAGGATCGGCCACCAGCATCCCGGGGCGGGAT
       <F  L  V  A  G  P  A  L  G  A  A  E  V  P  I  T  G  T  G  C  C  P  D  A  V  L  M  G  P  R  I
24636 GCCGGCCAGCCAGGCCAGGCCGGGCAGCGAGCGGGGAGGGATGCAGGGTCCTTGTAGGCCCGCCGGTTGCAGCGGCCGGT
       <G  A  L  W  A  L  A  A  A  L  P  P  H  L  T  G  P  T  S  S  R  K  Y  A  R  R  H  L  P  R  D
24728 CGGCCACCCGTACCGCCAGCCGTCCGCCCTGGGTGCCCTCGACGGTGACCGTGAGCGACACCCCGGGGGCCTCGGCGGCTCGGCGGCGG
       <A  V  R  V  A  L  T  A  Q  T  G  E  V  T  V  R  L  S  L  G  G  E  P  P  A  E  G  G  R  R
24820 GAGTGGTAGCGCAACCGGAGCGCGGCCACCGTGCCGCCCCACGGGCGTCCTCGATGTCGTTGTAGTTGCGGCGGCCGAGGAAGGA
       <S  H  Y  R  L  G  L  A  A  V  A  H  R  G  V  A  D  E  I  D  Y  R  N  Y  N  R  R  G  L  F  S
24912 GGCGGGCGACGTCCAACCGGGTCGCCGCGGTCGCGCCCGGGCACGGCCGCGGCACGGGCGCGGCCGCGGCCCGGCCAGCC
       <A  A  V  D  V  T  A  P  R  G  P  V  G  C  A  A  R  A  P  L  V  A  P  L  A  A  A  R  A  L  R
25004 GGGTGAAGGCCCTCCGGCTCGACGGCCTGGACGGCGGAGAACCTCGCCGGTGCCTGACCTCGGACCGAGGCCGCTCCTGATCCTCTGGGC
       <T  F  A  A  L  D  A  K  T  H  G  V  G  D  A  V  L  L  F  L  D  D  V  T  R  L  D  L
25096 AGGCGCGGCTCCGGACCGTCCGGCCTGGACGGCGGAGAACCTCGCCGGTGCCTGACCTCGGACCGAGGCCGCTCCTGATCCTCTGGGC
       <L  R  P  E  A  S  A  S  F  W  V  E  R  H  R  H  E  V  R  G  L  G  R  E  E  I  E  Q  A
25188 GGCCACCTCCTCGCCAGCCCTCGGCAGCCTCGCATGAAGGCGCACCGTCACCGTCCGCCATCGAAGCGCACCGGGACCGCCAGCGCCGACGCCGA
       <A  V  E  E  L  G  R  L  T  R  A  M
25278 GTGCCGGCCCGGACGCGCCGTCCCGGCCTACCACCGCCACCCCGGGGACCCAGCCAGCCCCCCGACGGGGAGCCGACGCCGA
25370 CCGGACCCGGCCAAGACTAGGTGAACCTCTATAGGAATTCGCGTGCCCCCTTCATAGGGTGCCGAAAGGGGTAATGAACCGTCCGGCACCGGA
```

FIG.11A(22)

FIG.11A(23)

```
26565 CGGGCGTGGTGTGTCGTGCCGATCGTCGTCCAGGTGCCGACGTGGCGGGAGTCGCCGACCTGGACACCTGCGGCGGGCCCGCCCA
      >P G V V S C A I V Q V I E S P T W R E .

26656 GCCCAGCAAACCGACAGCAGGGGATGATTGTTGGAAGCAGAGAAGGACACCGGTTGCGTCCGGTGGCGTCGCGTGGTGGGGA
      >V E A E K D R L R P V A S E A V A V V G

26746 TCGGCTGCCGGTTCCCGGGCGACGTCAACTCGCCCGACGAGTTCTGGGACCTTCTGACCGGGCGGAACACCACCGGGACGGTGCCCGAG
      >I G C R F P G D V N S P D E F W D L L T G G R N T T G T V P E

26838 GAGCGCTGGAGCGCGTACCGCGACCTGGGTCCGGCGTTCGAGTCCGCGCTCCGCTCGGCCACCCGGGCGGGCAACTTCCTGGCCGACATCTC
      >E R W S A Y R D L G P A F E S A L R S A T R A G N F L A D I S

26930 CGGCTTCGACGCGGACTTCTTCGGCATCTCCCCGCGCGAGGCCGAGCTGATGGACCCGCAGCAGCGGCTCATGCTGGAGGTGACCTGGCAGG
      >G F D A D F F G I S P R E A E L M D P Q Q R L M L E V T W Q

27022 CGCTTGGAGGACGCCGGGATCCCGCCCCGGACCCTGGCCGGCACCGACGTCGGCGTCTTCGCGGGCGTGTGCACCTACGACTACGGCGGCCAC
      >A L E D A G I P P R T L A G T D V G V F A G V C T Y D Y G G H

27114 CAGTTGGAGGACCTGCCGCACATCGACGCCTGGACCGGCATCGGCGCTGCCACCTGCGCCGTTGCCGTCGCGAACCGCGTCAGCCACGTGCTCGACCT
      >Q L E D L P H I D A W T G I G A A T C A V A N R V S H V L D L

27206 GCGCGGGCCCTCGCTCAGCATCGACACGGCCTGTTCGGCCAGTCTGGTCGCGCTGCACCTCGCCGCGGCGCAGAGCCTGCGCCTGGGCGAGAGCA
      >R G P S L S I D T A C S A S L V A L H L A A Q S L R L G E S

27298 CGCTGGCCCTCGCCGGCGGGGTCAACCTGATCGTCACGCCCGGGCAGTCGATCACCCTCGGCTCGGCCGGTGCCCTGGCACCTGACGGGCGC
      >T L A L A G G V N L I V T P G Q S I T L G S A G A L A P D G R

27390 AGCAAGTCCTTCGACGCCACAGCCGACGGCTACGGCCGTGGCGAGGGGTGTGGCGTCGTGCTCAAGCTGCTCTCCGACGCCCAGCGGGA
      >S K S F D A T A D G Y G R G E G C G V L V L K L L S D A Q R D

27482 CGGGGACCGGGTGCTGGCCGTGCTGCGCGGCTCGGCCGTCAACCAGGACGGCCGCACCAACGGGATCATGGCACCGTGCGGCCAGGCCCAGG
      >G D R V L A V L R G S A V N Q D G R T N G I M A P C G Q A Q

27574 AGCACGTGATGGTCCGCGCGCTGCGCTCGGCCGGCATCGAGGCGCACGGCACCGGCACCCCGCTCGGT
      >E H V M V R A L R S A G I E A H G T G T P L G
```

FIG.11A(24)

```
27666 GACCCGATGGAGGCCGCGGCGATCGGTTCGGTCTACGGGCAGGACCGGCCCGACGAGCCCTGCCTGATCGGTTCGGTCAAGTCCAACAT
     >D  P  M  E  A  A  A  I  G  S  V  Y  G  Q  D  R  P  D  D  E  P  C  L  I  G  S  V  K  S  N  I
27758 CGGCCACCTGGAGGGGGCGGCGGTGGCGGTCATCAAGGCGTTCTGGCTGCTGAACCGGGCCGAGGTGCCCGCCACCCTGCTGGTCA
     > G  H  L  E  G  A  A  G  V  A  G  V  I  K  A  V  L  A  L  N  R  A  E  V  P  A  T  L  L  V
27850 CCGAGGTCAACCCGGACATCGAGTGGAAGCGCCTGCGCCTGGTCACCCGCAACCAGCCCTGGCCGGACCGGCCCGGACCGCGCCGC
     >T  E  V  N  P  D  I  E  W  K  R  L  R  L  R  L  V  T  R  N  Q  P  W  P  D  R  P  G  P  R  R
27942 GCCGGAGTCTCCGGCTACGGCGGCGGTGGCACGGTGGCCCACGTGGTGCTGGAACAGGCCCCGGTTGCCGAGCAGCCGGCCCGGCGCT
     > A  G  V  S  G  F  G  Y  G  G  T  V  A  H  V  V  L  E  Q  A  P  P  V  A  A  E  P  A  P  A  L
28034 GACCGGGCGAGACGCTGTTCCCGATCTCGGCCGCACACTCCCTTCGCGAGCGGGCCCGGGCCCTGGCCGGTGGCCTCGGCGGACCTGGTC
     > T  G  E  T  L  F  P  I  S  A  G  S  A  H  S  L  R  E  R  A  R  A  L  A  G  I  V  P  D  V
28126 ACCTTCGCCGGCTCGGCCGCGTTGCGCCACACGCTGGCCACAGGCCGCGACGCGGCGGGGCCGTGGCCGGAAGCCGCCCGCACGGTGGGTGTT
     >D  L  A  A  L  G  H  T  L  A  R  R  S  H  L  T  H  R  A  V  A  V  A  A  G  R  D  D  L  V
28218 GCGGCCGTTCGCGGACGCCGACGGCCGTCACGACCGGGTGCGCACCGGAAGCCCCGTCGCGGAACCCGCCCGCACGGTGTGGGTGTT
     > A  A  F  A  A  L  A  D  D  R  P  H  D  R  V  R  T  G  S  P  V  A  E  P  P  R  T  V  W  V  F
28310 CTCCGGGCACGGGTCGCAGTGACTCGGTTTCTCACCCCCGCCAGCCGATCGTACGAGGCGATCGACCGGACCCAGACAATGATCTTCGCG
     > S  G  H  G  S  Q  W  T  G  M  G  R  E  L  L  A  T  E  P  A  F  A  D  A  I  D  R  I  E  Q
28402 TCTTCCTCGACGAGATCGGGTTTCTCACCCCCGCCAGCCGATCGTACGAGGCGGTCGATCGGCCACTCGGTGATGCCGGCGGT
     >I  F  L  D  E  I  G  F  S  P  R  Q  A  I  L  D  G  D  Y  E  A  V  D  R  T  Q  T  M  I  F  A
28494 ATGCAGCTCGGCGCTGGCCGAGATGTGGCGCGAGGGAGTCGAGCCGGACGCGGTCATCGGCCACTCGGTCGGCGAGATCGCCGCGGCGGT
     >M  Q  L  G  L  A  E  M  W  R  A  R  G  V  E  P  D  A  V  I  G  H  S  V  G  E  I  A  A  A  V
28586 GACCGCCGGCATCCTCACCGTCGCCGACGGCGCACGCCTGATCTGCCGTCGCCGCAGCCTGCTCCGCGAGGTCGCCGGGCAGGGCGCGATGG
     > T  A  G  I  L  T  V  A  D  G  A  R  L  I  C  R  R  S  L  L  R  E  V  A  G  Q  G  A  M
28678 CCCTGGTCACGCTGCCCTTCGAGGAGGTCGCCGCCCGGCTGGCCGGCCGCGTCGACGTGGTCGCCGCGATCGCCTCCTCGCCGTCGACC
     >A  L  V  T  L  P  F  E  E  V  A  A  R  L  A  G  R  V  D  V  V  A  A  I  A  S  S  P  S  S  T
```

FIG.11A(25)

```
28770 GTGGTCTCCGGCGACCCGGCCGCGCTGGACGCGCTGGTCGCCGAGTGGACCGAGGAGGGCCTGGGCGTACGCCGGGTCGCCTCCGACGTGGC
      > V V S G D P A A L D A L V A E W T E E G L G V R R V A S D V A
28862 CTTCCACAGCCCGCACATGGACCCGCCGCTCCTCGACCGGCTCCGCGCCGCTGTCGACTTCACCGCCCGCGCACCCCGGGTCGCGATCTACAGCA
      > F H S P H M D P P L L D R L R A A V D F T A R A P R V P I Y S
28954 CGGCGCTGGCCGACCCGCGGGCCCCGATCACCGCGGACGGCGAGTACTGGGCCGCGAATCTGCGCAACCCGGTCCGCCTCGCCGCAGCGGTG
      > T A L A D P R A P I T A D G E Y W A A N L R N P V R L A A A V
29046 GCCGCCGCCGTCTCCGACGGACACCGGGCCTTCATCGAGGTCTCCCCGCACCCGGTGGTGACCCACTCGATCCACGAGACGCTGGCCGGAAG
      > A A V S D G H R A F I E V S P H P V V T H S I H E T L A G S
29138 CCTCGACGACGAGGTCTTCGTCGGCGGCACCCTGCGCCGCGACACCCCGGAGGCCAGGCCTTCCTGTCCAGCCTGGGGGCCGCCACTGCC
      > L D D E V F V G G T L R R D T P E A Q A F L S S L G A A H C
29230 ACGGGGTCGCGACTGGGCGGTCGCCGACTGGGGCCGGGTGCATCCGTCCGGGCCGCTGGTCACCCTGCCCGGCTACCCCTGGCGCCACCGGAGTCACTGGCAC
      > H G V A V D W G R V H P S G P L V T L P G Y P W R H R S H W H
29322 TGGCCGACGCGGCCGCCGCCACGGGCCGCCACGACCCCGCGTCTGCCGCCCTCAACGTGGCGGGCAGCGACGT
      > W P T P A A A T G R G H D P A S H T L L G A V D N V A G S D V
29414 GCGGGTGTGGCGCACTCGACGACGACGCCAGCCGCCCGGTACCCGGGCAGCCACGCCCTCAACGGCGTGGAGATCGTTCCGGCGGCCGTGC
      > R V W R T A L D D A S R P Y P G S H A L N G V E I V P A A V
29506 CTGGTGGAGACCCTCATGGCTGCCGCCGCCGGGCGCGACGGTCGTGCCGAGGACGGCGCGTCCTCCGTTCCGTCCTGATGACCGCCGGG
      > L V E T L M A A A G R G D G R P L L T G L S M R Y P L M T A G
29598 CTGCACGAGGTCCAGGTGCGTCGCGACGGCGCGGAGGTGCGGCTCGCCTCGCGCGTGGACGCCGAGGCCGACCCGAGCCGGGACTGGCT
      > L H E V Q V V R D G A E V R L A S R S V D A E A D P S R D W L
29690 GATCCACACCGACGCCACCGTCGCCGACGCCACCGTGCTGGCCGCGCGCCTCGCCGACCCTGACGATCACCGGCACATGGAACCGG
      > I H T D A T V A D A D A T V L A A R A L A D P D D H R M E P
29782 GCGACCCGGGCTCCATCCACCGCCGCCTCGCCGAGGTCGGGGTGCCGTCGACGGGATTCGACTGGTCGGTGGAGGAGCTGCTCTCCGGGTAC
      > G D P G S I H R R L A E V G V P S T G F D W S V E E L L S G Y
```

FIG.11A(26)

```
29874 GGCGTGCTCCGCGCGGTGCGCTCGGCCGACTCGTCGGCCGACGCGCCGGTCATGTCGGTCGCCCCGCGTCTTCCC
      > G  V  L  R  A  R  V  R  S  A  D  S  S  T  W  A  P  V  L  D  A  V  M  S  V  A  P  A  V  F  P
29966 CGGCGTGCCGCAGCTACGGCATGGTCGTCTACGTCGTGGACGAGGTGCTGCTCACCGGCGAGCCACCGGAGGTGACGCTGATCGAGGTCGCCCTCG
      > G  V  P  Q  L  R  M  V  V  Y  V  D  E  V  L  L  T  G  E  P  P  E  V  T  L  I  E  V  A  L
30058 ACCCAGACCGGCCCGACACGGCGAACGCGCTGGTCGCGGACGCGGATGCTCAGGGCCGGGTCGTGGCCAGCCTTCCGGGCCTGCGCTACCCGGGTGATC
      > D  P  D  R  P  D  T  A  N  A  L  V  A  D  A  Q  G  R  V  V  A  S  L  P  G  L  R  Y  P  V  I
30150 GACCAGCCGGTCGCCCCGGCGCAGGACAGTTCCGGCGAGGTGGAGGAGGAGGCGGTCTCTTCGCGGCGTCCGACGAGAACTGACGAGCG
      > D  Q  P  V  A  P  A  Q  D  S  S  G  E  V  E  E  A  V  S  F  A  G  L  S  D  E  E  L  H  E  R
30242 GGTGTTCGACGAGGTGCGCCGGCAGATCGCCGGGGAGATGCGACTCGACGCGGACGATCTGCATCCCCGGCGTCCGGAGCAGGGCC
      > V  F  D  E  V  R  R  Q  I  A  G  E  M  R  L  D  A  D  D  L  H  P  R  R  P  L  A  E  Q  G
30334 TCGGACTCGGTGATGACGGTGGTGATCCGGCGGCGCCTGGAGAAGCGCACGGGGAGCCTCTTCTCCCCGACCGTCTTCTGGCAGCGGCCCACC
      > L  D  S  V  M  T  V  V  I  R  R  R  L  E  K  R  T  G  R  S  L  S  P  T  V  F  W  Q  R  P  T
30426 GTCGCCGCCATCGCCGACCACCTGGTCGAGCTGTTGAGCACGCCGCAGGAGTGAGGATCGCGACGAGACAGGAGGAGGGCCCGTGCGTTCCGGCA
      > V  A  A  I  A  D  H  L  V  E  L  L  S  T  P  Q  E  .
30517 CGGGACCCCTGCTGTCGACGGATCTTCAGGTGGCGGGGTCAGCGCCCCGGCATGGTCCACGGGTGGCGGCCCACTCCAGGTGGCG
                                     < .  G  P  R  Q  D  V  A  P  T  A  A  W  E  L  H  R
30608 GCTCTCCCCGGAGGTCTCCTCGGGCGTTCTGTTCGACGCGGCATGGCGACGCGCATCGGCGCGGAGCGCGAGGTGACGAGGTGACCGACCGCGA
      < S  E  R  L  T  E  E  A  N  Q  E  V  R  R  M  A  V  R  L  M  P  P  A  M  V  S  T  V  A  V
30700 CCAGCACCACGATGGTGTATGAGGGCGGTGTGTTCAGCAGCGCGCCAGCATCGCGATGATGATCGAGGTCCACGGCACCGCGCGCGTTG
      < L  V  V  I  T  Y  S  A  T  N  L  V  G  L  R  L  G  V  M  A  I  I  I  E  V  A  G  R  A  N
30792 AGCCCGGCGCCGAGGGCGACGCCGGGCTCTGCCGGGCACCGCCAGTGGCTGCGGCCAGGTACGCGGTGTACTTGCCGAGCACGGCGAG
      < L  G  A  G  L  A  V  G  E  W  H  S  Q  R  A  L  R  A  G  L  Y  A  G  T  Y  K  G  L  V  A  L
30884 CGCCAGGATCACCGCGCTGGAGGTCGGCGAGGGCACGCACCTCGGCCGCAGATCGACCGGAAGATCGGG
      < A  L  I  V  A  G  A  A  L  V  E  P  D  A  L  A  R  L  D  V  R  L  G  A  S  A  L  F  I  P  A
```

FIG.11A(27)

FIG.11A(28)

```
32077 GCCCGAACCTTGTCCTCCTCGGGCAGGCTGAGGCTGAGCACCGACATCTCGGCCGGCCACTGCACACGTTGGCCAGGTCCACGTCGAGCCCCTCGGC
       < A  R  V  K  D  E  E  P  L  S  L  V  S  M  E  A  P  W  Q  V  V  N  A  L  D  V  D  L  G  E  A
32169 CCGGGCGAACTCCAGCAGGTCGCGCAGGCCCCAGACGTTGTCCCGCTGGGGTGCCACCTGGAGCCAGAGGTTGACCTCGAGCGGGCCGGC
       < R  A  F  E  L  L  D  R  L  G  W  V  N  D  R  Q  P  A  V  Q  L  W  L  N  V  E  S  R  A  R  R
32261 GGACGTTCGCGATGAAGGTCTCCCACTTCGCTCGCCCCTGCCGGATCCGCTCGAACACCTCGAACCGTTGCAGGAGCGCCGATGCCGATG
       < V  N  A  I  F  T  E  W  K  A  G  Q  R  I  R  E  F  V  E  G  Y  G  D  C  S  A  G  I  G  I
32353 CTCTTGAAGTGCCGGAACCGGTCGAAGACCGACTCCGGCAACTCCGGCTGAGTTGTGTAGACGACGTTGAGTGCCGGCGTTACCGT
       < S  K  F  H  R  F  R  D  F  V  S  E  P  L  V  T  L  N  S  N  Y  V  V  D  V  N  G  A  N  G  T
32445 CTCCACCAGCAGGTCGAGTCGGCAGGGCGAAGTGGCCCCGGCTGCATGAAGTGGCCTCCCCACCGGCGAAGTACAGCCGCGGATGGGGCGTTCT
       < E  V  L  L  D  L  L  A  F  H  G  P  Q  M  F  P  E  G  G  A  F  Y  L  R  R  I  L  H  A  N  E
32537 CGGCGCAGGGTCTGCCACAGCTCGTCGTCGTCCCGGTAGGCGTCGATGACGCGGACGCGGATGGTCGCATGGGGCCCCAGCCGGAG
       < R  L  T  Q  W  L  E  D  D  D  R  Y  A  D  I  V  A  S  S  W  A  P  R  K  K  A  G  W  G  S
32629 CTGACCGGGTACGCGCACATCACGCACCGCAGGTTGCCAGTTGCCGAACCGGATGTCGAGGAAGAACGGGAAGTCCTCGACGGTGCCGTC
       < S  V  P  Y  A  C  M  V  C  R  L  N  C  T  N  G  F  R  I  D  L  F  F  P  F  D  E  V  T  G  D
32721 GGGCGCGGTGCCGGGCGGCCAGCCGGTCGGGCGAACCGCTCGGTCGGTACAGCAGCGCGTGGTCGTTGAAGGCGTC
       < P  A  T  R  A  A  L  R  D  P  D  A  I  D  R  F  R  Q  N  I  E  Q  R  Y  S  L  A  G  H  D  E
32813 CGCGGGTGGTAGCAGTAGGAGCAGGCCGTGGACCGTCGACCGGCAGCATGGCCGGCCAGCCGGACAGGCGTCGTTGGGGCGTGGGGAAGGCGTC
       < R  H  Y  C  Y  S  C  A  D  V  R  E  G  A  L  M  A  L  R  T  R  R  M
32904 CGGCAGGCCCATCACCCGGTCGACCGGGGTTGTCCGGCGTAGCGGGACCGGAGCGGCGACGGCGTCGTTGAGCAGGAACTCCGGCT
       < R  A  F  E  L  L  D  R  L  G  W  V  N  D  R  Q  P  A  V  Q  L  W  L  N  V  E  S  R  A  R
32996 CCTCCTCCTGCTCGTACAGCTTGTTGTGGTACATCGAGTGCTCCACGCCAGTGTCCACCGCCGTAGACGCAGAGATGGATC
       < P  A  T  R  A  A  L  R  D  P  D  A  I  D  R  F  R  Q  N  I  E  Q  R  Y  S  L  A  G  H  D  E
33088 CAGGGCAGCAGCACGCACCGGTCATGCCGGGCTTCCGGGTCAGTCGGGAAAGATCAACCGGGTGCCGCTGGCCAGCATCTCCGCCTCCCGGGCCGAGATCTGTCCCGGAAGT
       < G  V  T  E  V  R  P  L  P  F  F  I  L  R  T  G  S  A  L  M  E  A  E  E  R  A  V  I  E  D  R  F  H
33179 GCCGACGGTCTCGACCCGGGCAGGGGCAGGAGGGCAGCAGCATCTCCGCCTCCCGGGCCGAGATCTGTCCCGGAAGT
       <                                                                  G  P  R
```

FIG.11A(29)

```
33271  GCCAGGGCAGGACCAGGTAGTAGTCCGGGGGGCGCGACTCCTGCTCGCTGATGATTCGATGTCCGTGCCGAGGGTGCGCGCCC
        < W  P  L  V  L  Y  Y  D  P  R  A  A  R  S  E  Q  E  S  I  I  E  I  D  T  G  L  T  R  A  G

33363  ACCTTGTCCGGATTGCGCTCCGCGGGGTATGCCGCGGGTCTATGCCGCAGAACTGCCAGGAGGTGTTGCCCTTGCTGACGCGCC
        < V  K  D  P  N  R  E  A  A  Y  R  I  L  E  R  D  I  G  C  F  Q  L  L  T  N  G  K  T  S  A  G

33455  GTAGACGTGCACCGTGCCGCCTGGCCGCCCCAGCTGCGGCAGCTCGCGCAGCTGCGGCAGGAGGGCGCTCACCTGTCACGGTCACGGGCACCTGCTCGGCGAAGCGCT
        < Y  V  H  V  T  R  G  Q  G  R  L  E  R  L  L  A  S  V  E  D  R  H  Q  R  V  Q  E  A  F  R  Q

33547  GGGTACGGGGCGTGCGCCAGCCCAGCTGCCAGCCCCAGCGCGCCAGTCCCGGTCGGCGAGCTGCCTTGACGACCGCCGAACCGTCGGCCGCGCCACTGCCACCGCCCACCGGCC
        < Y  P  A  D  G  D  L  G  L  A  L  E  R  D  A  L  A  K  V  S  G  D  A  R  G  G  V  E  G  A

33639  CGGGTGACCACGCAGCAGATCGAGCAGGTCGTCGTGGCAGATGTCGTGGTAGCCGGCGATCTGCCAGGCCCGGCCAGGTAGGCGACCTCGACCA
        < R  T  V  C  C  I  S  G  N  V  G  N  L  S  A  R  V  I  E  L  G  A  A  G  L  I  R  S  L

33731  CGTGGCCAGGTAGTAGAAGCAGCAGCAGATGAGGACAGGTGCTCGTGGACAGGTGTCGTGGCAGATGTGTTCGTAGCCGGCGATCTCTGACCTGACGTAGGCGACCTCGACCA
        < T  A  L  S  Y  Y  S  L  H  E  H  C  I  S  D  Y  G  A  I  E  L  M  A  P  L  Y  A  V  E  V  V

33823  CCCAGACCCCGCGGGGCTGAAGTCGGAGGGACCAGTCGGGCTGGGGGCTGGAACTGGAAGTCGGCGCGTCGTCGGCGGGCGCT
        < W  G  G  P  A  L  L  A  E  V  Q  R  A  F  E  V  P  D  E  V  D  Y  F  M  A  I  S  T  V

33915  AGGTCGAAGCTGCCCGGCGTCGATGCCCACCGGTCAGGTTGCCAGCAGGTGCTCAGGCCGATGTCGAGCCGATGTCCTGCCGGGCCGCT
        < L  D  F  S  G  A  H  P  V  L  E  P  S  P  F  F  D  R  I  L  N  F  D  D  P  A  D  D  A  A  S

34007  GGAGGGGTCGATGCCGCCGTGCCCGGTCCAGGTTGCCAGCCGTGCCGTGTGCAGCCGATGTCGAGCCGATGTCGTTGATCCGAGCGGTACCAGTAGTGTCGTAG
        < S  P  D  I  G  W  R  Q  A  D  T  L  N  G  L  L  T  G  D  N  C  G  I  D  L  V  K  G  P  R  E

34099  CCCCCAACACCTGAGCCGCGGTCCAACTGCCGAGATGCGCGGCGACGCCGCACCAGGCCGCGACGGGTCACCCGTCCGCGCGTTCCGCGCGTCAGCTCCAGGGCACCTCCAGGGGGAA
        < G  L  V  E  V  A  A  D  V  V  D  A  L  H  R  R  M  T  D  N  I  R  S  R  Y  W  Y  T  D  Y

34191  AGCAGCCCACCCGGCCTGGGGCTCCGACACGCCGGGCTTCACGACCGCCTGAGGTACTGGGCACCCGGGGACAGCTCAGGCCGTACGCAGGGTCCGC
        < L  L  G  G  P  L  T  H  R  L  Q  V  L  G  C  P  D  G  G  D  R  E  A  C  R  T  L  E  L  P  F

34283  GCGCACCCTGGGCGGGTGGGCTGCGGACACGCCGGGCTTCACGAAGTCCGGGCACGACCGTCGAGGACCGTACGCAGGGTCCGC
        < R  V  R  P  P  D  S  V  G  P  K  V  F  S  G  Q  L  Y  Q  A  G  L  D  L  V  T  R  L  T  G  G
```

FIG. 11A(30)

```
34375 CACACACCCGGCAGGTGGTCCGCTCGACCACCTCCGACGCCAACTCCTCGCGGCGCGCCAACTGGCTCAGGTCCTCCTCGT
      < C V R C T T R E V V                                                 <. T R R T

34464 CTCGTGCCGGTGTGCCGGAGCCAGGCGCCCCGTCGTGCGGTTTGCTGGCGACCAGCAGGATGTCCAGATAGAAGGGCTGGTCGGGCCCTCGC
      < E H R H A P G P A G D H P K S A V L L I D L Y F P Q D P G E S

34556 TGCGGCCGAGATGCCGGAACGCCGGTCGAGGTACTCGTCGAGCGCGGGGGCCCGCAGCGCGCGGGGGACACCAGCGCGCCAGGGGCCAGA
      < R G L H R G A R D L Y E D L A R P R L R D V L W L A R L A L

34648 CCCACCGGGCCGCGGAGACGGCCAGCCGTGCAGCGGGCCCACTCGGCCTGGCGCGGCAGGAACAGCAGCAGCAACAGGCCCGCCAGGTCAGCTTGACGGT
      < G V P G G S P W G H E R G Y W E L L L L G R P G C T L K V T

34740 GCGGTCGACGGTGAAGCCGGTCCCACTCGGCCCACTCGGCCTGGCGCGGCAGGTCCGGCGGTCCACGGCCACAGGTCCTGGCCGTGCTCCTCCACA
      < R D V T F G A W E A Q R A L G D A T W R W L D Q G G H E E N V

34832 CCCCGTGGGTGGAGAGCACCAGACCCGTCGAACGTCGGCGGTCTGCAACTCGGCCCGGCGTACGCCTCCCAGGTACGCCGGGCCCGGGCTCCGAGACGTGTTCGAGC
      < G H T S L V R G G P R L L R Y A E R L Y A D S V H E L

34924 ACCTGGGTCGACAGTCCGGCCACTCCCGTCGAACGTCGAACGGTCGGCCGCGGTGGTCGGCCGCCGGGACTCACC
      < V Q T S L V G D F T G D P V P C R G D R D L A H D A P L S E G

35016 GCCCGGGATGTCGGCCAGCCGCTCCGCCAGCGCGTCGGCGGGTCTGCAACTCGGCGAGGTGCCCGCGGTAGTCGAGCCAGACTCCCGTGG
      < G P I D A T Q L E A S R F L G R Y P S T G A G Y D L W V G T A

35108 CGTCCCGGACCGCCATCACCTCGTCCAGCGACGGGCCCGGGGCGTAGGGGGTATGCCGGGGGCTCGATCCGCTCCCGGAAC
      < D R V A E A L A D R L D L F H A Y A W D G P R P E I R E R F

35200 CGTTCGCCACCATCACCTCGTCCAGCGACGGGCCCGGGGCGTAGGGGGACCAAGCCGGTCAGCAGGGCGGGACCGCCGCGCAGC
      < R E A M                              < W R W Y E E H P Y R M T T P E P L G E W R R L S A A P R

35290 AGGGTCACCAACGCCAGTACTCCTCGTGCCGGTACCGGTTGGTCCGGCCGCCGCAGCAGGCCCTCCCAGCGCCGGCCGCAGCGGCGGGCCG

35381 GTACTCGAAGGCTGCTCGCCGGCGTGCCGCCCCGCCCCGCCGCGGTGCCGCCGCGCGCGCCAGGCAGGAGAGCAGCACCTGCTGCTTGAGCCCGATGTACT
      < Y E F P Q E G A H E P A A R R Q A L C S L L V Q Q K L G I Y E
```

```
37679 CTCGTCCCGGAGGAACGCGGGTGCTGTTACGCACGTCCGTCCGGGCGGGTCGAGCTTGTGCCGTCGCACGCCGGGCCGGGTCTCCAGCC
       < E D R L F A P D S N R V T R G P P D L K H R R V G P R T E L G
37771 CGCCGGCCGTGGCGATCACGATCTGTCCCGGTGCGCGGGCAACAGGTCGGCGGGCAAGGGCCGCTCGGCGGCCCGCGCCG
       < G A T A I V I E D R H A P L L D A L G R A L A E A A G G
37863 TACGCGCGGGAGAGGTGTCGAAAAGGGTGACGCTCGAAGAGCCGGCCTGCGGCGACGGCCTGGTTCGATCCGCCGGCCCACTCGGCC
       < Y A R S T D F L T V G L D F A R R V A Q A G P E I R R G W Q G
37955 GCCGAGCGCGCCAGGCCGCCCGAGACCAGCGGCCCCGTCACCGAGCGCTGCCGCACGGCGTCCTCCCGCCCGGTG
       < G L A W T G L G L A S V L P G R E G I C R Q R V
38046 CCCCACCACCGCCCGTCGGCGCCCGTCACGCGCCGCCGTCAAGGAACCACCGCGTCGTGATTGATCATCT
       <* A A P E G D S R L T L F V G D H N I M K
38137 TGTCGGTGACCGGCGTCAGCCCGGCGATGCGGTCATCAACTCCACGCCGTGCCAGTTCAGGAACCCTTGAACTCCACGGGG
       < D T V P T L G A E A A I G T M L E V G H W N L F G K F E V P
38229 TTCGGCGTCGCGGTACCGCTCGGCGGGCGTGTTGTCGCCGAGTTCCAGGAAGTTGAAGCAGAACAGCCGCGGG
       < N A D R Y R E A Y T H F F G R T N D G L D L F N F C F L G G P
38321 CCGCAGGATCCGCCAGCTTCTCCAGGAAGTCGTTCTCCGATGTGGTAGGAGACGTTCTCGCCGGCCCGCCGCTGCCGATCTCGAAGAT
       < R L I R R I Q R F Y L F V E F V N L H I F V N L S F G A D F A
38413 CGGCCGGTCGGCCAGCTCGACGTCGCGCAGAGACACGGCGCGCACCCGGTCGGCGAGCCCCATGATGCCCTGCCGCTGCCGATCTGCGAAGAT
       < A T P L K E L F D N E I H H Y S V N E R G E C T A R A K D L
38505 AAGGATCGGCGACGTCGGCGAGCCCGAGCTGCTCGACGCGACGGTCGACACGGTTCGTCGAGGTACTCCTCGCGCGGCTGGTAGCCGG
       < F S R S V D A C L V A R V R D A L G A A M
38597 CTCCGATTCCGGGCGCGAGCCCAGCCCGAGCTGCTCGACGCGACGGTCCAGACGTAGTTGCACTCCAGAGTTGAGGTCGCCGGTCC
38689 CGAGCTGCATCTGCATCTCCTCCGCCGTGTTCCACTCCAGACGTAGTTGAGGTCGCCGGTGCTCCGGAGCGGACAGCCCGGGGGTCC
38781 TGCGGCGGCGGCCGTCGCCGTCGCGTCGTTCATCGGCCGCGATCTCGCCGGTCTTGTCGGGGCTCGCCGCGCCCGGCGCGTGTCGCCGGCGCTGCG
38873 GAAAACTGGGCCGCCGGGCGGTCGTCACGCAGCCTGCGGCCCGCGACGACGGGAACTCGGGCCGCAGCCCGGTGTCGCCAGCCGGGCAGGAG
       <* P R R A F E A V D E P S L A G T D A L R A L L
```

FIG.11A(34)

```
38964  TTCGGCCACCTGGACGGGTCGGCCCGGTGGTGACGGACTCCGGCATCCGCTGCGCCGGAATCGGTGGTCGTAGAGGACGGAGC
       <E A V Q V A T P G T T V S E R M R Q A A V R F R H D Y L V S G

39056  CGAGGGCCTCGTCGACCTCCTCGCGGGGACGCCTTCAGGCCGGGTCAGCCGTCTTCGTCGCCGCCGAGATCAGG
       <L A E D V E E R S A K L G P L T K T A G Q P D L R R G Y I L

39148  GCGTCGTAGTTGAGCGCCAGCGACAACTGCGGGCACGCCCATGCGAGCCGTTCATGTAGAGCAGGTTGGCGTGCCGTGGTGCACCAGCAAGTC
       <A D Y N L A L S L Q P V G N A L G N M Y C N A S G H H V L L D

39240  GCAGTCGGGGAGGATGAGCTCCAGCAGGTTGCTGAGCACCCGGCCGCCAGCGGCCCCCAGCCCTCCAACCTCGGAGGAGGCGG
       <C D P L I L E L P C N S L V R V N P P L A G L G E V E S S A A

39332  CGGTGATCACGACCTCCACGCCCCCGCTTGCCCCTGCCGAGCAGCAGGGGTCCACGTTCCTGGGAGCTGTTGTAGGGCTGGTAGCGGAT
       <T I V V E V G R Q A A A D V A H R L A P V Q A G F V G T A S

39424  TTGCCCCACCACCGCAGAACCCGTTGCCCTGCCGTTGCCCCTGCCGAGCAGCAGGGGTCCACGTTCCTGGGAGCTGTTGTAGGGCTGGTAGCGGAT
       <N G W V V C V R K G R R P G L L W P D V D Q S G N Y P Q Y R I

39516  CGGGATCGCAGCGCGTCGCCATCGGCGGGATCCGCGGGATCGCCGGGATCGCCTGCGCTCCACTCGCGC
       <P I R L A D G M P P I A V D P S P D I A Y R I Q H R S W E V G

39608  CGTACTTGGCGAACTCGGTGCAGCTCGGTGCGCCGGGTCGCCGGAGACCAGGTCGAGCCTCGGTCTCGATGGTCGTGATGAACCGGAGAAGTAG
       <Y K R F E T V P D G S V L D L G P E T E I T G I F G P S F Y

39700  ACGCTGGGATGGTGCAGCTCGTAGCTGCCCTCCACGGCCCTCCACGGCATGATGTCGTTGGACCACCAGGTCGGCGTAGTGGGCGGCGTA
       <V S P I H H L E A V L A G E V A M I D H V V L D P R Y H A A Y

39792  GTCGACGTCGTCGCGGGTCCACGCGTATCAACGGGTTCTCCACCATGTGCTGCGGGGTGTAGAGACGGTAGAAGCCTGGACGTAGAAGCCGAGT
       <D V A N D Y S R Q V A T V T R K W Y D A L L D T D F D A L S D

39884  CCATCGGCCGGGTCGAAAGGGGTTCAACGCAGCGTTGCTCCAGCGTCAACGGACAGGGGCATCATGCCCGGCGGACACAGGCGAC
       <M P R G T F P N L P L P Q E V M H Q P T Y L A Q V Y F G L R

39976  GCGCTCTCCATCATGTCCGGTCCGTCGAGCACCGGACAGGGCATCATCGCCCGGCGGACGGGCGAACAGGCGAC
       <A S E M M D P G D L V S P M M G A A A V G R V Q S P S C A V
```

```
42270  GTACTTGGCCAGGCCGTAGCTGTGTCCGCGGGGACGGGGACGACGGACTCGGCATCGGGTCTCGCCGTGGCGTAGACCGGCCACGGAGGAGG
       < Y  K  A  L  G  Y  S  D  A  P  V  P  V  S  E  R  M  P  T  E  G  H  G  Y  V  A  V  S  S  A

42362  CGAAACAGAAGAACCCGGTACGCCGGACGGTGTTGATCAGATTTATGCTCCCATCACATTGGTGCCGTAGTTGAGCTGCTTCACC
       < F  C  F  F  R  V  G  T  R  L  S  A  N  I  L  N  I  S  G  M  V  N  T  G  Y  N  L  Q  K  V

42454  GAATGGCTGATTCACCCCGGCGGAAGCGGCCACCCGGTCCACCCGGGAAAGTGGAAGACCGGTTCTCGGGAACAGTGAATCGACGAAGTCCACGTC
       < S  H  S  I  A  E  A  A  F  A  A  F  H  F  V  R  E  F  R  N  E  A  F  L  S  D  V  F  D  V  D

42546  GGTCACCACGAACCGACCAGGTCCACCCCGCGGAACCCGGAACCGGGAACCCGGGAACCGGTCGCAGAACGGTGACCCGGTGCCCAT
       < T  V  S  G  V  A  L  D  V  G  A  P  V  R  Q  R  S  G  G  S  L  D  D  L  V  T  V  R  H  G  N

42638  TCCTGACCAATGACTCACCAGTGCGAGCGGGCGATCTGCGGCGCGCCCTTCGTCGGCGAAACACCCGAGAGAAAGCTTCGCTCAGGGCAC
       < R  V  L  S  E  V  L  H  S  G  I  F  G  A  G  G  T  V  L  C  R  V  M

42728  GATCCGGAAAGGGTTGACGGGAACCACCGAGAGAAAGCTTCGCTCAGGGCAC
                                                          < ·      P  V

42819  CGGCGACGGTCGGCCTGCTTCTTCAGGCCTCCCACCAGTCCCGGTGCGTCGGTACCAGTCGATCGTCTCGGCCAGGCCGTCGGCGAAGG
       < P  S  R  D  A  Q  K  K  L  P  E  W  D  R  H  T  R  Y  W  D  I  T  E  A  L  G  D  A  F  A

42911  CGACCTCGGGCGGTAGCCGCGAGCGCCGCAGTTCGCGTCGAGTAGCGAGTAGCAGGGCGTCGTGGCCCTTGCCGTCGTGGCCACCCGCTCGACC
       < V  E  P  R  Y  G  L  A  R  L  K  A  D  T  L  S  Y  R  R  D  H  G  K  R  D  P  V  R  E  V

43003  CGGTCCCACCCGGCCCCCAAGGCGTCCAGCAGCCGGTCAGCTCCATGTTGGACAGCTCAGCTGCCGGCGATGTGCCGTAGACCTCGCC
       < R  D  W  G  A  G  L  A  D  L  L  R  G  T  L  E  M  N  S  L  E  A  T  G  A  I  H  Y  V  E  G

43095  GGGGACACCGGCGGTCGACGACGGCTGGAATGCCGGTCAGTGGTCGTCACGTGGATCCAGTCGCGAGCGTTCCCGCCGTCCGGCGTACAGCG
       < P  V  G  R  D  V  V  T  Q  I  G  R  C  H  D  T  V  H  I  W  D  R  V  N  G  G  D  G  Y  L  P

43187  GCACCCGTCGCCCGTCCAACAGCTCGGTCGACAGCTCGGTGACGACAGCGGGATCAGTCTTGTTGGAAACTTCTCGGAAACTTCTCCGGAAACTTCTCTGTTGTGCCACCGGGTG
       < V  R  R  G  N  L  L  E  T  V  F  L  P  I  L  K  E  P  F  Q  Y  P  G  Y  N  N  G  C  R  T

43279  AGGCAGACCGGCAGCCGGTGGGCGTGGGCCGTAGGCGATCAGGTCCAGGCCGATCAGGTCCCGCCGGCCTTCGCCGCCGCGTACGGGGAGTTCGGCGCCAG
       < L  C  V  P  L  G  H  T  R  A  Y  A  L  A  I  L  D  G  G  A  K  A  A  A  Y  P  S  N  P  A  L
```

FIG. 11A(38)

```
43371 GGGGGTGTCCTCCGGCCCAGGAACCCTCGTCGATGCTGCCGTCGGTGGAGAGACCTGGAGTGGGCGACCCCGGCGCGACGTGGAGTC
      < P  T  D  E  A  W  S  G  E  D  I  S  G  Y  V  E  D  T  S  V  Q  V  V  R  A  V  G  A  D  L  C
43463 ACGCCTGCATGAGCCTGGAGCGTCTGCACGTTGGTGCGGACAGTCGGCGATGGGACCGGTCGACGTGCGACTCGGCGCGCG
      < A  Q  M  L  T  Q  V  G  Q  V  N  T  R  V  F  E  A  S  D  A  I  S  R  D  V  H  S  E  A  A
43555 AAGTTGACCACCACGTCGTGCCGGGACAGCACCTCGGCCACCTCGCCGTGTCGCAGACGTCGCCCTGGACGAAGGTGATCGGTCCTGGAC
      < F  N  V  V  V  D  H  G  P  L  V  E  A  L  L  A  T  D  C  V  D  G  Q  V  F  T  I  R  D  Q  V
43647 CGGTTCGAGGTTGCGAGCGTTGCCCGCGTACGTCAGCTCGTTGCGCGTACCGGCACCTGTCGGAGTAGGCACCGGTGGCCA
      < P  E  L  N  A  L  N  G  A  Y  T  L  K  D  L  V  T  V  R  A  Q  A  T  D  P  Y  A  G  T  A  L
43739 GGTCGCGGACGTACTGCGAGCCGATGAAACGGCCAGCCGGTGACCAGGACGCGACGCATCAGACCCCCACCGGACTTCGCTGTGAT
      < D  R  V  Y  Q  S  G  I  F  G  A  G  G  T  V  L  V  R  R  M                                  
                                                       < *  V  G  V  R  V  E  S  H  D
43828 CGCCGAGGACGAACCGGTTGCGTCTTGGGCACCCGGGAACCACCCGGCGCCTCCCGGCCGATCATCGAGAACTCGATGCGCCGATG
      < G  L  V  F  R  H  T  K  P  V  R  P  G  P  V  V  R  A  E  R  G  I  M  S  F  E  I  R  G  I
43920 CCCTCGATGTAGCCACCGCAGCGGATGATGGAGTGCTCGATGCACCACCGGGACGATCCGGGAGCCGTCGGCGCTGACGTCGGCCGCTGATCGGCGTGATCACCG
      < G  E  I  Y  A  G  R  L  V  I  S  H  E  I  E  T  E  L  L  T  C  D  C  D  I  S  T  Y  P  G  L
44012 GTAGGAGTTGCGATCAGTTCGGTCGCGATCGTCGACCTTGCCCTCGACAAGGCTGCCAGGAGGACGAACCGGTTCATCTCCAGCATGTCGGCG
      < Y  S  N  R  I  I  S  G  A  G  V  V  P  G  V  I  R  S  G  S  V  D  A  G  A  S  I  V  P
44104 GGCCGATCAGTTGCCGGTGTCCTTCCAGTAGCCGGTGATCATGGTGGAGTCGACCCGGTGCGCGGTCGATCATCCACTGCACCGCGTCGGTGATCTC
      < G  I  L  E  T  R  D  D  V  K  G  E  V  L  P  E  V  S  G  L  V  F  R  N  M  E  L  M  D  A
44916 AGGTTGCCGGTGTCCTTCCAGTGCGATCTGGTCTGGATCCATGACCCGGTGGTCGGTCGTCAGGACGGGCAACACATCTGACGGCCGGCCCGGGCTCATGACGGC
      < L  N  G  T  D  K  W  Y  G  T  I  M  T  S  D  V  R  H  G  R  D  I  M  Q  V  A  D  T  I  E
44288 CAGCTCGTTGGCCAGGGCTTCAGCTGCCACGGCCATCGGTGAAGACTGTAGAGGACCAGGGCCAGGTCGGCTCT
      < L  E  N  R  W  S  P  K  L  E  A  V  A  D  H  V  V  P  S  F  V  Y  G  V  L  A  L  D  S  K
44380 TGGGGTGCTCGGGGCTTCTCTCCACCGGATCACCCGGCCGTGCCGAAGGCGGTGCGGGTGCGGGACCCGGGTC
      < P  H  E  P  K  E  E  V  G  I  V  R  G  D  A  G  M  E  A  V  G  F  A  H  P  D  A  V  R  T

FIG.11A(39)
```

```
44472 AGCATGATCGCCGTGCGGTCCTGCTCCTGCCGGAAGCGCTCGACGATGAAGTTGTCGCCGAGGTACATGAG
       L  M  I  Q  A  H  P  R  E  Q  R  F  R  E  V  I  D  K  I  G  G  V  I  F  N  D  G  L  Y  M  V
44564 GAAGTCGTCGCCGAGGTAGTCCGGGAGATCGCGCACGACGAGCACCTCCTGCCGAAAGGTAGGTCACCTGGAGGC
       F  D  D  D  G  L  Y  D  R  S  I  L  V  A  H  A  L  G  R  P  A  E  Q  P  L  Y  T  V  Q  L  G
44656 CGAACTGGGAACCATCGCCGACCACCGCGCTGAATTTCGGGCGCGGTGCTGCTGATACGCCCTCACGAATA
       F  Q  S  G  D  G  V  V  R  Q  I  E  P  A  T  S  G  V  V  I  G  V  E  E  I  G  G  E  R  I
44748 GCCTCGAGCCCGTAGAACAGCACCGGCCTTGTTGGCCACGGAATGAGTTGTTGGCGGACGTGTGGGTGATCGGACGCAATCTCGATCCAC
       A  E  L  G  Y  F  L  V  P  K  N  A  V  P  I  L  Q  K  A  S  T  H  T  I  P  R  L  R  S  G  V
44840 CCCTCCCGCAGGACCCAGCGCCTTCACGAACGCCCTCGAAAAGGATGGGACGTTCACGAGACTGGTTCACGGG
       G  G  A  L  V  L  A  K  V
44931 TGGACTGGGCTCTTCGTGAACGTACCGAAGGATCACTCGTGATTTCCTACTTATGGGCCACGAGGTGTGATCGTGATCTCTATGCGT
                                                                                   <  A  D
45022 CCGCCATTTCCGCAAACGGGGCGCCTGGCCGCGCCCGGCCACAGTTCGAGCACGGGGCCAGGCGTGTCCGGCGCACGGCTGGCC
       A  M  E  A  F  P  P  R  A  P  G  G  G  V  L  E  L  V  A  A  L  G  H  V  T  D  P  P  S  A
45114 GGCAGCAGCAGGGTCTGCAGGCCGTACACGCGGCCCGGCTGCGCCACCATCAGCGCCTCCGGGTCGGTCAGGTCGACCTTCAG
       P  L  L  L  T  Q  L  G  A  Y  V  A  G  G  D  A  L  T  D  G  V  M  L  A  R  E  P  A  V  K  L
45206 CTCGTCGCAGGCCGGTGCCGAAGATCCCGGCCTTGACCGCCACCTGGTGGGAGAAGACGTAGGCGTCCACCAGCTCCGCCATCC
       E  D  C  A  T  R  F  I  R  P  D  P  K  V  A  G  V  E  H  S  F  V  Y  A  D  V  L  E  A  M  G
45298 CGTACGCCGTCGCGGCCGGAAGGTCGGCCAGGCCGATGTTGCTGACGACCGGATTGCGCAGGCGCAACTCCGCCAGGACCGGG
       Y  A  A  F  T  P  R  L  D  W  A  I  N  S  V  V  A  T  G  C  G  R  R  L  E  A  L  V  P
45390 GCGGCGTCGCGGCTACGGCGGTAGGGCGCTGCGTTCCGGGCCAGGTCGACGGTCAGGTCGACGGTGGA
       A  D  R  Y  P  L  W  G  D  T  R  F  L  R  D  Y  L  A  E  A  L  G  P  H  P  L  D  V  T  S
45482 GAGCAGGCCCGTCGCGCTACGCGCTGCGTTCCGGCGGAGAGGTCCCGGCGAGCCGGGTACACCTCGGGCGGGGACGGCGTGCGGCT
       L  L  G  V  Y  Y  A  S  R  H  T  E  P  S  L  D  R  R  A  Y  V  E  A  L  G  P  P  V  A  H  P  E
```

FIG. 11A(40)

```
45574 CCGGCCCGCCGCGGGACGGCCGGGCCAGCAGCACCGGTCAGGGCCTCCTGCTGCGCCGGGTCGAGCTGGACGCCGAGCCGCGGGGACGGTGGCCGCCGCC
      < P  G  G  P  R  G  A  A  L  L  G  T  L  A  E  Q  A  P  F  L  Q  V  G  V  T  A  A  A
45666 GCCCGCAGCCAACGCTGCGCCAGTTCCACGGGCAGTCCTTCGACTTCCTCGTGGCCGACATCCCGCGGCTGCCGACCACGGGGCAGGGGGGTCGT
      <A R  L  W  R  Q  P  L  E  V  A  F  L  T  G  S  F  D  F  L  V  A  D  I  P  R  P  L  P  T  T
45758 CATCGCTCTCCTCGGTGCAGCCGCTCAGGGCGGCGGTCAGGGCGGCAGCCGGATGTCCATCATGGAGGAATGCGCCGGGTCG
      < M
45848 GGCGCGCCCGCCATGGCCGCCGGTCCGGCCGACAGGGCCATTTTCGGTCACTCTTGCCTTCTTAGGCGGATTTCTTCAAAGATGGCTGTCAATTC
                                       > V  T  R  T  R  T  A  L  R  R  L  L  A  A  G  L  A  S  L  A  T  A
45940 TTCAGCGATCCTGGAGGCATCCGTACCGAACCGTACCCGGTGCCGGGTGTCTGCGCCGGTCCGCCACCGGACGTGTCCACTACCACCGGGATCGATCAACTGGACGA
      A     > V  T  R  T  R  T  A  L  R  R  L  L  A  A  G  L  A  S  L  A  T  A
46030 CGCGACCCTCGTCGCCACCGCCGGTCCGGCCGCCGCCACCACCCCGGGCATCGACGTGTCCACTACCACCGGGATCGATCAACTGGACGA
      >  V  T  R  T  R  T  A  L  R  R  L  L  A  A  G  L  A  S  L  A  T  A
46122 GCGTCCGCAACGCGGGCATCCAGTTCGCGTTCATCAAGGCGACCGAGGGTACCAGCTACAAGGACCCCAACTTCGCCAACTACGTCAAC
      > A  T  L  V  A  T  A  G  P  A  A  A  A  T  T  P  G  I  D  V  S  H  Y  Q  G  S  I  N  W  T
46214 TCCTACAACGCCGGAGTGATCGCCGGGGCGGCCTACCACTTCGCCCGGCCCAACATCTCCTCCGGCGCCAACCGTACAGCGCAACGCCGTACGGCCTCA
      > S  V  R  N  A  G  I  Q  F  A  F  I  K  A  T  E  G  T  S  Y  K  D  P  N  F  A  N  Y  V  N
46306 CGGCGGCGCCTGGTCCGCGGACAGTCGCGGCGCACCCTGCCTGCGGCGCTGGACGTGGAGGCCAACCCGTACAGCGGTGGCACGTGTACGGCCTCA
      > S  Y  N  A  G  V  I  R  G  A  Y  H  F  A  R  P  N  I  S  S  G  A  T  Q  A  N  Y  L  A  S  N
46398 GCACGTCCGGAATGCCGCAGCTGGATCCAGGACTTCCTGAACACGTACAAGGCCCGTACCGGTCGTCATCTACACCACGAGC
      > G  G  A  W  S  A  D  S  R  T  L  P  A  A  L  D  V  E  A  N  P  Y  S  G  G  T  C  Y  G  L
46490 TGGTGGCAACCAGTGCACCGGCAGCTGGACCGGGCCCGTGGCCAACCACCCGCTGTGGCTCGCCCGCTGGTCGAGCACCCCTGCC
      > W  N  Q  C  T  G  S  W  T  G  P  W  A  N  H  P  L  W  L  A  R  W  S  S  T  P  G  T  L  P
46582 GGCCGGCGCTTCGGTGAGCTTCTGGCAGTACACGGCCAGCGGATCTCCCGGGATCAGCGGCGTCCCGGGATCAGCAGCGACAACGTGGACCGCAACAACTGGAACG
      > A  G  A  S  V  W  S  F  W  Q  Y  T  A  S  G  S  V  S  G  I  S  G  N  V  D  R  N  N  W  N
46674 GCGACCGCACCCGCCTGATCGCCCTGAACAACACCTGACCCGGGTAGGCGGTTGGCGGCAGGGAACCGATTGCGACCGT
      > G  D  R  T  R  L  I  A  L  A  N  N  T .
```

FIG.11A(41)

FIG.11A(42)

```
48052 CGTCCCCAGCCTCGGCGGCCGGGTCCGGCGGGCCGGTCACTCCTCCGGCCGGTGCCGGCAGCCTCGTCGGCGCTCGTCGGCGCGGTCG
       < D G A E E A A R D A P P G D S G G A P T G A A E D A S T A A D
48144 GGGGGCGGGGATCTTCGCGGTGGGACCGCCTGCCGGGCCGAAGTCGGTGACCTTCGCGGTCGGCGTCGGCGCTCGGCAGGTCGAC
       < P A P I K A T P D A A Q P G F D T V K A T P D A D A S P L D V
48236 CATCGCGGTCGGCGGCGGTCCAGCGGGTCCACCCCCGCGGGGACCTTCGCGGTCGCGGTCGCCGCGGCCGCCACCGGCGGGGCCAA
       < M A T P A A D V G A P V K A T A D G G G V G A A A G G A A L
48328 GACCACCTTCCGGGGTACGCGGTGCGGGCCGCCGGGTACGCGGTTCGGCGGGCGCGGGTGCGGGGCACCACCGGCGGTCGC
       < G G E P T R P A P R G T R Q E A P R P A P V V P P R
48420 GGCTCGCGGGGGCCGTTCGGCCCCGGCCTCGATCCGTCGATCAGCAGCGAGCGCGTCTTGGCGCGACGCCCGGCTTCAACGGGCCGGAGCCG
       < P E R P G N P G P R R V G D L L S I T K A R R G A R R L L R
48512 CTCGGCCACCTCGGCGTCGATCGCTCGACAGGGCCAGGGGCTGCGGATCGCCGCGCGCAGCCGGCGAAGCGGACCTTGCCCTCCACGGCGACGTACGCGGTCGCG
       < E A V E A D I R E A P D K R L L G N L V P K L P G A N R P P P
48604 GCATCGGCTCGGTGGCGACCAGAGGTCCGGCAACTAATGGCCGGCGAAATCGGTCAGGCCGGGGAGCCGGGTACGTCCACCATTCCGGT
       < M P E T A L A A L T A I A S P R A F P S K G E V A A Y L T A
48696 CCCAGCGACGTTCGGGTCACGGTGCCGGGGATGGTCGCCAGGCCGGAAATCGGTCAGCACGTTGCCGGAGCAGCACGTTGCCGGCT
       < G L S W L D A E P G A T G D R A R E P A I Y A P S G L V M G T
48788 CCGGCGTCACGTTCGGGTCACGGTGCCGGGGATGGTCGCCAGGCCGGAAATCGGTCAGCGCGTCGGTGCGCCGTCGAGCAGCACGTTGCCGGCT
       < R T V N P D G P I T A L G F D T L V V R G D T G L L V N G P K
48880 TGATGTCCCGGTGCATGACGCCGAGAGTCCTGAAAGGCGACTTCGACGCCACGTACTCATGACGATCCACGGGTCGCCAGAACGTCGAA
       < I D R H M V G A K H A A K L A G L V G L G I E V A K A P S V
48972 GGCCGGGACCGTCCTCGGAGTGCTTGACGTGGTTGAGTCGCGGGCCACGGCACTTCGCGCATCTCGCGGCGTTCCTCCGGGGTGA
       < P G D E A L T D Q L S K S A V Y E M V I W P D G D T R L V D F
49064 GATGGGACCACGTTGACGTGGTTGAGTCGCGGGCCACGGCACTTCGCGCATCTCGCGGCGTTCCTCCGGGGTGA
       < I R V V N V H N L R A I A R A E R L S R E R M E R R E E P T L
```

```
52557 ACGACGGGTGCCGAGCCGGCAGGCGAGGGTGACGATGGGGCAACGGCCTCGGCCACGTTGGGAGTCTGCCGAGTGATCGTGGCTGCTGCGGG
      >T T A V A E P A G E G D D G A T A R G L A T L G V I V A A A G
52649 CGCTTGGGCGCTGGTCGGCTGACGGGTCAGGTTGAGCGACGACCCGGCCCCCCCGGATCAGCCGGTTGACGACCCTGACGCCATGTCG
      >A W A L V A R R R L S D D P P P R I S R .
52740 GCGACATTGGGGGGTCGGGGTGGGGTGACGATACCGCTATTTGGCCGACATGAAGTCGATCAACAGCAGTGATCAACAGGCAGTGTGATCGGCGGGG
      >                                   >V P N S I S L R L V L A
52832 GTCGGTCGACGGCCAGGCGGGCGTCGACGAGGCGGGGACGGTAGCGTCGGCGACGTGCCGACGTGCGAATCGATTTCACTCCGACTCGTGCTCGC
      >S A S P A R R K L L H A A G I E P D V L V S G V D E S Q V T
52924 GTCGGGCGAGCCCTGCCCGTCGCAAGCTCCTCGCACGCCCGGCCATGAACCCGCGCTGGTCAGTGGGGTCGACGAGTCCCAGGTGACCA
      >S A S P A R R K L L H A A G I E P D V L V S G V D E S Q V T
53016 GCCGAGCGAGCCGGAGGATCTGTGCCTGGAGCTCGAGCTGGCGCTGCGCCGCCTGAAAGGCGCAGCAGCTGTCGTCGGCGACGAGGGACG
      >S E R A E D L C L E L A R L K A Q A V V G R L R P S A D E R T
53108 CTGGTGTCGGCTCGGCCGACTGCAGCGGGGTGTGCTGACACACGACTGCTGATCGACGTCATCATCCACGAGACGCGCGAGGCGGTCGCCTCGACCACCG
      >L V L G C D S V L A F D R E I L G K P A D E A D A T R R W E R
53200 GATGCGCGGTCCGGCGTGCTGCATACCGGCCATTGCCTGATCGACGTCATCCACGAGACGCGCGAGGCGGTCGCCTCGACCACCG
      >M R G R S G V L H T G H C L I D V I H E T R A E A V A S T T
53292 TGCGTTTCGCTGACATCAGCGACGAGGAGATTGCCGCGTAGCGGTCGCGGAACCGGCTCGCCGGCGCGTTCACCATCGACGGA
      >V R F A D I S D E E I A A Y Y A T G E P L A V A G A F T I D G
53384 ATGGGCGGGGCGTTCCTGGAGGGCGTTGTCGACGGGGATCCGGGCACGGTGGTCGGGCTCTCCCTGCCGTTGCTGCGCCGGCTTCTCGGCGAGCT
      >M G G A F L E G V D G D P G T V V G L S L P L L R R L L G E L
53476 GGACCTGCGGATCATCGACCTGTGGACGAAGGTCGCGCCGGGCGGCCAGGCGGTCGAGGCGGTGGGTACGGTGCAGCCAGGTT
      >                                                >M T T K
      >D L R I I D L W T K V A P G G Q A V E A V G T V Q P .
53567 CCCTGCCGCTGACCCCGGAACTGCATGCGTACGTCGTCGCCCACGGATCGGACCCGGATGAGGTGATGCGGGATCTGATCGAGGAGACCCTC
      >S L P L T P E L H A Y V V A H G S D P D E V M R D L I E E T L
```

FIG.11A(46)

```
53659  GCCGCGCTGCCCGCCGGAGGCGAGGATGCAGGCCGTTGCCCCGGAGCAAGCCGGTTCCTGACGTTCCTGACGCGTTGATCGGGGCGGGGGGGC
       > A  A  L  P  A  E  A  R  M  Q  V  A  P  E  Q  A  A  F  L  T  F  L  T  R  L  I  G  A  R  R  A

53751  GGTGGAGGTGGGCACCTTCACCGGCCTGTCCTCCCTGGCGATCGCGCGGGGCCTGGCCGAGGGCGGTTGACCTGCTTCGACATCTCGG
       > V  E  V  G  T  F  T  G  L  S  S  L  A  I  A  R  G  L  A  E  G  G  R  L  T  C  F  D  I  S

53843  AGGAGTACACAGGGCTCGCGGGGCGTCACTGGGCGTCGCGGGGCCGGAGGTGGCCGACCAGATCGGGATCGGCCGGGACACGCTG
       > E  E  Y  T  G  V  A  R  R  Y  W  A  R  A  G  V  A  D  Q  I  D  L  R  Y  G  P  A  G  D  T  L

53935  CGGGGGTTGCCGTACGACGGCCACTCGGCTTCATCGACGCGGACAAGGTCGGCTACGGGCTACTGGCGGAGTTGGTGCCCCG
       > R  G  L  P  Y  E  R  H  L  D  F  A  F  I  D  A  D  K  V  G  Y  P  V  Y  W  A  E  L  V  P  R

54027  CATGCTCCCGGGCGGAGGGTCATCGCGGTGGACAACACGTTGCGCGGGGGCCGGGTGCTCGCCCTGGCGATGCCGACGGCCATCGCCG
       > M  L  P  G  G  V  I  A  V  D  N  T  L  R  G  G  R  V  L  A  P  R  D  A  D  D  R  A  I  A

54119  CGTTCAACGACGAGGTGATGGCCGACGTCCGGGTGGAGCCGGTGCTGCTGCCGGTGTCGTCCGGCGTCCTTCACCGGGGTCGACCGGGTGAGGCGGGGTGT
       > A  F  N  D  E  V  M  A  D  V  R  V  E  P  V  L  L  P  V  S  P  I  A  D  G  L  T  L  A  R  V  R  .

54210  GGCGCCAGCCGACGATCGTGCCAGGTCGCCAGACCTTGTCGTTGTGCCAGGGCGGTTCGCCGGAGGTTGCCGAGGGTGAGCCAGGAATGCCGGAGA
                                        < .  R  V  S  R  A  F  Q  R  A

54302  AGGAAGGGGACCCTTCCTATACCGGAGCCCCCCTGGGGGGGAAGGTGAGCCAGGCTGGAGCCAGCGGCAGGATGAGGTGAAGGACAACGGCCTGGACGGCGCCTTCCTCGCCCGG
                                                      < A  N  A  V  K  D  N  G  L  D  G  A  F  L  A  R

54393  GCCCAGGCGACGGCAAGCACCGATGATGGGCCAGACCTTGTCGTTGTGCCAGGGCAGGTTCGCCGGCAGGTTCGTTGTGCCAGGGCGGTGAGCGGAGGCAGGATGAGGTGAAGGTTGAGCGGCAGGATGAGGTTCCCG
       < A  N  A  V  G  V  A  A  L  V  A  I  I  T  L  G  Q  W  V  K  D  N  G  L  D  G  A  F  L  A  R

54485  GGTGCCGTCCAGGAGAACCGGAGTTCCACTCCGGCGAGCTGGAGCGGCAGCTGAACGCGGGCCCTTTCCTGCCGTTGCCCCTGTTGGGAGC
       < T  G  D  V  A  W  S  F  P  N  W  E  A  I  R  Q  L  W  G  P  A  F  T  L  P  L  L  I  G  S  L

54577  GCAGCAGCACCAGGGCTGGGCCGTGTTCATCACCGGGGAGGCGTCTTGACCTTGAGCGGAGCTGAACAGCTGCCGATGAACAGCTGCCGATGAACAGCTGCCGAGGAGCGGCCGAG
       < L  L  V  P  Q  A  V  T  N  M  V  P  A  L  A  D  E  S  K  V  K  L  A  V  G  Y  S  V  A  S

54669  GTCATCATCCAGGCCGGATCCAGGGTACGACGACGACGATCAGGTACGACGACGACGATCAGGTACCTGTATGCTGCTGGATGCTGCTGGACGGGATCTTCGTGCGCCTTGAGTTCCTGCTGCTCACCATCTGAT
       < T  M  L  A  I  L  A  L  M  L  Y  A  L  L  L  D  G  I  F  V  R  L  E  F  L  L  A  L  L  T  I

54761  GATGACGAGGCCTGGGCCTGGGGCGCGGACGCCAGCATCAGGGGCAGAGGGCTGAACAGCTGCCGAGCAGCGGCCGGGGTGACCCGGGACGTT
       < I  V  A  Q  A  L  L  S  V  V  D  R  L  A  R  G  L  L  A  L  R  S  V  P  T  V  R  S  R  E
```

FIG. 11A(47)

```
54853  CGATGACGGCGGCGCAGCTCGGGGATCAGGCCGAAGCCCTGGAAGAGGCCGCCGAAGATGGCCCAGAGGCCGGGGAAGCCGGGCACGAAG
       < I V G A R L E A I L G F G Q F L G G F I A L L V L L G P V F

54945  ATCTTGTACGCCTCGGCCTTCGGGTCGGCGCGTTCAGCGCGCAGGGCCTTGAGCAGCAGGGCGAAGAGGAGCAGGTACATCACGGCGAAGACGCC
       < I K Y A E A Q T P A N L A P K L L P A F L L L Y N V P Q F V G

55037  GACGAAGACCCAGACCGGATTGCGGAGCAGGAGTTGCATCTGCCGCTGGGCGAGAGCAGGAGCCCAGGTGTCGCGGGCGAACTTCATGATCGGACT
       < V F V W V P N R L L Q M R Q A V L W T D R A F K M

55127  CCGGGCTGGTCAGGACTCGCGCAGCTCGCGCAGCCGGTCTTGGTGAGGAAGACGTCGTCGAGGCGGTGCAGCTCGTGATCGAGTCGAGCC
       < . S E R L S R G T K T L F V D D L S P R H L E I S S L R

55218  TGAGGCCGGACTGGTCGGAGCCCGACCTGAAGACGGTCACGTCCTCGCCAGGGATGGCCGGGATGGAAGACCTGCTGCCGGAGCCGCCAGGCCGCGCAGGCCGCGTCGACGGT
       < L G S Q D L R R L V Q P I A T A G E D V T L R L G G G D V T

55310  TCCAGCTTGGTGACGTTACGGCTCGGTGTCGTCAGGTTGGGCGCCGGCGTGGCCGGGATCTGGTGGGGTGGCGCGTCGCCTCGT
       < E L K T V Y P E T D L L Q A A Q P T A A A D L G V L V E G S

55402  GATCTCCCGCTTCAGCCCGTACGGTCCAGGCGTGGGCGACCACCACCTCGGTGTCCATGATCTCGCGAGACGATCTCGGGCGGCGCGTCGGCCACATGTGGGCGGCGGGGTCGAGG
       < I E R K L G G P T G E A V V E G H D M I A I R D C L A D A E D

55494  CCAGGTAGTGCGTGGTGATGAAGACGTCCTCAGGAAGACAGTTCCTCGCGGTAGCCCGGCCGGTCATCCCGGCCGGCGCGTTGGGCCTTGCCGATGCCGATACA
       < L Y H T T I F V T M G E A R L R R I E D W M H A R S Q P D L

55586  CCGCTGGTCGCGCTTGTCGTCAGGAAGACACCAGTTCCTCGCAGGAAGTGCGGGGCGATCTCGAGACGGATCTCGAGCGCGGCCTGCGCCTGGAGTAGGT
       < G S T P E D L F V I R P D H I I G L A I E V R R Q G G S Y T

55678  CTTGCACTTACGGTCGGCGTACTCGGTAGAAGCTGAGTGAGCGGAGCTCGGGCCGCTGGCGCGCTTGCCGATGCCGATACA
       < K C K R D A Y E T L Q F A A L A R E A R R L A D A K G I G Y M

55770  TCCGGGCGTGCAGGACCAGTTCCTCGCACCAGGCCGGCTTCGCGGCCTGGTGCGGCGACGATAGCCGATCCGGCGGCACTTCG
       < R A H L V L E E R A T S D D W T S G G Q A V Y G I R R V E

55862  GCCGGGTTCCGCCAGCAGGTCGGCCCCGGCCGATGGTGGCCTGGCCGCGTCGGGGGTGATGAGGGTGCCGCAGCATCCGGCAGGGTGGTCTT
       < A P N R L L D A G A I T A Q G G D P T I L T A L M R L T T T K
```

FIG.11A(48)

```
55954 CCCGGCGCCGTTGGGGCCGAGGAAACCCGAAGATCTCCCCCTCGGGCGACGTCGAGCGCCGCGCACGGCGTCGACGTCTTGTGCTGTC
      < G  A  G  N  P  G  L  F  G  F  I  E  G  E  A  V  D  L  D  V  G  R  V  A  D  V  T  K  H  Q  R

56046 GACCGGCGCGGGAGCGAAACGACTTCCGCAGCCCTCTGGTCTGGATCATCTTCGCTCCTGGTCGTCTTAGCCGGGACCGGCCGGCCCTC
      < G  A  R  S  R  F  S  K  R  L  G  R  T  Q  I  M

56136 TCTCCGGAACGCCACACGGGTGGCCCGGAAACGTCGGCGCCGAGGCTAACGCCGATATAACTCTAGTCAACTTTGATTAATGGCGA
                                                <•  R  S  I  V  E  R  T  L  K  S  •  H  R

56227 CCGTCGGCCCTCCCCACGTTCCTGACTGGCCGTCCTGACTGGCCAGATACGGCGGCCTCGGTCGGCGATCCGGTCGGCGACCCG
      < G  D  A  G  E  G  V  N  W  G  D  Q  S  A  L  G  E  P  L  Y  P  V  G  A  E  I  R  D  A  V  R

56319 CTCACACCAGGCCACCTTCGACCTCTCCCCGGGCAATCCACAGCTCGATCACATCCAGCTCGTACATCCAGCTCTTGGAGTCGCGGATCCAGGAGG
      < E  C  W  A  V  E  V  E  G  R  A  I  W  L  E  Y  M  W  S  V  G  V  P  K  S  D  R  I  W  S  S

56411 ACTCCATCGAGGCACGCATGGTTTCGACACTGGTCCAGGGGCCGCTCGCCCCCGACTGCGCAGCGCGGCCACCGCCTCCGGCCTGGGCAGCGCT
      < E  M  S  A  R  M  T  E  V  S  A  R  L  V  Q  G  R  S  R  L  A  A  V  A  E  P  R  P  L  A

56503 GGCAGGAACGCGAACGCCGGGAACCGATGCTCGTCTGATGATTGCCCACCACAGGCCGGTCTCGAACTCGTCGACCCC
      < P  L  F  A  F  A  A  V  F  P  D  S  T  Q  H  N  G  W  L  G  R  L  L  T  E  F  E  D  V  G

56595 CTTCGGGGTGATCTCGTAGCGCGTGTCCGGCGGGCTGCTCGTGGCGGAGCAGCCCCTCCTCGCGGAGCTTGC
      < K  P  T  I  E  Y  T  T  R  A  R  R  A  G  V  Q  E  T  A  V  E  R  L  L  G  E  E  G  L  K  R

56687 GCAGCGGCGTGGTAGATCGAGCGCGGCTGCAGCCGTTGGCCACTTGTCGGCAGCACCCCAACTGTTGCGCGGCGACGTCGTAGCCGTGCACC
      < L  A  H  Y  I  S  G  P  Q  V  N  A  W  K  D  A  G  W  S  L  L  E  R  R  V  D  Y  G  H  V

56779 GGCTGCATCCACTTGACCAGGCCGAGAATCATGCGAGTGGCAGACACCGGAAAAGAGTATTAGACAAGTTTGACTATCCAAGCATCTG
      < P  Q  M  W  K  V  L  G  L  I  M  M

56870 GGCAGTGCCTCATCCCACACTGAGCGATCGTTAGGGCCGGCCGATAAACTCCCGTCAGTAACATCCCGGGAGGAGCCACGAG

56961 GTGCGCAAGGTACTCATCGCCAACGCGAGGCGAGATCCGTCCCGCCTGCCGCGACGGCGCCTGGGCAGCGGTCGCCGTCT
      > V  R  K  V  L  I  A  N  R  G  E  I  A  V  R  V  I  R  A  C  R  D  A  G  L  G  S  V  A  V

57052 ACGGGACTCCGACCGGAGACGCCCTGCACCGGGCGGCGGTACCGCCGACGAGGGTACCGCGCCGACACCGGCGCCGAGACGTACCTGCGG
      > Y  A  D  S  D  R  D  A  L  H  A  T  L  A  D  E  A  Y  A  L  G  G  D  T  A  A  E  T  Y  L  R
```

FIG.11A(49)

```
57144 ATGGACAAGCTGATCGCCGTCGCGGCACAAGGCCGGGGGCCGGGGACGCCGTCCACCCCGGGTACGGCTTCCTCGCCGAGAACGCCGACTTCGCCCA
      > I  D  K  L  I  A  V  A  A  Q  A  G  A  D  A  V  H  P  C  Y  G  F  L  A  E  N  A  D  F  A  Q
57236 GGCCGTCCTCGACGCCGGGCTTACCTGGATCGGCCCGACCCCACAGGCGATCCGCGACCTCGGCGACAAGGTCACCCGCCACATCGCCC
      > A  V  L  D  A  G  L  T  W  I  G  P  T  P  Q  A  I  R  D  L  G  D  K  V  T  A  R  H  I  A
57328 AGCCAGGGCGCGCCCCTGGTTCCCGGTACCTCGGACCCGGTCGGCAGCCCGGACGAGGTGATCGCATTCGCGGTCGACCACGGCCTGCCG
      > Q  R  A  G  A  P  L  V  P  G  T  S  D  P  V  G  S  P  D  E  V  I  A  F  A  V  D  H  G  L  P
57420 GTCGCCATCAAGGCCGCCTTCGGCGGCGGCCGGCGCCTCAAGGTGGCCCGCACGATGGAGGAGATCCGCACCTGTTCGAGTCGGCCAC
      > V  A  I  K  A  A  F  G  G  G  R  G  L  K  V  A  R  T  M  E  E  I  P  H  L  F  E  S  A  T
57512 CCGGGAGGCGGTTCGCGGCGTTCGGCCGGGAGTGTTCGTGGAGCGGTACCTCGACCAGCCCGGCACGTGAGGCACGGTCCTCGCCG
      > R  E  A  V  A  A  F  G  R  G  E  C  F  V  E  R  Y  L  D  Q  P  R  H  V  E  A  Q  V  L  A
57604 ACCAGCACGGCAACGTGATCGTCGGGACTCGTCGGACAGCGCCAAGGCCAATCTGCCGGGGAGGCGCTACCACGGCCGGTGAGTACCT
      > D  Q  H  G  N  V  I  V  V  G  T  R  D  C  S  L  Q  R  R  H  Q  K  L  V  E  E  A  P  A  P  F
57696 CTCACCGACGCGCAGCGCCAGGCAGATCCACGACAGCGCCAAGGCCATCTGCCGGGAGGCCGGCTACCACGGCGCCGGTGAGTACCT
      > L  T  D  A  Q  R  R  Q  I  H  D  S  A  K  A  I  C  R  E  A  G  Y  H  G  A  G  T  V  E  Y  L
57788 GGTGGGCACGGACGGACAGCGGCACAGATCTCCTTCCTTGAGGTCGAACGGCTCCAGGTCCAGGACTCCGGGCACTCGAGTTCCGGATC
      > V  G  T  D  G  T  I  S  F  L  E  V  N  T  R  L  Q  V  E  H  P  V  T  E  E  T  A  G  I  D
57880 TCGTCCGAGCAGTTCCGGATCGCCGACGGCGAGAAGCTGCGGCTGGCCGAGGATCCGACCCCGCGCGGGCACTCCATCGAGTTCCGGATC
      > L  V  R  E  Q  F  R  I  A  D  G  E  K  L  R  L  A  E  D  P  T  P  R  G  H  S  I  E  F  R  I
57972 AACGGCGAGGATCCGGGCATCCCGGCGACTTGATCGGCGGCAACTTCGACTCCCTGCTGGCCAAGGTGATCATCACCGGGGAGACCCGGGAGACC
      > N  G  E  D  P  G  R  N  F  L  P  A  P  G  T  V  T  A  L  R  L  P  T  G  P  G  V  R  V  D  T
58064 CGGCATCTCCGCGGGCGACGTGATCGGCGGCAACTTCGACTCCCTGCTGGCCAAGGTGATCATCACCGGGGAGACCCGGGAGACCGAGGCCCTGG
      > G  I  S  A  G  D  V  I  G  G  N  F  D  S  L  L  A  K  V  I  I  T  G  E  T  R  T  E  A  L
58156 AGCCGGGCCCCGGCCGCCGCCTGGCTGACGAGATGGTGGTCGGGGAGGGAATGGCCACGGCGCTGCCGTTCCACCGCCTGGTGGTACGCGACCCGGCCTTC
      > E  R  R  A  L  D  E  M  V  V  E  G  M  A  T  A  L  P  F  H  R  L  V  V  R  D  P  A  F
```

FIG. 11A(50)

FIG. 11A(51)

```
59351 CGGTGCCGGGGAGCGGAGGACCGCGTACCGGATTCGACCGGCTCTCGGCGGGCGGCGGCGGTGGTGGACGGCGACGGCCGG
      > T   V  P  A  D  A  D  P  R  T  G  F  D  R  L  S  A  G  R  R  R  L  A  P  V  V  D  G  D  G  R

59443 CTCGTCGGGGTGTTGACCCGCAAGGGCGCGCTGCGCGACGGCGTGGACCGGCGTGGACGACCCGGCTGCGGATCGCGGCGGC
      > L  V  G  V  L  T  R  K  G  A  L  R  A  T  L  Y  T  P  A  V  D  D  R  G  R  L  R  I  A  A  A

59535 CGTCGGCATCAACGGCGACGTCACCGGCAAGGCCGCGGCGCTGCTCGAGGCTGGTGTGGACGCCCTGGTGGTGGACACCGCGCACGGCCACC
      > V  G  I  N  G  D  V  T  G  K  A  A  A  L  L  E  A  G  V  D  A  L  V  V  D  T  A  H  G  H

59627 AGGCGCGGATGGTCGCCGCGCTGCGGGCGGTTGCGCAAGCTTCACCCGGGCGTTCGGGTGTCGCGGCAACGTGGTCACCGCGATGGGGGTA
      > Q  A  R  M  V  A  A  L  R  A  V  R  K  L  H  P  G  V  P  V  A  A  G  N  V  V  T  A  D  G  V

59719 CGGGACCTCGTCGAGGCCGGCGCGACATCGTGAAGGTGGGCGTCGGTGGGGACCTCGGCGGCGCGGGAGACTCGGCCGCACGTCTGGGCCGACGGCTCTGGGCGCACGTCTGGGCCGACGGCGACCGCGCG
      > R  D  L  V  E  A  G  A  D  I  V  K  V  G  V  G  P  G  A  M  C  T  T  R  H  M  T  G  V  G  R

59811 TCCGCAGTTCTCCGCGGTGCTGGACTGCGCGGCGCGGCGGAAAGCGTGATGATGGCTTCCTGGTTCGCCGGCACGTACGAGTCCCGGGTGACCTGTACACG
      > P  Q  F  S  A  V  L  D  C  A  A  A  A  R  D  L  G  R  H  V  W  A  D  G  G  V  R  H  P  R

59903 ACGTGGCGCTGGCCCTCGCCGCCGGCGCGTCGAACGTGATGATCGGGATGATCGGGTCCTGTCGGCGGCGGTCAGGCCGCGTCAGGCGCTACGGGCGCAGCGCGCGAGCGCGTTCGACCG
      > D  V  A  L  A  L  A  A  G  A  S  N  V  M  I  G  S  N  F  A  G  T  Y  E  S  P  G  D  L  Y  T

59995 GACGCGGACGCGGATCGGAGGGTACAAGGAGAGCTTCGGCATGGCCTCGTCCGGGCGGTCAGGCGCTACGGCGGCGCGACCGGCGAGGACTCGGCGTTCGACCG
      > D  A  D  G  R  R  Y  K  E  S  F  G  M  A  S  S  R  A  V  S  A  R  T  A  E  D  S  A  F  D  R

60087 GGCCCGCAAGGGGATCTTCGAGGAGGGCATCTCCGGCGTGCGCAGCGCGTGCACCTACGCCGGCGCGCGGTCACGCGAGGACTGATCGACGAGA
      > A  R  K  G  I  F  E  E  G  I  S  S  A  R  M  Y  L  D  P  D  R  P  G  V  E  D  L  I  D  E

60179 TCATCTCCGGGGTACGGCGTGCGCAGCGCGTGCACCTACGCGGGCGCGCGGTCGCTGGCGGAGTTCGCCGAGCGGGCGCTCGGGGGTGCAGAGCACG
      > I  I  S  G  V  R  S  A  C  T  Y  A  G  A  R  S  L  A  E  F  A  E  R  A  L  V  G  V  Q  S  T

60271 GCCGGGCTACACCGAGGGGATGCCCTTACCGACGAGTTGGTGACCCCGGCGCGGCGTGAGGAAGGGTTCCCCTCTCTACCGGAGGCGTCAA
      > A  G  Y  T  E  G  M  P  L  P  T  S  W  .

60362 CAAGGGGCCCCTTCCTTCGTGCGCGCGGCTGCGCGTGACCGGCGTGGGTATCGGCGTGGGTATCGGCGTGACGCCGCCGCACTGAGCCGCCGTCGAGGGCCC
```

FIG.11A(52)

FIG. 11A(53)

```
61645 CGTCGTCGGCCAACGGTGGAACCGCTACCTCGCCGAGGAGCACGGCCTCACCCAGGCGGGCATGGTCACCCTGATGACCCTGGCCCGGCACG
       > V  V  G  Q  R  W  N  R  Y  L  A  E  E  H  G  L  T  Q  A  G  M  V  T  L  M  T  L  A  R  H
61737 GCGAGCTGCCGCACCGGGCGGTGCGCCGAGGCGTGTGCTTCATCCGCCCTACCCTCACACTCGACACTCGACACTGGAGCGCGACGGCCTC
       > G  E  L  P  H  R  A  V  E  A  C  F  I  R  P  A  T  L  T  G  I  V  D  T  L  E  R  D  G  L
61829 GTCGAGCGGCAGCGCGACGACGTCGACCGTCAGCGTGCTCCTGACCCCGGGCTCGTCCTGACCCCGGGAGAGGGTCACGGCCTCACCAACGT
       > V  E  R  Q  R  D  D  V  D  R  R  S  V  R  L  V  L  T  P  A  G  R  E  R  V  A  A  L  T  N  V
61921 CATGCAGTCCGGACCGATGACCTCGGTCGACGCCCCGGCGAAGGCCGTCATCCGGCAGTTCCTGCTCGAGGTCATCGGCAGTG
       > V  E  R  Q  R  D  D  V  D  R  R  S  V  R  L  V  L  T  P  A  G  R  E  R  V  A  A  L  T  N  V
       > M  Q  S  G  R  P  M  T  S  V  D  A  D  P  A  K  A  V  I  R  Q  F  L  L  E  V  I  G  S
62013 GAGAGGAACCTCGGGTGACGGCCCTCGACGCGAGGCCGGAGCGCGACATCATCGACCAGGG
       > G  E  E  P  R  V  T  A  L  D  A  R  P  E  A  P  A  C  .
62105 GACCGCTGGCGGCGGCGGTGATGGCGTTGCAGTTCGTCGGCACCATGGCCTCGCTCTACCTGCCGAGCCTCAACGCCGACATCATCGACCAGGG
       > M  A  L  Q  F  V  G  T  M  A  S  L  Y  L  P  S  L  N  A  D  I  I  D  Q  G
62196 TGTGGCCGGGCGCGACACCGGCTACATCATGCGCACCGGCGGATGGATGCTGCTGGTCAGCCTGGTGCAGATCGCCTGCTCCACCGCCGCGG
       > V  A  R  G  D  T  G  Y  I  M  R  T  G  G  W  M  L  L  V  S  L  V  Q  I  A  C  S  T  A  A
62288 TCTTCCTCGGCGCGAGCGCGATGGGCTTCGGCGACGTACGCGCGGAGGTCTTCGCGCACGTGAACCGGTTCAGCGCCCGCGAGGTG
       > V  F  L  G  A  R  S  A  M  G  F  G  R  D  V  R  A  E  V  F  A  H  V  N  R  F  S  A  R  E  V
62380 ACCCGCTTCGGCGCTTCGCCGCAGCCCTCGCTGATCACCCGCAACGACGTGCAACAGGTGCAGATGCTCGTCCTGATGAGCTGCACCATGCTGGT
       > T  R  F  G  A  P  S  L  I  T  R  N  T  N  D  V  Q  Q  V  Q  M  L  V  L  M  S  C  T  M  L  V
62472 CGGCGGCGTCGATCATCGAGCGTGTTCATGGCACTCGATGAGCCGGATGTCGGCCTGAGCTGGATGCTGGTCAGCGTGCCGGCGC
       > A  A  P  I  M  S  V  G  G  V  F  M  A  L  R  E  D  V  G  L  S  W  M  L  V  S  V  P  A
62564 TGGCGATCGCCCTGATGCTGATCATCCGGCGGATGGTCCCGGGTTCCGGCGTTCAACCGCGTCCTGCGC
       > L  A  I  A  L  M  L  I  I  R  R  M  V  P  G  F  R  L  M  Q  T  R  I  D  A  V  N  R  V  L  R
62656 GAGCAGATCACCGGCATCCGGGTGGTCGTCCGCGCGTTCGTCCGAGAGCCGTACGAGACGGCGCTTCGGCGCGCGAACGCCGACCTCACCGC
       > E  Q  I  T  G  I  R  V  V  R  A  F  V  R  E  P  Y  E  T  A  R  F  G  R  A  N  A  D  L  T  A
```

FIG.11A(54)

```
62748 GACCGCCCTGCGCACCGGTCGGTTGATGGCCCTGATCTTCCCCGTGGTCACGCTCCTGGTGCTCAACGTCTCCAGCGTGGCGGTGCTGTGGTTCG
      > T A L R T G R L M A L I F P V V T L V L N V S S V A V L W F
62840 GCGCGGACCGCGTCGACGCCGGTCCAGATCCAGGTCGGCGCGCTCACCGCCTTCCTGCAGTACCTCATGCAGATCCTGATGGCCGTCATGTTG
      > G A D R V D A G Q I Q V G A L T A F L Q Y L M Q I L M A V M L
62932 GCCACCTTCATCCTGATGATGGTCCCGCGCGCGGTCTGCGCCGAGCGGATCGTCGAGGTGCTCGACACCGACTCGACGGTGATCCCGCC
      > A T F I L M M V P R A A V C A E R I V E V L D T D S T V I P P
63024 GGCTGCCGACGGCGAGGTGACCGGCCGGGGCGAACTGGAACTCCGGGGCGTTCCAGTACCCCGGGGCGAGCGCGCCGGTGCTGC
      > A A P T A E V T G R G E L E L R G V R F Q Y P G A S A P V L
63116 ACGACATCTCGTTCCGGGCCACCCCGGGGCGTACCACCGCCATCATCGGCAGCACCGGTGCTGACGCTGATCCCC
      > H D I S F R A T P G R T T A I I G S T G A G K T T L L T L I P
63208 CGGCTGATCGACGCCACCGGCGCCGTGCTGGTCGACGGGGTGGACGTGCGCGACCTGGCCCCCGACGATTTGTGGCGCGGATCGGGCT
      > R L I D A T A G A V L V D G V D V R D L A P D D L W R R I G L
63300 GGTGCCGCAGCGGCGGCCGTACCGTTCAGCGGCACGATCGCCAGCAACCTGCGGTACGGCAACGCCGACGCGGAGCTGTGGGCCG
      > V P Q R P Y L F S G T I A S N L R Y G N P D A T D A E L W A
63392 CCCTGGAGATCGCCCAGGCCGACTTCGTCGCCGAGTTGCCCGAAGGCCTGAACGCCCCGATCACGCAGGGCGGCACCAATATCTCCGGC
      > A L E I A Q A R D F V A E L P E G L N A P I T Q G G T N I S G
63484 GGGCAGCGGCAGCGCCTGGCCATCGCGCGCGCCCTGGTCCGCAAGCCGGAGATCTACCTGTTCGACGACTCGTTCGCGCTCGACCTGGG
      > G Q R Q R L A I A R A L V R K P E I Y L F D D S F A L D L G
63576 CACCGACGCCCGGCTGGCCGCGCTGCGGCCCGTACGACGGTCACGGCGATGGGCCGGCACGCCGAACTGCTGGAAGACTGCCCGACG
      > T D A R L R A A L R P V T A D A T V L I V A Q R V S T I V D
63668 CCGACCAGATCATCGTCCTTGAGGACGGGGGCATCGTCGGGAATGGGCGGCATGCGGAGCTCGAAGACTGCCCGACGTACGCGGAGATC
      > A D Q I I V L E D G G I V G M G R H A E L L E D C P T Y A E I
63760 GTCGCCTCCCAGCAGACGGCCGGGGTGCCGGCATGACGGGCTACCAGGATCAGCGCGGATCAGCCGCGGGAGGGCCGGAGGGGCCGACGCCGAA
      > V A S Q Q T A G V P A
```

FIG.11A(55)

```
63851 GCGGCTGCCCTCCGGCAACCAGGGCAGCGGCCGGCATGCCGGCCGAGAAGTCGATGAACTTCGGGCCGTCCAC
      > M  S  A  G  M  P  A  E  K  S  M  N  F  G  P  S  T
63941 CCGCCGGCTGCTGCGCCGGCTGCGACGCGCACGCCTCCAGCTGGCCGCCATCGTCCTGCTCTCGGTTGCAGCGTCTGCAACGTGTACG
      > R  R  L  L  R  R  L  R  P  H  R  L  Q  L  A  A  I  V  L  L  S  L  V  S  V  G  C  N  V  Y
64033 GGCCGAAGGTGCTCGGCCACGCCACCGACCTGATCTTCAGCGGGGTGATCGGCCGGCAGTTGCCCGGGGCAGGCACCGCCGAGCAGGCGGTC
      > G  P  K  V  L  G  H  A  T  D  L  I  F  S  G  V  I  G  R  Q  L  P  A  G  T  T  A  E  Q  A  V
64125 GCCGCCCGCGCCGGCTAACGACAGCTTCGCCGACATGCTGGCCCGGCTGGTGCCGGGGGTGGGCATCGACTTCACCGCCCT
      > A  A  A  R  A  A  G  N  D  S  F  A  D  M  L  A  R  M  D  V  V  P  G  V  G  I  D  F  T  A  L
64217 GGGCCGGGTGCTGCTGTTCGTGCTGGCGCTCTACCTGGCCGCCAGCGTGCTGTTGTGGCAGGGCTGGCTGCTCAACGGGGTGGTGCAGC
      > G  R  V  L  L  F  V  L  A  L  Y  L  A  A  S  V  L  L  W  Q  G  W  L  L  N  G  V  V  Q
64309 GCACGGTGCTGCGCCTGCGCGCCGACGTGGAGGACAAGCTGAACCTGCGTCTGCAGCTACTTCGACCGCCAGCCGCGTGGTCGGCGT
      > R  T  V  L  R  L  R  A  D  V  E  D  K  L  N  R  L  Q  L  Q  Y  F  D  R  Q  P  R  G  E  L  L
64401 AGCCGGGTCACCAACGACATCGATGTTCTGGATCTCGCCGTGTTGGCGCTGTCCCTGGTCGCCGATGTCGGTGGTCACCAGCTGGTGTGGGT
      > S  R  V  T  N  D  I  D  N  I  S  Q  S  L  Q  Q  T  L  S  L  Q  T  L  S  L  L  T  V  V  G  V
64493 ACTGGCCATGATGTTCTGGATCTCGCCGTTCATCGCCGCCAGTCCAGTGGACCATACCGGAGAGCTGAACGGCCAGATCGAAGAGGCGTTCACCGGAGACGAGCTGGTC
      > L  A  M  M  F  W  I  S  P  L  L  A  L  V  S  L  V  A  V  P  M  S  V  V  T  S  L  V  A
64585 AGCCAGCAGCGGTTCATCGCCCAGTGGACGCATACCGGAGAGCTGAACGGCCAGATCGAAGAGGCGTTCACCGGACACGAGCTGGTC
      > K  R  S  Q  Q  R  F  I  A  Q  W  T  H  T  G  E  L  N  G  Q  I  E  E  A  F  T  G  H  E  L  V
64677 AAGGTCTTCGGCAGCCGCGAGGTGGAGGCCGAAGCCTTCACCGCCAAGAACGAGGAGCTGTTCCGGGCGCCAGTTCATCTC
      > K  V  F  G  R  Q  R  E  V  E  A  A  F  T  A  K  N  E  E  L  F  R  A  S  F  G  A  Q  F  I  S
64769 CGGGATCATCATGCCGGCAATGATGTTCATCGGGAACCTCAGTCTAGCGTCGCCGCGCGCGCGTTCATCCAGTACTCCCTCCAGTTCACCCAGCCGCTCACCCGGGTCGCCTCGATGGCCAACCTGCTCCAG
      > G  I  I  M  P  A  M  M  F  I  G  N  L  S  Y  V  A  I  A  V  V  G  G  L  R  V  A  S  G  S
64861 TGAGCATCGGCGACGTGCAGGCATTCATCCAGTACTCCCTCCAGTTCACCCAGCCGCTCACCCGGGTCGCCTCGATGGCCAACCTGCTCCAG
      >M  S  I  G  D  V  Q  A  F  I  Q  Y  S  L  Q  F  T  Q  P  L  T  R  V  A  S  M  A  N  L  L  Q
```

FIG.11A(56)

```
64953 TCCGGGGTGGCCTCCGCGAGCGGGTGTTCGCGGTGCTCGACGCCGAGGAGCAGAGCCCGGACCCGGCGGTGCCGGCCCGGGTCGCCGACCA
      > S  G  V  A  S  A  E  R  V  F  A  V  L  D  A  E  E  Q  S  P  D  P  A  V  P  A  R  V  A  D  Q
65045 GCGGCGGGTCGCGTCGAATTCGACCACGTCTCATTCCGGTACGAGCCGGACAAGCCGCTGATCACCGACCTGTCGCTGGTCGCCGAGCCGGGGC
      > R  G  R  V  E  F  D  H  V  S  F  R  Y  E  P  D  K  P  L  I  T  D  L  S  L  V  A  E  P  G
65137 ACACGGTTGCCATCGTCGGGCCGACCGGCGCGGCAAGACCACCCTGGTCAACCTGGTGATGCGCTTCTACGAGCTGGACGCCGGGATC
      > H  T  V  A  I  V  G  P  T  G  A  G  K  T  T  L  V  N  L  V  M  R  F  Y  E  L  D  A  G  R  I
65229 ACCCTCGACGGGGTGGACATCACCACGCTGAGCCGCGACGACCTGCGCGGCCGGATCGGCATGGTGCTCCAGGACACCGAGCTGTTCGGTGG
      > T  L  D  G  V  D  I  T  T  L  S  R  D  D  L  R  G  R  I  G  M  V  L  Q  D  T  E  L  F  G  G
65321 CACGATCCGCGACAACATCGCTACGGCGGCCGCGAGGAGGAGATCGTCGCCGCCGCCCGGGCGACGTTCGTGGACCGGTTCG
      > T  I  R  D  N  I  A  Y  G  R  P  D  A  S  E  E  E  I  V  A  A  A  R  A  T  F  V  D  R  F
65413 TGCGTAGCCTCCCGACGGCGTACGACGCTCATGACTCCGAGGCGCCGGAAGCAGCTCATCACCATCGCCCGG
      > V  R  S  L  P  D  G  T  D  T  V  I  D  S  E  G  S  N  V  S  A  G  E  K  Q  L  I  T  I  A  R
65505 GCGGTTCCTGGCCGAGCCGTCGCTGCTGATCCTGCTGATCCTCGACGAGGCGACCAGTTCGTCGTGCTCCAACGGGCCATGGC
      > A  F  L  A  E  P  S  L  L  I  L  D  E  A  T  S  S  V  D  T  R  T  E  V  L  L  Q  R  A  M  A
65597 GGCGCTGCGCGAGCAGGGGACACCCGAGGGCACCCATGAGCAGCTTGTCCACCATCCGCGACGCGGACCTGATCCTGATGGAGCACGGTC
      > A  L  R  S  D  R  T  S  F  V  I  A  H  R  L  S  T  I  R  D  A  D  L  I  L  M  E  H  G
65689 GCATCGTCGAGCAGGGCACCCACGAGCAGCTGCTCGCGGCGCGTACCCACCAGTTCACCCAGGCCGGACCG
      > R  I  V  E  Q  G  T  H  E  Q  L  L  A  A  R  G  A  Y  H  R  L  Y  A  Q  A  F  T  Q  P  D  P
65781 GCCGCCGTCGGGGACCCCGAGCCCCAGCCCCCGAGCGCGTCCGGGCTCGTGCGCGTGTACCATCCCGGACCCGCAG
      > A  A  V  G  D  P  E  P  Q  P  Q  P  A  S  V  R  G  .
65872 GGGCAGCTCCCCCCGGGCCCCCGGAAGACACTGTGTGCGGCAGAACCGTGTGGGCAGCGGAGCGCGGGGCCCAGCCG
65964 CATCCGCGGGAACATGTCGTCGGCGAAGTGGCCGAGGTGCGGAGGTCAGTGACGGTGACTGTCGGGCCCGCGGGTTCCCCGACGTCG
66056 TGGTCGCGTACCGCGCTGCCGCTGGAGACGTAGCCGGAGCGGCATCCGAATTCGGGGCGCCCGGCCCGACGCCAGCCGAGACG
66148 CATCCGGTTACCGCGAAGGCGACAGGCCGCAACCGTCGGCGCTACAGTCGGCGATGCACAGCGCGCCTCGGGGCGGCCGGGCCGGCAC
```

FIG.11A(57)

```
66240 GGGACCTGCCGGCGGCCCATGGCGGCCCGGTCGTCGGCTACGGGGGGTCCGACACTCGAGGCCGGCCGGCCGACTACGCCGGTACGCCGGCCGTCGGC
66332 GATCCGCCGACGCCTCCACCCGCGTACGCGGCCGAGGTTGCCGGCCCCCAGGGGACCTCCCGGCCGTCCCCGACCGGCGTCGGCCGTCGCCGGGCCC
66424 GACGACCGGTTCGTGCGGGTGCCGGCGAGGTGGAGCCTCGCGGCCCAGTTACTCCAGCTCGTGGAGCATGAGCTGCGGGCGGCCTCGGTGATC
                                     <· E L E H L M L Q R A A E T I
66515 GAGCCCGACAGGCTCGGGGTAGATGGTCTGGGTCTGTTGACCGTGAGGTTGTTCTCCACGCGTCGGTCGATCGGCAGGATCAG
      <S G S L S P Y I T I T Q A L E N V T L N N E V A M T I P L I L
66607 CTCGCTGGCCTTCGGTGCCAGCTCGGCCAGCTCGTCGACGATCGCTGGCCTGGCCGCGCCCTGGGCGCTGGCCCAGGGCGGCAGAACAGCTTCACGAAGCCGTCGGCGAGGTCGT
      <E S A K P A V V G G I V Q G S A P R C G L K V F G D A L D D
66699 CCATCTTCGCCCCAACAGCGCGTTGCCGACAGCGGCACATCACCTGCCGGGGTCTTGCCGGCGGTCCAACTCGTCCTGGGAGACGCCGACG
      <M K A R A N G S L P L M V Q R A P T K G A S V E D Q S V G V
66791 GTGGCCAACTCCGGTCGTGAAGAGTTCGGTACGCGGTCGAGCGGCCCGACCGGCGGGCCGAGGCGCTGCCACATCGCGAT
      <T A L E P D T F V N A A V T R L R L P R V A E G L A H W M A I
66883 CCGGCCCCTGCAGGCCGGCGAGCTGCCCCGGTCAGGCGACAACACCCCGGTAGATCCCGGGGACGTTGGTCGCGGACACCC
      <R G Q M A A V S A L P L V G T C D G A A Y I G P V N T R S V R
66975 GGTCGACGGTGACGCTAGCGCCCCCGGGGATCGCCAGTCCGAGCCGTACTCGGCGGAGGCTGATGCGCTGGACCCTCCACCCGTCGGCGATGCTGGACCCTCTCGGCGCGGGAGTTGTT
      <D V T V Y G G R A L E V G T E A L G L N A T N P I S G V A I
67067 AGCGCGTCGAGCGTGCAGACCGGCACCAGCCGGCAGCCGCCGATGCGCTGGACCTTCCACCCGTCGGCGATGCTGGACCCTCTCGGCGCGGGAGTTGTT
      <L A H S G H V L R G D A L E V E V G D A I R Q V R E A R S N N
67159 GAGGATCGTCATGCCGGGGAGCGGAACACGCCTCGATCGCCATGGCGGCGTCGGCGTCGGCGTCCTCGTCGGCGCATCCGGTTCCCGGCTGGAGA
      <L I T M G R S R F V R E I A M A A D A D E H P M V R D R S S V
67251 CGAGGGTGACGGAGCGTGTACACCTGCCGCCGTCGGAACTGGCGGCCACCGGTGACGCCGGAACCGGCACCAGGATCACCGGTACGCCGGTGCTCGGGCAGG
      <L T V P V G M A L Y A S A F E A G T V G S G V V I L H E P L
67343 TGCGGACGGTCGTACACCTGCCGCCGTCGCGGCCGATGCCGGTCAGGATGCCGGCACGCCGTGGCGGGGAGCTGGCCGCCGGTGCGGAC
      <H P L D Y V Q E W T L I R E G D P V A T P L Q R P T A G T A V
```

FIG.11A(58)

```
67435 CAGCACGGTCGACGCGGTCGATCGAGTGCTTCTCGGAGCCGGTCGGCGACGACGGTGGGTGTGGCCAGCATGTCCTCGCCGA
       < L  V  T  S  A  D  I  S  H  K  E  S  G  D  A  P  T  V  V  V  R  H  T  H  G  L  M  D  E  G  L
67527 GCCGGGGCCGTGCCGGCCACGAAGGTCACCGCCTTCGCGGCCTTTGCGCTGGGCGACCGGTGAGCCGCTTGACCCGC
       < R  A  T  G  A  V  F  T  V  G  A  K  V  L  K  A  H  I  D  A  S  Q  A  L  A  L  R  K  V  R
67619 TCGTGCACGGCCCGGGCGTCGACGGTGACGGTAGCGCTCGGAGTGCACCTCGGTGTCCGGTGTCCGGTGACCACCTC
       < E  H  V  A  R  A  D  V  T  V  A  E  L  G  D  S  H  V  G  F  E  E  T  D  R  Y  G  T  V  V  E
67711 CGAGCTGGGCGATGAACGTTTTCGACCAGTCGGACACGCAGGTACGGTGGCCTCCACCACGGTGACATCAGCGT
       < S  S  A  I  F  T  K  S  P  V  C  D  S  L  V  C  A  G  G  A  G  E  A  E  V  V  T  V  D  A  D
67803 CCAACTGGGCGGCGACCAGGGCCGACTCGTACCCGGCCGGCCCGATGATCACGATCTGGCTCACAGAGTATCGCCCTGTCCGT
       < L  Q  A  A  V  L  A  A  E  Y  G  A  P  G  G  G  I  I  V  I  Q  S  V
67893 GCTCACAGTGACTTTCTCCCCGACGCGTCCGACACGCGTCGTATTCTCCCAGCCGTCCGGCCGTATCGTCATCGCCGTGGCG
                                                                                              > V  R
67984 TCACTACTAGCGCTCAAACCTGGACCCCGCCGGATGCGCGCTACTGCCGCACTCCCGATGGTCGGCGTGGCTGGAGG
       > H  Y  A  A  Y  G  S  N  L  D  P  A  R  M  R  A  U  C  P  H  S  P  M  V  G  V  G  W  L  E
68076 GCTGGCGCTCACCTTCGCGGGTGAGGGCGATCGGCTGGGCCTGCAGGGGCGCGTCAGTCCCCGGTGATCGGTGTTCGTG
       > G  W  R  L  T  F  A  G  E  G  A  I  G  W  E  G  A  V  S  T  I  V  E  S  P  G  D  R  V  F  V
68168 GGGCTCTACGACATCCACCCGTACGACGCCGTCCAGCTCGACGAGATCGAGGGGGCGTACGCGACGTACGCAAGCTGCAGTCCGGCGT
       > A  L  Y  D  I  H  P  Y  D  A  V  Q  L  D  E  I  E  G  V  A  S  G  T  Y  R  K  L  H  V  R  V
68260 CTTCACCCTCGACGGCGACGTGACGGCGTGGTCTACGTCTTCGACGGGTACGAGGGCGGCCTGCCGACGGCGTGGTATCTGTCGGAGATCG
       > S  T  L  D  G  D  V  T  A  W  V  Y  V  F  D  G  Y  E  G  G  L  P  T  A  W  Y  L  S  E  I
68352 CCAACGCCGCCGAGAAGGCCGGGGCCCCCGACGACTACGTCAGCGAGCTGCGGTCCCGGCACGGGCGTCGGCGTAGCGCGTCTC
       > A  N  A  A  E  K  A  G  A  P  D  D  Y  V  S  E  L  R  S  R  P  T  G  T  A  S  A  .
```

FIG. 11A(59)

```
68443 CCACACTCCCAGTCTGCTCCCCGAGACGGGGCCGGCACGCGGGTCGTCTGTCACACATCATGGTCGCGCCGTCACA
                                                                        < . V
68534 CCGCCGTGGCGGGGACGGTGCTCGTGTACATGTCGGTCCAGGGATCTCGGCAGCCCCACCGAGCGGTAGAGCGTCCGGGGGAGGTC
      < A T A A P V T R E Y M D T W R M E R L G V S R Y L T A P S T
68626 GGGTTGGTCAGGTCGAGGCGGTGCTGGGACTCGAGGTCCCTTCGCCGCGTAGAGCCTGAAGGCCGCCACAGCAGCGGCGGGCGCCGACCCC
      < P N T L D V G L G A H R R G K A A Y V T F A R W L L A A G V G
68718 GTGCCGCGGTACTTCGGCAGCAGCAGCGACAGGGTCGCGCACCCAGTCCTGTTCCCAGCGCCTGGTCGGACGACTGCAACGCGCGGCCG
      < H R R Y K P L V S L T R V W G S D Q W L A Q D S S Q L A G A P
68810 GCTCCCCGTCGACCTGCGGGACGAACCACTCGTCGTAGAGCGGCAGAACGCTCCCGGCAGTGGTCGTACCCGGCGGCCTCG
      < E G D V E A V F W E D W T R D Y A P L R E R W H D Y G A P E
68902 TAGTCCGGGGTGTCCGGAACGCGTCGATCCGTGTAGATCCGGGCAGCCAGGTCGTCGTCGTCGTCGCAGCGGCCCAGCCTCGGTCA
      < Y D P T D R F A T D Y I R H F L R L D D E D G A R L P R V T V
68994 CCCGGGGTGGGGCGGCGGCCTCGGGGCAGCCCAGAGCGCGCAGGATTCGTGCAGGTCAGCGACGGGGTCAGCGCGCCCGTCGGCCTCGGTCA
      < G P P P P E A P L G A L D R S M R V Y R K V R S F G A E T L
69086 GCTCCGTCACCCAGCGAGAGCGAGCAGGGTACCCGCTTCGGGGGTTGGCCGAGAGCGCGCCGCTGACGGAGCTGCGGCCGCCACCCGGTCGG
      < E T V W R T E P P Y A S A R V T L A P L S R E A A R E A V R
69178 TCCAGCATCGAGAGCGACCAGGCGCCCTGCGGGGTCCTGAGGGTCAGCAGCCAGGAGGAGCTGCGCGGCCGGGGTCGGCCACCCGGTCGG
      < D L M L A L L P A R V A E A R E P D V L V D V F E R G V T P
69270 GTTGTCGACCACGACCAGGCGACGGGTCGCGGGCCGGGTGCCGCCGGATCGCGCCGGGTCGCAAGAAGGGGCCGTCAGGG
      < N D V V D Q A V L R G Q P D S V L W S D R A P D F F P A T L A
69362 CGGCCTTGACGTCTTCGGCGTGGCCGATCGCGAAGTGTCTGCGGCCGTGCACGACGGCGAGGATCCAGGACGTCGTCG
      < A K V D E A D F D P H G I A F T D A A H V V A L I G P V D D
69454 AGGGGCGGCGGCGGCGCCCCAGTCAGCGGCGAAGAGTCACGGGGCGATCCTGGCAGCCACCCGGTCCCGCGCCCTCATTTTTCAACCGC
      < L T P R R A A W D A P L T V
```

FIG. 11A (60)

FIG.11A(61)

```
70556 GCTCGATGCCGGTCAGTTCCTCGGCACCGTCGTCGGGCTCCACCGCGCGGCGGCAGCTCCGGCCTCGGGCCCGCTCCTGGTCGTCGGTACGCGCC
       < E I G T L E E A G D H E A E V A G A L E A E R E Q D T R A
70648 CGCGGCCAGTTCCGTTCCGCTGCTCCAGCATCCGGCGTTGCCGGCCACGGGCGGCCGCCTCCCGGGCGGCCCGCTTCGGCGCGCGG
       <R A L E R E L M R R Q R A R E A R A A R E A E R A A R K A R P
70740 TGGTGGGTGGGTGGGGCGGTGCTGCTCCGCCGGTGACCAAACGGAGCTGGGGCGGGGCACCTGCGAGCCGGCGTAGCTGGCGG
       <P P H T P P P Q E E G G T V L R L Q P R P V E G F G A Y S A A
70832 CCCGCAGCAGCCGGCCGGAGCGCGTGCCCGGCCACCTGCCCGTGTCGGAGAGCGCGGGCGTCGAGCGTCGCCACTCGCCCAGCGGCCAGC
       < R L L R G S R V Q G A V E T D S L A A D L T A E V E G L P L
70924 TTCCCGGCCGGCCGGGCCGCCTCGGGCGTCGGGCCCTCTGGGCGCGGCCAGGTTGGGTCAGTTGGGCGACCAGTCGGCGGCGCA
       <K G A P P G G E A D A A L R R A E A V L A A V A A R R Q A S L
71016 TTCCCGCGAGCAGCCGGGGGCGCCAGGTCGCGCTCGGCGCGCAGGCTCGCCGGCGATCTCGCCGTGCCGGGTCGCCGAGCGCCGGCC
       <E R L R P G R L D R Q A R R L A E A L Q T L D A V L E P R R L
71108 GGGCGAGCAGGTTGACCAGGTTCGCGGTGAGGATCGCGGCGGGCGGGCGGCGGTTGTGGCGCGGCGAGAGGCTCTGCGGGGCGGCACGGCTC
       < A L L N V L W A A V T P R R L R A I E R A T A P D G S R R A
71200 TCGGCGACGGTCGCGGGGTGGCGACGAAACTTCTCCGGCTTCACGGCGCTACGTCGGCGTACTGAGCGTGTGCG
       <E A V A A D R T A V F K E P P E T Y L R R L L S Q P P P V .
71291 AGACGTCGAGCGCCGGCTCGGCCTGAGCCTGCAGGGCGAAGGCTCGGCGCGGATGAAGTCGACCACGTCGAGAACTTCGACGGTTGTCG
       < V D L R S G P Q E L R Q U D T G S L A A Y Q R N L V A L G N D
71383 TTGAGCAGCCGTCGTGCAGGGCGCTGCCACCGGGCGTCCTGGGTGCCAGGGGCGTGAGACGCTCGTTCAGCAGATACCCGA
       <N L L G D H L A F A R R P A V A R I F D L V E S F K S W P A H
71475 GATCGGCGCGAAGAGGGTGTCCACGGGCGTCCTGGGTGCCAGGGGCGTCCTGGGTGCCAGGGGCGTCTGAGACGCTCGTTCAGCAGATACCCGA
       <I P A F L T D V P A D E P A V L A D G P H Y V V D N L L Y G L

FIG.11A(62)
```

```
71567 GGTTGTCCACGACCGGATGTCGGGATGACGGCCGTGCCGACGCGCCACGCGCCCGCGCGGTGAAGCTGCCCG
      < N D V V P I D P H I V A H R G G Y A R V A V G A A T F A Q G
71659 GGTGAGATGGGCTCCAGGGCTCGCCACGTCGCCGAGGCACCGGCCAGCGAGGCCGTAGATGCGGAACGGCAGCGGTGAGCTG
      <P S I P E L A E A V D G L A G A L S A P G Y I R F P W R D L Q
71751 CCGGGTGAGAGCGCGACGTGGTCCACGTGGCTGCTCATGGGTGTCCAGCGCGTCGCACGCGCCGGTCGGGTCGCTGAAGA
      <R T L A A V D V H D P H E H T I L V A D A G D L A T P D S F V
71843 CGCCCGGGTCGACGACCAGCACACCCGTCGTCGACGGAGTGGGCAGGAGTTGGTGAGCTGCATCGTGACTCCTCGAT
      < G P D V V L V G G D H E V R L C S H A F K T L Q M
71933 TGACCCAATCGTGATGTCCCTCAGCGCAGTCTGCCGGAACCGGCGCGGTCTGAGGTATCGCCGATGGGGCGTAGACGAT
                                                              > M R V R V
72025 CGGAGCGGGAATGGACGGACACGCAAGACGCAGGTTGCTGACCGCGGTGGGGCGGCACCTGCCGAGCGCGGTTGCAGCGCCGACA
72117 GCGATGGGGCGGGAGAGCCTTCGGCGCGCCGGGTGCGCTCACCGGAGCAGGCGCAGCGGAGCAAGGCAGGGTGCCGATGCCGGG
72209 GGAACGCGGGTTCCGGCGCTGCGGTGGCCTCACCGGAGCGGGTCAATCATCTACACCGGAACCATGCGGGGTGCGGGTGG
      > M R V R V
72300 ACGATGTGGACGCCGCCGGTTCGCTGCGGCGACGAGCGCAGCGCAGCGGCGGAACC
      >D D V D A A A R S A I T A V T G V G G F V G G D E R S S G G T
72392 GCCGACGCCCGGGGCGGAGTTGCAACTGCGGCGTGCCGGCGGAGTTGGCGCCGTCCTGGAGGAGCTCGGCCGAGGCTGGCAGGAGCA
      > A D A R A E L Q L R V P A E R F T A V L E E L A R L G R Q E Q
72484 GCGGGGCGGATCCGCACGCGAGGACGTGACCGAGGACGACCCTGGTGACGCTGGTGACGGTGGCTAGGCGGGAGAGCGAGGCCGACCTGCGCTCGCTGGAGGCG
      > R A I R T E D V T E E T V D L D A R I A T Q R A R V E S G R
72576 AGCTGCTGGCCGCGGCCACCTCGATCGGCGACCTGGTCACCCTCGAGTCGGAAGAGCGAGGCCGAGGCCGAGGCCGACCTGGCGAGCCTGGAAGCC
      >K L L A R A T S I G D L V T L E S E V A R R E A D L A S L E A
72668 AAGAAGCGCCGGCTGGCCGACCTGACCAGCCTCTCCACCATCACCCTGGTGGGCCCTGAGGCGGAGGACACCGAGCCCGACC
      >K K R R L A D L T S L S T I T L T L V G P E A E A R D T E P D
72760 CACCGGCTTCGTGGTCGGCCTGCGGCGGGGCTGGACGGCGGCGGCGTCCCTCGGGGTCGTGCTGCTCACCGTGCTGCTGGGGGCGCTGCTGCCGT
      > T G F V V G L R R G G W T A F V A S L G V L L T V L G A L L P
```

FIG.11A(63)

```
72852 TCGCGGTGGCCCTCGGCGTGCCGGTGGCGGTGCTGCTTGCCGTGCTGCGGCGGCGGCCCGGGCGGCCCCGTCAACGCGCC
     >F  A  V  A  L  G  V  P  V  A  V  L  L  A  V  L  R  R  R  R  R  P  P  A  P  A  V  N  A  P
                                                                                    <.  R  A

72943 GCCGCCAGTGCCCCGACAGCGCGGTCTGACCATGACCCGCGATGCCGACCGCGATGAGGCCCGGTGCAGGT
      >  P  P  V  P  P  A  A  R  S  A  P  .
     <A  A  L  A  R  L  A  T  Q  V  M  V  R  I  G  V  A  I  A  G  E  D  V  D  F  S  A  R  H  L  D

73034 CGACGTTCGGGCCGGACGGCGGAGGCGGGCCAGCGCGCCGGGACGTACTCCAGGTACCAGGAGAAGTCCTCGCCGCCATGCTC
      <V  N  P  G  S  R  G  V  G  L  R  A  L  A  G  P  V  Y  Y  E  L  Y  W  S  F  D  E  G  G  M  S

73126 TGCGGGGTCTCCGCGACCCCCTCGGGCCGCGAGCGCGTGGGTCGCCGCCGTGAGCACCTGGATCGCCCGGGCGTCGTTGGTCACCGGCGG
      <Q  P  T  E  A  V  G  E  P  G  L  A  A  H  T  A  A  T  L  V  Q  I  A  R  A  D  N  T  V  P  P

73218 CCGGGCGCGTAGGTACTCCAGGTCGACGGTGCCGGTGGGGACGACGCCGGTGCCCAGGGATCACGTTGTACCCGGGCCGAGGCGTGGCCGAAC
      <R  G  R  L  Y  E  L  D  V  T  A  G  T  P  A  I  V  D  R  V  V  Q  A  V  I  K  P  A  Q  D  W

73310 AGGTGTCGCGGGTCCATCACCCGACAGCGCCGCAGGGATGCCGGAGCGGGCACCCGCTGACCAGCGCGTCGACGGTGAC
      <T  D  R  D  M  V  R  L  T  G  S  A  S  A  E  S  P  I  V  N  Y  R  T  G  A  S  A  H  G  F

73402 ACGAGCAGCAGCCCGCTGTTGGGCGGCGAGCGGTGTGCCCGCCCGGTGAGCGCAGGCGGTGATCGGCCGACCGCCAGGC
      <V  L  L  L  G  S  N  A  P  V  R  R  S  V  L  A  P  V  E  T  V  L  R  G  L  A  D  V  L  D  V

73494 GGTCAGGTGCGGGGCGAGCGGTGTGCCCGGAGCCGGGTCTGTCGAGCGGAAGATCTGCACGACGTCGTCAGTGCGATCACCGGCGCTGCGGTTGTC
      <T  L  H  P  R  A  T  H  G  G  P  G  T  L  R  V  T  V  N  D  A  A  A  T  I  P  G  V  E  L  G

73586 CGACCTTGCCGACGCAGGAGGATCTCCTGCGGCTGGAAGATCAGCCGGACGGTCGTCAGTGCGATGACCTGCAGCCAGCGAG
      <V  K  G  V  P  Q  N  P  D  V  H  L  A  F  I  Q  V  V  D  D  L  G  G  A  E  I  V  E  L  S

73678 CCGCAGGGCAGGATCTCCGGCGTGTGCACCGGTGTGCCAGCGCGTCGTGGCCGGCAGAGACACCGTCGTTGGTGGACCGGTAGGGACCGGTACGCGCC
      <G  C  P  L  I  E  E  A  P  Q  F  I  L  R  V  R  G  D  L  E  G  L  N  A  L  Q  A  L  L  V  G

73770 GACGCCGAGCAGCAGTGCCACGGTGTGCACGTCGTTGGCCGCAGTGCCAGACACCGTCGTCCTTGACGTCGG
      <V  G  L  L  V  T  T  H  V  D  H  G  C  A  H  C  V  G  D  K  T  S  R  Y  P  V  D  K  V  D  T
```

FIG.11A(64)

```
73862  TCAGCGGGCAGGCGGTCGATGTCGAGGCGGCGGAGGCGGACCACCGGCCGTCGGGGGCGGCCGTGGGGGACCCCGTTGCCCTTTGGC
        < L  P  L  A  D  I  D  A  R  L  A  V  V  P  G  D  P  R  G  D  I  C  I  V  G  N  G  K  P

73954  AGCAGGCGCGGGGCGCAACCCGGCGAGCGACAGTCGCGGGGCGATCAGGGCGAGCATCCGAGGGGCGATGGTCGAGTCGAAGGCTGCGACCCGGCGGCGACT
        < L  R  P  R  L  G  A  L  S  L  E  R  A  I  L  A  A  T  E  F  E  E  G  S  L  E  P  H  S  H

74046  GATGTGCGGCGGGTGGGCGGTGGCGATAAGGCGGGCATCCGGAGGGCGAGCGTCGACGCAGATGGTCGAGCTCGAAGGGCAAAGGCTGCGACCGGCGGCGACT
        < I  H  R  R  T  A  I  L  G  P  M  R  L  A  L  L  H  D  L  E  F  F  P  L  P  Q  S  G  S  P  S  E

74138  CCGGGCAGGCCGGACGACGCCAGGTGGCTGCCGTTCGGCAGCGTCAACGCACTCGTCACGTCGAAATCTCGATCACTAGAAACGGATGGATC
        < P  W  A  S  S  A  L  H  S  G  N  P  L  T  L  A  S  T  V

74229  ATCAGGGATGACAGCCGCCAGCTTGACCTTCAGACCTCTGTGCAACATCATTCCGTAGCGATCGGACCGCGCAGCGTCACGAATAC
        <  F  R  D  S  P  R  Y  T  G  W  V  Q  R  L  T  G  C  V  E  G  V  T  A

74321  CCTGGTGGAAGGGCTCCATAATCGCGGGACAGCAGGTAGATCGCGGGCCGTCATCTGCCCCGTCACACCTCTACACCGTAACCGA
        < R  A  R  L  A  E  K  M  P  H  L  V  N  A  T  G  E  A  A  A  R  L  E  G  L  A  R  E  V  A  D

74413  TTCGGCGGTCACGAAATCACGTCGATCGGAGACTCCGGCGGTGACACTCCCGACCTGCTGCCGTCCAATCACTGCCGGGACGGG
        < S  D  R  E  V  R  L  K  A  L  R  E  A  Q  A  A  E  I  T  P  D  V  R  L  P  E  Y  P  E  D  A

74505  CGACCGCACTCGGCGGCAGTGCCCCGGTGGCACACCAGGGGCGACCTGCGCCCGGGGCGAACGGTTACGCCCGCGACCC
        < D  V  T  F  R  N  L  G  V  V  V  R  E  G  S  D  I  E  Q  A  I  R  Y  A  S  Q  E  I  E  R

74597  TTACCCACTGCCCCGGGTGGCACAGGGGGTCAGAACGGGGCGCGTACGTCCCCACCTGCGCACAGACCTCGCCCACCGTGGCC
        < K  Q  F  G  A  E  I  A  D  V  V  S  G  H  D  A  V  R  E  M  L  E  V  V  A  A  E  I  E  A  T

74689  CTCATCCGAGACAAGGGGTCAGAACGGGGCGCGTACGTCCCCACCTGCGCACAGACCTCGCCCACCGTGGCC

74780  CGGGCCCCGCAGCGCCTCCTTCATCGGGTGCAGCACGTTCGCGTAGCGATGGGCTCATCCCGAGTCGTCGGCCGATCTCCCGC

74872  GCTGTCGCGCTCACTCGCGAGCTTGGCCAGCCGCTCGGCCTTCGATCGTCGGCCAGCGCTCGTCCACCGGCTCGTACGGCTCGTCGG

74964  CGTCGACCGGTGAACCGTTGAGGCCGACCACCGAGTCGATCTCCTGGCGATCGGTACGCGACTGCTCGATCTCCCGC

75056  TTCTGGAAGCCGAACTGCTTCGAGATGGCCTCGGCTCCAATGGTCACCACCGAGCCGGCGTGGTCGCACCGCCCTCGGATCTCGGCGGT
```

FIG.11A(65)

```
75148 CATCGCCTCCACCACGTACGACCGGGTCGACGGGTCGGCGGTCAGGTCCGGTCTCGTCGTACGGAGCACCTGCTGGGTGCGCAGGCCA
       < M  A  E  V  V  Y  S  G  A  F  P  D  V  T  A  T  L  D  T  E  Y  A  L  V  Q  Q  T  R  L  A  L
75240 GCCGGGCGGCCTTCTGGTGGGCGCGATGGCCTCGTCGAAGCTGTTCGTGTGTAGGACTGGGTGCCGAGCACCGCCCAGCCCC
       < R  A  A  K  E  T  P  L  A  I  A  E  D  F  S  N  T  H  L  S  Q  T  G  G  L  V  A  G  L  G
75332 TGGATCGCCACCCCGGACCAGGTTCACCTCGGGCGGTGAGCTCGGTGAGCGGAACTTCGCGACTCCTCCAGCAGGGTGGTCC
       < Q  I  A  V  R  V  L  N  V  E  P  Q  Q  A  T  L  Q  V  G  A  T  Q  T  H  F  R  L  M  M  S  K
75424 CGGGTTCTTCGCGCGACGAAGAAGACGACAGCCGGGGCGCGGAACTCGTCGAAGTCGTCAAGGCGCAGGATCGTGCCAGGCGCAAGGGCC
       < P  N  K  A  G  F  E  D  R  M  L  R  A  Q  I  R  R  A  A  R  F  K  A  V  E  E  L  T  T  R
75516 GGGCGACGAAGAAGAACGACAGCCGGGGCGCGGACGCCTGCGCCCGGAGCGCGGCCTACTGACGCTACTGAGACGCGTTGGCC
       < A  V  F  F  F  S  L  R  P  A  F  D  D  V  A  L  G  A  A  L  A  A  R  V  Y  E  V  G  N  A
75608 AGCGTGAACGGATCTCCTGCGGGCGACGCGTCGGCAGCGCCATGCATGGTAGCCGGAGATGGTGTTCCACTTCGGCACCTCCGC
       < L  T  F  A  I  E  Q  A  P  S  A  G  A  E  A  M  H  Y  G  S  I  S  I  T  N  W  K  P  V  E  A
75700 CCGGCAGTAGGCGAACGTGTCGGACCAGCGCGGACCAGCCCGGAGGGCTTCGGCCCTCCTGGCGACGAGCAGCACCGACCCCGGGGCG
       < R  C  Y  A  F  T  S  A  V  L  R  L  S  P  K  P  F  I  Y  T  G  R  A  I  Y  E  K  L  I  D
75792 CGTTCTGGGATCGTTGAGCGTGGCCGCGCGGCCGATCGAGCGGATCCATGTCCTGAGTCGAGTGCGACGCCGACCTT
       < N  Q  I  T  G  N  L  A  A  G  P  V  G  A  E  E  A  V  L  Q  Y  L  L  L  V  S  G  P  A
75884 TTGATCGTCATCGAGGTGGAAACCTTGTCCAACGGGATGCCTGCAGATCGTGGAGTCGTCGTCCTGAGTCGAGTGCGACGCCGACCTT
       < N  I  T  M  S  T  S  V  K  D  L  P  I  G  H  F  L  L  R  M  D  E  I  S  D  I  A  V  G  V  K
75976 GCCGACCTCGCCGTGGCGATCGGGTCGTCGAGTCGTAGCGCAGATCAAAAGCGACGAGGAGGCCCATGGTGCCGGCGC
       < G  V  E  G  H  A  I  P  D  D  S  D  Y  G  M  Q  T  P  L  D  F  A  V  S  L  G  M  T  G  A  R
76068 GCAGGAGCTGGTGTAGCGCGTTGCTCTCCGTGCCGGTGCCAGCCGCATCGTCCACGGCCGCGAGGTGTACATGGTG
       < L  L  Q  H  Y  R  A  N  S  E  T  A  T  G  F  G  A  Y  Q  R  M  T  W  P  R  S  T  Y  M  T
76160 GAGTAGACCCCACGGGTGTACGGGAACTCCCCAGCACCTCGGGCAGACCCTCCTCTGGGTGTAGACACCCTT
       < S  Y  V  G  R  T  Y  P  F  E  G  P  E  G  L  R  E  P  L  G  E  E  P  L  D  R  Q  T  Y  V  G  K
```

FIG.11A(66)

```
76252 GATCGGGAAGCCGGACTCGCTCGACCGCGGTTCACTCACTCATCCCCGGATGTAGGACGTGCCACCGCGCCGGAGGGTGAGGGATTGGGCACAT
      < I  P  P  F  G  S  E  S  S  R  P  E  S  M
76343 CGCACCCCTGTCTTTCCCGCCGACTCCGAGGGTGAACACCTGGCTCCTCGATTAGGTAAACGTTCCGCCGCTCGGGTTCGCA
76435 TCGGGGCGTCGGAACCAGCAAGATAGAGAGGAGTTGTGTCCAGCCCCTCGATTTCCCCCGGTGGCTCTTCTGTGACTCAGATCCGACGTGGA
76527 GCGGGGACCAGTCAGCCACCCCGACGGTGCGCGAGCGGCACCATCGGGTGCGGCGTACTGCGTCGCTCCGGTCCGGTGGGCAATGGC
76619 GGCATGGGCACGGTCTGGCGTGCCACAGACACCCTGCTGCGGCGGGATGTGGCGGTGAAGGAGGTCGTCTTCCCGCCCGGCCTCGCCCTGA
      > M  G  T  V  W  R  A  T  D  T  L  L  R  R  D  V  A  V  K  E  V  V  L  P  P  G  L  A  P
76710 GCGACCGGCGACGTACGAACGCCATGTACGAGCGCACGCTGCGCGAGGCCCGCGCCGCGGCCATCCAGCACCCCGCGTGGTCCAGGTGTACGACGTG
      > S  D  R  D  A  M  Y  E  R  T  L  R  E  A  R  A  A  A  I  Q  H  P  A  V  V  Q  V  Y  S  V
76802 GTCACCGAGGGTGGTCGCCCTGATCGTCGCCCTGCTGGTGATGGAGCTGCTGGACATGGTCGATCGAGGACGGGCCGGTGGCCCC
      > V  T  E  G  G  R  P  W  I  V  M  E  L  L  D  A  R  S  L  A  D  M  V  I  E  D  G  P  V  A  P
76894 CCGCGCGGTGCCAAGATCGGCATCGCCCTGCTCGGCGTGCTGACCGATCGGGGTGCTGCACCGGGACGTGAAGCCGGCCA
      > R  A  V  A  K  I  G  I  A  L  L  G  A  L  E  V  A  H  A  I  G  V  L  H  R  D  V  K  P  A
76986 ACGTGCTGATCTGCACCGACGGCCGCTGCGTGCTCCCCGAGTTCGGCGCCGCAAGCTCCCCACGACGTGCAGCTCACCACGCCGGGGATG
      > N  V  L  I  C  T  D  G  R  C  V  L  T  D  F  G  V  A  K  L  P  T  D  V  Q  L  T  T  P  G  M
77078 GTGCTCGGCTCGCCCCACTTCATCTCCCCGAGCGAGTTCGGCCCGGCCCGGAGCCAGGAGTTCGGCGTCCCCCCTGTTCTCCCTCGGCGTCACGCT
      > V  L  G  S  P  H  F  I  S  P  E  R  A  M  G  Q  E  F  G  P  P  S  D  L  F  S  L  G  V  T  L
77170 CTACACGGCGGTCGAGGGCCGTCCGCCGTTCGACAGGGGCGATCGAGACCCGGATCGAGAAGGACCCTGACCGCCGCCGCGATGCTC
      > Y  T  A  V  E  G  R  P  P  F  D  R  G  D  P  I  E  T  M  H  A  V  V  E  D  P  A  T  P
77262 AGCGCAGCGGCCCGCTGACCCGGGTGCTGATGGGGCTGCTGGAGAAGGACCCCGCCCGCCGCCTCGACGTGCACACCGCCGGCGATGCTC
      > Q  R  S  G  P  L  T  R  V  L  M  G  L  L  E  K  D  P  A  R  R  L  D  V  H  T  A  R  A  M  L
77354 CGCGAGCTGCTGCCGGCCCGCTGACCAGCACCCTGACCACCGCCGTCAACTCGGTACGACCCGTACGGGGTGCGGTCGGTGCCGGTCAAGCAGCGGCCC
      > R  E  L  L  A  G  P  L  T  S  T  A  T  A  V  N  S  V  T  D  P  Y  A  V  V  P  V  K  Q  R  P
```

FIG. 11A(67)

```
77446 GGCCGTCGCCCCACCGCCCTCCGCTGCGGAGCCGAGAAGCCGAGAGCCGAGAAGCCGAGGAGCCAGATGCTGGCGGGGGGAGATGCTCGCCCCGGGCGAGTCGCTGACCG
       > A V A P P P S A A E P K P S G Q I G G R A M L A P G E S L T
77538 ACCGGCTGGCGGCCCTGCGCGGGCGAGAAGACGAGGAAGAAGACGAGGAAGAGAAGACGAAGAAGACGAGGCCCGCGCCCTGGAGACGACACCAGCGACGCGCTT
      >D R L A A L R G E K T R K R K T T T A A L D D T S A D A L
77630 GCCGGCCCGCTGCACACCCCCACCGGAGCCATGCCCCCGCCGCCCGGGCCGACGTACGGCGGTTCGTCGGAGGCCACCCAGCGAGT
      >A G P L H T P T G A M P A P P P A G R T Y G G S S E A T Q R V
77722 CGACGCGGGGACGGCCGGGGAGGCCACCCAGCGGATGACGTACGGCTCGGGCGGGTCCCCCGACGCGACCCAGCGTGTCCACGGAGAGCGGCCCGT
      > D A G T A P E A T Q R M T Y G S P P D A T Q R V S H G S G P
77814 CGGAGGCCACCAGCGGGTGCCCTACGGCGGCGGCTCGGCCGACGCCACCCAGCAGGTGCCCTTCGGTCGCCGGCCCGACGCGACGCAGCGG
      >S E A T Q R V P Y G G S A D A T Q Q V P F G R R P D A T Q R
77906 GTCCCCCTACGGCAGCCCGGCCACCCAGCCGGTCCCCGGCTTCGGCGACGCGCCGCCCGACGCGACCCAGCGGGTCGGCGGCGCCTACGG
      >V P Y G S Q P G A T Q P V P G F G A S P D A T Q R V G G A Y G
77998 CGGCGGCCAGTGGTCGGTCCCCGGCACCGGCCAGCCCTGGGCCACCCCGGCCACCGCGCCCGCCACCGCGCCGGCCACCGCCGGCGGCGGGGTCG
      > G G Q W S V P G T G Q P W A T P A T A P A P A T A G G G V
78090 GCCGCCCTGCGTCGCCAAGGGCTGGCCCGCGCGCAAGGTGCAGCTGCGCGCCGCGGCCGTGGCGGTGCTGCTCATCGGCGTGTTC
      >G R L V A T V K G N P R K V Q L A A A G G V A V L L I G V F
78182 GCCCTCTTCGGCGGCGACGACCCCGAGCAGCCCGACCACCCTGCCCAAGGGCCTGGGAGCCGGTGCCAGTGCCGACGCCAGGGTGGAGATGCA
      >A L F G G D D P E Q P T T P Q G Q P S A G A P A G P G V E M Q
78274 GGAGCAGTCGGCCAAGGGCGTCACGGTCCAGGTGCCCAAGGGCTGGGAGCGGCGGAGCGCCGACGGCGGTGTGTGGGTCGACTACATCGATC
      > E Q S A K G V T V Q V P K G W E R R S A D G G V W V D Y I D
78366 CGGAGGACAACAGCGCCAAGGTGCGCATCCTCGCCGAGCGGTGGAGCGGCACGTCGACGCGCTGGGCGGAGACGGCCGCGAACGGCCTGCGG
      >P E D N S R K V R I L A E R W S G T S T R W A E T A A N G L R
78458 ACCCGGTCGGCCCTCCTGCCAGAAGCGTACAACCAGGTGTCCATGACGGAGCAGGAGCTCGACGGCAAGGCGGCCGCGGAGTTCGAGTACAC
      >T R S A S C Q K P Y N Q V S M T E Q E L D G K A A A E F E Y T
```

FIG.11A(68)

```
78550 CTGCGGCGACGGCGAGGGCAAGCGGCACGGCGTGTTGGCGCGGGGTGGTGCACGAGGGCAAGGTCTACTCTTCTCTGACCGACG
      > C G D G E G K R H G V W R G V V H E G K V Y S F Y L S S T D
78642 CCCGCTTCGCCGAGAGCAAGCCGATCTTCGATCAGATGGTGGCGTCGTTCAAGCTCCGGGGAGCGACTGAGCGCGGGCCGACGC
      >A R F A E S K P I F D Q M V A S F K L R G S D .
78733 GACGGCCGGCCGGGCGGGCGACGCCGTGGTGAGCGCCATGGCCGACGACGACCACTGACCTGACGACACG
                                          >M A A D T T D L D D T
78824 CGCGATCTGGACGACCTTCGCGACGGCGGTGGCTCGACGACCCCGACCCCGGCCACCCGAGACGAGCTGGAGGCCGTGGTCGA
      >R D L D D L R D D P A T R D E L E A V L D
78916 CGGGCTGCCGGCCGAGCGCGGCGAGCTGGCCGACCGGTTCGCCGGCCCACTGACCTTCGGCACCGCCGGGCTGCGCGGTCCGCTGCGCGCCG
      > G L P A S A A E L A D R F A G P L T F G T A G L R G P L R A
79008 GCCCCAACGGGATGAACCTCGCCGTGGTCACCCAGGCCGCGGCCGGCCTCGTCGCCTGGCTGGCGGCCCAGGACGCCACCGGGCCGCTGGTC
      > G P N G M N L A V V T Q A A A G L V A W L A A Q D A T G P L V
79100 ATCGGGTACGACGCCCGCACGCCCGGCAGTTCGCCGGCGAGTTCGCCCACGACTCGCGGGTACGGTGGCCACCGGCGGCGGCCCGGCGCTGCTGCCC
      > I G Y D A R H G S R E F A E R T A Q V A T G A G R P A L L P
79192 CCGCCCGCTCCAGCCACCCGGCGTGCTCCAGCTCGACGTACGGCGTGATGGTGACCGCCAGCCACAACCCGCCCC
      > R P L P T P V L A Y A V R Q L D A A A G V M V T A S H N P P
79284 AGGACAACGGCTACAAGGTCTACCTCGGCGCGCAGCTCGGCGGCGGCGAGCTGGGCGCCCAGGCGCAGATCGTGCCGCCGGCCGACACCGGCATC
      >Q D N G Y K V V Y L G A Q L G G G E L G A G A Q I V P P A D T G I
79284 AGGACAACGGCTACAAGGTCTACCTCGGCGCGCAGCTCGGCGGCGGCGAGCTGGGCGCCCAGGCGCAGATCGTGCCGCCGGCCGACACCGGCATC
      >Q D N G Y K V V Y L G A Q L G G G E L G A G A Q I V P P A D T G I
79376 GAGGCCGCCATCCGCGCCGGCGTCGGCCCGCTGGCCGACGTACCCGCTGGGCCCGGCCCAGGTCGTCGGCGACGTGGTCGTGTCGTACGT
      >E A A I R A V G P L A D V P L G P A G Q V V G D D V V S Y V
79468 CGACCGGGCCGCCGCCGTGGTCGACCCCGCGGGGCCCCGAGCCTGAAGGTGGCCTACACGCCGCTGCACGGCGTGGGCGCGGCCGTGCTGA
      > D R A A A V V D P A G P R S L K V A Y T P L H G V G A A V L
```

FIG.11A(69)

```
79560 CCGCCGCCTTCGCCGCCGGCTTCGGCATCCCCGGCGTGGTGCCGGAGCAGGCGGTTGCCGGACCCCGGACTTCCCC
      >T  A  A  F  A  R  A  G  F  G  I  P  G  V  V  P  E  Q  A  V  P  D  P  D  F  R  T  V  S  F  P

79652 AACCCGGAGGAGCCGGGGGCGGTGGACCTTCTCGTCGCGGTGGCGCTCGCGGAGCGGACCGGCGATCTGGCGGATCTGGCCGATCGCCAACGACCCCGACGCGGA
      >N  P  E  E  P  G  A  V  D  L  L  V  A  L  A  E  R  T  G  A  D  L  A  I  A  N  D  P  D  A  D

79744 CCGCTGCGCCGGGTGGGGGCGTCCGGGGGCCGGGGCGCTGGCCGTCCACGGCCGTGACGGGCCTGTGTACGGGCCTGTCCTGTCGTCCTCGCTACGGGCCATGTGC
      >  R  C  A  V  A  V  R  D  G  R  A  A  G  P  A  P  V  S  G  G  A  W  R  M  L  R  G  D  E  V

79836 GGGCGCTGCTCGCCGACCATCTCATGCGCCGTGTGCACGGGCTCCACGGCCTGTACGCCACCATCGTCGTCCTCGTCCTCTACGCGCTGTGAGGCCGGCTCGA
      >G  A  L  L  A  D  H  L  M  R  R  G  V  H  G  L  Y  A  T  T  I  V  S  S  S  L  R  A  M  C

79928 GCCGCCCGTGGCCTGGAGCTTCAAGTGGCTTCAAGTGACCGCTGACCGCGGAGGAGGAGGAGGAGGAGACGGCATCACCGCGCTGACCG
      >A  A  R  G  L  P  Y  D  E  T  L  T  G  F  K  W  I  V  R  A  G  G  P  L  G  E  A  G  S  D

80020 CCCGCTGGTCTTCGGCTACGAGGAGGCGCTGGGCTACTGCGTCGCCCCGGAGCACGTCCGCGACAAGGACGGCATCACCGCGCTGACCG
      >  P  L  V  F  G  Y  E  E  A  L  G  Y  C  V  A  P  E  H  V  R  D  K  D  G  I  T  A  A  L  T

80112 TCGCCGAGCTGGCCGCCGAGTTCGGCGTGCACCACACC
      >V  A  E  L  A  A  G  L  K  A  Q  G  P  T  L  T  D  R  L  D  E  L  A  A  E  F  G  V  H  H  T

80204 GACCAACTCTCGGTGCGGTGGACGACGTCGACGACCTGCGCATCATCGCCGACGCGATGGCCCGGGTCCGGGCGGATGGCCGACGCGCTGCTCGGCCG
      >  D  Q  L  S  V  R  V  D  D  L  R  I  I  A  D  A  M  A  R  V  R  A  A  T  P  T  T  L  L  G  R

80296 CCCGGTGACCGAGGCGCGGGACCTGCTCCCCGAGGCGGACGTGATCCTGCGTACGGACGGTGGTGATCCGCGTGGGCA
      >  P  V  T  E  A  R  D  L  L  P  E  A  D  V  I  L  R  T  D  G  A  R  V  V  I  R  P  S  G

80388 CCGAGCCGAAGCTCAAGGCGTACCTGGAGGTGGAGCCGGTTGAGCCGGTCGCGGCCCGCACGCGGGCGGCCGCCCTG
      >T  E  P  K  L  K  A  Y  L  E  V  V  E  P  V  A  D  G  D  V  P  A  A  R  T  R  A  A  A  T  L

80480 GCGGCACTCCGCACGGAAATCGCCGCCCTGGTCAGGAGGATGTGTCCCGCTTCCAGCGGGTTGGCGTGTCGCCCC
      >  A  L  R  T  E  I  A  A  L  V  Q  G  .

80571 CAGGTTCGTGGTGATATGCGGGTAAGGCCAGGTACCCGGGCCCTGTTTGAGCGTGTACGTAGAACATGATGTGTGCCACTTGGATGTAGTAG

80663 GTGACCAATGAGGTGAACCCGGAACCGCAAGCCACTGGCCAGTCACATCGTCACGGCGGGCTTTCCCGTT
```

FIG.11A(70)

```
80755  AGCGCTCGCGTAGCTCAGCGCAGCAGGAACATCCTCCCCGCCATAGGGATACAGCAGCTGGCTGGTGTATCCTTCTCGAAGGGCTTTGCAG
80847  GTTCTGCGCGGCAAGGGCGAGAGGTCCTGGGCTTCGTCCGTCTTGATCACGATCTCGTAGAGCCGGACATCGGCCGTCTCGGTGTTGTACGCCAGG
80939  ATGACCGGCACCGGCCAAGGTGTTTGGGAGGGTCAAGCTGGACCGGAACATGGACGTGAACCGGGTCCGGGTGCTGCGTCGGCCGCTGCCCGGCTTGGGT
81031  GGCGGGCCCGTCCGAGGGGCTACGGACGACCATCCAGCGCCCCAGTTGTCCTTCTGGCCATCAGGCGGCCACACCTGCTCGCAACCGTCTTCGTTG
81123  TCACCTGGAAGGGCGCTACGGACGACCATCCAGCGCCCCAGTTGTCCTTCTGGCCATCAGGCGGCCACACCTGCTCGCAACCGTCTTCGTTG
81215  TCCACAACCTGCCACACGGGCGTGTTGCCCAGCGGAGGGGAGGCCACTGTAGTGCCCGTCTAGGGATCTCGTTGGCATTCTCGTCGTTGACTGGCATGGCCGTGCCGT
81307  CCACCCCTTCCCGAAATTGCGCTGCCAGCGGGCTGGCCCACTGTAGTGCCCGTCTAGGGATCTCGTTGGCATTCTCGTCGTTGACTGGCATGGCCGTGCCGT
81399  CATTGTGTTGTAGAACAGCATTCCGGAGTGACATGGGCTTTACCCGTCCATCACGGCCTCACTGGCATCAGTATGATCGCCATGGCCCGTGAAACGGAG
81491  TCATAGAGAGAGCATTCCGGAGTGACATGGGCTTTACCCGTCCATCACGGCCTCACTGGCATCAGTATGATCGCCATGGCCCGTGAAACGGAG
81583  CAATCGGGTGGAAGAAGAGCCAGCATGACCCGGCGTGTCGGTCGGCGTGGAAGGTGCGGCTGTTCGCCACGTGCCGGCAGCCCAGGGTGCCTCACGGGT
81675  AGCGTTCCGCGCATCTGTCGGTCGGCAGGACCCAGGACCCGGGAACGGCGCACCCGGCGGCAGGGACCCGGGAACGGCGCACCCGGCGGCAGGGACCCGGGAACGGCGC
81767  TCTGCCACGAGGGCCCTCCGCGCCGCCCACCATTGGCTCGCCGGGAACCGGGCACCATTGGCTCGCCGGGAACCGGGCACCATTGGCTCGCCGG
81859  CGGGAGGCCCTCCGCGCCGCCCACCATTGGCTCGCCGGGAACCGGGCACCATTGGCTCGCCGGGAACCGGGCACCATTGGCTCGCCGG
81951  CAGGCCCCACCATTGGCTCGCCGGGAACCGGGCACCATTGGCTCGCCGGGAACCGGGCACCATTGGCTCGCCGGGAACCGGGCACCATTGGCTCGCCGG
82043  TGCACGGGTGCGGTGAAACAAATGGCTCGAAACCGGGAACCGGGCACCATTGGCTCGCCGGGAACCGGGCACCATTGGCTCGCCGGGAACCGGGCACCATATCAGCA
        > V P R R Q L G R L L T Q L R E S A H I S
82134  TCGACGCGGCGGCCGCGGCGAGCTGGACTGCTCGCGGACAAGCTCTGGCGGATCGAGCGGGGGCTGACCTCGGCCAAGACACCGGACGTCCGG
        > I D A A A G E L D C S R Q K L W R I E R G L T S A K T P D V R
82226  GTGCTCTGCGAGCTGTACCGGGCCACGCCCGACCAGGCGAGCGTGCTGCTCGGGCTCGCCGAGGTGAGCCGGGCCGAGGGGTGGTGGCACGC
        > V L C E L Y R A T P D Q A S V L L G L A E V S R A E G W W H A
82318  CCACGGGCAGCTCCGTGCCGGCCTGGTTCTCGCTCTACGTCGGGCTGGAGAACGTCGGAGCAGCATTCGGCACTACAACGCGGAGCTGGTGC
        > H G S S V P A W F S L Y V G L E N V A S S I R H Y N A E L V
82410  CGGGGCTGTTGCAGCGCCCGGGCTACGCCACCGCGCTCTTCGAGCACAACCGGCCCGAGCTGGGCGAGGAGGAGCGAAAGAAGGCGGTGGCC
        > P G L L Q R P G Y A T A L F E H N R P E L G E E E R K K A V G
```

FIG. 11A(71)

```
82502 TTCCGGACTCAGCGGCAGGGGCTGCTGGCCCGGCGGCTGCCCCCGGCCCCCGAGCTGACCGTTGATCCTCAGCGAGGCGGTTGCTGCGCCGCCC
     > F  R  T  Q  R  Q  G  L  L  A  R  R  L  P  P  A  P  E  L  T  V  I  L  S  E  A  V  L  R  R  P

82594 GGTGCCGGGCCGATCGGTGATGGCCGACCAGCTCCGGCACCTGCTGGCCGTCGGCGAACATCACCGTACGGTGTGCTGCCGCTGG
     > V  P  G  R  S  V  M  A  D  Q  L  R  H  L  L  A  V  G  E  R  H  N  Q  T  V  R  V  L  P  L

82686 CCGCCGGGCCGCTGGCCGCCGAGGCGGCAGGCACGTTCGTGCTGCTGGACTTCCCGCTCTCGGCAGCCCTGGGCAGCCCGACC
     > A  A  G  P  P  L  A  A  E  A  G  T  F  V  L  L  D  F  P  L  S  A  L  G  S  P  T  E  P  P  T

82778 GTCTACGTCGGAGGGCGCTCACCGGCGCTCTACCTCGACCAGCCGACGGAGATCGCCGCGTACGAACGGGTCTGGAGGGGTCTGGATTCGCT
     > V  Y  V  E  G  L  T  G  A  L  Y  L  D  Q  P  T  E  I  A  A  Y  E  R  V  W  R  G  L  D  S  L

82870 CGCCCTCGGCGCGCGACAATCAGCGGAGCTGATCGATGCCATCCGGGGAGAGTGCTATGAGTGATCGACGCGCCGCTGGCCACCAG
     > A  L  G  A  R  Q  S  A  E  L  I  D  A  I  R  G  E  C  Y  E  .

82961 CACCGGCAGCGGCACCAGCGGGCACTGCGTGTGCCGGACATCGTCGGGACAGCGTCCGGGACGTCCGGGACAGCAAGGACCCGGGCG
                                                      < .  A  R  K  G  L  A  A  D  V  A  K  G  L  A  T

83053 GGCGGGCCTGACGGTCCGTCGCCCTGTCGTTGTGGAAGGTCAAGGCCCCGCTGACAGCTCCGACGAA
     < V  V  L  A  V  S  P  R  V  V  S  D  D  L  S  V  T  G  S  F  G  A  G  G  A  I  E  E  L  R  R

83145 CCAACCCCGGCTACGCCTCAGACGCCTGCGCAGGGCTGCGCCCTCAGGGCCTGCGGCGTGCCGAGGGCGTGACGCCTTGCGCGCTCAGAC
     < R  A  D  V  A  A  D  G  T  L  G  L  A  P  E  M  R  L  V  A  V  L  T  A  L  A  A  T  A  E

83237 AGCCCGGGGATCTGCCGGGCAGCCTGCGCCAGCGCCTCCGGCGCCGGAGTCCTCCACGGTGGCGTCGGTGCGGTG
     < D  P  I  Q  G  G  A  L  A  E  A  L  R  R  R  S  D  R  R  V  T  A  D  A  T  P  Y  R  H  V  H

83328 GACGACCAGGGCACCGAGGGCCGGACCGATCGTCTCCAGCGAC
     < V  V  L  A  V  S  P  R  V  V  S  D  D  L  S  V  T  G  S  F  G  A  G  G  A  I  E  E  L  R  R

83420 GCCGGGCCGTCGCGGCGGTCGCCGGTGTCGCCGAGCGCCAGGGTGGCGACCAGGGTGGCGTCGGGTGTAGCGGTCACGTG

83512 TCGGGGGATCTGCCGGGCAGCCTGCGCCAGCGCCTCCGGCGCCGGAGTCCTCCACGGTGGCGTCGGTGCGGTG

83604 GATGAAGCCCAGCTCGGTCTCCTCGGTGAAGAGGCGCCACCAGGTCGCCGTGGAGGATCGCGCCGACCAGGCCGCGCAGCC
     < I  F  G  L  E  T  E  E  V  D  R  V  V  G  R  A  V  L  D  G  L  I  R  D  R  L  G  H  R  L  R
```

FIG. 11A(72)

FIG.11A(73)

```
84980 GGCGTGGACCAGTCGGCGCGGAGCAGCGGGCGGCCGCCAAGGCCCAGGGGGATCGACCTGGC
      > G V D Q V G A E Q R A A Q L G T R S I K T T A K A R A I S L A
85072 GATCCGGATGGTCGACCTGACCACCCTGGAGGGGGCCGACACCCCTGGCAAGGTGCGGGCCCTCGCGGCCAAAGCACTGCGCCCCGACCCGG
      > I R M V D L T T L E G A D T P G K V R A L A A K A L R P D P
85164 CCGACCCCGTCTGCCCGCACGTCGGCGCAGTCTGCGTCTACCGGTCTACCGGAGGTGCTGCGGAGCGCCGGGTCC
      > A D P S C P H V G A V C V Y P A M V P Y V A E V L R G S A G S
85256 GGGCGGCCGTCCGGCGGCCCGGACGGCAACGCGGGCCCGGGCGTGGTGCACCTGGCGTCGGTGGCCACCGCGTTCCGTCCGGGCCA
      > G R P S G G P D G N A P A G P G V V H L A S V A T A F P S G Q
85348 GGCACCCCTGGAGGTCAAGCTCGCGGACACCCGCGCGGCGGTCGCGGCGGGCGCAGTGACGAGATCGACATGGTGATCAACCGGGCGGTTCC
      > A P L E V K L A D T R A A V A A G A D E I D M V I N R G A F
85440 TGGCCGGCGCTACCGCGAGGTCTACGACGAGATCGTGCCCAAACGTCCTGGCCACCGACGCGACGGGGCGACGATCTGAAACCGGC
      > L A G R Y R E V Y D E I V A T K Q A C G D A H L K V I L E T G
85532 GAGCTGGCCACGTACGACAACGTGCGCCGCGCAAGCTGGCTGGATGCTGGAGGCGGTCCGCGACTTCATCAAGACCTCAAGGTCAAGGTTCC
      > E L A T Y D N V R R A S W L A M L A G G D F I K T S T G K V P
85624 CGTCGCGGGCGACCCTCCCCCGGTCGATGCTGGTGGAGGCGGTTATGGTCCGGACGCGTCGGCCGGACTGGCTCGGACCTGGAAGCCGG
      > V A A T L P V T L V M H L E A V R D F R A A T G R Q V G V K P
85716 CCGGCGCGGCATCAAGAACACCAAGGACGCGATCAAGTACCTGGTTATGGTCAACGAGACGGTCGGCCCGGACTGGCTGGACCCGGACTGGTTC
      > A G G I K N T K D A I K Y L V M V N E T V G P D W L D P D W F
85808 CGGTTCGGCGCGTCCAGCCTGCTCAACGACCTGCTCATGCAGCGCACCAAGCTGACGACGGGCGTCTACGTGTCCGGACTACTTCACCCT
      > R F G A S S L L N D L L M Q R T K L T T G V Y V S G P D Y F T L
85900 GGACTGAGCGTGATCTTCGAATACGCGCCGGCGCCGGAGTCCCGCTCGGTGGTGGAGCCCGGGCTGTTCGTCGACGG
      > D . > V I F E Y A P A P E S R S V V D L K P S Y G L F V D G
85989 GGAGTTCGTCGACCCGGCCGACGGCGGCGGCTTCAAGTCGGTCAACCCGGCCTCCGAGGAGGTGCTCGCCGAGGCGGGGCAGCG
      > E F V D P A D G G G F K S V N P A S E E V L A E I A E A G S
```

FIG.11A(74)

```
86081 CCGACGTGGACCGGGCGGTCCGCGCCGGCCGACGGGCTACGAGAAGGTGTGGGGCCCGATGCCGGGCCGGGACCGGGCCAAGTACCTGTTC
      >A D V D R A V R A A R T A Y E K V W G P M P G R D R A K Y L F
86173 CGGATCGCCCGGATCATCCAGGAGCGCTCCCGCGAGCTCGCCGTGCTGGAGTCCCTGGACAACGGCAAGCCGATCCGGGAGTCCCGGGACGT
      >R I A R I I Q E R S R E L A V L E S L D N G K P I R E S R D V
86265 CGACCTGCCGCTGGTCGCCGCACTTCTTCTACTACGCGGGCTGGGCAGACAAGCTGCCGTACGCGGGCTTCGGCCGGCCGAACCCGCGCCGC
      >D L P L V A A H F F Y Y A G W A D K L P Y A G F G P N P R P
86357 TCGGCGTGGCCGCCAGGTCATCCCGCAGAACTTCCCGCTGCTCATGCTGGCCCAGAAGATCGCGCCTGGCGCTGGCCGGCAACACGGTG
      >L G V A A Q V I P Q N F P L L M L A Q K I A P A L A A G N T V
86449 GTGCTCAAGCCGGCGGAGACCACCCCGCTGACCGCTGCTGCTGCCCAGGCCGAGCTCGCCGGCGTGACCGGAGGTCGGCAAGG
      >V L K P A E T T P L T A L L F A E I C Q Q A E L P A G V V N I
86541 CGTCACCGGCGCGGGCGACACCGGCCGTCGTCGGCGGGCACCGGCAAGAAGGTCACCCTGGAGCTGGGCGGCAAGGCCGCGAACATCGTCTTCGACGACGCCCCGGTC
      >V T G A G D T G R A L V E H P G V D K V A F T G S T E V G K
86633 CCATCGCCCGGGTCGCGGGGCACGGCAAGAAGGTCACCCTGGAGCTGGGCGGCACGGGCACCCTGCAAGATCGTCTTCGACGACGCCCCGGTC
      >A I A R S V A G T G K K V T L E L G G K A A N I V F D D A P V
86725 GACCAGGCCGTGGAGGGGATCGTCAACGGCATCTTCTTCAACCAGGGCCACGTGTGCTGCGCCGGCTCGGAGCTGCTGGTCCAGGAGTCGGT
      >D Q A V E G I V N G I F F N Q G H V C C A G S E L L V Q W S V
86817 CGCCGAGCAGGTGCTGGAGTCGCTGAAGCGCCGGATGGCGCTGCTGCGGGTCGGCGACCCGTTGGACAAGAACACGGACATCGGGGCGATCA
      >A E Q V L E S L K R R M A L L R V G D P L D K N T D I G A I
86909 ACTCGGCCGCGCAGCTGGCCCGGATCCGCGAGCTGTCCGCGGCCGGCGAGGGCGAGGCGGAGCGCTGGTCCCCGTGCGAGCTGCCC
      >N S A A Q L A R I R E L S A A G E A E G A E R W S P P C E L P
87001 GAGCGCGGGTTCTGGTTCGCGCCGACGATCTTCACGGGGGTGACGCAGGCCCACCGGATCGCCCGGGAGGAGATCTTCGGTCCGGTGCTGTC
      >E R G F W F A P T I F T G V T Q A H R I A R E E I F G P V L S
87093 CGTGCTGACCTTCCGCACCCCGGCCGAGGTCGTCGAGAAGGCCAACAACACGCCGTACGGCCTGTCGGCCGGGATCTGGACCGACAAGGGCT
      >V L T F R T P A E A V E K A N N T P Y G L S A G I W T D K G
```

FIG. 11A(75)

```
87185 CCCGGATCCTGTGGATGGCCGACCGGGCTGCGCCTGCGCGGGGTGGTGTGGGCCAACACGTTCAACAAGTTCGACCCGACCTCGCCGTTCGGCGGG
     >S  R  I  L  W  M  A  D  R  L  R  A  G  V  V  W  A  N  T  F  N  K  F  D  P  T  S  P  F  G  G
87277 TACAAGGAGTCGGGCTACGGCCGCGAGGGCGGCCGGCACGGGCTGGAGGGGTACCTCGGTGTCTGAGGGGTACGGGGTCGCGGTACGCAAGACGTAC
     >Y  K  E  S  G  Y  G  R  E  G  G  R  H  G  L  E  G  Y  L  G  V  .
87368 AAGCTCTTCATCGGCGGGAAGTTCCCGCGACCGAGTCGGGGAGCCAGCGAGTCGGGACGCCGAGTCGGGGAACGTCGCTGGCCTCCCGCAAG
                       >V  Q  S  A  N  V  S  L  A  S  R  K
87458 GACGCGCGGGACGCGTGGTCGCCCGCGCCCGTCGAAGGGCTGGGCCGGGGCGACGCGTACAACCGGGGTCAGATCCTCTACGGGT
     >D  A  R  D  A  V  V  A  A  R  A  A  V  K  G  W  A  G  A  T  A  Y  N  R  G  Q  I  L  Y  R  V
87550 CGCCGAGATGCTGGAGGGCCGCGAGCAGTTCGTCGCGCTCGGCGTGCCGGCCGACGAGGTCGACGCGGCGATCGACCGCTGGGTCTGGT
     >A  E  M  L  E  G  R  R  E  Q  F  V  A  L  G  V  P  A  D  E  V  D  A  A  I  D  R  W  V  W
87642 ACGCGGGCTGGTCCGACAAGCTCCCCCAGGTCGTACGGGGTGCGAACCTGTCGCGGGCCGTACTTCAACCTGTCCGCGCCGAGCCGACG
     >Y  A  G  W  S  D  K  L  P  Q  V  Y  G  G  A  N  P  V  A  G  P  Y  F  N  L  S  A  P  E  P  T
87734 GGGGTGGTGGCCGTTGGCGGGATCCGCCGACCCCCTGGCCTCGGTGACCCTCGCCGAGGTGCTGGCCACCTCCGAGGTGCTGGTCAACGTCC
     >G  V  V  A  V  V  A  P  E  A  P  A  L  L  G  L  V  S  V  I  A  P  A  I  V  T  G  N  T  V  V
87826 GGTGGCGGCCGACGACGCCCAGCCCCTGGCCTCGGTGTGCGACCTGAGAACCTCAAGCGGGTGATTCGCCCGGCCGCGGACTACGGGCCT
     >V  A  A  S  P  T  Q  P  L  A  S  V  T  L  A  E  V  L  A  T  S  D  L  P  G  G  V  V  N  V
87918 TGACCGGTGCCAGCTCGGATCACCGAGACGGTCGGAGGTCAGGGGGTCGGGAGAACCTCAACGGGTGATCGCCGGCCCGGCGACGACCTGACGGTGGCTC
     >L  T  G  A  I  T  E  T  V  P  T  L  A  A  H  L  D  V  N  A  I  D  L  T  G  V  G  F  A  S  L
88010 GCCACCGAGCTGGAGGTCAGGGTCGGCGGAGAAGCTGAAGGAACCTCAAGCGGGTGATTCGCCCGGCCGCGGACCACGACTGGTACGCCGACCCGGGCCT
     >A  T  E  L  E  V  R  A  A  E  N  L  K  R  V  I  R  P  A  P  A  D  H  D  W  Y  A  D  P  G  L
88102 CACCCGGGATGACGACGCTGCTGGAGACGAAGACGAAGACGGTCTGGCACCCGAAGGGCGTCTGAGCGCCCCGGCCCCACCCGGCCAC
     >T  R  M  T  T  L  L  E  T  K  T  V  W  H  P  K  G  V  .
88193 CCGGCCGGCCGGAGGCAGGGGTGGGCGGCGGGTGGCGGCGGTGACTCGGTTGGGTGATCTTGAGC
```

FIG. 11A(76)

```
88284 GGGCCGGTGTGATGGACGTGCTGTGTGTCCCGGGACACCGTCGGACGGGGTGACGGTGCGCCGAGGTCGCCGAGGCCCTCGACGGCCGCGA
      >M  D  V  L  W  D  T  V  P  G  T  S  D  G  V  T  V  R  E  V  A  E  A  L  D  G  R  E
88375 GCTGGCCTACACGACGGTGATGACCGTGCTGGACCGTCTGGCAGGGCAAGGGCATGGTGCGCCAGCGCCAGCGGGAGGGCCGGGCCTGGCTACC
      >L  A  Y  T  T  V  M  T  V  L  D  R  L  A  G  K  G  M  V  R  R  Q  R  E  G  R  A  Q  R  Y
88467 AGGCCCGGGCCCAGTCCGAGGCCCACATCGCCCAGCTCATGCTGGACGCGCTCGACGGCCTGGGCAGCCGGGACGCGGCGCTGGTGCGCTTC
      >Q  A  A  A  S  R  E  A  H  I  A  Q  L  M  L  D  A  L  D  L  G  G  S  R  D  A  A  L  V  R  F
88559 GCCCGGTCGGTGACCGGGCGACCGGCAGCCCGGCCCTGGCCGACGAGGCCGGTGAGGCGGGACCCCTGACGGACCGTGACGCGCCG
      >A  R  S  V  T  G  T  E  A  E  V  L  R  A  A  L  G  A  E  A  G  G  P  L  T  D  R  V  D  A  P
88651 GCGGCGCCGACCGGGGCGGGCCAGCCGGCCCTGGCCGACGCCGAGGCCACGGACCGTAGGGCCGTCATGGCGTACGCCGTCCACTTCGCCG
      >R  A  D  R  A  G  Q  P  A  L  A  D  E  A  T  D  R  .     >M  A  Y  A  V  H  F  A
88741 CGACGGTCCTGGCCTGCTACCTGACCGCTCAGGTCCTCGGCGCGTCCACCTGGACGTGGCGGGCCCCCGAGATCGGCATCGTCTGCTGGCAG
      >A  T  V  L  A  C  Y  L  T  A  Q  V  L  A  A  S  T  W  T  W  R  A  P  R  I  A  I  V  C  W  Q
88833 GCGGTCGGGCTCGCGCTGGGGCTCTCCGCGATGGGCCTGCCGATGGCGCTCGGCGTGGCCGCGTACGACCGCCCGACCGGCAGCGCGTTGCT
      >A  V  G  L  A  L  G  L  S  A  M  G  L  P  M  A  L  G  V  A  A  Y  D  R  P  T  G  S  A  L  L
88925 CGCCCTGGCCACGGACCTGACCCACGGCACCCTGCCGGCCGGCCTCGGGGCGGTCCACCTCGGTCTGGTCGGCGGCTTCGGCATCGGGGG
      >A  L  A  T  D  L  T  H  G  T  L  P  A  G  L  G  A  V  H  L  G  L  V  G  G  F  G  I  G
89017 CGGCGCTGCTCGCCACGACGGTACGCAGCGTCCAGGCGACCGTCCGGGCCCAGCGCCAGCACCGGGACCTGCTGGCCCTGGCGGTGGCCCGG
      >A  A  L  L  A  T  T  V  R  S  V  Q  A  T  V  R  A  Q  R  Q  H  R  D  L  L  A  L  V  A  R  R
89109 GACCCGGAGGTGCCGGGCGCGCTGGTGCTGGACCATCCGAGCGCGGCGGCGTACTGCCTGCCGGGCGTGGTCGGGTCGGTGGTCAGCGGC
      >D  P  E  V  P  G  A  L  V  L  D  H  P  S  A  A  A  Y  C  L  P  G  V  R  P  R  V  V  V  S  A
89201 CGGGGCGCTCAGCATGCTCGACCGGGCCGAGCTGGCCGCGGTGCTGACCCACGAGCGCGCCCAGGAGCGCCACGACCTTGTCGTGCT
      >G  A  L  S  M  L  D  R  A  E  L  A  A  V  L  T  H  E  R  A  H  A  Q  E  R  H  D  L  V  L
89293 TGCCGTTCACCGCGCTGTGCCGCGCGCTGCCCTGGTTCCGTTGGGTACGCGACGCGGGGTCGCCCTGCCTGGTCGAGATGCGGGCC
      >L  P  F  T  A  L  C  R  A  L  P  W  F  R  W  V  R  D  A  H  E  R  V  A  L  L  V  E  M  R  A
```

```
92781 CGCACGGCTGCGGATCGGCGGTTCCTGTCCGCACCCTGTCGGTGGTGCTGGAGAGCTGGTGCGGCTGGGTGCCGGTGGGCATCCG
      > R T L R I A F L S A L V L E L V A T L S V A L V A V P V G I R
92873 GCTGCTCGGGGGCGGGCTGGCTAGTACTCCACCGGCTGTCGCTGGTGCTGCTGCTGCTGACTCCGGAGGCGTACCTGCTGCCGCTGCGGGCCAGCC
      > L L G G L A L S T A L L V L L L T P E A Y L P L R A A G S
92965 GGTTCCACGGCAGCATGGAGGGGCTGGCAGCGCTGGACGAGGCCCTCTCCGCCGCCGACCCGACCGCCACGGCCGGCTCG
      > R F H A S M E G L A A L D E A L L S A A D P T A T A G S
93057 CGGCCCGTCCCCGACGGCCGCGCGAGATCCGGTGTCGCGGGCCGTGACGAGCGTGCCGCTACGGACGTCAGCTGACT
      > R P V P D G R A E I P F E G V T V A Y E R T V A L R D V T L T
93149 AATCCGGCCCGGAGCGGGATCGCAGTCGTCGGGCCCAGCGGGCGCAAGAGCACCCTGCTCAACCTGCTCCTCGGCCCCGA
      > I R P G E R I A I V G P S G A G K S T L N L L L G F V A P
93241 CGCAGGGCCGGGTCACCGTGGGTGGCGTCGACCTGGCCGGAGCCGACCCGGACGGCTGGCGCCGCAGGTCGCAGGTGCGCAACGGCC
      > T Q G R V T V G G V D L A G A D P D G W R R Q V A W V P Q R A
93333 CACCTCTTCGCCGCCTCGCTGACCGACAACATCCGGCTGGGCTCGGGTCGCTGGAGGCTGTCGGCCACGGGCACGGCTGAAGCGGGG
      > H L F A A S L T D N I R L G A P G T P D A A L A G A V A A A A
93425 GCTGGACGAGGTGGCGGCGCTGCCCGACGGCCTGGACACCGTGCTGGGCGAGCGCGGCCACGGCCTGTCCAGCGGCCAGGGGCAGCGG
      > L D E V A A L P D G L D T V L G E R G H G L S S G Q R Q R
93517 TCGCCCTGGCACGCGTTCCTGCGCGACGCGCCGGTGGTGCTGCTGGACGAGCCGACCGCGCGGCTGGACACGGCCAGCGAGGCCGGGGTG
      > V A L A R A F L R D A P V V L L D E P T A R L D T A S E A G V
93609 CTGGCCGTCCACCGCCCGGCGCTGCTCAGCGACGCCGATCGGATCCTGCGG
      > L A A T R R L V A G R T A L L V A H R P A L L S D A D R I L R
93701 GGTCGAGGAAGGCCGGGTCACCGAGCTGACCACCACCCCGGCCACGGGCGTGACCCCGGGCCCGGAGGCGGCGGCGGGACCGGCCGGGC
      > V E E G R V T E L T T T P A T G V T P G P G E A A A G P A G
```

FIG.11A(81)

```
93793 AGGTCGCCCCGCCCCGGCCGGAGAGGGGCGGCCGATGAGCACCGGTCCCGCCGACGACGCCTTCCGCGCCATCCCGCTGCCGGCCGACGGG
     >Q V A P A P A G E G G A A R .
     >M S T G P A D D A F A I P L Q A D G
93884 GCCCCGGTGGCCGGCGGCAGCGTCCGGGCCGAGGCCCGCGAGGCCGTCCTGCGCCTGGCCCGGCCCTACCTCGGCCGGCTGGTCGGCGGGTCT
     >A P V A G G S V R A A E R A V L R L A R P Y L G R L V G A G L
93976 GCTCGCCGCCGCCACGGAGTTCGCCGGGCTGGCCCTTGATGGCCACCGCCCTGCTGATGAGCGCCGCCGGCCGGCCACCTGGACC
     >L A A A T E F A G L A L M A T A T W L L M S A A G R P P L D
94068 GGCTCACCGTGGCGATCGTCGCGGTCCGGGCGCTGGCGATCAGCCGAGGCGTGTTCCGCTACACCGAGCGCCTCGCCGGCCACGATGCCGTG
     >R L T V A I V A V R A L A I S R G V F R Y T E R L A G H D A V
94160 CTGGCGGATGATCACCGACGTCCGGGCCGGGGTCTTCGCCGCCCTGGCCGCGCGCGACGCCGCCCGGCAGCGCACCGGCGACCGGGGACGCGGCTGAG
     >L R M I T D V R A G V F A A L A A R R D A A R Q R T G D A L S
94252 CCGGCTCGTGTCCGACGTGGAGGCCGTGCAGGACCTGCTGCTGCGCGTGCTGGTGCCGGGGGCCGCCGCCACGGTGGTCAGCGTGCTGGCCG
     >R L V S D V E A V Q D L L L R V L V P G A A A T V V S V L A
94344 TGGCCGGGGCCACCACCATCTCGCTCCCCGCCGCCGGGGTGCTGGCCCTGGGGCTGCTCGTCGCCGGGGTGCCCTCGCCGTGGCCCACC
     >V A G A T T I S L P A A G V L A L G L L V A G V A L P L A A T
94436 GCGCTGACCCGGCACGCCGACCGGGTTGCCCCGCTGCGCGGCGCTCGCCACGGACGCCGTGGACCTTGTCCACGGCGCCGACCT
     >A L T R H A A D R V A P L R G A L A R D A V D L V H G A A D L
94528 GGCGCGCGTTCGGTGCCACCGGGCTACGACGGCGCTGGACGCCGCCCGGCTGGAAACGACGGGCCTGCGGCCGCCACCG
     >A A F G A T G Y A L D A A A A D R A R R L A R L E R R L A A T
94620 GCTTCGCCGTGGACGCCGGGGCCGCCGGGGCGCTGGTCGCCGGCGTGACCGCCGGAGTGGTCGTCGGGGCCCGGCAGCGCCAGCTCCGGGC
     >G F A V D A A G A L V A G V T A G V V V T A L R D G V G G V
94712 CTGGTCGGGGTGCTGGCCGGGTCACTTGCCCCTGCTGACCGCCAAGGCCGGACGCCAGCGCACCCGGCTGTTCGCCGCGCGCCAGGC
     >L V G V L A V G S L A A V E V A L V G A A R Q R T R L F A
94804 CGGGCTGGTCCGGGTGGCCGCCCTGCTGACCGCCCCGCAGGCCGACGCCCCCGCCGCCACCCCGCCGGGTGCCGCGCCGTCG
     > G L V R V A A L L T A P Q A D A P A A T P P G A A R A A A V
```

FIG. 11A(82)

```
94896 GTGCGGCCCGCACGACGTGCGCTTCGAGACGGTGCGGGTACCGGGCCCGGCCACCGCCCCGGGCCCTGGACCGGGTCACCCTGGACCTG
    >G   A  G  P  H  D  V  R  G  D  A  V  T  V  R  Y  R  A  G  T  A  P  A  L  D  R  V  T  L  D  L

94988 CCGGCCGGCCGCCGGTGGTCGGGCCGTGGTCGGGGCGGCCGGCGCCAAGAGCACCCTCGCCGCGTCCTCACCGGCACGGTGCGACCCGAGCA
    >P   A  G  R  R  V  A  V  V  G  P  S  G  A  G  K  S  T  L  A  A  V  L  T  G  T  V  R  P  E  Q

95080 GGGCCGGGTCACCCTCGACGGAGCAGACCTGTCCGCCTACCCGGTCGAGGAACTGCCGCGCGTGGGCGGCCTGCTCGCCGAGGCGTACG
    >G   R  V  T  L  D  G  A  D  L  S  A  Y  P  V  E  E  L  P  R  A  V  G  G  L  L  A  E  A  Y

95172 TCTTCCACGCGGTCCGGGAGAACCTGCTCGGACGGCCCGCCGCCGACGAGGCCGAGCTGACCGCCGCGGCCACCCGGGCGGCCGGCCTG
    >V   F  H  A  T  V  R  E  N  L  L  G  R  P  A  A  D  E  A  E  L  T  A  A  T  R  A  A  G  L

95264 CTGGACTGGGTGCACGCCCAGCCCGCCGGGTGGGACACCGTGGTCGGCGAGGAGGGCCAGCTCTCCGGCGGCCAGCGGCAGCGCCTCGC
    >L   D  W  V  H  A  Q  P  A  G  W  D  T  V  V  G  E  E  G  Q  L  S  G  G  Q  R  Q  R  L  A

95356 GCTGGCCCGGGCGCTGCTCGCCGCGCCCGGCGTCCTGGTGCTCGACGAGCCGACCGAGGGCCTCGACCCGTCCGCCGCGGACGCGGTGCTCG
    >L   A  R  A  L  L  A  A  P  G  V  L  V  L  D  E  P  T  E  G  L  D  P  S  A  A  D  A  V  L

95448 CCTGCGCGCTGGCGGCGACCCCGGCCCGGCCACGAGCGTGCTCCTCATCAGCCACCGGCTCAGCGGCCTCGCCGACTTGGACGAGATCGTGGTG
    >A   S  A  L  A  A  T  P  A  G  H  S  V  L  L  I  S  H  R  L  S  G  L  A  D  L  D  E  I  V  V

95540 CTCGACGCCGGCCGGGTCGGTCCAGGCCGGTGCGCCAAGACCGAGCGCCACGACGAGCTGGTCGCCGCACCAGGCTGGTACCGGGACCAGTGGCTGCTCCAGGAGGC
    >L   D  A  G  R  V  V  Q  E  G  R  H  D  E  L  V  A  A  P  G  W  Y  R  D  Q  W  L  L  Q  E  A

95632 GGCCGAGCGCGGGAGTTCCCCGACGCCCTGGGCCTGACGCGCCGGCCTCGGGACGCGTCGGCAGTCACCGGCATGGCAGGCT
    >A   A  P  G  W  Y  R  D  Q  W  L  L  Q  E  A  .

95723 CGTCGCATGGTGCGCTGCGACGACGTACTCGTGAAGGAGCGGCTGCGCGAGTTGAGCGACCGGCTGCACGGCCCGGCCCGGCTCAAGGCCG
    >M   V  R  C  D  D  V  L  V  K  E  R  L  R  E  L  S  D  R  L  H  G  P  A  R  L  K  A

95814 ACCTGCTGGCCGAGGCCCGCCACGCGTTGCAGGACGCGGTGGAGGCGTACCGGGACGGCGGCCTGCCGGCGGCCGAGGAGCGGCGGGCA
    >D   L  L  A  E  A  R  H  A  L  Q  D  A  V  E  A  Y  R  D  G  G  L  P  A  A  E  E  R  R  A

95906 GTGGCCGAGTTCGGCGAGCCGGCCCGGCTCGCCCCGGCGTACCAGGCGGAGCTGGCCGGCGGCTCCCTGCGCGGCCTGTCCCTGCGGGTGCT
    >V   A  E  F  G  E  P  A  R  L  A  P  A  Y  Q  A  E  L  A  A  G  S  L  R  G  L  S  L  R  V  L
```

FIG.11A(83)

FIG.11A(84)

```
97006 AGGACGGCGCGCGCCCGTCGGCGCAGGACGCCGACGCGCGCCTCTGGGACGAGCTGCGCATCGACCCGGTCGAGATCGCCCTGCCCGCCGGC
     >E  D  G  A  R  P  S  A  Q  D  A  D  R  A  L  W  D  E  L  R  I  D  P  V  E  I  A  L  P  A  G
97098 ACCGGCTACACGCTGCGGGCGTACCGGCCGGCACGGGAGTTGACCCCGACGGACGTGGCCGAGCGGGACGCGGAGCGGGACCAGGACGACCCGTTCCTGGCCCG
     >T  G  Y  T  L  R  A  Y  R  P  A  R  E  L  T  P  T  D  V  A  E  R  D  Q  D  D  P  F  L  A  R
97190 CCGGCAGGCGGTCGAGACCGACGAGGACGAGGACGAGGTGATCATCCTCGACGAGGAGGTGGCCGCCGAGTTCGCCGAGGCGGACGCGGAGG
     >R  Q  A  V  E  T  D  E  D  E  D  E  V  I  I  L  D  E  E  V  A  A  E  F  A  E  A  D  A  E
97282 AGGCCGGCGGGAAGTCCCGCAAGCCCCGCGCGGACGCTCCGACGAGCCGCACAGACGCGGAGAGGAG
     >E  A  G  G  K  S  R  S  R  K  P  R  A  D  A  D  S  D  D  A  G  A  A  T  D  A  D  A  E  E  E
97374 CCGGACTCCGACGAGGACGAGGCGGGCGACGAGGAGGTTCCGGTCTTCCTCAGCCACCGGGGCAGGCTGCTGCTGTTCAAGACGCCCGAATC
     >P  D  S  D  E  D  E  A  G  D  E  E  V  P  V  F  L  S  H  R  G  R  L  L  L  F  K  T  P  E  S
97466 CCTCGTCAGCTTCGTCCGGTCCGGCGCCACCCAACGACAGTCTCAACTGGAATGAACTGCGCGGGGTGGAGCCGGCCGACA
     >L  V  S  F  V  R  S  G  A  P  N  D  M  S  Q  L  D  S  W  N  E  L  S  E  R  V  E  P  A  D
97558 TCGTCCCGCTCGACGAGGTTGCCCGGAGCTGCCTATGCCGTCGCTCGCCCCCGTGTTGGACATGTCTCCCGGCTCCAGCCTCGACGACCTG
     >I  V  P  L  D  E  D  T  Y  E  L  D  L  V  V  E  N  L  R  G  G  H  D  T  W  D  S  A  L  L  I
97650 GAGCCGGCGGAGGTGGCCCGGCAGGTCGCCGTGTTGGTCTGCGTCTGCCCTCCCGGCTCCCCGGCTCCGGAGATCGGCGGCGACCAGCCGGCTACGCCTG
     >E  P  A  R  W  P  G  T  S  R  M  P  C  V  C  P  P  C  W  T  C  S  P  P  A  P  A  S  T  T  W
97742 GACGAGGCGCTGCCGCGCCAACGGCGGGCCTCGGGGGCTTCCTCGGCGGCTGAGGAAAATCGGCGCGCAGACGGCGAGTC
     >T  R  R  C  A  P  R  P  T  A  G  S  G  A  S  S  A  A  G  G  .
97833 TCGGTTGGCGCCACCATTGTCGGCAAGATCTCTGCGGTCGTGGACTGGCGCGACGTTCCAGGGAGCATCAGTCTCTGGCAGAGAAAG
                                                              BamHI
                                                              junction marker 97925 ACCAGTCCCGGAGGAGGACGACGCTGTGGCGCTCGTGCGCGTGTACTGCGGTGGCGGTCGGTCCGGCGCGCTCGGCGGATCGGCGCCGACCGACCGGCCCTCGGCC
98017 GGTTCGGCGTGACGTCCGCTGTGGTCGGCGACGAGGTCAGGTGGCGCGACGACGCAGGTCGGCGGCGACGACCAGCCGCGGCTACGCTCAGCT
98109 GGTCGTGCTACTCGTGTGGAGCGGGTCGGGGCGGGCCGGAGCCGGGGCTGCGAGCCGCCGACAGGCGGACGACCACAGGTCACCTGCTGCTGAGTG
```

FIG.11A(85)

FIG.11A(86)

```
99304  CGGCAGCGCACCATCATCCGCCTCGCCCCAAGACGACGGGCGAGTCCGGGGCGCCGCCCACCGGCGGCTTCAGCGCCACCGACCTGAGCGT
       >R Q R T I I P P R P K T T G E S A P P P T G G F S A T D L S V
99396  CCCGGTGCCGACCCCGCGTCCCGGAGTCCGCTCCCCGGCTCGCGGGCGAACTGGCCGCTGGTCAACAACCCGGAGGACCCGCCG
       > P V P T P R P G Q E S A P P G S R A N W P L V N N P E D P A
99488  ACAGTCCCCGAACATCCCGTCGCGGCCCTTGGAGGATCGGGCGAAGCGGCAGATCGACGCGCCACCCAGGTGGTCCCGCCGCC
       >D S S P N N P V A R R P L E D R A K R Q I D A P T Q V V P P A
99580  GAGGGCCGGGTCACCCCGCCTGGCTGGCTCGCCGACGACCTGCCCCAGAGCGCCTGCTGGGCTGCGAGCGCCACCGCTGGCCGACCG
       >E G R V T P P W L A D D L P Q R P P M L R L V E P P L A D R
99672  GGCACTGCGCGGATGGGCCGGCCAGGCTGCCGCCGCCGACCCGCGCCTGGAGCCCCCGCTGCGCCTGCTGGTCGACCGCGGCGAGGCAGCCCGCGCG
       >A L R D G P G Q A A A D P R L E P P L R L V D R G E A A R A
99764  GCCGTCCCGCGCCGGAGCCCCGAGCCCCGCGGGCCCCCGCTGGGTCCCCGCTGGGTCAGCGGGTCCCGTTGGAGGAGCGGCCCGAC
       >G R P A P E P P E R A P A E H R S P L G Q R V P L E E R P D
99856  ATGGAACATCGGACCGCCCCCCAGCCAGCCGCAGTCCGCCGATGGAGCGCCGCACCCCGCCGATCTCCGACGAGGGGACGGCGACCT
       >M E H R T A P P Q P S R S A P M E R R T P P I S D E G D G D L
99948  GCTGATCTTCGCCGCGAAGTCGGCCTGGTTGCGTTCGTGGGCGTGGCGCCAAGTCCGAGATGGACTGGTCGAGCACGGCGACACCGGGGTGGC
       >L I F A A K S A W F V G H G D E S E M D W S S T A S T G W
100040 AGGCCGCGAGCAGGCCGCCCCGGCGGTGGGCGCGGGCGATACCAAGGCCGGCCTCCCGAGCTTGCCCAAGCGGGTGCCCAGGCAACACGACCGGCCAACCTGGTTCCGGGC
       >Q A A E Q A A R P A V G A D T K A G L P K R V P Q A N L V P G
100132 TCCCCCTGCGCGAGGAGCGTCCCCTGCGCGTCCGCGATAGTCCGGCGACCGGGCAGCTCGCCGAGAACACGACCGGCTACTTCCGGGACTGGCGGCGG
       >S P L R E E R P L R I V R D A A S L A E N T T G Y F R G W R R
100224 CGGGCAGGAGATCGGCGGGTTCGCCGTCGGCGGCCGCCCGCCTACCGGTCCGCTCCTGACCATCGCGCCGGGACTGGCGGCGGGGTGGGGACTTCACCCGGGACACCGGGACCGAG
       >G Q E I G G F A V G G R P G R E A A G G W D F T R D T G D R
100316 ACGACGACCGGGACTACGAGTACGAGTACCGGTCCGCGGGCTACCGGTCCGGCGACGACCGGACACACCGAAGAGCAACCCTGGCCGGCCGACGTC
       >D D D R E Y E Y R S A G Y R S *
100407 CCGTGCTGGCTACGCCGTAGCAACCCGACGCCCACCCGACCGGTGGGACGACACACCGAAGAGCAACCCTGGCCGGCCGCCTGACGTC
```

FIG. 11A(87)

```
100499  CCGCAGGGACGGTGACGGCTACTGGGCCGTCCCCCCGGGAAGGTTGCGAGGCGGTCGGGAGCGCACAGGGCGCTGTCAGGGCCGCTCCTGAGCCG
100591  CCCTACGGATGGGCTAGCCCTACGGAATCGAGCGCCGGGCCGGGTTCGCCTGTCGAGTTCGCCTCCAGCGGTCCCCAAACAGCCGGAC
100683  GCGCCGACGGCCCGGCGGGTGCCGGTCGCCGGGCGCGGCGGCGCGTCCCGTCGATCAGGCGGCGGACGGCGAGCGCGCATCGTGAGCA
        < .   A P A V A R S R R M T L V
100774  CGTACTCGACCAGCGAGATCAGCCTGGTCGTTCCGGGCCGTCGCCAGGCCACCGGCGTGCGAGATCGCGAGC
        < Y E V L S I L V H K T S E R N R A D C A V V P V D H S I A L
100866  GCGTCCCGACGTCCTCGCGGGTCTCGTGTACTGCCCGTCGATGGCCAGCAGTTGATGGCCAGGACCGCCGATGCTCGAAGAAGTC
        < A D R V D Q P D H Y Q M G D F C N I A V L Y P L R R H E F F D
100958  GATGGCCGCGAAGCAGTCGGCCGCGCGGGTGTCGACCAGGACCACGCGCGATGGCGCCCAGGACCTCGTCCACATGAACCAGA
        < I A A F C D A L R R T D V L V V A G I A G R C L E D W M F W F
101050  ACCGGGTCTGGCCCGGGGGTGCCGAACAGGTACAGGATCAGGTCCCGGTCGATCGAGAGTACGACGGTCCATGCCGAAGTCCATCCGAGACCGAGCC
        < R T Q G P T G F L Y L I L D R D I S I R G F D M A V T T T
101142  TCGCCCGGCACCTGGCCGGGTGTCGTGGGGTGCCCGGTTGATCTCCGAGACCGAGCC
        < E G P V Q R T D D V G V G A S T M I A E T T L P T I E S V S G
101234  GACCAGGCTGTCTTGCCGACGACGCCGAACCACCGGCGATAACGATCTTCGCCGACGTCACGCGCCCGGTCACGCGCGGCGGTGCGACA
        < V L T T K G V G F G G A I V K A S T V R G S P V P P R H S M
101326  TGTCAGAGCCTGCGAAGTCCACTCAGCGTCCTCTCCAGCACCCTGTCGTCGGAGTCGTCCAGGATGGTCGGCTCGTGGA
        < < . L R R L G S L V R E L L E T G V A D D S D D L I T P E H V
101417  CTGCGACCAGGCCGTCGTCGCCATGTCGGCGATGAGCACCCTTAGCGCGGAGCTGCATCCGCGCGATCTCGGCAAGCGAC
        < A V L G D T A M D A I L V R A V G L P L Q M R A A I E A L S
101509  TGCACGCGTCCGTCGCACAGCGGCGGCGATGTACTGGTGCTCTCGGCCCTTGGCCAGCGGCCGACCGGCGCGCCGTCGT
        < Q V R G D C L A A I Y Q H E R G Q G G N S S A A A R G V T T
101601  CTCGACGAGCGCCTCCAACGCGATGTTCCAGCCGAGGGCGGGTACGACCGGGTGACGGCGTACGGACGACGCCAACGACGGCCAGTCGGCTCGT
        < E V L A E L A I D L R P R T R G R T V A Y P R V L A G T P E D
```

FIG.11A(88)

101693 CACGATCCATGTCGCCGCTCACCTCCTTGTCCCGACACCGTCGTTCTTGTCCTTGCCACCCGCCGAC
       < · R D M D G S V E K T G S V

101784 CCATCGGCCAGCGCGTGGGTCAGCCCCATCATCCCACAGTCGTCGCGGCTCGCGGGTCAACGCGTCGCGGGGTCAACGCGGAGGC
       < · G M M G V T T R P Q P T L A D G V R D V L L A

101875 CATCTCGTATCCGACCTGCCCGACGTCGGCAGTCTGCAGCGACCACGGCGAGCGGCGAGGACACGGAGCACGGACATCAGGAACAGGAAGC
       < M E Y G V Q G V D C S R A A L V A F S S G D S I S M L F G

101967 CGTTGTCCATCTCGACCACGGTCTGCAGCACCGGCGTCTCGTTGACGACGCGGAAGGCTGAGGCTGACCAGCCTGACGCGATC
       < N D M E V V T Q L V A G G E F C R A A G Q T L S V L G S A I

102059 GCGGCGAGCTGGTCGGCCGTCAGCCGGTCACGCGGAAGGTTCTCGTTGACGACGCAGGAGCAGACCGTCCGGAGACGGCGACGGCGGTGCGGACACC
       < A A L Q D A R D R P L D R S S A L L G D A S V A H A V G

102151 GGGCACCCGGTCGGGCGAAGTTGCCCAGCAGCCAACGAGATCCTGCGTAGTTGTCATCCTTGTTCTTGCTCCCCTCCCGGCCACCG
       < P V · G Q Q E K Q G S G A V P

102242 GGCCTGAGCCAGACTGCCGAGGATTGCTGCCCACCCGGAGCTGCCCTCGGGGTTGGTCGGTGCCCGTACGCTCGGGTACGCTGCACG
       < G S G S Q S S Q Q G G P A A E P N T P N G D P E T R G R Q V

102334 CCTCGATGGTATGCCGAGACGCTGGGAGACGCCCTCCGGCGTACGGCGCTGGACGACGTGGTGCGACGTGGGCTTCTCCACCGGCAGGCACGAG
       < G R H Y A S L L G R V G E P T R R Q V S T T P K E V G G P V L

102426 TTGGGCCATCGGCCACCGCTTCCGGCAGGCCCTTGCCGGGTCGGTGCTGGCCCGAGGCGGCCCGCAGCCGTCGT
       < Q A M P V R K P L G K R T T E A V P V E T A A S A A R W S P P

102518 CCGCGGCCAGTCTGCGCGGCCATTCCTCGCGGCCGTCCGGCGTCTGCCTCGTCGTTACCTGGTCGTTGTTCGGC
       < A A T Q W A H A Q P T P R R G A F G E A P G P R T G G N T P

102610 GACCCGTTGTCGCGCGGATCGACCGCGGAGAACTGTTGGGTCACGGCGGTTCCGGCGGCGCCATTGGTCGCGCTGGGACGGGCCG
       < S G N D R P M G G A M P R D A M P A N G T T G P A P T Q V P R

102702 GCCGGTGACGTCGACGTCGGCGAGCTTCGGCAGTCGGGCGTTGGGTCACGGCGGTTCCCGGCGGCGCCATTGGTCGCGCTGGGACGGGCCG
       < G T V D V A A S F Q Q T V A A N A P S G A G N T A R Q A V G A T

FIG.11A(89)

```
102794 TCTCCTCCGAACCCGAGCGGCGGGGTACGGAACCAGGCCGACTCGAGCTCCCGGAAGATCGGCAGCTCCATCGTCTCGTCCGCGTACCGCTGC
        < E E S G S R R T R G W A S E L E R G I P L E M T E D A Y R Q
102886 TGCCGGTTCTGGGCCTGCACGGGCCTGCGACCGCGTCGACGGGCGTCGGGTCTCGTCGGTGCCGGTGCTGCGGTGTCGGTGCACCTCGGTGCTCGG
        <Q R N Q A Q V P T S R A P T P P T T P Q T A P T S P V E T S P
102978 CACCCGGGGGCAGCTCCGTGGTCATGTCCGAGCGCTGCGGCGGAGGCGCTGCGGACGCCGAGGTGACCGGCTCCGGCGCGGCCACCGGGCGGCC
        <V R P L E T T M D L A A A L R E P V P P T V P E P A A V P P W
103070 AGGCCGGCGGCGCCACGGCGGCCTGGGCCGACTGGACCGCGAGCGCTGCGCCAGCGCGGCTGACCGGACGCCGACTACGGCCTGACGCTGCCG
        < A P P A V P A Q A D P V P R S P L P Q A S Y P Q G S V P T G
103162 AACGGCTGACCGGACCGCGTGCCGAGACCGGAACGCTGCCGGGTGCCCGGGTCCAGCCTGTCGGGGATGGCCGCGGCTGCT
        <F P Q G S V P T G F P Q G S V P A A S V P Q G S V P F V S V P
103254 CGGTGCGGACACCGGCGGCGGATCGCCGGAGAGGTGCCCGCCGCCCCGGGCTGCCAGCCTGTCCAGCTGTCTCGAGGTGCGGCGGCGGCA
        <P A S V P P V S V P P P P T W G R A E P S S P L Q R P I A P Q Q
103346 GGGCCGCTGCTGCCGGATCGCCGGCCACTGGCCGTCCAGGGTCCGGTGCAGGATGCATGGAACCGGTGCGACGCGTGCCGTTGCG
        <G S S A P D G D G S A R R Q P L P D S S Q G N S T R G A A A
103438 CCGGCCAGCGGGCTGCCCGAGCGGGTGCTCGCCGGAGTTCGTCCCGCCGGTTACCTGCCACAGGCGGCGCCGGTGTTGCCGGGGTTGTTGC
        <G G A T G S A G T L D S W A P M S R M S G T S A P T G H G N R
103530 CGAGGCGCGGGTCGAACGACCAGGCCGCCCAGGGTTACCTGCCCCGAGTGCTGTTCGCCGGCCTGGAGCTGAGCCGGCGAGAGCGCTGC
        <S A P D G D R G G L T V Q N G S H G P R Q T P A P T A P N N G
103622 CGAAGGCCGCGGGTCGAAGGCACCACCAGGCGCGGGACGTGGTGGGCAGGGTCCCGGCCGCAGGTCGGTGCAGCCGGCCGAGCTC
        <S A P D G D R G G L T V Q N G S H G P R Q T P A P T A P N N G
103714 TGGAACCGGCCGGGAGCGCGGAGAGCGCGGCGGGCACCGGCCCGGTCCTGGTCACACACCGGGTGACGGTGGACGCCACGTCCACCTGGT
        <Q F R G S L A R P V L V T T P L T V D A V T G R D T G P R L E
103806 GACCTTGACCGCGGCCGCGGACGCGCAACCAGGCCCATCATCCGGGAGGACACCAGGTCCCACGTCCACCTGCGCGGCGGCGAGGCGA
        <V K V G H R S A L R A V V V L G M M R S V A V D V Q P P S A L
```

FIG. 11A(90)

```
103898 GGCGGTCGTTGAGGTCGTGTAGCTGCTCGGGCGCTGATGCCGGATGCCCGGTCTCGAGTGTAGAGGTTGGCCGGTCGCCGGTCGCCGGCC
         < R  D  N  L  D  H  L  Q  E  A  S  I  G  I  R  D  E  V  Y  L  N  A  R  D  G  V  R  R  A
103990 TCCACCATCACTGCGAGTCGGGCGGCGGCGAGAAGGCGGTCGCGTTGTCGCGTTGACCCAGGTGGACCAGGTCGTTGACCCGGTCGCGC
         < E  V  M  V  Q  S  D  P  P  S  F  A  T  A  N  D  G  L  E  A  V  L  H  V  L  D  N  V  A  H  A
104082 GGCGACCTGCGATGTCACGGTCGATCACCCGAACTCGATCCGGGTGTAGTGCTGAACCAGCAGGTTCTCGTAGTGCACGTCGATCAGTG
         < A  V  E  I  D  R  D  I  V  G  F  E  I  R  T  Y  H  E  V  E  S  Q  A  A  R  L  V  D  I  L  A
104174 CCGCCCGGCTGCGCTGCACGCGGGTGGAGTCGGCGCCCGGCGACGAGCACCAGGTTCTCGTTGTCGGGCGCATCCGGGTGCCAGGTGGTCG
         < A  P  E  R  Q  V  R  T  S  D  A  G  A  L  V  L  L  N  E  D  N  R  R  M  R  T  A  L  H  D
104266 AGCTGGAAACAGCTCGGGCAGGTTCGACGAACATGGTCGCGAACTCGTCCTTGCTGCGCAGCGGGAGGCGCGCCAGCGGCCGGATCAGCACCAGAGATCTGCGA
         < L  Q  F  L  E  A  L  R  D  P  D  E  E  G  R  E  L  R  D  L  H  F  I  L  R  D  V  L  I  Q  S
104358 ACGGCGGGGCAGGTTGACGAACATGGTCGCGAACTCGTCCTTGCTGCGCAGCGGGAGGCGCGCCAGCGGCCGGATCAGCACCAGAGATCTGCGA
         < R  R  A  L  N  V  F  M  T  A  V  S  A  R  L  A  A  Q  E  A  A  T  R  V  A  E  L  H  V  A  N
104450 TGAAACGCCTCGGTCACCTGGCGAACTCGTCCTTGCTGCGGCAAACGTACTGGGGCAAACGTACTGCTGAGCGCCACCCTGGCGCAGGTCGGCAGCGA
         < F  A  E  T  V  Q  G  F  E  D  K  S  R  V  P  L  P  E  A  I  Q  N  A  A  Q  V  P  S  L  Q
104542 CTGGAAACTGCGACCGGGCAGCGCGGATCGCGGCGAACAGGATACGCGAACAGGATGCCGAGCAGCATGCCGAGCAGGTCGGTTCGGAGGAACACCGTGCGCT
         < S  S  G  Q  P  D  R  L  R  A  V  A  Q  P  L  G  T  Q  A  I  S  L  A  G  Q  R  L  D  R  L  S
104634 GCGGGGCCATCGACCGGGCGGAGCGGAGCGCGTCGGCGTCGGCCTGCGTCGAACAGGATGCCGAGCTTGCCTCGACCAGCAGGTTTGGCGCTCTGGAGGAACACCGTGCGCT
         < R  A  M  S  R  A  V  L  Y  A  F  L  I  A  L  L  L  M  G  L  L  L  G  T  Q  L  F  V  T  R  Q
104726 GTACGTCGGAGCGGAGCGGCGTCGGCGTCGGCCTGCGTCGAACAGGATGCCGAGCTTGCCTCGACCAGCAGGTTTGGCGCTCTGGAGGAACACCGTGCGCT
         < V  D  S  R  L  A  D  A  Q  K  V  V  N  G  D  L  K  A  E  V  T  R  I  L  K  A  S  A  V  M
104818 GCCGCGTCCCACTGACCGGCCCGAAACGGCCGTTGGCATTGGCCATGCCGTTGGTGTTGCCGTCGAGCCAGCCCAGGTAGTTCGCGCTGTAGTTCGCGCCTGCCG
         < A  A  D  W  Q  D  P  G  F  P  A  N  A  M  S  G  N  T  N  G  D  L  W  G  T  Y  N  Q  A  E  R
104910 CCGGTCGCCGGCCGGCCGACGGTCGTTGGTGCCGGAGTCCAGGTCGTGCAGGTCGTGCAGGCTTTGAAGCTTTGCAGTGCCTGCTGTGCCTGCTGCCGG
         < R  D  G  G  A  V  T  Q  D  H  L  D  S  E  D  L  S  A  V  A  K  F  S  Q  L  A  Q  Q  G  T
```

FIG. 11A(91)

```
105002 TGCCGCTGGGCGATGTAGTCGGTGCGCAGGATGAGGGGTCAACTCGCGCTGGATCAGGCGCCGGTGCCACCACGACCCGGCTGGTGCGCACCGAGAGGTAT
       < G  S  A  I  T  D  T  R  L  I  P  T  L  E  R  Q  I  L  A  R  H  V  V  V  R  R  V  S  L  Y
105094 TCCTTCTCCCGGGCGACGGCTGCCGCGGCCGCCGCATCCGGTCGCTCAGGTCGTTGTCACCGGCGAGGTGGGTGGCGGAGTCGCGGAGTGGATGGACAG
      <E  K  E  R  A  V  A  A  A  R  M  R  D  S  L  D  N  D  G  A  L  H  T  A  S  D  R  I  S  L
105186 CAGGTCGTTGATCAGGCCCTCGTACGCATGGCGCTCGAGGAGGCCCTCCAGGCCGTGCTCGGACCCGTCGTTGCAGGTACGGCACCTTGTCC
      < L  D  N  I  L  G  E  T  A  Q  M  A  D  I  I  K  L  K  G  N  F  V  Q  S  R  T  G  P  L  D  K
105278 TCAGGTTCTGGTCGATCCGTCGAGGAGGCCCTCCAGGCCGTGCTCGGACCCGTCGTTGCAGGTACGGCACCTTGTCC
      < L  N  Q  D  I  G  D  L  L  G  E  L  S  S  P  L  G  D  V  E  G  R  Q  Q  L  Y  P  V  K  D
105370 TGGTCGAACCCGGATGTTGACCGGCGTTGTACGCCTTGGCTGTACGCGCTCCTGGTACTGCGCCCCGAGCAGCAGACCGGGAGGT
      < Q  D  V  R  I  N  V  R  N  Y  A  E  Q  Y  Q  A  K  A  Q  D  G  S  A  G  L  L  V  A  S  T
105462 GCGTTCGTCCTGAAGGCTGTTGACCAGGTCGCCGGAGTAGCCGACGACAGATTGGCCAGGTCGCGGAGCGGTTGGGCGTTGTTCAGGCATGTCC
      <R  E  D  Q  L  S  N  V  L  D  G  S  Y  G  V  L  N  A  L  D  G  S  R  N  A  N  N  L  T  E  L
105554 GGTTGTCGACGAGGCCACTGGTCGCCGAGCAGGTCGACGACAGAGCCTTGGACCAGATCGGCATGTC
      <  N  D  V  L  G  S  T  G  V  V  T  A  I  T  P  V  I  M  I  L  G  L  K  S  E  I  P  M
105645 GCGGAGCCCGGCTGCCGCCGGCACGGCAGGAGAAAGAAACCCGCGTCTTCGGTCGTTGCTCACGTCGCCCTCGCGATCACAGC
105737 GTTCGCGCGTTGCCCCGGCAACGCTCAGCGAGCGGCTCGGACCTCCGAGATTCCATCACGCGTCCAAAGAGAAAGCCCA
105829 GGCTGGCCGTCGCCGAGGTGTGCGAGAGATGTTGATGAGACAGTAATGGGACAGAGTGATGAGCGAGATGGATCACCCC
      >M  D  H  P
105919 CACCGCCTCGTCGCCGCCCTTCGGGCTCACGCGAAAGTCGTACATAGCCAACAAAACCGGCGGCCTTCCTGTCTTTGTCTGGACGACTT
      >H  R  L  V  L  L  A  G  P  S  G  S  G  K  S  T  I  A  Q  Q  T  G  L  P  V  L  C  L  D  D  F
106011 CTACAAGGATGGTGATGACCCTACGTTGCCCGCGCAGTTCTGTGGACTCGTCGTCGGGACGCGGGGCGCGGCCGTGG
      > Y  K  D  G  D  D  P  T  L  P  R  Q  N  G  L  V  D  W  D  S  P  Q  S  W  D  A  G  A  A  V
106103 AAACGATTGCCCGGCCTGCCCGGGACGCCAAGGCCGAAGTGCCGGTTTATGCGGTCGCCGGGGTGCCACCCGGACATTCGAG
      >E  T  I  A  R  L  A  R  D  G  K  A  E  V  P  P  V  Y  A  I  G  A  D  R  R  V  A  T  R  T  F  E
```

FIG.11A(92)

```
106195  GTCGCCGGATCGCCACTTTTCGTCGCCGAAGGGATTTTCGCGCGCGAGATGTCGACGGGCGAGGAGGGCTGCTCGCCGGGGCGTA
        > V A G S P L F V A E G I F A A E I V E E C R R R G L L A G A Y
106287  CGGCCTGCGCCGGCCGGCGAGCCCCACCTTTTTCCGGCGGCTCCGCCGACCTGGCCGAGCAGCGCAAGGCTCCCGGATGCTGCTGCGGC
        > A L R R P R G T T F F F R R L A R D L A E Q R K A P G M L L R
106379  GCGGGCCTGGCCCTGCTGCGCGCGGAGCCGGCGGTGCTGCGCGAGCCCGCCGCAGGGCGGTCAGCCAGCTTCCGGTGCCGGCCCGGAGGTGCTGCCG
        > R G L A L L R A E P A V L R R Q A G L G A H P A P A R E V L P
106471  CGGGTGGCCGACCTGCTCGCCGGCCACCCGCACCACCCGATCAGCAGCTTCCGGTACGCCGGCTTGATCACCTGTCGATGAT
        > R V A D L L A G H P H H P • • G L L K G Y A P K I V E D I I
106561  GGCCAGCGCGCTCGTGAACGCGGGGATGAACGCGCTCTTCATGCGGTTGATGGTGAACCATTGGAACTCTTCCAGCGTAGCGAAGGCCTCCG
        > A L R E D F P I F A S K M A N I T F W Q L E K W G Y G F A E A
106653  CCAGCAGCGCCATCTCCCGGACATCGAGGTGCCGCTCATCAGCCGGTTGTCGGTGTTCACCGTTCACCGTGTTCGGTTTCGCCTTGACTCGACGAAGC
        < L L A M E R S M S T G S M L R N D T N V T V R F R L D R L L
                                                                       BamHI
                                                                       junction marker
106745  CCGATCGGGGTGCTCGGCGATCGACGGCCGCCCGGGCTCTGCAGACGTTCGACGACGGGCACAGCTCCAGCGGGATCCGCTTGTCCCGCACGTA
        < G I P H E A I S A A A G T Q V N S S P C L E L P I R K D R V Y
106837  CGGGGCCAGCCAGCCGGCCGGCACGGGAATCGCCCGGGCGGTCGCCGGGGATGTCGTCCACGATGCTGCTCAGGAGGCGGTCCGGCCGCCACCACT
        < A A L R G L V P P D G P T I D D V I R V G H G L R D A G C W Q
106929  GGATGGCCTGCCAGATCGACGGCAGCCGGTCGAACGCCTCGGCCTCGCCCGAAGTGGAAGTGGAAGTTCTCCGTTGCAGGTACTGCAGGCGTCC
        < I A Q W I S P L G F A E G A H I T F H F N E R Q L Y E F A D
107021  AGGTGCCGGGTGGGGCGGGAATCCCGGCCCTCGAAGGCGGGCGATGTCGAAGCCGGTGCCGGCACCCGGCCAGTTCGGCGAT
        < L H R T P P F G A E G A I D F G V V G A D R H R V A L E A I
107113  CTCCTGCGACCGGGCCGGGGCATGGCGGTGCGAGCAGGGGTGCGAGCAGGGTGACCGGGGATCGGAATGGGCGCAGGGATGAGCGAAGCGCCCTCGG
        < E Q S R A A H R M A T L L T G V R I P H G A D A A L A A G E A
```

FIG.11A(93)

```
107205  CGAACCCGGGCGACGACCGCCTCGACCACCTGTCCAGGGTCCAGGTGTCCAGGTGCTGCTCCAGGTGTGCTCGGGGGCGAACCGACCTCGGCGTAGACG
         < F  G  A  V  V  A  E  V  V  E  D  L  T  L  D  R  E  L  H  Q  E  P  A  F  R  V  E  A  Y  V
107297  ACCCCGTCGGCGGTCCAGGCCGTGGCGGCAGGTCCAGGGCCACTCCTCGCCGCCGCGGTCTGCAGTGCGCCGGTCTGCATGACCGCCGCCACGGTGTGGGCGAACGT
         > V  G  D  A  A  L  D  L  A  C  E  Q  A  V  R  R  L  A  P  A  T  Q  M  V  A  V  T  H  A  F  T
107389  CTCCAGGTAGCGCTCCAGCGAGCGGAGTTCGCCGCCGCCGCCGCGAACCAGCGGGCGAGCGCTTCCGGGTCGGTGGTGCAGTCGTCGGTGGCCGA
         < E  L  Y  R  E  L  S  G  S  N  A  A  V  F  W  R  G  L  A  E  P  D  T  T  P  L  E  H  G  V
107481  CCTCGGCGGCCAGCTCGACGATCGTGCCGGCCGCCCAGGCCGCGTCGTTGCAGCCAGCGGCGCTGGGGACCGCTTGACGATGTCCTCG
         < E  A  A  L  E  V  I  T  A  P  R  L  G  G  D  L  H  D  H  L  L  A  K  P  V  K  V  I  D  E
107573  TATGAGATTGCGACCATGCCCAGACCCTAGTAGCGACGACGCGGCGGGTCTGCCGGTGAGGATGTCCAGGTGATGACCCC
         < Y  S  I  A  V  M                                                > M  D  P
107662  CGCATCGTCGACGGCGCTGCCGGTTGCCGGTCTGCGCGGAACGCTCACCGAGGCCGGACCGGACCGGGCGCTGCGCTGCCCGCGCCG
                                                                            > R  I  V  D  R  L  R  C  P  V  C  A  E  P  L  T  E  A  A  G  T  T  R  A  L  R  C  P  R  R
107754  GCACAGCTTCGACGTGGCCCGCCAGGGGTACGGCGGGGCACTACGACACGCGCTCTCGGCGCGCCCGAGCGCCACCCGGAGCGCTGAGCCACCCGGGAGGCC
         > H  S  F  D  V  A  R  Q  G  Y  V  D  L  L  A  G  R  A  P  H  V  G  D  T  A  E  M  V  A  A
107846  GCGCCGACTTCCTCGCCGCGGCCGGTCACTACGACACGCTCTCGGCGGCCCAAGCGCTGGACATGCGTCGCCGGACAGCCC
         > R  A  D  F  L  A  A  G  H  Y  D  T  L  S  A  A  L  A  A  A  A  L  S  H  P  P  E  A
107938  CCCGGAGCGGAGCGTCGGCGGCAAAGACGGGCAGGATGCCCAAGCGCCGGATGCGTCCGCGTCCGGAGATCGCCGGAGACGAGCC
         > P  G  A  D  A  S  A  G  K  D  G  Q  D  A  Q  G  R  D  A  S  A  G  H  D  A  S  A  G  Q  P
108030  GGCCGTGCGGGACGTACCGCTGGTGGTGGACGCGGGCGCAGCGGCAGCGCGGGCCGGCAGCCGGCACCTGCTCGCCGCGGTCCTGGCCGTGCTGGCGCTGCCCGACGCGCCGGTGG
         > A  V  G  T  Y  P  L  V  V  D  A  G  A  G  T  G  R  H  L  A  A  V  L  A  A  L  P  D  A  V
108122  GCCTGGCCCTGGACGTCTCCAAGCCGGCCCTGCGCGTCTCGCGACGTCCCGGCGCGCGCGCACCGCCCGCGCGGCCGCGGCCGCGCGG
         > G  L  A  L  D  V  S  K  P  A  L  R  R  A  A  A  R  A  H  P  R  A  A  A  L  A  D  T  W  R  R
108214  CTTCCGGCTGGCCCGACGCCAGCGTGCTGCTCGACGTCTTCGCCCCGCGCAACGGCGCGGAGTTCCGCCGCGTGCTCCACCCGGCCGG
         > L  P  L  A  D  A  S  V  A  V  L  L  D  V  F  A  P  R  N  G  A  E  F  R  R  V  L  H  P  A  G
```

FIG. 11A(94)

```
108306  CGGCTGCTCGTGGTCACCCCCGCCGAGGA CACCTCGCCGAACTGGTCGACTCGCTGGACTCGCTGAAGGTCGACCCGACAAGGCGGACC
         > A  L  L  V  V  T  P  A  E  D     H  L  A  E  L  V  D  S  L  D  L  L  K  V  D  P  D  K  A  D

108398  GGGTCGCCGGAGCCTGGCTGCGCACCGCCGAGCAGACCGCCGAGACCCTTCGAGACCGTGCTGCGGGCCCGACGAGCGTGCTGCGGGCCCGGGAGCTGGAAACTCACCGGCCGGCAGGTGGCCACC
         > R  V  A  G  S  L  A  G  H  F  E  Q  T  A  E  S  V  L  R  A  R  L  E  L  T  G  R  Q  V  A  T

108490  CTGGTCGGGATGGACCCAGCCTGGCACACCGACCCGGCCACCCTGGCCGCGCGCATCGCCGCGCTACCCGAGCCGGTCCGGGTCGACCCT
         > L  V  G  M  G  P  S  A  W  H  T  D  P  A  T  L  A  A  R  I  A  A  L  P  E  P  V  R  V  T  L

108582  CGCGGTACGGCTCGGCGTGTACCGCCCCCGCTGACCGGGGCGCGCCCCGGGCTCCAGGTGGAAAGGTGACCTCTTCCAGCCGGCGGCTC
         > A  V  R  L  G  V  Y  R  P  R  *                       < • T  S  L  D  V  E  E  W  G  P  P  E

108674  CTCGTGGTAGGGCCCTCGCAGGACCACCGCCGCCACTCCAGGCGCTGCCGGATCGCGTTGGCGTCGACCAGGCCGGCGGCGGACC
         < E  H  Y  P  G  R  L  V  V  A  W  E  L  A  W  R  R  Q  G  I  A  N  A  D  V  L  G  P  P  S  R

108766  GCCCGTCGCGCTCCAGTCCAGGTACGCCCAGTGAGGCAGTAGTGCAGGTCGAGTGCTGCGGCGCGGCC
         < G  D  R  E  L  E  L  Y  A  W  D  L  C  Y  H  L  D  L  L  A  A  A  D  A  P  H  Q  P  A  A

108858  AGGATGCGGGAGGCCACTGCTGCAGGGTCTCCCCGGCGATGTGCGCTCCACCAGCGCTCGTCGACCGGCCAGCGTCGGGTC
         < L  I  R  S  R  W  Q  Q  F  S  E  G  G  A  I  H  P  L  R  E  V  L  R  E  D  V  P  L  T  P  D

108950  GAGCTGCTTGGCCAGGCCCAGCACCCAGGCCAGGCTGAGAACAGCGTGTGGTGCAGACGACGGTCGCCGGCCGTTCGCGCCCATCA
         < L  Q  K  A  L  G  L  V  W  A  L  S  F  L  A  D  H  H  L  V  F  S  R  H  D  G  R  G  G  M  V

109042  CGAACTGCCACTCCGGCCACTCCGGGGGTGACCAGGTCGACCAGGTTGAGCAGCCAGTCATCGCCGGCATGCCGAAACACCGG
         < F  Q  W  E  P  P  T  V  L  D  V  L  H  S  N  L  L  W  S  M  A  A  Q  A  P  M  G  F  C  R

109134  GCCAGGATCACGTGCAGCACGGGCGATGCGCCGGGGGCGCTCGGCGGCGTCAGGCCTGCGTCCCAGCCCGGGGAA
         < A  L  I  V  H  L  V  A  I  R  A  E  I  E  V  T  P  R  L  E  I  E  D  G  P  E  W  V

109225  ACTGGCTCGGTGCAGGCCAGCCCAGCCCGGGACAGGCCCAGCTCGTCCAGGACAGCTCTCGCGGGGTCGGGAGCGGAAACGCGCACG
109317  GCTCAGATCCCTGTCAGTCGCATCGTGTCAGTGCCGGTCGTCCCCCTTGGCCTGGGGAGGATAGCGGTTCACGACGGGGCGGG
109409  CGGGGGCGGGGCCCGGGGCTGCAGTTCAGCAGCGGCGGTTCAGCGGCGATCCGCTGATGACCAGCGGCTGCCGGGGGTGCGGGGTACCGCGGAGATCCGGTACCCGGACCGCCTCG
         BamHI
109501  GCCAGCGCCGCCGGGATCC
```

FIG.11A(95)

FIG. 12A

```
1235 GAC CTG GAG CGA CGG GTC GAC GAG GCG GTG CAC GCC GGA TCG GCG GTG TCC AAG CAG CAC GCC CGG CGT GCG GGC AAG AAG ACG GCG CGG
    > D   L   E   R   R   V   D   E   A   V   H   A   G   S   A   R   A   V   S   K   Q   H   A   R   R   A   G   K   K   T   A   R

1325 GAG CGG ATC GGG CTG CTG GAC CTC GAG GGG TCC TTC GTC GAG CTG GAC GGG TTC GCC CGG CAC CGG TCC ACC AAC TTC GGC CTG GAC CGC
    > E   R   I   G   L   L   D   L   E   G   S   F   V   E   L   D   G   F   A   R   H   R   S   T   N   F   G   L   D   R

1415 ACC CGC CCG TAC GGC GAC GGG GTG ATC ACC GGC TAC GGG GTC CGG CAG GTC TGC GTC TTC GCG GAC GTC TTC ACG GTC TTC
    > T   R   P   Y   G   D   G   V   I   T   G   Y   G   V   R   Q   V   C   V   F   A   Q   D   E   T   V   F

1505 GGC GGC TCC CTC GGC GAG GTG TTC GGC GAA AAG ATC GTC AAG GTG ATG GAC CTG GCC ATG AAG ATC GGC TGC CCG GTC GTC GGC ATC AAC
    > G   G   S   L   G   E   V   F   G   E   K   I   V   K   V   M   D   L   A   M   K   I   G   C   P   V   V   G   I   N

1595 GAC TCC GGC GGC GCC CGC ATC CAG GAG GTG CTC CTC GGG CTC TAC GGC CTC TTC TTC CGC AAC GTG CGG GCC AGC GGC GTC
    > D   S   G   G   A   R   I   Q   E   V   L   L   G   L   Y   G   L   F   F   R   N   V   R   A   S   G   V

1685 ATC CCG CAG ATC ATG CTG ATC TCC GCG GGC TGC GCG GTC ACC GAC GTC ATG GTC GAC CAG
    > I   P   Q   I   M   L   I   S   A   G   C   A   G   G   A   V   Y   S   P   A   V   T   D   F   T   V   M   V   D   Q

1775 ACC TCG CAC ATG TTC ATC ACC GGC GAC GTC ATC AAG ACG GTG GAG GAA CTG GGT GCC GGC ACC
    > T   S   H   M   F   I   T   G   P   D   V   I   K   T   V   T   G   E   D   V   G   M   E   E   L   G   G   A   R   T

1865 CAC AAC GCG CGC AGC GGC AAC GCG CGG TAC GTC GAG GAG GCC ATC GAG TAC GTC AAG GCG CTC CTG TCG TAC CTG CCG
    > H   N   A   R   S   G   N   A   H   Y   L   G   T   D   E   E   D   A   I   E   Y   V   K   A   L   L   S   Y   L   P

1955 TCG AAC AAC CTG GAC GAG CCG CCC GTC TTC GAC GCC GTG GCG GAC ATC AGC GAC CGG GAG CTG GAC AGC CTC GTC CCG
    > S   N   N   L   D   E   P   P   V   F   D   A   P   A   D   V   A   I   S   D   A   R   E   L   D   S   L   V   P

2045 GAC GCC TCG GCG AAC CAG CCG TAC GAC ATG CAC CGG GTC ATC GAG CAC GTC CTG GAC GAC GGG GAG TTC CTG GAG GTC CAG CCG CTG TAC GCG
    > D   A   S   A   N   Q   P   Y   D   M   H   R   V   I   E   H   V   L   D   D   G   E   F   L   E   V   Q   P   L   Y   A

2135 CAG AAC ATG GTG GTC GGC TTC GGT CGA ATC GAG GGA CGG CCG GTC GGC AAC CCG ATG CAC CTC GCC GGC ACG CTG GAC
    > Q   N   M   V   V   G   F   G   R   I   E   G   R   P   V   G   N   P   M   H   L   A   G   T   L   D

2225 ATC GCC GCC TCG GAG AAG GCC GCC CGG TTC GTG CGC ACC TGC GAC GCG TTC GTG CGC GAC GCG TTC GTG CGC GAC GTG CCC GGG TTC
    > I   A   A   S   E   K   A   A   R   F   V   R   T   C   D   A   F   N   I   P   V   L   T   F   V   D   V   P   G   F
```

```
11289 TTC CGC GCC ATC GCC GCC CTG GTG GCC GAG CGG ACC GGT CGG CCA CCG GTG CCG GTG CTG GCC GTG CCC CCC GAC GAG GCC CGG GTC
      >F   R   A   I   A   A   L   V   A   E   R   T   G   R   P   P   V   P   V   L   A   V   P   P   P   D   E   A   R   V

11379 GCC TTC CAC GAC ATG GTC GTT GAC GCC TCG GCC TTC CAG GCG GTC ACC GGG TGG GCC CCG CGG GTG CCC GGG TTG CGC CTC GCG CTG GAC
      >S   D   F   H   D   M   V   D   A   S   A   F   Q   A   V   T   G   W   A   P   R   V   P   R   L   R   L   A   L   D

11469 CGC ACC GTC GCG GCG CTC GCC CGC GAC AGC GAC CCC GAG GCC GTC GGC CGG ACG CGG GAT CAG GCC CGG
      >R   T   V   A   A   L   A   R   D   S   D   P   E   A   V   G   R   T   R   D   Q   A   R

11553 AAG CCG GAC TCG ATC TCC AGG CAG GTC CGG TCG GGG CAG CGC CAA CCC GAG CGC CTG GTC CGG GAA GGT ACT CCT GGA GAC GTG TTC TCG AAG ACG TAC CGG
      >K   P   D   S   I   S   R   Q   V   R   .

11663 GTC CTC CGG GAT GGG CAG CCC AGG CCC GAG CGC CTG GTC CGG GAA GGT ACT CCT GGA GAC GTG TTC TCG AAG ACG TAC CGG
11784 ATG CGC GCG ACC CGA CGG CAG TCA GAA CTC CTG CTG TCG AGC GCG CAC CAC CCG GTC CCC ACT TGC CGA AGC GTG TCA GCG GAC CAG GTC GAG CAC ACC
11905 GGC CCG TGC GGG CAG GAG AAC TTC GCG CGT GCG CCG GGT CAG GCC CCG GGG TAC AGC GAG TCA GCC CGC GCT GTA GCT TGT GTA CGT CGG CAC GGG GAA CAC GCC GGT A
12026 CCG GAC CGT GTC CCC GGA ACG GGT GAC ATG CGG AAG GGC GAA GGC GAA GCG GTA CGG CGC CTT GCG GCC GAG ATA CGG CGC GGT CAG CGG GTC AGC GGC GGC GGG AAC ACC
12147 GGC GGG
```

FIG.12K

EVERNINOMICIN BIOSYNTHETIC GENES

This application is a continuation of U.S. patent application Ser. No. 11/739,945; filed Apr. 25, 2007 which is a continuation of U.S. patent application Ser. No. 11/021,825; filed Dec. 23, 2004, now U.S. Pat. No. 7,229,813; which is a divisional application of U.S. patent application Ser. No. 09/758,759; filed Jan. 11, 2001, now U.S. Pat. No. 6,861,513, which claims the benefit of U.S. Provisional Patent Application No. 60/175,751; filed Jan. 12, 2000 each of which is herein incorporated by reference in its entirety.

FIELD OF THE INVENTION

This invention is directed to nucleic acid molecules which encode proteins that direct the synthesis of the orthosomycin everninomicin. The present invention also is directed to use of DNA to produce compounds exhibiting antibiotic activity based on the everninomicin structure.

BACKGROUND OF THE INVENTION

Everninomicin Biosynthesis

Everninomicin is an oligosaccharide antibiotic belonging to the orthosomycin group of antibiotics produced by *Micromonospora carbonacea* var. *africana* (ATCC 39149, SCC 1413) and is useful as a human medicine. Everninomicin chemically consists of several glycosyl residues attached to modified orsellinic acid. Everninomicin's antibiotic activity is believed to be due to its inhibition of protein synthesis by a mechanism that involves binding of the antibiotic to a ribosome (McNicholas et al., Abstract C-846, ICAAC, San Francisco, Calif., 1999). Everninomicin is structurally similar to the antibiotic avilamycin produced by *Streptomyces viridochromogenes* Tu57.

The biosynthesis and enzymatic steps necessary for synthesis of homologs of the chemical moieties contained in the everninomicin structure have been studied in other systems. These include synthesis of orsellinic acid (Type I polyketide), glycosyl group synthesis (deoxysugars), and glycosyltransferase responsible for covalent attachment of glycosyl groups. Orsellinic acid biosynthesis in *Penicillium patulum* and *Streptomyces viridochromogenes* Tu57 has been investigated (Beck et al., European Journal of Biochemistry, 1990, 192:487-498; and Gaisser et al., Journal of Bacteriology, 1997, 179:6271-6278). Glycosyl biosynthesis has been reviewed (Hung-wen et al., Annual Review of Microbiology, 1994, 48:223-56; Williams et al., "The Carbohydrates: Chemistry and Biology" Vol. 1B, 1980, 761-798; and Johnson et al., Current Opinion Chem. Biol., 1998, 5:642-9), and been studied in the erythromycin biosynthetic cluster (Summers et al., Microbiology, 1997, 143:3251-3262). Glycosyltransferases have been studied in a number of systems (Olano et al., Molecular Gen. Genetics, 1998, 3:299-308; Fernandez et al., Journal of Bacteriology, 1998, 18:4929-4937; and Wilson et al., Gene, 1998, 214:95-100).

Polyketides are synthesized via a common mechanistic scheme thought to be related to fatty acid synthesis. The cyclic lactone framework is prepared by a series of condensations involving small carboxylic acid residues (acyl groups). Modifications of the structure, such as ketoreduction, dehydration and enolylreduction, also occur during the processing. The synthesis is driven by a set of large multifunctional polypeptides, referred to as polyketide synthases.

PCT Publication No. WO 93/13663 describes the organization of the gene encoding the polyketide synthase of *Saccharopolyspora erythraea*. The gene is organized in modules, with each module effecting one condensation step. The precise sequence of chain growth and the processing of the growing chain is determined by the genetic information in each module. This PCT publication describes an approach for synthesizing novel polyketide structures by manipulating in several ways the DNA governing the biosynthesis of the cyclic lactone framework. In order to adapt this methodology to other polyketides, however, the DNA molecules directing the biosynthetic processing must first be isolated.

Combinatorial biosynthesis with bacterial deoxy-sugar biosynthetic genes has been demonstrated (Madduri et al., 1998, Nature Biotechnology, 16:69-74) with the antitumor drug epirubicin (4'-epidoxorubicin) produced by *Streptomyces peucetius*. The heterologous sugar biosynthetic genes avrE from *Streptomyces avermitilis* and eryBIV from *Saccharopolyspora* were introduced into an *S. peucetius* dnmV mutant blocked in the biosynthesis of dausosamine, the deoxysugar component of epirubicin. Product yields were enhanced with avrE complementation demonstrating heterologous expression of sugar biosynthetic genes in combinatorial biosynthesis. Glucosylation of the glycopeptide antibiotic vancomycin (Solenberg et al., Chem Biol, 1997, 4:195-202) demonstrated that the heterologous glycosyltransferases gtfB and gtfE from *Amycolatopsis orientalis* expressed in *E. coli* produced glycosyltransferase capable of adding glucose or xylose to the vancomycin heptapeptide. Additionally, expression of gtfE from *Amycolatopsis orientalis* in *Streptomyces toyocaensis* resulted in glucosylation of A47934, producing a novel antibiotic. Thus, cloned glycosyltransferases can be used to produce novel hybrid antibiotics by glycosylation. In order to adapt this methodology to other glycosyl synthetic genes or glycosyltransferases, however, the DNA molecules directing the biosynthetic processing must first be isolated.

Orsellinic acid is synthesized by AviM, a Type I polyketide synthetase in *Streptomyces viridochromogenes* Tu57. An acytyl-CoA is used as the "starter" unit and three manonyl-CoAs are used as "extender" units for the synthesis of orsellinic acid. AviM has been shown to synthesize orsellinic acid by introduction of aviM into *S. lividans* TK24 (Gaisser et al., Journal of Bacteriology, 1997, 179:6271-6278). AviM has homology to the *Penicillium patulum* Type I polyketide synthase for 6-methylsalicylic acid (MSAS). The *M. carbonacea* EvrJ protein has homology to both AviM and MSAS and contains polyketide synthetic active site motifs resembling acyl carrier proteins, β-ketoacyl:ACP synthetases, and acetyl-CoA/Malonyl-CoA:ACP acetyltransferases. Thus EvrJ contains motifs necessary for the condensation of malonyl extender units with the starter acetyl-CoA unit.

The *M. carbonacea* EviI protein has homology to DpsC from *S. peucetius* ATCC 29050. Purified DpsC has been shown to use propionyl-CoA as substrate and to be acylated by propionyl-CoA at the Ser-118 residue (Bao et al., J. Bacteriol, 199, 181:4690-5). This has led to the proposal that DpsC is responsible for the choice of proponyl-CoA as the starter acyl unit in the biosynthesis of daunorhubicin by acting as an β-ketoacyl:acyl carrier protein (ACP) synthetase three (KSIII), and catalyzes the first condensation of the propionate-starter unit with malonyl-ACP. Thus EvrI may be responsible for specifying the choice of acetyl-CoA as the starter acyl group in orsellinic acid biosynthesis and condensation with the first malonyl extender unit. EvrI contains a possible Cys-127 acylation site to form the EvrI-Cys-S-acetyl moiety. This active Cys is similar to the active Cys found in the *Streptomyces glaucescens* FabH (KSIII) enzyme.

The success in cloning and manipulating biosynthetic pathways for the products mentioned above demonstrates a need in the art to isolate and harness the biosynthetic pathway for everninomicin. Moreover, there is a need to employ everninomicin biosynthesis in the development of novel molecules by combinatorial biosynthesis.

Genetic Manipulation of Actinomycetes

The ability to insert genes into the actinomycete chromosome is important to avoid plasmid inhibition of secondary metbolite production and to allow the construction of recombinants that do not require antibiotic selection to maintain cloned genes. Vectors have been developed for use in actinomycetes that contain att/int functions for site-specific integration of plasmid DNA. The two systems available make use of the att/int functions of bacteriophage phiC31 (U.S. Pat. No. 5,190,870) and plasmid pSAM2 (U.S. Pat. No. 5,741,675). However, there is a need for additional vectors with att/int functions for site-specific integration in *M. carbonacea*.

The present invention addresses these and other needs in the art.

SUMMARY OF THE INVENTION

The present invention advantageously provides the DNA sequence for the gene cluster responsible for encoding everninomicin biosynthetic genes, which provide the machinery for producing everninomicin. As a result, the present invention provides the information needed to synthesize novel everninomicin-related compounds based on everninomicin, arising from modifications of this DNA sequence designed to change glycosyl and modified orsellinic acid groups contained in everninomicin.

Figure 7A:
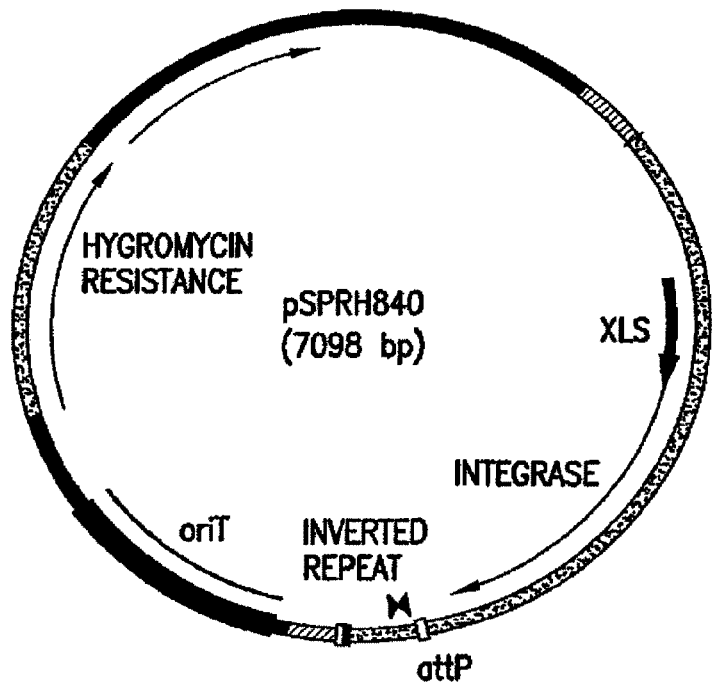
Figure 8:
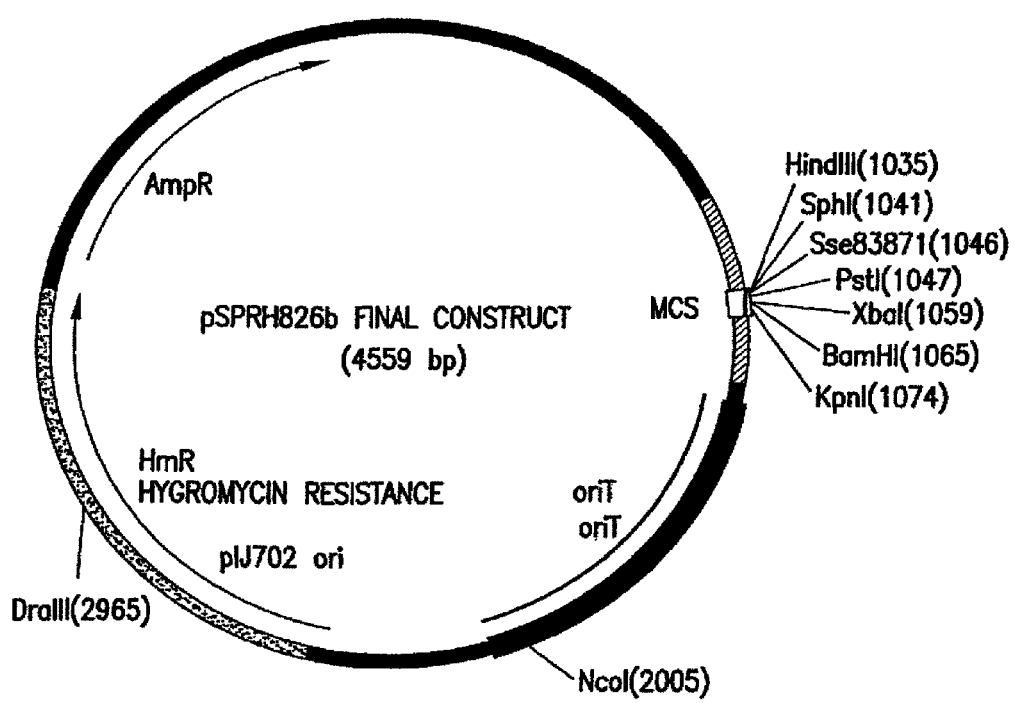

Thus, in one embodiment, the invention provides a nucleic acid comprising an everninomicin biosynthetic pathway gene product from a *Micromonospora carbonacea*, e.g., encoding a protein as set forth in Tables 1a and 1b, and in a specific aspect having a coding region (CDR) as set forth in Tables 1a and 1b.

The invention further provides expression vectors, host cells, and related methods of expression of protein gene products, comprising the isolated nucleic acids of the invention.

In addition, isolated polypeptides corresponding to an everninomicin biosynthetic pathway gene product are provided. Specific open reading frames and amino acid sequences of the polypeptides are set forth in FIG. 11 (SEQ ID NOS: 2-175) and FIG. 12 (SEQ ID NOS: 183-204).

Furthermore, the invention provides modified *M. carbonacea*, in which an everninomicin biosynthetic pathway gene is knocked-out, or, alternatively, over-expressed (or both). Similarly, the invention provides for metabolic engineering of new everninomicin analogs.

A particular advantage of this invention is the discovery of various everninomicin resistance genes, which can be used as selection markers. Thus, the invention provides a vector comprising an *M. carbonacea* everninomicin biosynthetic pathway resistance gene, and related methods of selection of transfected or transformed host cells.

In a related but distinct aspect, the inventors have discovered a *Micromonospora* site-specific integrase. The gene for the integrase can be incorporated in a vector for integration into any actinomycete, and, particularly *Monospora*. Thus, the invention further provides a method for introducing a heterologous gene into an actinomycete chromosome using this particular vector.

These and other aspects of the invention are better understood by reference to the following Detailed Description and Examples.

DESCRIPTION OF THE DRAWINGS

FIG. 1. The structure of everninomicin.

FIG. 2A-C. (A) Map of cosmid clones and subclones that span the whole region of the everninomicin biosynthetic locus and surrounding genomic DNA. Heavy cross-hatching indicates sequenced regions; light cross-hatching indicates regions for which a cosmid restriction map was obtained. (B) Restriction map of cosmid pSPRX272. (C) Restriction map of cosmid pSPRX256. In (B) and (C), cross-hatched regions have been sequenced and cloned fragments are indicated by clone designations beneath the fragment.

FIGS. 3A-D. Map of the everninomicin biosynthetic region of *Micromonospora carbonacea* var. *africana* DNA. Distances in bf are shown relative to the beginning of the DNA region. Open reading frames (ORF) are indicated by block arrows. The restriction sites for BamHI, BglII, EcoRI, KpnI, PstI and XhoI restriction enzymes are indicated.

FIGS. 4A-B. Proposed biosynthetic pathway for orsellinic acid synthesis by evrJ and malonylCo-A synthesis by evbD. (A) Orsellinic acid biosynthesis. (B) Malonyl-CoA biosynthesis.

FIG. 5A-B. Biosynthetic pathway for D-6-deoxysugar and L-6-deoxysugar biosynthesis by evrV, evrW, and evrX.

FIG. 6. Map of pSPRH830B *E. coli-Micromonospera* shuttle vector.

FIG. 7A-B. (A) Map of pSPRH840 integrating vector. (B)(1)-(4) Sequence of integrase gene (SEQ ID NO: 176) and deduce amino acid (SEQ ID NO: 177).

FIG. 8. Map of pSPRH826b insertion plasmid.

FIGS. 9A-B. Analysis of *M. carbonacea* and *M. halophytica* pSPRH840 insertion site att-B/attP region. (A)(1)-(2) Alignment of pMLP1 attP region with religation clone edge sequences.

*H. halophytica* PstI relig-9: SEQ ID NO: 205
*M. Carb* PstI relig-1: SEQ ID NO: 206
*M. Carb* PstI relig-4: SEQ ID NO: 207
pMLP1.intTGA.att region: SEQ ID NO: 208
Consensus: SEQ ID NO: 209

(B) pMLP1 attP. (SEQ ID NO: 210)

FIG. 10. Schematic of specific resistance gene-containing fragments for cloning in the pSPRH830 vector.

FIG. 11A (1)-(95). Everninomicin biosynthetic pathway locus sequence (SEQ ID NO:1) with open reading frames and deduced amino acid sequences (SEQ ID NOS: 2-175).

FIG. 12A-K. Everninomicin biosynthetic pathway locus sequence (SEQ ID NO: 182) with open reading frames and deduced amino acid sequences (SEQ ID NOS: 183-204).

DETAILED DESCRIPTION

*Micromonospora carbonacea* var. *africana* produces several antibiotics, including everninomicin, thiostrepton, chloramphenicol and lasilosid. As noted above, the present invention advantageously provides the DNA sequence for the gene cluster responsible for encoding everninomicin biosynthetic genes, which provide the machinery for producing everninomicin. As a result, the present invention provides the information needed to synthesize novel everninomicin-related compounds based on everninomicin, arising from modifications of this DNA sequence designed to change glycosyl and modified orsellinic acid groups contained in everninomicin.

The invention also advantageously provides an *M. carbonacea*-specific integrase gene and integration sites (see, FIGS. 7B, 9A, and 9B). Use of the pMLP1 att/int site specific integration function allows for increasing a given gene dosage and for adding heterologous genes that lead to the formation of new products, such as hybrid antibiotics. This procedure has many advantages over methods involving autonomously replicating plasmids. In particular, a plasmid containing pMLP1 att/int functions would integrate as a single copy per chromosome. Plasmids comprising the site-specific integrating function would introduce the gene of choice into the chromosome of actinomycetes. Vectors lacking actinomycete origins of replication can only exist in their integrated form in actinomycetes. Integrated vectors are extremely stable which allows the gene copies to be maintained without antibiotic selective pressure. The site-specific nature of the integration allows analysis of the integrants.

"Everninomicin" refers to a lipophilic oligosaccharide antibiotic of the orthosomycin family of antibiotics, which contain at least one acidic phenolic hydrogen, and two orthoester linkages associated with the glycosy residues (FIG. 1; see, PCT Publication No. WO 93/07904). These include for example everninomicin, curamycin, avilamycin and flambamycins (Ganguly et al., J.C.S. Chemical Communication, 1976, pp. 609-611; "Kirk-Othmer, Encyclopedia of Chemical Technology", Vol 2, 1978, Third Edition, John Wiley and Sons, pp. 205-209; Ollis, et al., Tetrahedron, 1979, 35:105-127). These lipophilic oligosaccharide antibiotics exhibit broad spectrum biological activity against gram positive and some gram negative bacteria in various in vitro assays, and in vivo activity, for example, in animal models such as murine models of gram positive infection.

Figure 2A:
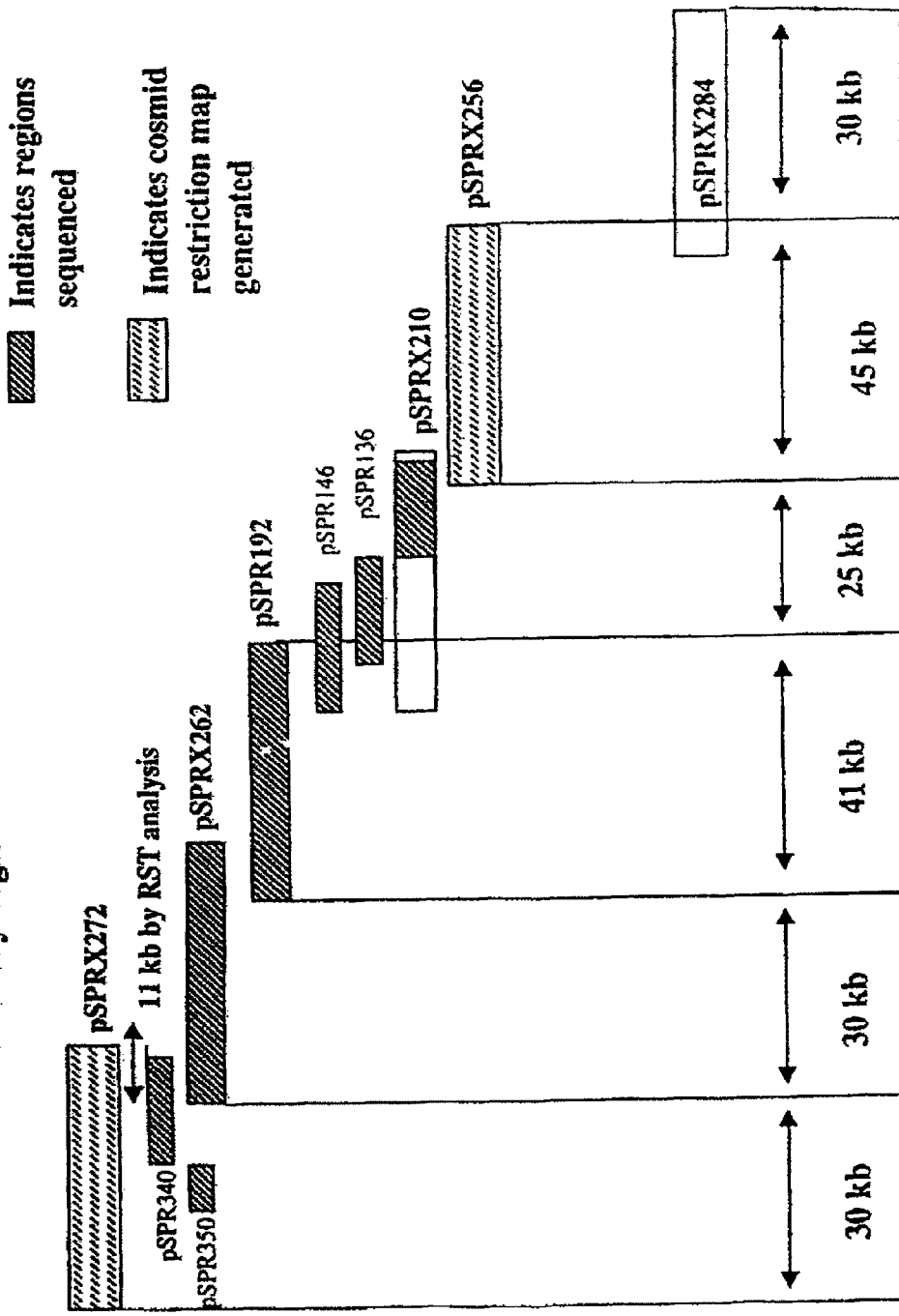

An "everninomicin (EV) biosynthetic pathway gene product" from a *Micromonospora carbonacea* refers to any enzyme ("EV biosynthetic enzyme") involved in the biosynthesis of everninomicin. These genes are located in the EV biosynthetic locus on the *M. carbonacea* chromosome. This locus is depicted in FIGS. 2A and 3. Since everninomicin is only known to be produced in *M. carbonacea*, for the sake of particularity the EV biosynthetic pathway is associated with this microorganism. However, it should be understood that this term encompasses EV biosynthetic enzymes (and genes encoding such enzymes) isolated from any *M. carbonacea*, and furthermore that these genes may have novel homologues in related actinomycete bacteria that fall within the scope of the claims here. In specific embodiments, these genes are depicted in FIG. 11 (SEQ ID NO:1; open reading frames and polypeptides designated as SEQ ID NOS: 2-175) and FIG. 12 (SEQ ID NO: 182; open reading frames and polypeptides designated as SEQ ID NOS: 183-204). It is noted that the sequences of FIGS. 11 and 12 are linked (contiguous) or connected such that they are part of the same cluster, i.e., the sequence in FIG. 12 precedes that of FIG. 11. Moreover, the present inventors have identified specific categories into which many of the genes from the EV biosynthetic pathway fall, including but by no means limited to, orsellinic acid biosynthetic enzymes, sugar biosynthetic enzymes, glycosyltransferases, tailoring enzymes, regulatory enzymes (serine-threonine kinases), and resistance mechanism enzymes (rRNA methylases and transporter enzymes). These categories are discussed in greater detail, infra. The gene products are listed in Tables 1a and 1b.

TABLE 1a

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
| --- | --- | --- | --- | --- | --- |
| evdA length 416aa | (132 ... 1382)* | (1389 ... 1394)* | 2, 3 | similarity to hydroxylase (CAA11782; 6.5e−137) | sugar biosynthetic |
| evdB length 373aa | (1490 ... 2611)* | (2618 ... 2622)* | 4, 5 | hexose aminotransferase, dnrJ homolog (daunorubicin) (P25048; 2.8e−65) | sugar NH2 addition |
| evdC length 412aa | (2622 ... 3860)* | (3867 ... 3870)* | 6, 7 | similar to flavoprotein, oxidase (S39965; 4.4e−92) | sugar biosynthetic |
| evdD length 389aa | (4143 ... 5312) | (4134 ... 4138) | 8, 9 | dNTP-hexose glycosyltransferase (AAC01731; 4.6e−49) | Glycosyl transfer |
| evdE length 308aa | (5309 ... 6235) | | 10, 11 | hexose dehydratase (CAA18814; 8.0e−58) | sugar biosynthetic |
| evdF length 347aa | (6232 ... 7275) | (6226 ... 6229) | 12, 13 | dNTP-hexose glycosyltransferase (CAB07092; 3.4e−18) | Glycosyl transfer |
| evdG length 351aa | (7272 ... 8327) | | 14, 15 | unknown | unknown |
| evdH length 340aa | (8342 ... 9364) | (8333 ... 8336) | 16, 17 | dNTP-hexose glycosyltransferase (CAA19930; 0.8) | Glycosyl transfer |
| evdI length 253aa | (9463 ... 10,224)* | (10,232 ... 10,235)* | 18, 19 | hydrolase (AAB81835; 6.8e−10) | sugar biosynthetic |
| evdJ length 250aa | (10,424 ... 11,176) | | 20, 21 | unknown | unknown |
| evdK length | (11,208 ... 12,455) | | 22, 23 | hexose dehydratase or empimerase | sugar biosynthetic |

TABLE 1a-continued

Gene Products and Putative Enzymatic Functions
Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| 415aa | | | | (CAB08849; 3.3e−26) | |
| evdL length 304aa | (12,108 ... 13,022)* | (13,027 ... 13,030)* | 24, 25 | dNTP-hexose glycosyltransferase (S37028; 0.010) | Glycosyl transfer |
| evrA length 317aa | (14,410 ... 15,363)* | (15,369 ... 15,373)* | 26, 27 | hexose epimerase (CAA12010.1; 1.3e−40) | sugar biosynthetic |
| evrB length 344aa | (15,380 ... 16,414)* | | 28, 29 | hexose oxidoreductase (ACC01734; 1.3e−65) | sugar biosynthetic |
| evrC length 484aa | (16,419 ... 17,873)* | | 30, 31 | hexose dehydratase (CAA12009; 2.2e−107) | sugar biosynthetic |
| evrD length 354aa | (17,870 ... 18,934)* | | 32, 33 | GDP-mannose 4,6-dehydratase (BAA16585; 1.0e−88) | sugar biosynthetic |
| evrE length 510aa | (19,374 ... 20,906) | | 34, 35 | multidrug efflux transporter (CAB15277; 1.4e−59) | resistance mechanism |
| evrF length 492aa | (21,064 ... 22,542) | (21,056 ... 22,542) | 36, 37 | similar to non-heme oxygenate/halogenase (CAA11780; 4.3e−58) | orsellinic acid chlorine addition |
| evrG length 474aa | (22,748 ... 24,172) | (22,736 ... 22,740) | 38, 39 | oxidase (Q12737; 5.5e−67) | tailoring |
| evrH length 348aa | (24,177 ... 25,223)* | (25,230 ... 25,233)* | 40, 41 | unknown (AAB89073; 3.2e−6) | unknown |
| evrI length 358aa | (25,550 ... 26,626) | | 42, 43 | acyl starter unit fidelity (daunorubicin homology) (AAA65208; 5.7e−56) | PKS acyl Carbon choice |
| evrJ length 1264aa | (26,685 ... 30,479) | (26,672 ... 26,676) | 44, 45 | orsellinic acid synthase 6-methylsalicilic acid synthetase (CAA72713; 0.0e) | polyketide synthetase |
| evrK length 439aa | (30,557 ... 31,876)* | (31,885 ... 31,888)* | 46, 47 | Na/H antiporter (BAA16991; 2.1e−14) | unknown |
| evrL length 313aa | (31,941 ... 32,882)* | | 48, 49 | similar to gene essential to heme biosynthesis (BAA12681; 0.0012) | unknown |
| evrM length 412aa | (33,167 ... 34,405)* | (34,414 ... 34,418)* | 50, 51 | similar to p450 hydroxylase (S18530; 3.8e−70) | tailoring |
| evrN length 253aa | (34,449 ... 35,210)* | (35,219 ... 35,221)* | 52, 53 | methyl transferase (CAB10751; 0.00061) | tailoring |
| evrO length 314aa | (35,294 ... 36,238)* | | 54, 55 | unknown (BAA20094; 0.56) | unknown |
| evrP length 242aa | (36,235 ... 36,963)* | | 56, 57 | unknown (CAB05421; 0.00020) | unknown |
| evrQ length 342aa | (36,998 ... 38,026)* | | 58, 59 | similar to oxidoreductase and heat stress protein (P80874; 7.8e−31) | tailoring |
| evrR length 164aa | (38,072 ... 38,566)* | | 60, 61 | low similarity to hexaheme nitrite reductase regulator (P30866; 0.0034) | regulatory (methyl transferase) |
| evrS length 423aa | (38,892 ... 40,163)* | | 62, 63 | dNTP-hexose glycosyltransferase (AAD15267; 1.9e−36) | Glycosyl transfer |
| evrT length 224aa | (40,216 ... 40,890)* | (40,899 ... 40,902)* | 64, 65 | similar to L-proline hydroxylase (BAA 20094; 5.5e−7) | tailoring |
| evrU length 229aa | (40,887 ... 41,576)* | | 66, 67 | methyltransferase (CAB02029; 5.6e−6) | tailoring |
| evrV length 342aa | (41,679 ... 42,707)* | (42,714 ... 42,717)* | 68, 69 | dTDP-glucose epimerase (AAB84886; 3.5e−36) | L-dTDP-glucose biosynthetic |
| evrW length | (42,810 ... 43,799)* | (43,807 ... 43,811)* | 70, 71 | dTDP-glucose dehydratase (CAA72715; 5.1e−136) | D-dTDP-glucose |

TABLE 1a-continued

Gene Products and Putative Enzymatic Functions
Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| 329aa | | | | | biosynthetic (GDH) |
| evrX length 355aa | (43,799 ... 44,866)* | | 72, 73 | dTDP-glucose synthetase (A26984; 1.2e−118) | D-dTDP-glucose biosynthetic |
| evrY length 248aa | (45,014 ... 45,760)* | (45,767 ... 45,770)* | 74, 75 | dehalogenase (P24069; 5.8e−8) | drug resistance |
| evrZ length 250aa | (45,962 ... 46,714)* | (45,952 ... 45,956)* | 76, 77 | similar to muramidase/lysozyme (P25310; 1.2e−77) | drug resistance |
| evsA length 692aa | (47,156 ... 49,234)* | | 78, 79 | serine threonine kinase (BAA32455; 2.0e−76) | regulatory |
| evsB length 362aa | (51,627 ... 52,715) | (51,620 ... 51,622) | 80, 81 | similar to proteases | unknown |
| evsC length 222aa | (52,889 ... 53,557) | | 82, 83 | similar to MAF involved in septum formation (BAA18425; 1.3e−21) | unknown |
| evbA length 217aa | (53,554 ... 54,207) | | 84, 85 | O-methyl transferase (AAC44130; 8.6e−38) | tailoring; possible resistance |
| evbB length 251aa | (54,362 ... 55,117)* | (55,125 ... 55,128)* | 86, 87 | membrane pump, homolog mithramicin resistance (AAC443581; 2.9e−24) | resistance mechanism |
| evbC length 319aa | (55,135 ... 56,094)* | (56,100 ... 56,103)* | 88, 89 | membrane pump, homolog mithramicin resistance (AAC44357; 1.0e−69) | resistance mechanism |
| evbC2 length 198aa | (56,184 ... 56,813)* | | 90, 91 | ankrylin like (AAC44356; 0.0041) | resistance |
| evbD length 582aa | (56,961 ... 58,709) | (56,947 ... 56,951) | 92, 93 | acyl-CoA carboxylase (CAB07068; 7.3e−201) | malonyl-CoA biosynthesis |
| evbE length 479aa | (58,873 ... 60,312) | | 94, 95 | IMP dehydrogenase (CAA15452; 4.1e−165) | tailoring |
| evbF length 185aa | (60,472 ... 61,029)* | (61,038 ... 61,040)* | 96, 97 | hypothetical protein Rv0653c, mycobacterium (CAB07128; 3.8e−06) | regulator |
| evbF1 length 90aa | (61,288 ... 61,560) | | 98, 99 | unknown | unknown |
| evbF2 length 152aa | (61,610 ... 62,069) | (61,597 ... 61,599) | 100, 101 | ORFI Streptomyces peucetius (CAA06602; 0.024) | regulatory/ resistance |
| evbG length 557aa | (62,122 ... 63,795) | | 102, 103 | ABC transporter (Q11046; 2.7e−170) | drug resistance |
| evbH length 645aa | (63,891 ... 65,828) | (63,884 ... 63,887) | 104, 105 | ABC transporter (Q11047; 5.6e−166) | drug resistance |
| evbI length 467aa | (66,469 ... 67,872)* | (67,883 ... 67,886)* | 106, 107 | lipoamide dehydrogenase (CAA17075; 1.6e−140) | tailoring |
| evbJ length 151aa | (67,979 ... 68,434) | | 108, 109 | hypothetical protein Rv3304 [Mycobacterium tuberculosis] (CAA17076; 7.6e−40) | unknown |
| evbK length 321aa | (68,529 ... 69,494) | | 110, 111 | protease synthase and sporulation regulator; homology to resistance proteins streptomyces (029729; 7.3-7) | regulatory |
| evbL length 249aa | (69,610 ... 70,359)* | | 112, 113 | acetyltransferase/ phosphotransferase | tailoring |
| evbM length 306aa | (70,365 ... 71,285)* | | 114, 115 | hypothetical protein Rv 1584c [Mycobacterium tuberculosis] (CAB09085; 0.32) | unknown |
| evbN | (71,289 ... 71,918)* | (71,926 ... 71,929)* | 116, 117 | hypothetical protein | unknown |

TABLE 1a-continued

Gene Products and Putative Enzymatic Functions Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| length 209aa | | | | SC3A7.08 [S. coelicolor] (CAA20071; 4.0e−40) | |
| evbO length 230aa | (72,284 . . . 72,979) | | 118, 119 | putative lipoprotein [S. coelicolor] (CAA19252; 2.6e−20) | unknown |
| evbP length 420aa | (72,933 . . . 74,195)* | | 120, 121 | peptidase (CAA17077; 6.5e−88) | unknown |
| evbQ length 527aa | (74,707 . . . 76,290)* | | 122, 123 | methylmalonyl-Coa mutase (BAA30410; 1.8e−149) | acyl precursor biosynthesis |
| evbR length 696aa | (76,622 . . . 78,712) | | 124, 125 | protein serine/threonine kinase note eukaryotic type (BAA32455; 1.1e−71) | regulatory |
| evbS length 576aa | (78,791 . . . 80,521) | | 126, 127 | phosphomannomutase (CAA17080; 5.4e−91) | sugar biosynthesis |
| evbT length 286aa | (82,073 . . . 82,933) | | 128, 129 | hypothetical protein SC5C7.22c (CAA20634; 5.7e−28) | 10-28 |
| evbU length 202aa | (83,280 . . . 83,888)* | | 130, 131 | glucose-6-phosphate 1-dehydrogenase low BLAST homology (S61167; 0.00039) | unknown |
| evbV length 193aa | (84,080 . . . 84,661)* | | 132, 133 | uracil phosphoribosyl transferase (CAA17081; 5.6e−60) | unknown |
| evbW length 338aa | (84,890 . . . 85,906)* | | 134, 135 | deoxyribose-phosphate aldolase (AAA79343; 1.3e−54) | unknown |
| evbX length 477aa | (85,909 . . . 87,342) | | 136, 137 | aldehyde dehydrogenase (AAB84440; 4.2e−103) | tailoring |
| evbY length 245aa | (87,422 . . . 88,159) | (87,407 . . . 87,411) | 138, 139 | aldehyde dehydrogenase (CAA71003; 3.4e−16) | tailoring |
| evbZ length 137aa | (88,292 . . . 88,705) | (88,280 . . . 88,282) | 140, 141 | hypothetical protein (CAB06141; 1.3e−16) | unknown |
| evcA length 301aa | (88,716 . . . 89,621) | | 142, 143 | hypothetical protein, putative integral membrane protein [Streptomyces coelicolor] (CAB06143; 4.5e−28) | unknown |
| evcB length 416aa | (89,817 . . . 91,067) | | 144, 145 | cytochrome D oxidase subunit I (P94364; 3.0e−65) | tailoring |
| evcC length 335aa | (91,078 . . . 92,085) | (91,068 . . . 91,072) | 146, 147 | cytochrome D oxidase subunit II (CAA71118; 1.9e−15) | tailoring |
| evcD length 561aa | (92,148 . . . 93,833) | | 148, 149 | ABC transporter (CAA22219; 2.6e−107) | resistance |
| evcE length 613aa | (93,830 . . . 95,671) | | 150, 151 | ABC transporter (AAC44070; 3.4e−32) | resistance |
| evcF length 229aa | (95,729 . . . 96,418) | | 152, 153 | unknown | unknown |
| evcG length 111aa | (96,440 . . . 96,775)* | | 154, 155 | unknown (AAB84787; 1.9e−8) | unknown |
| evcH length 303aa | (96,894 . . . 97,805) | | 156, 157 | unknown (CAA17083; 9.2e−5) | unknown |
| evcI search length 691aa | (98,287 . . . 100,362) | | 158, 159 | unknown (CAA19992; 6.0e−6) | unknown |
| evcJ length 197aa | (100,733 . . . 101,326)* | | 160, 161 | putative ATP/GTP binding protein (CAA19989; 7.9e−59) | unknown |

TABLE 1a-continued

Gene Products and Putative Enzymatic Functions
Involved in Everninomicin Production

| Gene Product | CDS[1] | RBS[2] | SEQ ID NO.[4] | Enzymatic Function (Protein ACC No; BLAST Score) | Class |
|---|---|---|---|---|---|
| evcJ2 length 134aa | (101,328 ... 101,732)* | | 162, 163 | unknown (CAA19986; 8.6e−23) | unknown |
| evcK length 117aa | (101,803 ... 102,156)* | | 164, 165 | unknown (CAA19991; 1.7e−36) | unknown |
| evcL search length 1145aa | (102,204 ... 105,641)* | | 166, 167 | unknown (CAA19992; 4.6e−99) | unknown |
| evcM length 201aa | (105,907 ... 105,641) | | 168, 169 | putitive uridine kinase (CAA19591; 1.0e−9) | unknown |
| evcN length 358aa | (106,513 ... 107,589) | | 170, 171 | unknown (CAA17085; 7.5e−120) | unknown |
| evrMR length 320aa | (107,653 ... 108,615) | (107,637 ... 107,641) | 172, 173 | homology to 23S rRNA methylase for mycinamicin resistance (myrA) (BAA03674; 1.4e−79) | resistance |
| evrMR2 length 193aa | (108,635 ... 109,216) | | 174, 175 | homology to gene linked to myrA | resistance |

TABLE 1b

Gene Products and Putative Enzymatic Functions
Involved in Everninomicin Production

| | | | | | |
|---|---|---|---|---|---|
| ORF1 length 291aa | (189-1064)* | (1069-1073) | 183, 184 | Transcriptional regulator Biotinylation H70979; 8e−31 | unknown |
| ORF2 length 527aa | (1184-2767)* | | 185, 186 | Propionyl-CoA carboxylase T42208; 0.0e | unknown |
| ORF3 length 296aa | (2863-3753)* | | 187, 188 | unknown | unknown |
| ORF4 length 166aa | (3776-4276)* | (4280-4284) | 189, 190 | ECF sigma factor T36644; 8e−26 | regulation |
| ORF5 length 280aa | (4526-5368)* | | 191, 192 | Membrane protein CAB94598.1; 5e−50 | unknown |
| ORF6 length 251aa | (5392-6147)* | (6152-6156) | 193, 194 | rRNA methyltransferase AAG32067.1; 4e−49 | resistance |
| ORF7 length 362aa | (6194-7282)* | | 195, 196 | O-methyl transferase PP42712; 4e−59 | modification |
| ORF8 length 284aa | (7280-8133) | (8141-8145) | 197, 198 | unknown | unknown |
| ORF9 length 354aa | (8254-9318) | (9324-9328) | 199, 200 | oxidoreductase AAG05128.1; 3e−51 | modification |
| ORF10 length 309aa | (9575-10,504) | (9568-9571) | 201, 202 | unknown | unknown |
| ORF11 Length 333aa | (10,584-11,585) | | 203, 204 | deoxyhexose ketoreductase T17473; 1e−49 | sugar modification |

Legend for Tables 1a and 1b
*CDS, RBS complement on full length biosynthetic locus sequence
[1] CDS is then putative coding sequence.
[2] RBS is the putative ribosome binding site.
[3] GenBank protein database (www.ncbi.nih.gov/Entrez/protein.html)
[4] The first number corresponds to the nucleotide sequence and the second number corresponds to the amino acid sequence.

Although the term "enzymes" is used to refer to the EV biosynthetic pathway gene products, such gene products may be proteins with non-enzymatic functions. Such proteins are also contemplated as falling within the scope of the present invention.

An "EV biosynthetic pathway bottleneck gene" is a gene encoding a product whose level limits the rate of synthesis of everninomicin. Examples of such gene products include, though are not limited to, evrJ (involved in orsellinic acid biosynthesis); evrV, evrW, and evrX (involved in dTDP-glucose synthesis); evbD (involved in malonyl-CoA-synthesis, which is required for orsellinic acid synthesis); and oxidases responsible for oxidation of the amino group on the terminal sugar to produce everninomicin that contains a nitrososugar group. Other likely bottleneck genes include those encoding glycosyltransferases (evdD, evdF, evdH, evdL, and evrS) and tailoring enzymes, particularly sugar modification enzymes.

A modified *Micromonaspora carbonacea* refers to a microorganisms that has been genetically engineered to overexpress or suppress expression of an EV biosynthetic pathway gene product (enzyme). Such genetic engineering and manipulation is described in detail, infra. Preferably, to increase the level of production of everninomicin, the modified microorganism overexpresses one or more bottleneck genes. To produce an everninomicin analog or homolog, various tailoring enzyme genes (e.g., evdB, a hexose aminotransferase that produces an amino sugar; evrF, a nonheme halogenase that chlorinates the orsinillic acid; or an oxidase gene that produces a nitrososugar by oxidation of an aminosugar) may be knocked out. Other knock-outs may be made of putative key genes, resulting in all likelihood in blockage of everninomicin biosynthesis. These include the orsellinic acid synthase (evrJ), dTDP-glucose synthases (evrV, evrW, and evrX), and glycosyltransferases (evdD, evdF, evdH, evdL, and evrS). A knockout of the glycosyltransferase that adds the terminal glycosyl group is expected to produce an everninomicin analog lacking the terminal glycosyl group.

Such genetic construction can be replicated in a different actinomycete, such as a *Streptomyces*, as described infra, by introduction of all or part of the modified everninomicin biosynthetic pathway described here into such a host cell.

A *Micromonospora carbonacea* "everninomicin biosynthetic pathway resistance gene product" is a protein or enzyme that confers resistance to everninomicin (and related compounds) to a host cell. Expression of such a gene on a vector provides an alternative selection mechanism for transformed host cells in vitro or in vivo, and thus can be used in molecular biological manipulations of cells independently of the EV biosynthetic pathway. For example, such a vector can be used to select for a transfected or transformed host cell by culturing the cell in the presence of an amount of everninomicin that is toxic to the host cell lacking the vector.

A *Micromonospora* site-specific Att/Int functions consist of an integrase protein and AttP site, e.g., as depicted in FIG. 7B (SEQ ID NO: 177) and in a specific embodiment encoded by a nucleic acid having a sequence as depicted in FIG. 7B (SEQ ID NO: 176), that permits site-specific integration of a vector into an actinomyce, and particularly a *Micromonospera*, genome.

GENERAL DEFINITIONS

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other to proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, especially in biological systems, the term "about" means within about a log (i.e., an order of magnitude) preferably within a factor of two of a given value, depending on how quantitative the measurement.

The use of italics indicates a nucleic acid molecule (e.g., *enrJ* cDNA, gene, etc.); normal text indicates the polypeptide or protein.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when the encoded polypeptides are at least 35-40% similar as determined by one of the algorithms disclosed herein, preferably at least about 60%, and most preferably at least about 90 or 95% in a highly conserved domain, or, for alleles, across the entire amino acid sequence. Sequence comparison algorithms include BLAST (BLAST P, BLAST N, BLAST X), FASTA, DNA Strider, the GCG (Genetics Computer Group, Program Manual for the GCG Package, Version 7, Madison, Wis.) pileup program, etc. using the default parameters provided with these algorithms. An example of such a sequence is an allelic or species variant of the specific everninomicin biosynthetic genes of the invention. Sequences that are substantially homologous can be identified by comparing the sequences using standard software available in sequence data banks, or in a Southern hybridization experiment under, for example, stringent conditions as defined for that particular system.

Cloning and Expression of EV Biosynthetic Pathway Genes

The present invention contemplates analysis and isolation, and/or construction, of a gene encoding a functional or mutant EV biosynthetic enzyme, including a full length, or naturally occurring form of an EV biosynthetic enzyme, and any antigenic fragments thereof from any source. It further contemplates expression of functional or mutant EV biosynthetic enzyme protein for evaluation, diagnosis, or, particularly, biosynthesis of everninomicin or other secondary metabolic products.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et al. (eds.), *Current Protocols in Molecular Biology*, John Wiley & Sons, Inc. (1994).

Molecular Biology-Definitions

"Amplification" of DNA, as used herein, denotes the use of polymerase chain reaction (PCR) to increase the concentration of a particular DNA sequence within a mixture of DNA sequences. For a description of PCR see Saiki et al., Science, 239:487, 1988.

A "nucleic acid molecule" refers to the phosphate ester polymeric form of ribonucleosides (adenosine, guanosine, uridine or cytidine; "RNA molecules"); or deoxyribonucleosides (deoxyadenosine, deoxyguanosine, deoxythymidine, or deoxycytidine; "DNA molecules"); or any phosphoester analogs thereof, such as phosphorothioates and thioesters, in either single stranded form, or a double-stranded helix; or "protein nucleic acids" (PNA) formed by conjugating bases to an amino acid backbone; or nucleic acids containing modified bases, for example thiouracil, thio-guanine and fluorouracil. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide (although only sense stands are being represented herein). This includes single- and double-stranded molecules, i.e., DNA-DNA, DNA-RNA and RNA-RNA hybrids.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Furthermore, the polynucleotides herein may also be oligonucleotides modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a minimum nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG, though as shown herein, alternative start codons can be used) and a stop codon.

The term "gene", also called a "structural gene" means a DNA sequence that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including a 5'-untranslated region (UTR) and 3'-UTR, as well as the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control of" or "operably (or operatively) associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a heterologous nucleic acid into a host cell. The term "transformation" means the introduction of a heterologous gene, DNA or RNA sequence to a host cell, so that the host cell will express the introduced gene or sequence to produce a desired product. The introduced gene or sequence may also be called a "cloned" or "heterologous" gene or sequence, and may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which heterologous DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra. In a preferred aspect, a host cell of the invention is an actinomycete, preferably of the genus Streptomyces (e.g., a host cell as described in Ziermann and Betlach, BioTechniques, 1999, 26:106) or alternatively Micromonospera. Additional examples include, but are not limited to, the strains S. pristinaespiralis (ATCC 25486), S. antibioticus (DSM 40868), S. bikiniensis (ATCC 11062), S. parvulus (ATCC 12434), S. glauescens (ETH 22794), S. actuosus (ATCC 25421), S. coelicolor (A3(2)), S. ambofaciens, S. lividans, S. griseofuscus, S. limosus, and the like (see also Smokvina et al., Proceedings, 1:403-407).

The term "expression system" means a host cell and compatible vector under suitable conditions, e.g., for the expression of a protein coded for by foreign DNA carried by the vector and introduced to the host cell. Common expression systems include E. coli host cells and plasmid vectors, although the actinomycte host cell expression systems are preferred for biosynthesis of everninomicin and related products.

The term "heterologous" refers to a combination of elements not naturally occurring. For example, heterologous DNA refers to DNA not naturally located in the cell, or in a chromosomal site of the cell. A heterologous gene is a gene in which the regulatory control sequences are not found naturally in association with the coding sequence. In the context of the present invention, an EV biosynthetic enzyme gene is heterologous to the vector DNA in which it is inserted for cloning or expression, and it is heterologous to a host cell containing such a vector, in which it is expressed, e.g., a K562 cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}P$-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of EV biosynthetic enzyme, or to detect the presence of nucleic acids encoding EV biosynthetic enzyme. In a further embodiment, an oligonucleotide of the invention can form a triple helix with a EV biosynthetic enzyme DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

EV Biosynthetic Pathway Nucleic Acids

A gene encoding EV biosynthetic enzyme can be isolated from any everninomicin-producing Micromonospora source. Methods for obtaining EV biosynthetic enzyme gene are well known in the art, as described above (see, e.g., Sambrook et al., 1989, supra). The DNA may be obtained by standard procedures known in the art from cloned DNA, by chemical synthesis, by cDNA cloning, or by the cloning of genomic DNA (e.g., DNA having a sequence as deposited with the ATCC and accorded accession no. 39149), or fragments thereof, purified from the desired cell (see, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene can be molecularly cloned into a suitable vector for propagation of the gene. Identification of the specific DNA fragment containing the desired EV biosynthetic enzyme gene may be accomplished in a number of ways. For example, a portion of an EV biosynthetic enzyme gene exemplified infra can be purified and labeled to prepare a labeled probe, and the generated DNA may be screened by nucleic acid hybridization to the labeled probe (Benton and Davis, Science, 1977, 196:180; Grunstein and Hogness, Proc. Natl. Acad. Sci. U.S.A., 1975, 72:3961). Those DNA fragments with substantial homology to the probe, such as an allelic variant from another species, will hybridize. In a specific embodiment, highest stringency hybridization conditions are used to identify a homologous EV biosynthetic enzyme gene.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of EV biosynthetic enzyme protein as disclosed herein. Thus, the presence of the gene may be detected by assays based on the physical, chemical, immunological, or functional properties of its expressed product.

Other DNA sequences which encode substantially the same amino acid sequence as an EV biosynthetic enzyme gene may be used in the practice of the present invention. These include but are not limited to allelic variants, species variants, sequence conservative variants, and functional variants.

The genes encoding EV biosynthetic enzyme derivatives and analogs of the invention can be produced by various methods known in the art. The manipulations which result in their production can occur at the gene or protein level. For example, the cloned EV biosynthetic enzyme gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of EV biosynthetic enzyme, care should be taken to ensure that the modified gene remains within the same translational reading frame as the EV biosynthetic enzyme gene, uninterrupted by translational stop signals, in the gene region where the desired activity is encoded, unless the gene will be used to knock-out or disrupt an endogenous EV biosynthetic enzyme.

Additionally, the EV biosynthetic enzyme-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Such modifications can also be made to introduce restriction sites and facilitate cloning the EV biosynthetic enzyme gene into an expression vector. Any technique for mutagenesis known in the art can be used, including but not limited to, in vitro site-directed mutagenesis (Hutchinson, C., et al., J. Biol. Chem., 1978, 253:6551; Zoller and Smith, DNA, 1984, 3:479-488; Oliphant et al., Gene 1986, 44:177; Hutchinson et al., Proc. Natl. Acad. Sci. U.S.A., 1986, 83:710), use of TAB linkers (Pharmacia), etc. PCR techniques are preferred for site directed mutagenesis (see Higuchi, "Using PCR to Engineer DNA", in *PCR Technology: Principles and Applications for DNA Amplification*, H. Erlich, ed., Stockton Press, 1989, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Finally, the vector may include a fusion polypeptide sequence such that the construct with the EV biosynthetic enzyme encodes a chimeric protein, such as a poly-histidine tag, FLAG tag, myc epitope tag, or some other such sequence for ease in purification.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired.

Expression of EV Biosynthetic Enzyme Polypeptides

The nucleotide sequence coding for EV biosynthetic enzyme, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, a nucleic acid encoding EV biosynthetic enzyme of the invention can be operationally associated with a promoter in an expression vector of the invention. Such vectors can be used to express functional or functionally inactivated EV biosynthetic enzyme polypeptides.

The necessary transcriptional and translational signals can be provided on a recombinant expression vector.

Expression of EV biosynthetic enzyme protein may be controlled by any promoter/enhancer element known in the art, but these regulatory elements must be functional in the host selected for expression. Promoters which may be used to control EV biosynthetic enzyme gene expression include, but are not limited to, prokaryotic expression vectors such as the β-lactamase promoter (Villa-Komaroff, et al., Proc. Natl. Acad. Sci. U.S.A., 1978, 75:3727-3731), or the tac promoter (DeBoer, et al., Proc. Natl. Acad. Sci. U.S.A., 1983, 80:21-25; see also "Useful proteins from recombinant bacteria" in Scientific American, 242:74-94, 1980). Among regulable promoters which can be used in the context of the present invention, mention may be made more especially of any regulable promoter which is functional in actinomycetes. These can comprise promoters induced specifically by an agent introduced into to the culture medium, such as, for example, the thiostrepton-inducible promoter tipA (Murakami et al., J. Bact., 1989, 171:1459), or thermoinducible promoters such as that of the groEL genes, for example (Mazodier et al., J. Bact., 1991, 173:7382). They can also comprise an actinomycetes promoter which is specifically active in the late phases of the proliferation cycle of actinomycetes, such as, for example, certain promoters of genes of the secondary metabolism (genes for the production of antibiotics, in particular).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Antibodies to EV Biosynthetic Enzymes

According to the invention, any EV biosynthetic enzyme polypeptide produced recombinantly or by chemical synthesis, and fragments or other derivatives or analogs thereof, including fusion proteins, may be used as an immunogen to generate antibodies that recognize the EV biosynthetic enzyme polypeptide. Such antibodies include but are not limited to polyclonal, monoclonal, chimeric, single chain, Fab fragments, and an Fab expression library. The anti-EV biosynthetic enzyme antibodies of the invention may be cross reactive, e.g., they may recognize EV biosynthetic enzyme from different species. Polyclonal antibodies have greater likelihood of cross reactivity. Alternatively, an antibody of the invention may be specific for a single form of EV biosynthetic enzyme, such as murine EV biosynthetic enzyme. Preferably, such an antibody is specific for human EV biosynthetic enzyme.

Various procedures known in the art may be used for the production of polyclonal antibodies to EV biosynthetic enzyme polypeptide or derivative or analog thereof. For the production of antibody, various host animals can be immunized by injection with the EV biosynthetic enzyme polypeptide, or a derivative (e.g., fragment or fusion protein) thereof, including but not limited to rabbits, mice, rats, sheep, goats, etc. In one embodiment, the EV biosynthetic enzyme polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the EV biosynthetic enzyme polypeptide, or fragment, analog, or derivative thereof, any technique that provides for the production of antibody molecules by continuous cell lines in culture may be used. These include but are not limited to the hybridoma technique originally developed by Kohler and Milstein (Nature, 1975, 256:495-497), as well as the trioma technique, the human B-cell hybridoma technique (Kozbor et al., Immunology Today, 1983, 4:72; Cote et al., Proc. Natl. Acad. Sci. U.S.A., 1983, 80:2026-2030), and the EBV-hybridoma technique to produce human monoclonal antibodies (Cole et al., in Monoclonal Antibodies and Cancer Therapy, Alan R. Liss, Inc., 1985, pp. 77-96).

According to the invention, techniques described for the production of single chain antibodies (U.S. Pat. Nos. 5,476, 786 and 5,132,405 to Huston; U.S. Pat. No. 4,946,778) can be adapted to produce EV biosynthetic enzyme polypeptide-specific single chain antibodies. Indeed, these genes can be delivered for expression in vivo. An additional embodiment of the invention utilizes the techniques described for the construction of Fab expression libraries (Huse et al., Science, 1989, 246:1275-1281) to allow rapid and easy identification of monoclonal Fab fragments with the desired specificity for an EV biosynthetic enzyme polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an EV biosynthetic enzyme polypeptide, one may assay generated hybridomas for a product which binds to an EV biosynthetic enzyme polypeptide fragment containing such epitope. For selection of an antibody specific to an EV biosynthetic enzyme polypeptide from a particular species of animal, one can select on the basis of positive binding with EV biosynthetic enzyme polypeptide expressed by or isolated from cells of that species of animal.

The foregoing antibodies can be used in methods known in the art relating to the localization and activity of the EV biosynthetic enzyme polypeptide, e.g., for Western blotting, imaging EV biosynthetic enzyme polypeptide in situ, measuring levels thereof in appropriate physiological samples, etc. using any of the detection techniques mentioned above or known in the art.

In a specific embodiment, antibodies that agonize or antagonize the activity of EV biosynthetic enzyme polypeptide can be generated. Such antibodies can be tested using the assays described infra for identifying ligands.

Techniques of isolating bacterial DNA are readily available and well known in the art. Any such techniques can be employed in this invention. In particular DNA from these deposited cultures can be isolated as follows. Lyophils of *E. coli* XL1-Blue/pSPRX272, *E. coli* XL1-Blue/pSPRX2262, *E. coli* XL1-Blue/pSPR192, *E. coli* XL1-Blue/pSPRX210 or *E. coli* XL1-Blue/pSPRX256 are plated onto L-agar (10 g tryptone, 10 g NaCl, 5 g yeast extract, and 15 g agar per liter) plates containing 100 µg/ml ampicillin to obtain a single colony isolate of the strain. This colony is used to inoculate about 500 ml of L-broth (10 g tryptone, 10 g NaCl, 5 g yeast extract per liter) containing 100 µg/ml apramycin, and the resulting culture is incubated at 37° C. with aeration until the cells reach stationary phase. Cosmid DNA can be obtained from the cells in accordance with procedures known in the art (see, e.g., Rao et al., Methods in Enzymology, 1987, 153: 166).

DNA of the current invention can be sequenced using any known techniques in the art such as the dideoxynucleotide chain-termination method (Sanger et al., Proc. Natl. Acad. Sci., 1977, 74:5463) with either radioisotopic or fluorescent labels. Double-stranded, supercoiled DNA can be used directly for templates in sequence reactions with sequence-specific oligonucleotide primers. Alternatively, fragments can be used to prepare libraries of either random, overlapping sequences in the bacteriophage M13 or nested, overlapping deletions in a plasmid vector. Individual recombinant DNA subclones are then sequenced with vector-specific oligonucleotide primers. Radioactive reaction products are electrophoresed on denaturing polyacrylamide gels and analyzed by autoradiography.

Fluorescently labeled reaction products are electrophoresed and analyzed on Applied Biosystems (ABI Division, Perkin Elmer, Foster City, Calif. 94404) model 370A and 373A or Dupont (Wilmington, Del.) Genesis DNA sequencers. Sequence data are assembled and edited using Genetic Center Group (GCG, Madison, Wis.) programs GelAssemble and Seqed or the ABI model 670 Inherit Sequence Analysis system and the AutoAssembler and SeqEd programs.

Polypeptides corresponding to a domain, a submodule, a module, a synthesis unit (SU), or an open reading frame can be produced by transforming a host cell such as bacteria, yeast, or eukaryotic cell-expression system with the cDNA sequence in a recombinant DNA vector. It is well within one skilled in the art to choose among host cells and numerous recombinant DNA expression vectors to practice the instant invention. Multifunctional polypeptides of polyketide everninomicin synthase can be extracted from everninomicin-producing bacteria such as *Streptomyces ambofaciens* or translated in a cell-free in vitro translation system. In addition, the techniques of synthetic chemistry can be employed to synthesize some of the polypeptides mentioned above.

Procedures and techniques for isolation and purification of proteins produced in recombinant host cells are known in the art. See, for example, Roberts et al., Eur. J. Biochem., 1993, 214: 305-311 and Caffrey et al., FEBS, 1992, 304:225-228 for detailed description of polyketide synthase purification in bacteria. To achieve a homogeneous preparation of a polypeptide, proteins in the crude cell extract can be separated by size and/or charge through different columns well known in the art once or several times. In particular the crude cell extract can be applied to various cellulose columns commercially available such as DEAE-cellulose columns. Subsequently the bound proteins can be doted and the fractions can be tested for the presence of the polyketide everninomicin synthase or engineered derivative protein. Techniques for detecting the target protein are readily available in the art. Any such techniques can be employed for this invention.

In particular the fractions can be analyzed on Western blot using antibodies raised against a portion or portions of such polyketide everninomicin synthase proteins. The fractions containing the polyketide everninomicin synthase protein can be pooled and further purified by passing through more columns well known in the art such as applying the pooled fractions to a gel filtration column. When visualized on SDS-PAGE gels homogeneous preparations contain a single band and are substantially free of other proteins.

Actinomycetes are prolific producers of secondary metabolites with antimicrobial and antifungal activity and represent a significant source of active compounds for pharmaceuticals. The genus *Streptomyces* produces a wide variety of secondary metabolites including antitumor, antifungal, and antimicrobial agents. The biosynthesis of these compounds has been shown to be directed by large multi-functional proteins or a number of proteins each catalyzing specific steps in the biosynthesis of the secondary metabolite (REF—Biotechnology of AB etc.) The genes encoding actinomycete secondary metabolite biosynthesis have been found to be clustered on contiguous segments of each producing organisms genome (Strohl, William R., 1997, Biotechnology of Antibiotics, $2^{nd}$ Ed., Marcel Dekker, Inc., New York, N.Y.). This makes it feasible for complete pathways to be cloned, analyzed, genetically manipulated and expressed in surrogate hosts.

Components of The Everninomicin Biosynthethic Pathway

Orsellinic Acid Biosynthesis

The term "polyketide" refers to a class of molecules produced through the successive condensation of small carboxylic acids. This diverse group includes plant flavonoids, fungal aflatoxins, and hundreds of compounds of different structures that exhibit antibacterial, antifungal, antitumor, and anthelmintic properties. Some polyketides produced by fungi and bacteria are associated with sporulation or other developmental pathways; others do not yet have an ascribed function. Some polyketides have more than one pharmacological effect. The diversity of polyketide structures reflects the wide variety of their biological properties. Many cyclized polyketides undergo glycosidation at one or more sites, and virtually all are modified during their synthesis through hydroxylation, reduction, epoxidation, etc.

For the purposes of the present invention, "polyketide" refers to the orsellenic acid moiety in everninomicin. Thus, the invention provides, in particular, the DNA sequence encoding the polyketide synthase responsible for biosynthesis of this orsellinic acid moiety of everninomicin, i.e., the everninomicin orsellinic acid synthetase. The everninomicin orsellinic acid synthase DNA sequence, which defines the orsellinic synthase gene cluster, directs biosynthesis of the orsellinic acid polyketide by encoding the various distinct activities of orsellinic synthase. The skilled artisan recognizes, however, that the everninomicin orsellinic synthase genes are useful in the production of other polyketides, e.g., by recapitulating all or part of this component of the biosynthetic pathway, or by modulating biosynthetic pathways to (see, the discussion about combinatorial biosynthesis, infra).

Figure 4A:
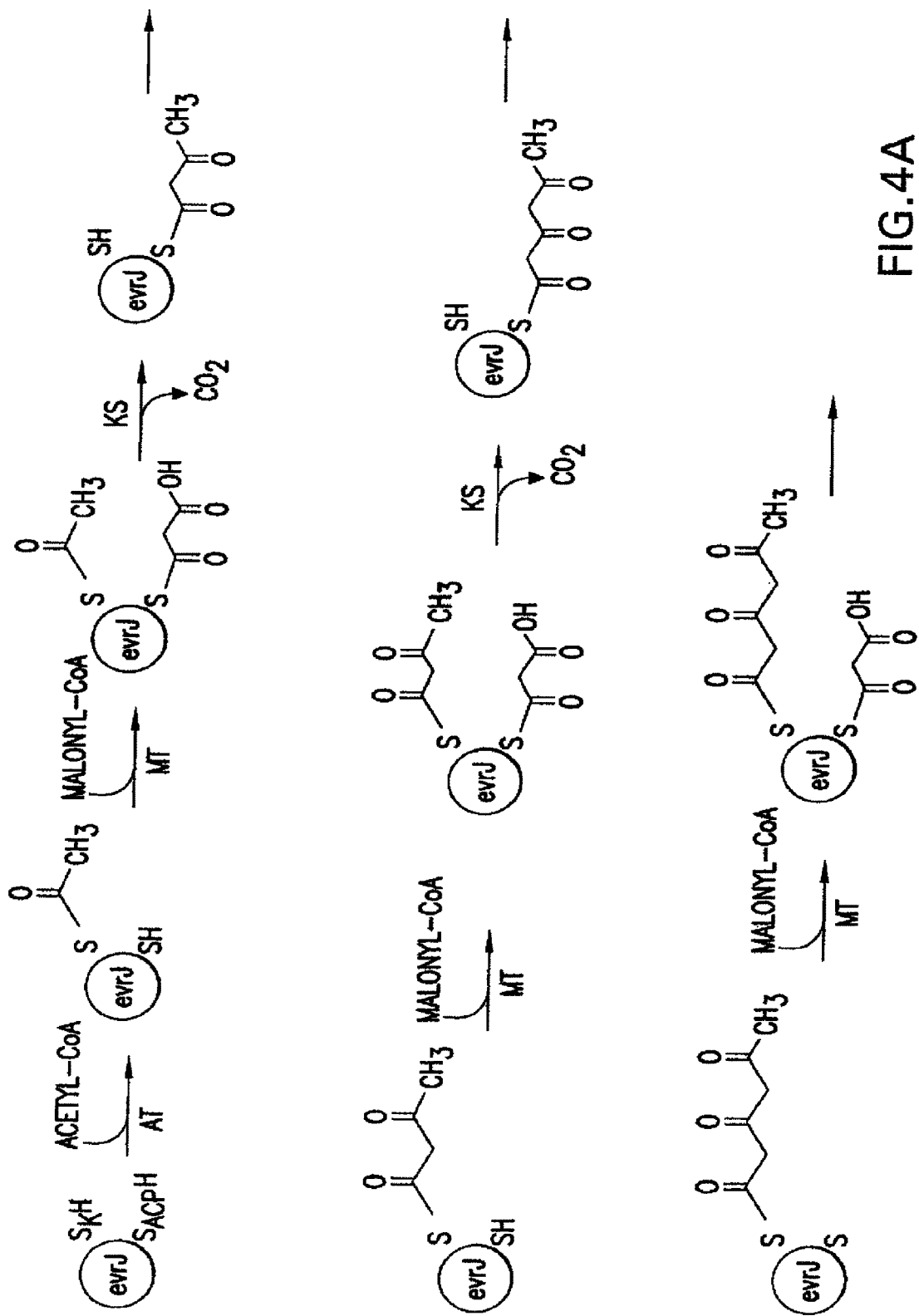
Figure 4B:
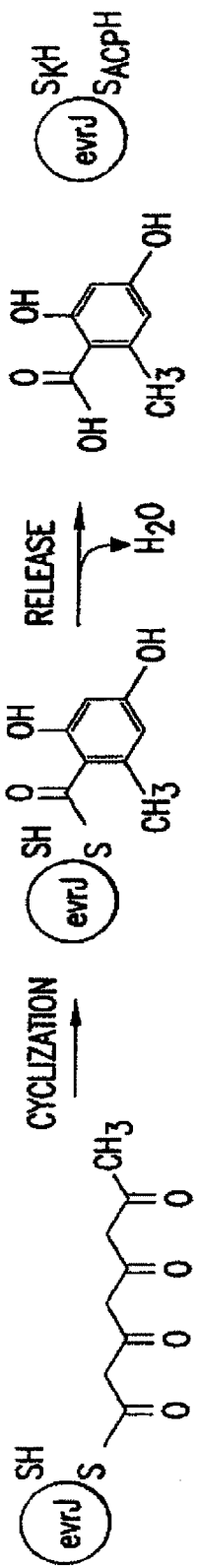
Figure 5:
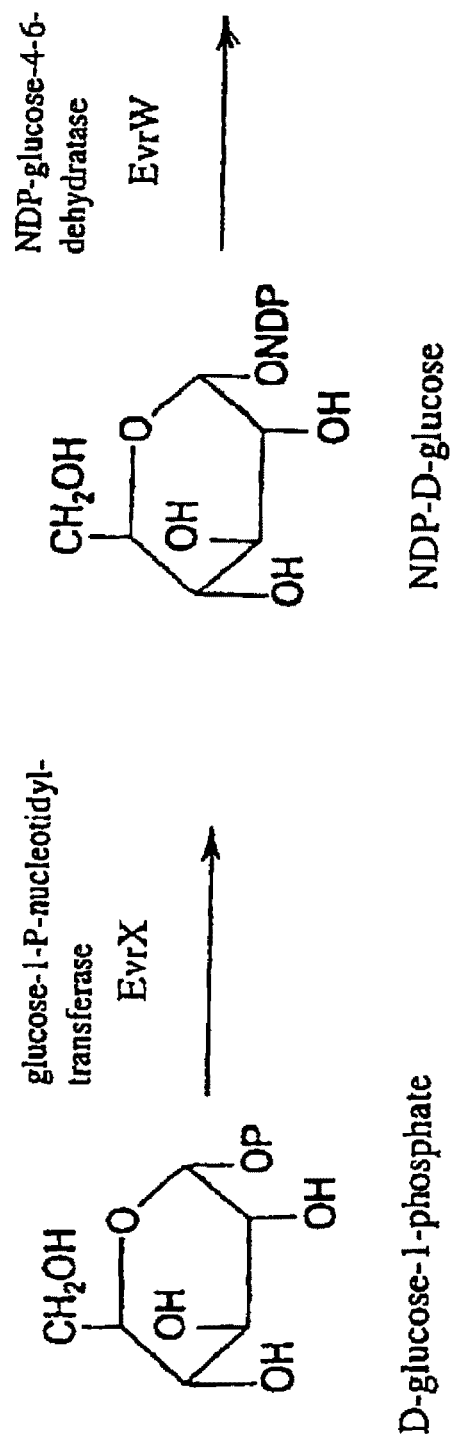

The gene cluster for orsellinic synthase, like other Type I polyketide biosynthetic synthase genes whose organization has been elucidated, is characterized by the presence of an ORF encoding a multi-functional protein which contains separate, active sites for condensation of acyl groups as defined above. The map of the orsellinic synthase gene derived from *Micromonospora carbonacea* var. *africana* is shown in FIG. 3. The accompanying synthetic pathway and the specific carboxylic acid substrates that are used for each condensation of orsellinic acid synthesis are indicated in FIG. 4.

Polyketides are complex secondary metabolites synthesized from the condensation of acetyl-coenzyme A (CoA) or related acyl-CoAs by polyketide synthetase enzymes. Other acyl groups forming the acyl-CoA include malonyl, proponyl, and butyryl. Condensation of extender units requires the action of β-ketoacyl ACP synthetase, acetyltransferase and acyl carrier protein enzymatic sites. Each module processes one condensation step and typically requires several activities accomplished by several active sites including acyl carrier protein (ACP), β-ketosynthase (KS), and acyltransferase (AT). The specific gene products identified with orsellinic biosynthesis are listed in Table 2.

TABLE 2

Orsellinic Acid Biosynthetic Gene Products

| Gene Product | CDS | SEQ ID No. | Enzymatic Function |
|---|---|---|---|
| evrF | 21,064 ... 22,542 | 36, 37 | non-heme oxygenase/halogenase addition |
| evrI | 25,550 ... 26,626 | 42, 43 | acyl starter unit |
| evrJ | 26,685 ... 30,479 | 44, 45 | Orsellinic acid synthase/6-methylsalicilic acid synthase |
| evbD | 56,961 ... 58,709 | 92, 93 | acyl-CoA carboxylase |
| evbQ | 74,707 ... 76,290* | 122, 123 | Methylmalonyl-CoA mutase |

Polyketide synthetases are classified as either iterative Type I, iterative Type II or modular polyketide synthetases. Iterative Type I synthetases resemble the multifunctional fatty acid synthases from animals and are composed of multifunctional proteins with separate protein domains encoding each active sites. This is exemplified by the actinomycete *S. erythrea* polyketide synthetase for the biosynthesis of erythromycin, the *Streptomyces viridochromogenes* Tu57 AviM synthesis of orsellinic acid and the *Penicillium patulum* polyketide synthase for 6-methylsalicylic acid (Hutchinson et al., Annual Review of Microbiology, 1995, 49:201-238; Gaisser et al., Journal of Bacteriology, 1997, 179:6271-6278; Beck et al., European Journal of Biochemistry, 1990, 192: 487-498). Iterative type II synthetases have separate proteins for each active site. These are exemplified by the polyketide synthetases from *S. coelicolor, S. violaceoruber* and *S. glaucescens* synthesizing the aromatic polyketides actinorhodin, granaticin and tetracenomycin respectively (Hopwood, et al., Annual Review of Microbiology 1990, 24:37-66). The modular polyketide synthetases are large proteins that contain several domains with each domain containing several active sites. An example of a modular polyketide synthetase is the 6-deoxyerythronolide B synthetase from *Saccharopolyspora erythraea*. Recent reviews of polyketides and polyketide synthetases elaborate on these pathways (Hopwood, et al., Annual Review of Microbiology, 1990, 24:37-66; Hutchinson et al., Annual Review of Microbiology, 1995, 49:201-238).

Although not wishing to be bound to any particular theory or technical explanation, a sequence similarity exists among domain boundaries in various polyketide synthase genes. Thus, one skilled in the art is able to predict the domain boundaries of newly discovered polyketide synthase genes based on the sequence information of known polyketide synthase genes. In particular, the boundaries of submodules, domains, and open reading frames in the instant application are predicted based on sequence information disclosed in this application and the locations of the domain boundaries of the everninomicin synthase (Donadio et al., GENE, 1992, 111: 51-60). Furthermore, the genetic organization of the everninomicin synthase gene cluster appears to correspond to the order of the reactions required to complete synthesis of everninomicin. This means that the polyketide synthase DNA sequence can be manipulated to generate predictable alterations in the final everninomicin product.

Acyl Precursor Formation

EvrJ (orsellinic acid synthetase) requires one acetyl-CoA starter and three malonyl-CoA extender units to synthesize orsellinic acid. The acetyl-CoA and malonyl-CoA units most likely are derived from glycolysis and fatty acid biosynthesis (Tang L, et al., Ann. N Y Acad. Sci., 1994, 721:105-16). The malonyl-CoA can also be derived from acetyl-CoA by carboxylation by acetylCoA carboxylase, (Scott Eagleson, Concise Encyclopedia of Biochemistry, $2^{nd}$ Ed., Walter de Gruyler; Berlin, 1988). The *M. carbonacea* EV region contains an evbD which has strong homology to know acetyl-CoA carboxylases. Thus evbD is responsible for the synthesis of the malonyl-CoA unit required for orsellinic acid biosynthesis as shown in FIG. 4.

Sugar Biosynthetic Products and Glycosyltransferases

Glycosyl groups (6-deoxysugars) are synthesized by a common mechanism involving hexose-1-P nucleotidyltransferase, dTDP-D-glucose synthetase and dTDP-D-glucose 4,6-dehydratase. L-deoxysugars are synthesized by the action of a NDP-4-keto-6-deoxyhexose 3,5-epimerase. Deoxysugars can be modified by deoxygenations, transaminations, methylations and isomerization or epimerizations prior to covalent attachment by a glycosytransferase.

Biosynthesis of the sugars (see Liu and Thorson, Annu. Rev. Microbiol., 1994, 48:223) that are attached to the orsellinic acid/polyketide, and the enzymes that mediate attachment of the sugars, are also key elements of the everninomicin biosynthetic pathway. Genes encoding such sugar biosynthetic enzymes and glycosyltransferases are typically found in the biosynthetic pathway locus (see Summers et al., Microbiology, 1997, 143:3251). The genes identified from the EV biosynthetic locus are listed in Tables 3 and 4.

TABLE 3

Sugar Biosynthetic Gene Products

| Gene Product | CDS | SEQ ID No. | Enzymatic Function |
|---|---|---|---|
| evdA | 132 ... 1382* | 2, 3 | Hydroxylase |
| evdB | 1490 ... 2611* | 4, 5 | hexose aminotransferase |
| evdC | 2622 ... 3860* | 6, 7 | oxidase (flavoprotein) |
| evdE | 5309 ... 6235 | 10, 11 | hexose dehydratase |
| evdI | 9463 ... 10,224* | 18, 19 | Hydrolase |
| evdK | 11,208 ... 12,455 | 22, 23 | hexose dehydratase or epimerase |
| evrA | 14,410 ... 15,363* | 26, 27 | hexose epimerase |
| evrB | 15,380 ... 16,414* | 28, 29 | hexose oxidoreductase |
| evrC | 16,419 ... 17,873* | 30, 31 | hexose dehydratase |
| evrD | 17,870 ... 18,934* | 32, 33 | GDP-mannose 4,6-dehydratase |
| evrV | 41,679 ... 42,707* | 68, 69 | dTDP-glucose epimerase |
| evrW | 42,810 ... 43,799* | 70, 71 | dTDP-glucose dehydratase |
| evrX | 43,799 ... 44,866 | 72, 73 | dTDP-glucose synthetase |
| evbS | 78,791 ... 80,521 | 126, 127 | Phosphomannomutase |
| evbU | 83,280 ... 83,888 | 130, 131 | Glucose-6-phosphate 1-dehydrogenase |
| ORF9 | 8254 ... 9318 | 199, 200 | Oxidoreductase |
| ORF11 | 10,584 ... 11,585 | 203, 204 | Deoxyhexose ketoreductase |

TABLE 4

Glycosyltransferases

| Gene Product | CDS | SEQ ID No. | Enzymatic Function |
|---|---|---|---|
| evdD | 4143 ... 5312 | 8, 9 | DNTP-hexose glycosyltransferase |
| evdF | 6232 ... 7275 | 12, 13 | DNTP-hexose glycosyltransferase |
| evdH | 8342 ... 9364 | 16, 17 | DNTP-hexose glycosyltransferase |
| evdL | 12,108 ... 13,022* | 24, 25 | DNTP-hexose glycosyltransferase |
| evrS | 38,892 ... 40,163* | 62, 63 | DNTP-hexose glycosyltransferase |

These genes are important targets for modulation. They are likely to be bottleneck genes, and thus increased expression using an exogenous or integrating vector can increase the yield of everninomicin (or its analog). Alternatively, knocking out these genes may result in complete elimination of everninomicin biosynthesis.

Tailoring Enzymes

Various types of EV biosynthetic enzymes fall into the tailoring enzyme category. These are listed in Table 5. Increasing or decreasing expression of these enzymes permits production of everninomicin analogs. Moreover, expression of these enzymes in other actinomycetes permits production of novel secondary metabolites by the action of the everninomicin tailoring enzymes on these metabolites.

TABLE 5

Tailoring Gene Products

| Gene Product | CDS | SEQ ID No. | Enzymatic Function |
|---|---|---|---|
| evrG | 22,748 ... 24,172 | 38, 39 | oxidase |
| evrL | 31,941 ... 32,882* | 48, 49 | heme biosynthesis |
| evrM | 33,167 ... 34,405* | 50, 51 | p450 hydroxylase |
| evrN | 34,449 ... 35,210* | 52, 53 | methyl transferase |
| evrQ | 36,998 ... 38,026* | 58, 59 | oxidoreductase/heat stress protein |
| evrT | 40,216 ... 40,890 | 64, 65 | L-proline hydroxylase |
| evrU | 40,887 ... 41,576 | 66, 67 | methyltransferase |
| evbA | 53,554 ... 54,207 | 84, 85 | o-methyltransferase |
| evbE | 58,873 ... 60,312 | 94, 95 | IMP dehydrogenase |
| evbI | 66,469 ... 67,872* | 106, 107 | lipoamide dehydrogenase |
| evbL | 69,610 ... 70,359* | 112, 113 | acetyltransferase/phosphotransferase |
| evbX | 85,909 ... 87,342 | 136, 137 | aldehyde dehydrogenase |
| evbY | 87,422 ... 88159 | 138, 139 | aldehyde dehydrogenase |
| evcB | 89,817 ... 91,067 | 144, 145 | cytochrome D oxidase subunit I |
| evcC | 91,078 ... 92,085 | 146, 147 | cytochrome D oxidase subunit II |

Regulatory Products

Serine-Threonine Kinases

Protein serine (Ser), threonine (Thr), and tyrosine (Tyr) kinases play essential roles in signal transduction in organisms ranging from yeast to mammals, where they regulate a diverse cellular activities. Genes that encode eukaryotic-type protein kinases have also been identified in different bacterial species, suggesting that such enzymes are also widespread in prokaryotes. Although many of them have yet to be fully characterized, several studies indicate that eukaryotic-type protein kinases play important roles in regulating cellular activities of these bacteria, such as cell differentiation and secondary metabolism (Cheng-Cai, Molecular Microbiology, 1996, 20:9-15). Examples that have been studied include the pknD Ser/Thr kinase from *Anabaena* sp. PCC7120, which is involved in nitrogen metabolism control (Zhang et al., Molecular and General Genetics, 1998, 258:26-33); the pkn9 Ser/Thr kinase from *Myxococcus xanthus*, which is involved in development of fruiting bodies (Hanlon et al., Molecular Microbiology, 1997, 23:459-71); and the afsK Ser/Thr kinase from *Streptomyces coelicolor*, which is involved in aerial myceliaum formation (Ueda et al., Gene, 1996, 169:91-95). These genes from the EV biosynthetic locus are listed in Table 6.

TABLE 6

Regulatory Gene Products

| Gene Product | CDS | SEQ ID No. | Enzymatic Function |
|---|---|---|---|
| evrR | 38,072 ... 38,566 | 60, 61 | hexaheme nitrite reductase regulator/methyltransferase |
| evsA | 47,156 ... 49,234* | 78, 79 | serine-threonine kinase |
| evbF | 60,472 ... 61,029* | 96, 97 | |
| evbF2 | 61,610 ... 62,069 | 100, 101 | |
| evbK | 68,529 ... 69,494* | 110, 111 | protease synthase/sporulation regulator |
| evbR | 76,622 ... 78,712 | 124, 125 | protein serine-threonine kinase (eukaryotic type) |
| evcJ | 100,733 ... 101,326* | 160, 161 | ATP/GTP binding protein |
| ORF1 | 189 ... 1064* | 183, 184 | Transcriptional regulator biotinylation |
| ORF4 | 3776 ... 4276* | 189, 190 | ECF sigma factor |

The evsA and evbR proteins within the everninomicin cluster have a high degree of homology to Ser/Thr kinases and may play a role in regulating the expression of the pathway. Manipulation of the evsA and evbR proteins could enhance the expression and yield of everninomicin from *M. carbonacea* by providing positive signals for biosynthesis. Thus, these genes are preferred elements in a vector to enhance the efficiency of everninomicin biosynthesis.

Resistance Mechanisms

Actinomycetes utilize a variety or mechanisms to confer resistance to secondary metabolites they produce. These include membrane pumps, rRNA methylases, O-phosphorylation, N-acetylation, and production of resistant target proteins (Cundliffe, Annual Review of Microbiology, 1989, 43:207-33). The genes from the EV biosynthetic locus that have this function are listed in Table 7.

TABLE 7

| Resistance Mechanism Genes | | | |
|---|---|---|---|
| Gene Product | CDS | SEQ ID No. | Enzymatic Function |
| evrE | 19,374 . . . 20,906 | 34, 35 | multidrug eflux transporter |
| evrY | 45,014 . . . 45,760* | 74, 75 | dehalogenase |
| evrZ | 45,962 . . . 46,714* | 76, 77 | muramidase/lysozyme |
| evbB | 54,362 . . . 55,117* | 86, 87 | membrane pump |
| evbC | 55,135 . . . 56,094* | 88, 89 | membrane pump |
| evbC2 | 56,184 . . . 56,813* | 90, 91 | ankrylin-like |
| evbG | 62,122 . . . 63,795 | 102, 103 | ABC transporter |
| evbH | 63,891 . . . 65,828 | 104, 105 | ABC transporter |
| evcD | 92,148 . . . 93,833 | 148, 149 | ABC transporter |

TABLE 7-continued

Resistance Mechanism Genes

| Gene Product | CDS | SEQ ID No. | Enzymatic Function |
|---|---|---|---|
| evcE | 93,830 ... 95,671 | 150, 151 | ABC transporter |
| evrMR | 107,653 ... 108,615 | 172, 173 | 23S rRNA methylase |
| evrMR2 | 108,635 ... 109,216 | 174, 175 | |
| ORF6 | 5392 ... 6147* | 193, 194 | rRNA methyltransferase |

Multi-drug transporters are membrane proteins that are able to expel a broad range of toxic molecules from the microbial cells. These multidrug transporters belong to the ATP-binding cassette (ABC) family of transport proteins that utilize the energy of ATP hydrolysis for activity. In microorganisms, multidrug transporters play an important role in conferring antibiotic resistance on pathogens, and in actinomycetes confer resistance to the antibiotic secondary metabolites produced by these organisms themselves (Fath et al., Microbial Reviews, 1993, 57:995-1017). A second class of membrane transporters that are found in actinomycetes include MDR (multiple drug resistance) type pumps found in eukaryotes (Guilfoile et al., Proc. Natl. Acad. Sci. USA, 1991, 88:8553-8557). The EV cluster contains evbB and evbC, which are homologouse to the ATP-binding cassette (ABC) family of transport proteins and specifically to the mithramycin resistance pump from *Streptomyces argillaceus* (Fernandez et al., Molecular and General Genetics, 1996, 251:692-698). In addition the EV cluster contains evrE, an MDR type pump with homology to the *Streptomyces peucetius* drrA MDR type pump that confers resistance to daunorubicin. Ribosomal methylases have also been found to confer resistance to producing organisms. The tlrB 23S rRNA methylase from *Streptomyces fradiae* and the myrA 23S rRNA methylase from *Micromonospora griseorubida* have been found to confer resistance to tylosin and mycinamicin respectively.

The EV cluster also contains evrMR, a 23 RNA methylase with (loc.) homology to both tlrB and myrA.

The EV pathway also contains evrZ, a gene with homology to muramidases. Muramidases (lysozyme) cleave β1,4 linkages between N-acetylglucosamine and N-acetylmuramic acid (Scott and Eagleson, Concise Encyclopedia Biochemistry, 2$^{nd}$ Ed., Walter de Gruyter: Berlin, 1988 p. 353). Thus, evrZ may inactivate everninomicin by cleavage within the glycosyl bonds.

Increased levels of expression of one or more of these resistance genes is expected to enhance the efficiency of everninomicin biosynthesis in an enhanced biosynthetic system by reducing toxicity to the host cell.

Furthermore, these resistance genes are good candidates for use as positive selection markers in recombinant systems. By including an everninomicin resistance gene in a vector, a host cell successfully transformed with the vector will demonstrate everninomicin resistance. Thus, everninomicin becomes a useful tool for selecting transformed host cells.

Biosynthetic Production and Modification of Everninomicins

There are a number of uses for the cloned *Micromonospora carboonacea* EV cluster DNA. The cloned genes can be used to improve the yields of everninomicins and to produce novel everninomicins. Improved yields can be obtained by introduction of a second copies of genes for enzymes that are rate limiting in the pathway ("bottleneck genes"). This can be accomplished by cloning genes onto vectors, preferably integrating vectors, then obtaining integrants in the chromosome. Alternatively, a rate limiting enzyme gene can be modified by associating it with a strongly expressing promoter sequence and then integrating this construct into the chromosome. Manipulation of regulatory proteins including the Ser/Thr kinases can enhance yields by obtaining mutants that express EV pathway genes at higher levels than parental organisms.

Novel everninomicins can be produced by using cloned fragments to disrupt steps in the biosynthesis of everninomicin. Disruptions can lead to the accumulation of precursors or "shunt" products. To generate disruptions, DNA fragments of internal segments of genes (lacking 5' and 3' sequences) can be cloned into insertion vectors. These constructs can be introduced into the parental organism and homologous recombinants selected for that result in two copies of the gene in the chromosome. One copy lacks 3' sequences and the second copy lacks upstream native promoter sequences and 5' sequences. Alternatively, DNA fragments of genes containing internal deletions or insertions can be cloned into gene replacement vectors. Recombinants can be obtained that contain internal deletions or insertions of genes, which results in a non-functional chromosome copy of the gene. Constructs that allow a frequency of recombination into the chromosome to obtain disruptions should contain fragments of sufficient size for recombination to occur (300 to 600 bases). Modified everninomicins produced by disrupting the genes may be antibiotics themselves, or serve as substrates for further chemical modification, creating new semi-synthetic everninomicins with unique properties or spectra of activity.

Novel everninomicins can also be produced by mutagenesis of the cloned genes, and replacement of the mutated genes for their unmutated counterparts in the everninomicin producer. Mutagenesis may involve, for example, (1) manipulation of the orsellinic acid PKS TypeI gene by introduction of KR, DH or ER domains (see, Donidio et al., 1993), e.g., to yield a modified orsellenic acid nucleus; (2) manipulation of the glycosyltranferase to relax substrate or glycosyl specificity, e.g., to yield everninomicin containing novel glycosyl groups or additional glycosyl groups; and/or (3) manipulation of glycosyl biosynthetic genes, e.g., to yield novel glycosyl groups and everninomicin containing novel glycosyl groups.

The DNA from the everninomicin biosynthetic cluster can be used as a hybridization probe to identify homologous sequences. Thus, the DNA cloned here could be used to obtain uncloned regions flanking the region described here but not yet isolated. In addition DNA from the region cloned here may be useful in identification of non-identical but similar sequences in other organisms.

The modified strains provided by the invention may be cultivated to provide everninomicins using conventional protocols.

Genetic Manipulation of Actinomycetes

Protocols have been developed to genetically manipulate actinomycete genomes and biosynthetic pathways. These include *E. coli* actinomycete shuttle vectors, gene replacement systems, transformation protocols, transposon mutagenesis, insertional mutagenesis, integration systems and heterologous host expression. These techniques are reviewed in numerous articles (Baltz et al., Trends Microbiol., 1998, 2:76-83, Hopwood et al., Genetic Manipulation of *Streptomyces*: A Laboratory Manual, 1985; Wohlleben et al., Acta Microbiol. Immunol. Hung, 1994, 41:381-9 [Review]).

The development of vectors for the genetic manipulation of actinomycetes began with the observation of plasmids in actinomycetes and the development of a transformation protocol of actinomycete protoplasts using polyethylene glycol (Bibb et al., Nature, 1980, 284:526-31). Many standard molecular techniques for *Streptomyces* were developed by Hopwood and colleages for *Streptomyces coelicolor* and *Streptomyces lividans* (Hopwood et al., Genetic Manipulation of *Streptomyces*: A Laboratory Manual, 1985). These techniques have been adapted and expanded to other actinomycetes.

Vectors incorporating antibiotic-resistance markers (AmR, ThR, SpR) that function in *Streptomyces* spp. and other features have allowed the development of vectors for (a) integration via homologous recombination between cloned DNA and the *Streptomyces* spp. chromosome, (b) autonomous replication, and (c) site-specific integration at the bacteriophage phiC31 attachment (att) site or pSAM2 attachment site, and (d) gene replacement vectors. Homologous recombination between the cloned DNA and the chromosome can be used to make insertional knockouts of specific genes. Autonomously replicating plasmids and integrating plasmids can be used to introduce heterologous genes into actinomycetes for complementation or expression studies.

Many actinomycetes contain restriction systems that limit the ability to transform organisms by protoplast transformation. More recent gene transfer procedures have been developed for introducing DNA into streptomycetes by conjugation from *Escherichia coli*. This employs a simple mating procedure for the conjugal transfer of vectors from *E. coli* to *Streptomyces* spp. that involves plating of the donor strain and either germinated spores or mycelial fragments of the recipient strain. Conjugal plasmids contain the 760-bp oriT fragment from the IncP plasmid, RK2 and are transferred by supplying transfer functions in trans by the *E. coli* donor strain. Other recent developments that increase the frequency of recombination of non-replicating plasmids into the recipient actinomycete chromosome include transformation of non-replicating plasmids into protoplasts using denatured plasmid DNA (Oh and Chater, J. Bacteriol., 1997, 179:122-7) and conjugation of non-replicating plasmids from a methyl minus strain of *E. coli*. (Smith et al., FEMS Microbiol. Lett., 1997, 155:223-9).

Various strategies have been used to obtain gene replacements in streptomycetes, for the construction of mutations and the modification of biosynthetic pathways (Baltz et al., 1998, supra; Hopwood et al., supra; Wohllenben et al., 1994, supra; Baltz and Hosted, TIBTECH, 1996, 14:245; Baltz, Curr. Op. Biotech., 1990, 1:12-20). These methods have typically employed a two or three step procedure that results in allelic exchange. Initial crossover events between a non-intergrating phage, non-replicating plasmid, or temperature sensitive plasmid and the streptomycete chromosome are selected for by antibiotic resistance. Subsequent recombination events that result in gene replacement can be detected by screening the progeny of the initial recombinants by PCR analysis, Southern analysis, appearance of an expected phenotype or screening for the loss of a resistance marker which had previously been exchanged into the loci to be replaced. The last of these methods has been employed by Khosla et al., Mol. Microbiol., 1992, 6:3237-49; Khosla et al., J. Bacteriol., 1993, 175:2197-204, to successfully modify the polyketide biosynthetic route of *S. coelicolor*. The strategy employed by Khosla et al., 1992, supra, also has the advantage of allowing placement of non-selectable and phenotypically silent alleles into chosen positions of the chromosome. Donadio et al., Proc. Natl. Acad. Sci. U.S.A., 1993, 90:7119-23 has also successfully reprogrammed the erythromycin pathway of *Saccharopolyspora erythrae* by gene replacement.

Non-replicating plasmids for gene replacement were initialy utilized by Hilleman et al., Nucleic Acids Res., 1991, 19:727-31, who used a derivative of pDH5 to construct mutations in the phosphinothricin tripeptide biosynthetic pathway of *S. hygroscopicus*. Plasmid-integration events were obtained by thiostrepton selection, subsequent screening of the primary recombinants indicated that 4 of 100 isolates had undergone a double-crossover gene replacement.

Use of counterselectable or negative selection markers such as rpsL (confers streptomycin sensitivity) or sacB (confers sucrose sensitivity) have been widely employed in other microorganisms for selection of recombination that results in gene replacement. In *S. coelicolor*, Buttner utilized glk as a counterselectable marker in an minus phiC31 phage to select for recombination events to construct gene replacement mutants of three *S. coelicolor* RNA polymerase sigma factors (Buttner et al., J. Bacteriol., 1990, 172:3367-78). Hosted has developed a gene replacement system utilizing the rpsL gene for counterselection (Hosted and Baltz, J. Bacteriol., 1997, 179:180-6).

The construction of recombinant streptomycete strains to produce hybrid secondary metabolites has been accomplished. Current procedures use recombinant DNA techniques to isolate and manipulate secondary metabolic pathways and to express these pathways in surrogate hosts such as *Streptomyces lividans*. Heterologous expression of diverse pathways, polyketide, oligopeptide and β-lactam biosynthetic pathways, has been achieved. Furthermore novel polyketide structures have been generated through the manipulation of polyketide genes forming chimeric pathways. Recently novel polyketide modules have been isolated from environmental sources using PCR amplification and expressed in *Streptomyces* to yield novel chemical structures (Strohl et al., J. Industr. Microbiol., 1991, 7:163; Kim et al., J. Bacteriol., 1995, 77:1202; Ylihonko et al., Microbiology, 1996, 142:1965).

Knowledge of the everninomicin synthase DNA sequence, its genetic organization, and the activities associated with particular open reading frames, modules, and submodules of the gene enables production of novel everninomicins that are not otherwise available. Modifications may be made to the DNA sequence that either alter the structure or sequence of addition of building blocks. The principles have already been described above. In addition, any product resulting from post-transcriptional or post-translational modification in vivo or in vitro based on the DNA sequence information disclosed here are meant to be encompassed by the present invention.

Combinatorial Biosynthesis

The EV biosynthetic enzymes described here are ideal candidates for combinatorial biosynthesis to generate libraries of orthomycins, particularly everninomicin analogs and homologs, for testing and drug discovery (see Altreuter and Clark, Curr. Op. Biotech., 1999, 10:130; Reynolds, Proc. Natl. Acad. Sci. USA, 1998, 95:112744). Moreover, unlike chemical synthesis, which may depend on the efficiency of a specific reaction to determine product yield, a biosynthetic system can be amplified and propagated to produce high yields of the desired product.

Actinomycetes are well known microbial biosynthetic factories, and have been modified to produce novel compounds by mutation of specific biosynthetic genes (see Hutchinson, Bio/Technology, 1994, 12:375; Piepersberg, Crit. Rev. Biotech., 1994, 14:251). In addition to mutagenisis in situ, rapid evolution by DNA shuffling, particularly with related genes from other species or from the EV biosynthetic locus itself, provides for more directed evolutionary mutagenesis (Stemmer, Nature, 1994, 370:389). This technique can be practiced, for example, by shuffling EV biosynthetic gene products with their closest homologs, as determined by BLAST (or some other homology algorithm) analysis. For example, gene shifting of two or more transferases can yield new enzymes with altered function. Similarly, sugar biosynthetic genes, orsellinic acid biosynthetic genes, and tailoring genes can be manipulated by the techniques of directed evolution, e.g., gene shuffling, to produce mutants with novel enzymatic and synthetic function. Tailoring enzymes are particularly attractive targets for mutagenesis, since these will not affect synthesis of the core structure, but yield a variety of novel products.

An Integration Vector for *Micromonospera*

In a specific embodiment, the present invention relates to a new nucleic acid sequence, to vectors for its expression and to its use in fermentation processes in actinomycetes. This nucleic acid sequence encodes a *Micromonospera*, and particularly *M. carbonacea*, var. *africana*, att/int functions and thus permits development of an integrating vector. In a specific embodiment, the att/int functions has an amino acid sequence as depicted in SEQ ID NO: 177. In a more specific embodiment, the integrase is encoded by a nucleic acid having a nucleotide sequence as depicted in SEQ ID NO: 176 (FIG. 7B). A preferred integrating plasmid is shown in FIG. 7A.

Advantageously, the integrative vectors derived from this novel integrase also comprise a recombinant DNA sequence coding for a desired product, including but by no means limited to an EV biosynthetic gene. The product can be a peptide, polypeptide or protein of pharmaceutical or agrifoodstuffs importance. In this case, the system of the invention makes it possible to increase the copy number of this sequence per cell, and hence to increase the levels of production of this product and thus to increase the yields of the preparation process. The desired product can also be a peptide, polypeptide or protein participating in the biosynthesis (synthesis, degradation, transport or regulation) of a metabolite by the actinomycete strain in question. In this case, the system of the invention makes it possible to increase the copy number of this sequence per cell, and hence to increase the levels of production of this product, and thus either to increase the levels of production of the metabolite, or to block the biosynthesis of the metabolite, or to produce derivatives of the metabolite.

Plasmids comprising the site-specific integrating function of the invention can be used to permanently integrate copies of a heterologous gene of choice into the chromosome of many different hosts. The vectors can transform these hosts at a very high efficiency. Because the vectors do not have actinomycete origins of replication, the plasmids cannot exist as autonomously replicating vectors in actinomycete hosts. The plasmids only exist in their integrated form in these hosts. The integrated form is extremely stable which allows the gene copies to be maintained without antibiotic selective pressure. The result is highly beneficial in terms of cost, efficiency, and stability of the fermentation process.

Those skilled in the art will readily recognize that the variety of vectors which can be created that comprise this fragment is virtually limitless. The only absolute requirement is that the plasmid comprise an origin of replication which functions in the host cell in which constructions are made, such as *E. coli* or *Bacillus*. No actinomycete origin of replication is required. In fact, in a specific embodiment the plasmid comprising the inetegrase comprises no actinomycete origin of replication. Other features, such as an antibiotic resistance gene, a multiple cloning site and cos site, are useful but not required. A description of the generation and uses of cosmid shuttle vectors can be found in Rao et al., (Methods in Enzymology, 1987, 153:166-198). In short, any plasmid comprising the integrase is within the scope of this invention.

The integrating vectors can be used to integrate genes which increase the yield of known products or generate novel products, such as hybrid antibiotics or other novel secondary metabolites. The vector can also be used to integrate antibiotic resistance genes into strains in order to carry out bioconversions with compounds to which the strain is normally sensitive. The resulting transformed hosts and methods of making the antibiotics are within the scope of the present invention.

The integrase of the invention may thus be used in any actinomycete, in the genome of which the vector of the invention or its derivatives are is capable of integrating. In particular, they may be used in fermentation processes involving strains of *Streptomyces*, of mycobacteria, of bacilli, and the like. As an example, there may be mentioned the strains *S. pristinaespiralis* (ATCC 25486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens, S. lividans, S. griseofuscus, S. limosus*, and the like (see also, Smokvina et al., Proceedings, 1:403-407).

In this connection, European Patent Publication No. EP 350,341 describes vectors derived from plasmid pSAM2 having very advantageous properties. These vectors are capable of integrating in a site-specific manner in the genome of actinomycetes, and possess a broad host range and high stability. Moreover, they may be used for transferring nucleic acids into actinomycetes and expressing these nucleic acids therein. U.S. Pat. No. 5,741,675 describes tools capable of improving the conditions of industrial use of the vectors derived from pSAM2 by increasing the copy number of pSAM2 or its derivatives, since the free forms are present in a high copy number per cell. This patent also describes cassettes for the expression of this gene, vectors containing it and their use for inducing the appearance of free copies of pSAM2 or integrative vectors derived from the latter.

Alternatively, U.S. Pat. No. 5,190,871 provides methods for increasing a given gene dosage and for adding heterologous genes that lead to the formation of new products such as hybrid antibiotics using plasmids comprising the site-specific integrating function of phage phi.C31.

EXAMPLES

The following examples are provided for illustration purposes only and are not intended to limit the scope of the invention, which has been described in broad terms above.

Example 1

Sequencing of Orsellinic Acid Synthetase

The DNA sequence of the *Micromonospora carbonaceae* var. *africana* (ATCC 39149) everninomicin biosynthetic region was obtained by sequencing inserts of recombinant DNA subclones containing contiguous or overlapping DNA segments of the region indicated in FIG. 2A. All sequences representing the everninomicin region were fully contained in the overlapping cosmid clones pSPRX272, pSPRX262, pSPR192, pSPRX210, and pSPRX256 (FIG. 2A). The sequence was obtained by subcloning and sequencing fragments bounded by restriction site as indicated in FIG. 2A.

Figure 2B:
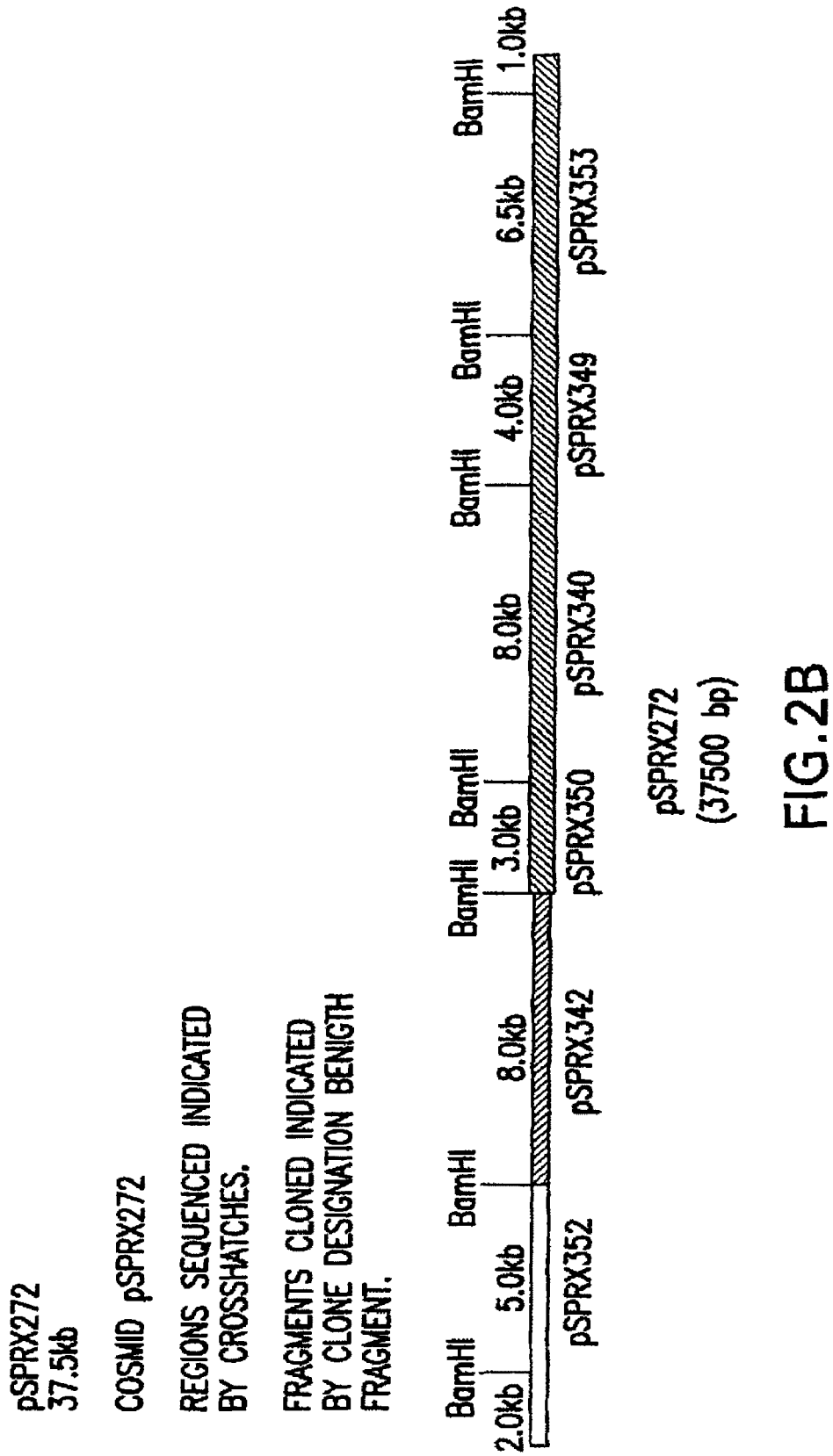
Figure 3A:
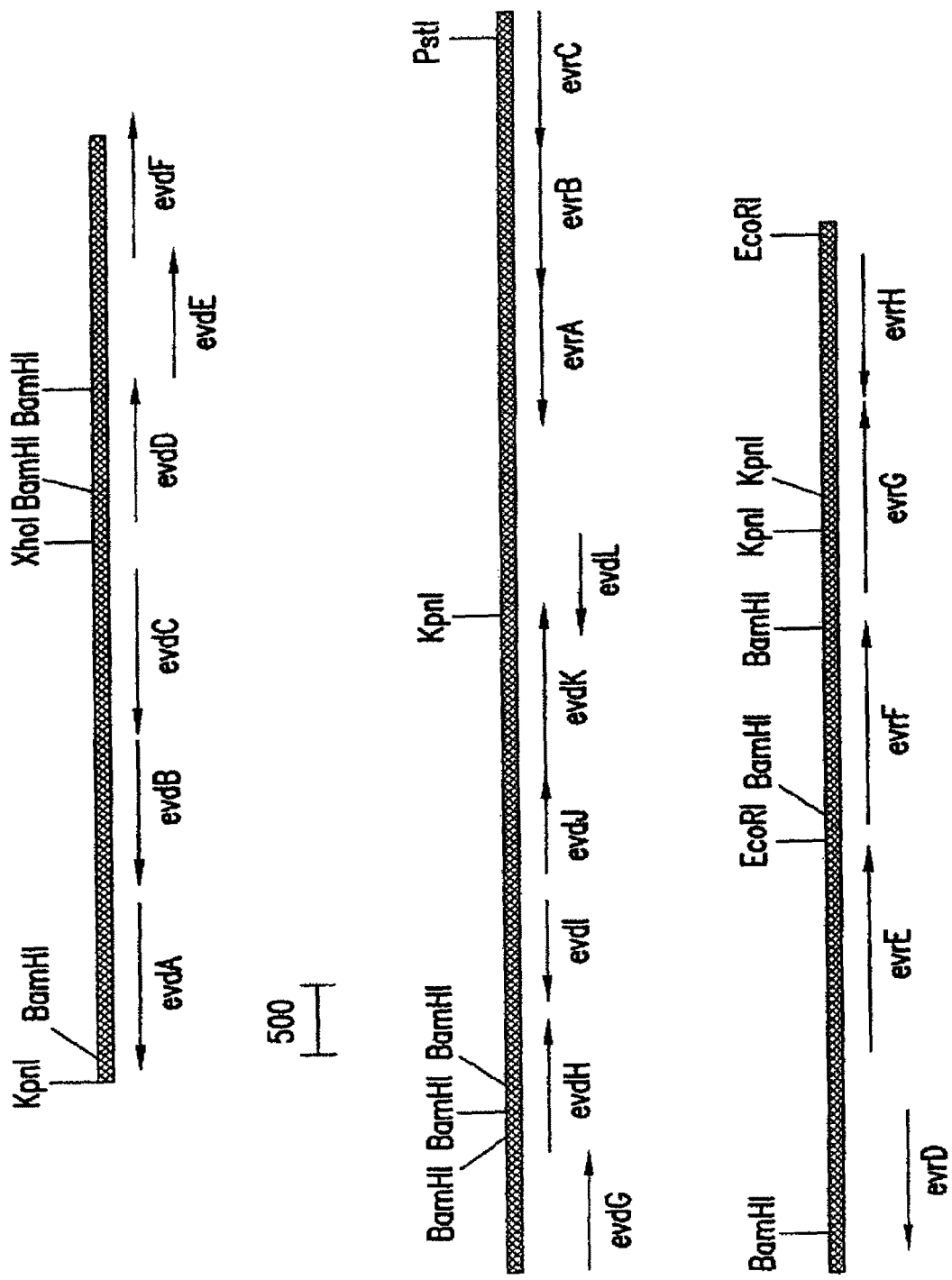
Figure 3B:
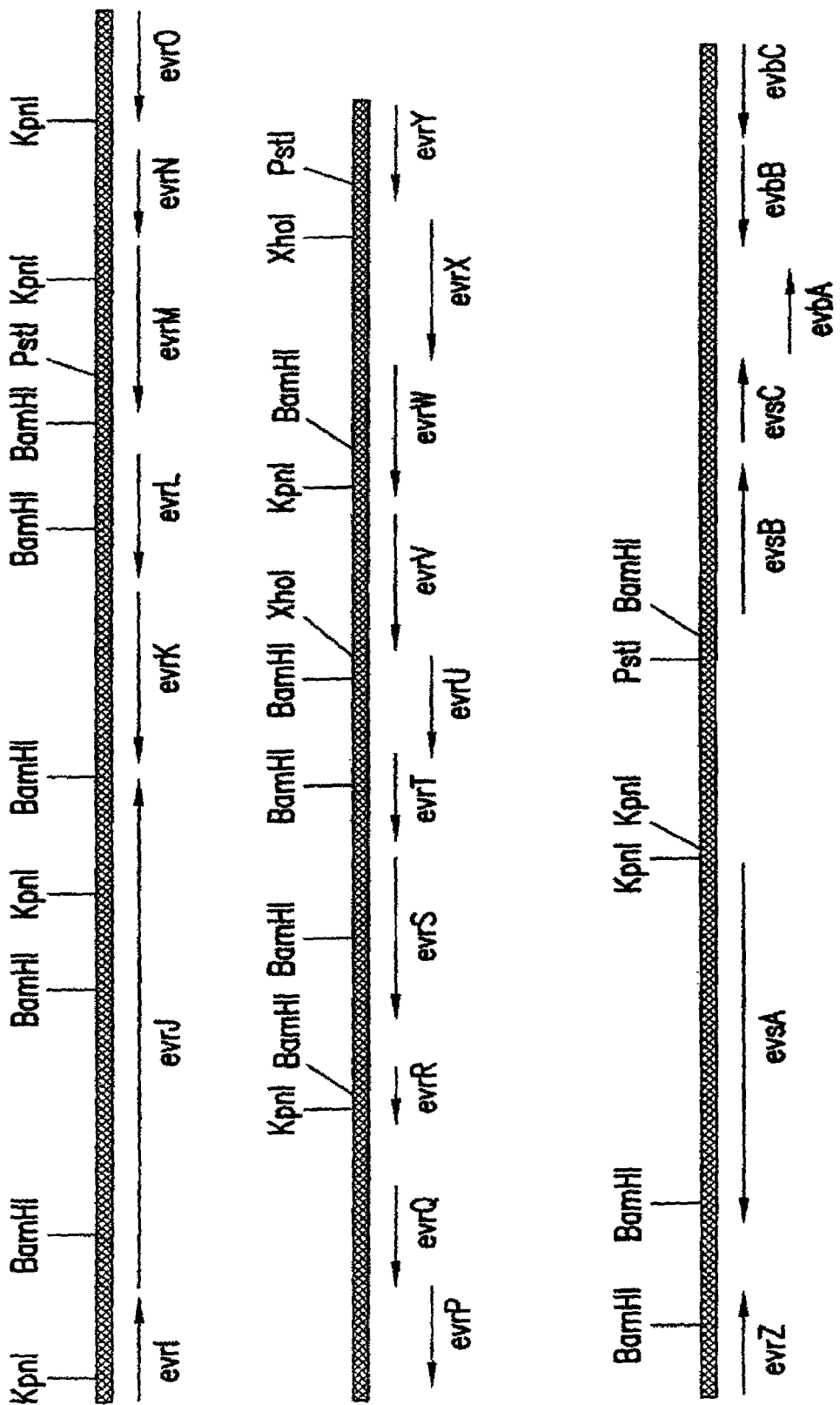
Figure 3C:
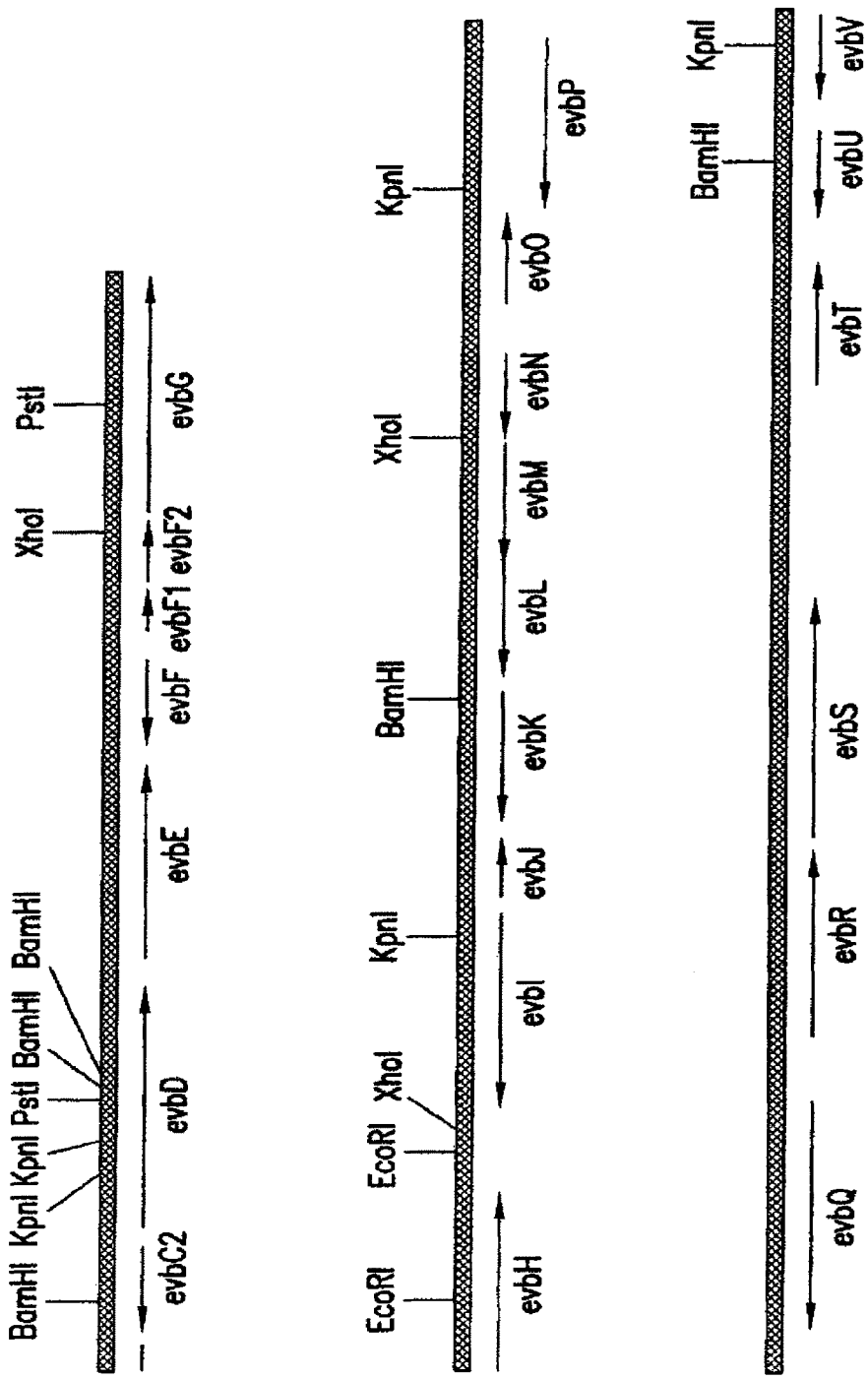
Figure 3D:
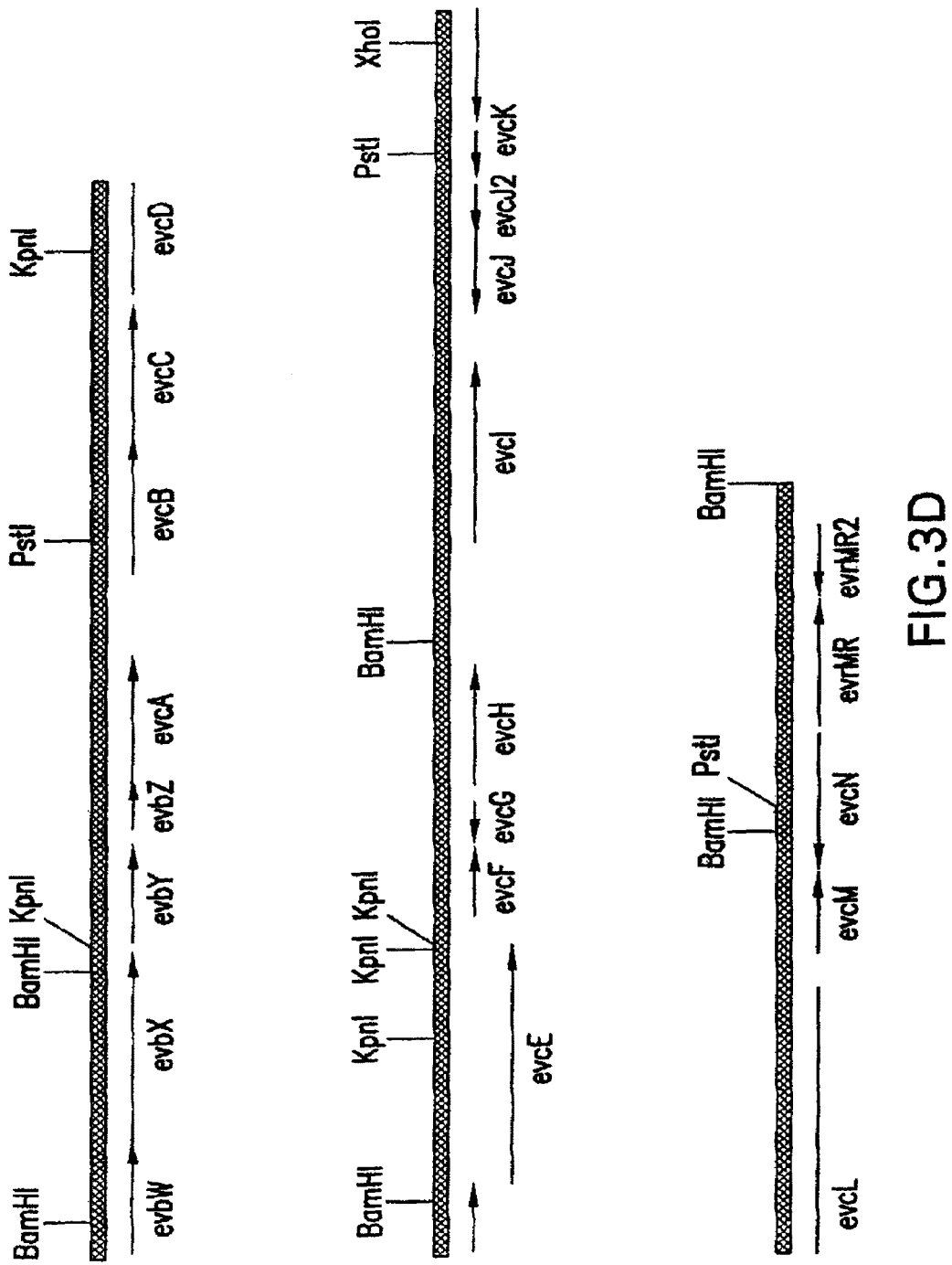

Preliminary sequences were also obtained for the cosmids pSPRX272 and pSPRX256. Restriction maps for these two cosmids are shown in FIGS. 2B and 2C, respectively. These restriction maps are characteristic of these two isolated cosmid clones of the *M. carbonaceae* everninomicin biosynthetic pathway or flanking regions thereof.

In order to obtain the evrJ gene, the sequence can be obtained by subcloning and sequencing of the fragments bounded by the KpnI sites at position 1, 25.9 kb, 29.6 kb, and 34.2 kb. The sequence can also be obtained by subcloning and sequencing of the fragments bounded by the BamHI sites at position 1, 24.5 kb, 27.0 kb, 28.8 kb and 30.5 kb. The resulting fragments should be ligated and cloned in an appropriate recombinant DNA vector. Clones containing the correct orientation of the fragment can be identified by restriction enzyme site mapping.

Example 2

Transformation of *M. carbonacea* with pSPRH830

Figure 6:
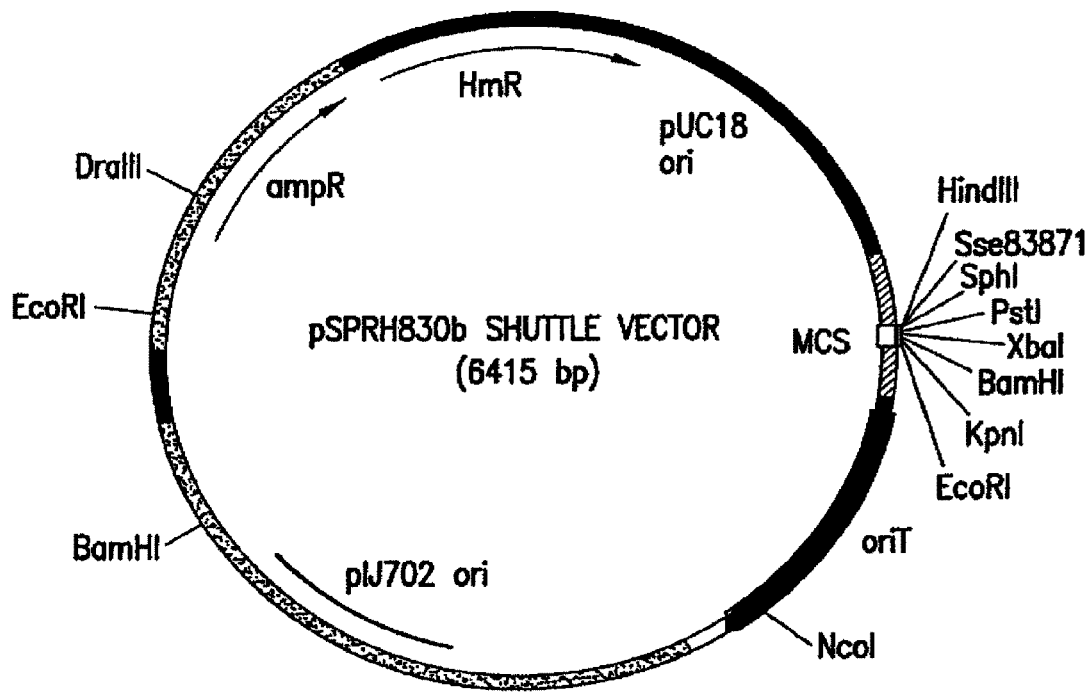

*M. carbonacea* was transformed with pSPRH830b (FIG. 6) by conjugation from *E. coli* S17-1 (Mazodier et al., Journal of Bacteriology, 1989, 6:3583-3585) to *M. carbonacea*. *E. coli* S17-1 containing pSPRH830b was grown overnight at 37° C. in LB supplemented with 100 µg/ml Ampicillin (Amp). The culture was inoculated into LB containing 100 µg/ml Amp at an 1:50 ratio and grown with shaking at 37° C. to an $OD_{600}$ of 0.4 to 0.5. Cells were harvested by centrifugation and washed three times with fresh LB lacking Amp. *M. carbonacea* was grown in TSB medium at 30° C. with shaking to stationary phase. *E. coli* S17-1 containing pSPRH830b prepared as described above was mixed with *M. carbonacea* in a total volume of 100 µl and plated on AS1 plates using a plastic hockey spreader. Plates were incubated for 15 hours at 29° C. and then overlaid with 50 µg/ml naladixic acid and 200 µg/ml Hygromycin for selection. Transconjugants appearing in 2-3 weeks were picked, homogenized and grown in TSB media with 50 µg/ml naladixic acid and 200 µml hygromycin. Presence of pSPRH830b in *M. carbonacea* transformants was confirmed by PCR analysis and isolation of pSPRH830b from exconjugats.

The ability to transform *M. carbonacea* with pSPRH830b (on a multicopy plasmid) allows the introduction of second copies of genes contained in the everninomicin biosynthetic pathway or heterologous or mutated genes into *M. carbonacea*.

Example 3

Transformation of *M. carbonacea* with pSPRH840

The pSPRH840 integrating vector (FIG. 7A) was constructed as follows. A 4.0 kb KpnII fragment from the pSPR150 cosmid containing the *M. carbonacea* pMLP1 intM gene was ligated with BamHI cleaved pBluescriptII (Stratagene) to yield pSPRH819. Sequence analysis of the 4.0 kb KpnI fragment from the cosmid revealed the presence of an integrase gene designated intM, an excisionase gene designated xis, and an integrase attachment site designated attP (FIG. 7B).

BLAST analysis of intM showed homology to other integrases in the NRRL database. Analysis of the predicted attP site showed homology to the attP sites found phage phiC31 and plasmid pSAM2.

A 2.5 kb NruI to XhoI fragment from pSPR819 was treated with T4 polymerase to generate blunt DNA ends, alkaline phosphatase treated and ligated into the pCRTopo 2.1 vector (Invitrogen Corp, Carlsbad Calif.) to yield pSPRH853. A 2.6 kb KpnI to PstI fragment from pSPRH853 was ligated to KpnI and PstI digested pSPR826*b* (FIG. 8) to yield pSPRH840 (FIG. 7A). pSPRH840 was transformed into *M. carbonacea* SCC1413 and *M. halophitica* SCC760 as described in Example 2. Transconjugants appearing in two to three weeks were picked, homogenized, and grown in TSB medium supplemented with 50 μg/ml naladixic acid (Nac1) and 200 μg/ml Hygromycin. DNA was prepared from transconjugants, cleaved with BamHI, separated by gel electrophoresis, a Southern blot prepared, and probed with radiolabeled pSPR826b. Southern hybridization analysis confirmed the presence of pSPR826b sequences integrated into the *M. carbonacea* and *M. halophitica* chromosomes. Regions including pSPRH840 and chromosomal flanking sequences were cloned by digesting chromosomal DNA with PstI or KpnI, ligating digested DNA and transforming *E. coli* XL10 (Stratagene, LaJolla, Calif.). *E. coli* transformants were isolated, plasmid DNA prepared and analyzed by digestion and gel electrophoresis. The attB/attP regions *M. carbonacea* and *M. halophitica* were each sequenced. Sequence analysis of this region confirmed that pSPRH840 had integrated into the *M. carbonacea* chromosome, specifically into a tRNA region (FIGS. 9A and 9B).

The ability to transform *M. carbonacea* with pSPRH840 allows the high frequency integration of second copies of genes contained in the everninomicin biosynthetic pathway or heterologous or mutated genes into *M. carbonacea.*

Example 4

Overexpression and Isolation of Proteins From the EV Region

The coding region of evrF gene was amplified with PCR primers:

```
                                        (SEQ ID NO: 178)
5' PR 657 CCC TCG AGA TGT CCA GCA AGA TCC TA;

(SEQ ID NO: 179)
3' PR 658 CGA ATT CTC AGG CAG ACT GCT CTG;
and (SEQ ID NO: 180)
5' PR 659: CCC TCG AGA ATG TCC AGC AAG ATC CTA;

(SEQ ID NO: 181)
3' PR 660: CGA ATT CAG ACT GCT CTG CCG CCG C;
``` using the Advantage-GC Genomic PCR kit and Advantage HF polymerase (Clontech, Palo Alto, Calif.) and a Perkin-Elmer 9600 PCR machine (Foster City, Calif.). The 1.5 kb PCR products were digested with XhoI and EcoRI and the fragments were ligated to XhoI and EcoRI digested pBADHisA (primer pair PR657/PR658 product) and pBADMycHisC (primer pair PR659/PR660 product) and transformed into *E. coli* Top 10 (Stratagene, LaJolla, Calif.). Transformants were analyzed by plasmid isolation followed by digestion and gel electrophoresis analysis. Appropriate clones were also verified by sequence analysis. This yielded the evrF expression clones pSPRE59 (pBADHisA) and pSPRE19 (pBADMycHisC). Top 10 cells containing either pSPRE59 and pSPRE19 were grown overnight at 37° C. with shaking in LB containing 50 ug/ml AMP. Overnight cultures were used to innoculate fresh LB containing 50 µg/ml and grown at 37° C. with shaking to an $OD_{600}$ of 0.4 to 0.5. L-arabinose was added to a final concentration of 0.02% and the culture was incubated for an additional 4 hours. Cells were collected by centrifugation, resuspended in 100 µl Tris-Glycine buffer and boiled for five minutes. Whole cell protein lysate was loaded onto a SDS-PAGE gel, electrophoresed, and stained with coomassie blue to determine protein expression.

To isolate sufficient amounts of protein for raising antibodies, 100 ml of culture was processed as described above and the His-tagged EvrF protein was purified by Ni-NTA column chromatography using the Xpress Protein Purification System (Invitrogen, Carlsbad, Calif.). The recombinant EvrF protein was purified to over 90% homogeneity. This preparation was fractionated on SDS-PAGE gel, excised, and used to immunize New Zealand white rabbits to raise antibodies. Antisera were generated following standard protocol, i.e., priming with complete Freund's adjuvant, (CFA) and boosting with incomplete Freund's adjuvant (IFA).

Example 5

Everninomicin Pathway Expression of Putative Resistance Genes

Figure 10:
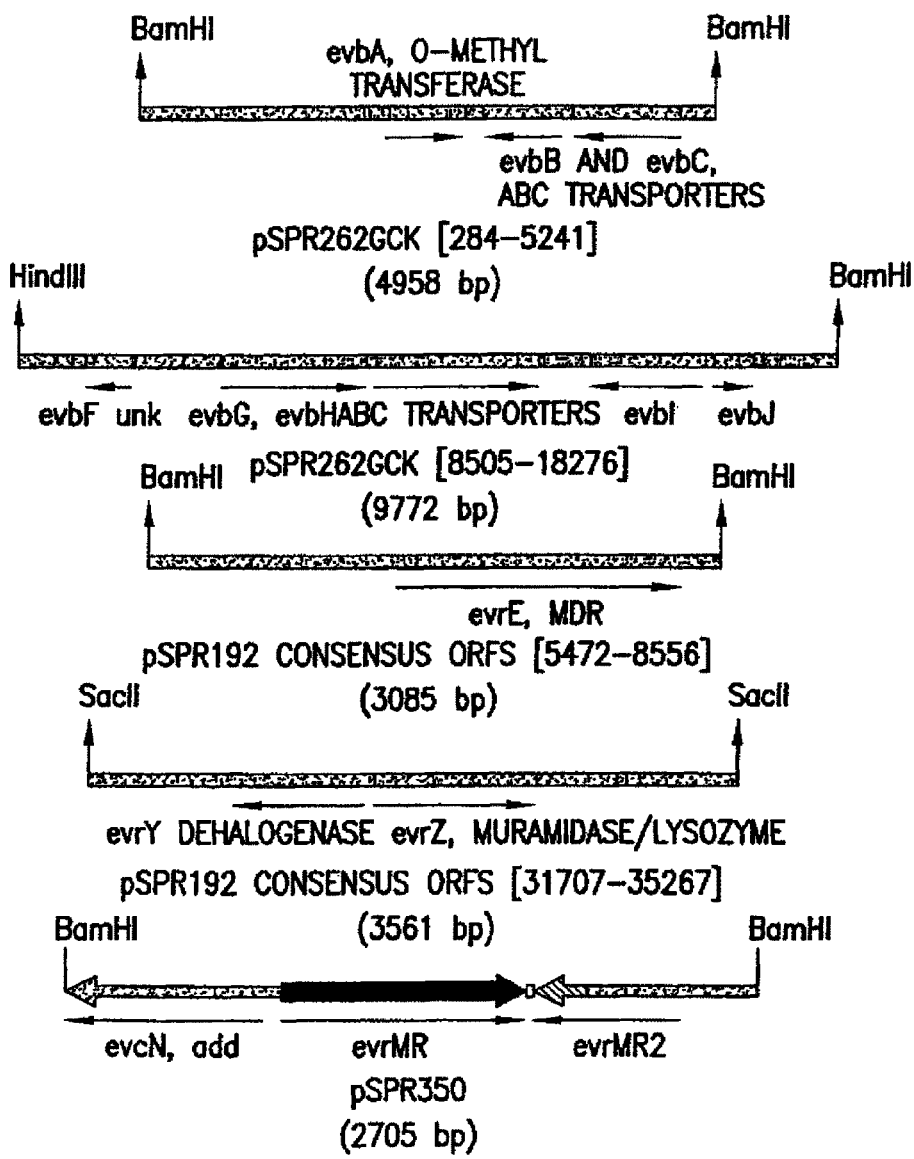

Putative everninomicin resistance genes are expressed in the actinomycete vector pSPRH830b. Clones are obtained using standard molecular biology procedures. Plasmids are transformed into *Streptomyces lividans* or *Streptomyces griseofuscus* by PEG protoplast transformation or other standard actinomycete transformation procedures. Transformants are tested for increased resistance levels to everninomicin. A schematic of pSPRH830 the specific fragments to be cloned into is attached and shown in FIG. 10.

The EV biosynthetic gene DNAs to be expressed by this recombinant vector are:

1) 4.9 kb BamHI fragment containing
   evrB, evrC—membrane pumps similar to mithramycin resistance.
2) 9.7 kb HindIII/BamHI fragment containing
   evbG, evbH—ABC transporter pumps, possible resistance mechanism.
3) 3.0 kb BamHI fragment containing
   evrE—MDR (Multiple drug resistance-type pump) transporter, possible resistance mechanism.
4) 3.56 kb SacII fragment containing
   evrY—dehalogenase, possible resistance mechanism
   evrZ—muramidase/lysozyme homology, possible resistance mechanism.
5) 2.7 kb BamHI fragment containing
   evrMR—23S rRNA methylase
6) A PCR fragment containing
   evcD and evcE—ABC transporters

Example 6

Insertional Inactivation of EV Pathway Genes

To confirm involvement of evrJ, (orsellinic acid synthetase) evrF, (halogenase) and evrW (dTDP-glucose dehydratase) in EV biosynthesis these genes were disrupted in *M. carbonacea* via homologous recombination using the conjugative suicide vector pSPRH900b. Internal fragments of evrJ, evrF, and evrW were cloned into pSPRH900b to yield pSPRX572, pSPRX570, and pSPRX589 respectively. Plasmids pSPRX572, pSPRX570, and pSPRX589 were inserted into the chromosome by conjugation from *E. coli* into *M. carbonacea* to yield strains 572X, 570X and 589X respectively. Southern analysis confirmed insertion into the correct chromosomal loci for each plasmid. 572X, 570X and 589X strains showed a loss of EV production as shown by fermentation and analysis by HPLC indicating these genes are essential for EV production.

Production and determination of EV production was determined as follows. A mycelia stock of *M. carbonacea* was inoculated into the seed medium SIM-1 (10 ml) and incubated at 28° C. and 300 rpm. The seed inoculum (5 ml) was then added to 4I+Co production medium (100 ml) and incubated at 28° C. and 300 rpm for 96 hours. A 10 ml aliquot of the fermentation broth was extracted with 20 ml of EtOAc, and the organic phase was evaporated to dryness. After resuspension in 2 ml of MeOH, 10 ml of the extract was subjected to HPLC analysis on a YMC-pack ODS-A C-18 column (3 mm, 150×4.6 mm, Waters Corporation, Milford, Mass.). The column was equilibrated with 3 mM tetramethyl ammonium hydroxide (pH to 7.2 with glacial acetic acid) with 70% (vol/vol) MeOH and developed with a 24-min linear gradient from 70 to 90% MeOH in the same 3 mM tetramethyl ammonium hydroxide buffer at a flow rate of 0.8 ml/min. EV was detected at 270 nm by UV-Vis detection using a Agilent Series1100 HPLC system (Agilent Technologies).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all sizes and all molecular weight or molecular mass values are approximate, and are provided for description.

Patents, patent applications, procedures, and publications cited throughout this application are incorporated herein by reference in their entireties.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07947480B2). An electronic copy of the "Sequence Listing" will also be available from the USPTO upon request and payment of the fee set forth in 37 CFR 1.19(b)(3).

We claim:

1. An isolated polypeptide comprising the amino acid sequence:

(SEQ ID NO: 7)

```
Val Ala Ala Asp Leu Arg Ala Pro Leu Thr Pro Ala
 1               5                  10

Gly Arg Thr Val Val Asp Leu Leu Ala Gly Val Ile
            15                  20

Pro Arg Ile Ser Ala Glu Ala Ala Asp Arg Asp
 25              30              35

Thr Gly Thr Phe Pro Val Glu Ala Phe Glu Gln Phe
                40                  45

Ala Lys Leu Gly Leu Met Gly Ala Thr Val Pro Ala
 50                  55                      60

Glu Leu Gly Gly Leu Gly Leu Thr Arg Leu Tyr Asp
 65                  70

Val Ala Thr Ala Leu Met Arg Leu Ala Glu Ala Asp
            75                  80

Ala Ser Thr Ala Leu Ala Trp His Val Gln Leu Ser
 85                  90                      95

Arg Gly Leu Thr Leu Thr Tyr Glu Trp Gln His Gly
            100                 105

Thr Pro Pro Val Arg Ala Met Ala Glu Arg Leu Leu
 110                 115                     120

Arg Ala Met Ala Glu Gly Glu Ala Ala Val Cys Gly
                125                 130

Ala Leu Lys Asp Ala Pro Gly Val Val Thr Glu Leu
                135                 140

His Ser Asp Gly Ala Gly Gly Trp Leu Leu Ser Gly
 145                 150                     155

Arg Lys Val Leu Val Ser Met Ala Pro Ile Ala Thr
                160                 165

His Phe Phe Val His Ala Gln Arg Arg Asp Asp Asp
     170                 175                 180

Gly Ser Val Phe Leu Ala Val Pro Val Val His Arg
                185                 190

Asp Ala Pro Gly Leu Thr Val Leu Asp Asn Trp Asp
     195                 200

Gly Leu Gly Met Arg Ala Ser Gly Thr Leu Glu Val
 205                 210                     215

Val Phe Asp Arg Cys Pro Val Arg Ala Asp Glu Leu
                220                 225
```

-continued

```
Leu Glu Arg Gly Pro Val Gly Ala Arg Arg Asp Ala
 230                 235                     240

Val Leu Ala Gly Gln Thr Val Ser Ser Ile Thr Met
                245                 250

Leu Gly Ile Tyr Ala Gly Ile Ala Gln Ala Ala Arg
         255                 260

Asp Ile Ala Val Gly Phe Cys Ala Gly Arg Gly Gly
 265                 270                     275

Glu Pro Arg Ala Gly Ala Arg Ala Leu Val Ala Gly
                280                 285

Leu Asp Thr Arg Leu Tyr Ala Leu Arg Thr Thr Val
     290                 295                 300

Gly Ala Ala Leu Thr Asn Ala Asp Ala Ala Ser Val
                305                 310

Asp Leu Ser Gly Asp Pro Asp Glu Arg Gly Arg Arg
                315                 320

Met Met Thr Pro Phe Gln Tyr Ala Lys Met Thr Val
 325                 330                     335

Asn Glu Leu Ala Pro Ala Val Val Asp Asp Cys Leu
                340                 345

Ser Leu Val Gly Gly Leu Ala Tyr Thr Ala Gly His
     350                 355                 360

Pro Leu Ser Arg Leu Tyr Arg Asp Val Arg Ala Gly
                365                 370

Gly Phe Met Gln Pro Tyr Ser Tyr Val Asp Ala Val
                375                 380

Asp Tyr Leu Ser Gly Gln Ala Leu Gly Leu Asp Arg
 385                 390                     395

Asp Asn Asp Tyr Met Ser Val Arg Ala Leu Arg Ser
                400                 405

Arg Thr Ser Ala.
 410
```

2. An isolated polypeptide that is encoded by a polynucleotide that hybridizes to the full length complement of a polynucleotide consisting of the nucleotide sequence set forth in SEQ ID NO: 6 under high stringency conditions, said conditions being in the presence of 50% formamide and 0.2×SSC at 68° C.; wherein SCC is a 0.15 M NaCl, 0.015 M Na+ citrate.

3. The polypeptide of claim 1 which is a chimeric polypeptide fused to a heterologous polypeptide.

4. The polypeptide of claim 3 wherein the heterologous polypeptide is a member selected from the group consisting of a poly-histidine tag, a FLAG tag, a glutathione-S-transferase tag and a myc epitope tag.

5. A method for making an isolated polypeptide comprising the amino acid sequence:

```
Val Ala Ala Asp Leu Arg Ala Pro Leu Thr Pro Ala Gly Arg Thr Val
 1               5                  10                      15

Val Asp Leu Leu Ala Gly Val Ile Pro Arg Ile Ser Ala Glu Ala Ala
                 20                  25                      30

Asp Arg Asp Arg Thr Gly Thr Phe Pro Val Glu Ala Phe Glu Gln Phe
         35                  40                      45

Ala Lys Leu Gly Leu Met Gly Ala Thr Val Pro Ala Glu Leu Gly Gly
 50                  55                      60

Leu Gly Leu Thr Arg Leu Tyr Asp Val Ala Thr Ala Leu Met Arg Leu
 65                  70                      75                      80
```

-continued

```
Ala Glu Ala Asp Ala Ser Thr Ala Leu Ala Trp His Val Gln Leu Ser
                 85                  90                  95
Arg Gly Leu Thr Leu Thr Tyr Glu Trp Gln His Gly Thr Pro Pro Val
            100                 105                 110
Arg Ala Met Ala Glu Arg Leu Leu Arg Ala Met Ala Glu Gly Glu Ala
            115                 120                 125
Ala Val Cys Gly Ala Leu Lys Asp Ala Pro Gly Val Val Thr Glu Leu
            130                 135                 140
His Ser Asp Gly Ala Gly Gly Trp Leu Leu Ser Gly Arg Lys Val Leu
145                 150                 155                 160
Val Ser Met Ala Pro Ile Ala Thr His Phe Phe Val His Ala Gln Arg
                165                 170                 175
Arg Asp Asp Asp Gly Ser Val Phe Leu Ala Val Pro Val His Arg
            180                 185                 190
Asp Ala Pro Gly Leu Thr Val Leu Asp Asn Trp Asp Gly Leu Gly Met
            195                 200                 205
Arg Ala Ser Gly Thr Leu Glu Val Val Phe Asp Arg Cys Pro Val Arg
            210                 215                 220
Ala Asp Glu Leu Leu Glu Arg Gly Pro Val Gly Ala Arg Arg Asp Ala
225                 230                 235                 240
Val Leu Ala Gly Gln Thr Val Ser Ser Ile Thr Met Leu Gly Ile Tyr
                245                 250                 255
Ala Gly Ile Ala Gln Ala Ala Arg Asp Ile Ala Val Gly Phe Cys Ala
                260                 265                 270
Gly Arg Gly Gly Glu Pro Arg Ala Gly Ala Arg Ala Leu Val Ala Gly
            275                 280                 285
Leu Asp Thr Arg Leu Tyr Ala Leu Arg Thr Thr Val Gly Ala Ala Leu
            290                 295                 300
Thr Asn Ala Asp Ala Ala Ser Val Asp Leu Ser Gly Asp Pro Asp Glu
305                 310                 315                 320
Arg Gly Arg Arg Met Met Thr Pro Phe Gln Tyr Ala Lys Met Thr Val
                325                 330                 335
Asn Glu Leu Ala Pro Ala Val Val Asp Asp Cys Leu Ser Leu Val Gly
            340                 345                 350
Gly Leu Ala Tyr Thr Ala Gly His Pro Leu Ser Arg Leu Tyr Arg Asp
            355                 360                 365
Val Arg Ala Gly Gly Phe Met Gln Pro Tyr Ser Tyr Val Asp Ala Val
            370                 375                 380
Asp Tyr Leu Ser Gly Gln Ala Leu Gly Leu Asp Arg Asp Asn Asp Tyr
385                 390                 395                 400
Met Ser Val Arg Ala Leu Arg Ser Arg Thr Ser Ala
                405                 410
```

(SEQ ID NO: 7), said method comprising transforming an isolated host cell with a vector comprising a polynucleotide encoding the polypeptide under conditions wherein the polypeptide is expressed by the host cell.

6. An isolated antibody or fragment thereof that binds specifically to the polypeptide of claim 1 which consists of the amino acid sequence:

```
                                              (SEQ ID NO: 7)
Val Ala Ala Asp Leu Arg Ala Pro Leu Thr Pro Ala
1               5                   10
```

-continued
```
Gly Arg Thr Val Val Asp Leu Leu Ala Gly Val Ile
            15                  20
Pro Arg Ile Ser Ala Glu Ala Ala Asp Arg Asp Arg
25                  30                  35
Thr Gly Thr Phe Pro Val Glu Ala Phe Glu Gln Phe
                40                  45
Ala Lys Leu Gly Leu Met Gly Ala Thr Val Pro Ala
            50                  55                  60
Glu Leu Gly Gly Leu Gly Leu Thr Arg Leu Tyr Asp
            65                  70
```

-continued

```
Val Ala Thr Ala Leu Met Arg Leu Ala Glu Ala Asp
         75                  80
Ala Ser Thr Ala Leu Ala Trp His Val Gln Leu Ser
 85                  90                  95
Arg Gly Leu Thr Leu Thr Tyr Glu Trp Gln His Gly
            100                 105
Thr Pro Pro Val Arg Ala Met Ala Glu Arg Leu Leu
        110                 115                 120
Arg Ala Met Ala Glu Gly Glu Ala Ala Val Cys Gly
                125                 130
Ala Leu Lys Asp Ala Pro Gly Val Val Thr Glu Leu
            135                 140
His Ser Asp Gly Ala Gly Gly Trp Leu Leu Ser Gly
145                 150                 155
Arg Lys Val Leu Val Ser Met Ala Pro Ile Ala Thr
            160                 165
His Phe Phe Val His Ala Gln Arg Arg Asp Asp Asp
        170                 175                 180
Gly Ser Val Phe Leu Ala Val Pro Val Val His Arg
                185                 190
Asp Ala Pro Gly Leu Thr Val Leu Asp Asn Trp Asp
            195                 200
Gly Leu Gly Met Arg Ala Ser Gly Thr Leu Glu Val
205                 210                 215
Val Phe Asp Arg Cys Pro Val Arg Ala Asp Glu Leu
            220                 225
Leu Glu Arg Gly Pro Val Gly Ala Arg Arg Asp Ala
        230                 235                 240
Val Leu Ala Gly Gln Thr Val Ser Ser Ile Thr Met
                245                 250
Leu Gly Ile Tyr Ala Gly Ile Ala Gln Ala Ala Arg
            255                 260
Asp Ile Ala Val Gly Phe Cys Ala Gly Arg Gly Gly
265                 270                 275
Glu Pro Arg Ala Gly Ala Arg Ala Leu Val Ala Gly
                280                 285
Leu Asp Thr Arg Leu Tyr Ala Leu Arg Thr Thr Val
            290                 295                 300
Gly Ala Ala Leu Thr Asn Ala Asp Ala Ala Ser Val
                    305                 310
Asp Leu Ser Gly Asp Pro Asp Glu Arg Gly Arg Arg
            315                 320
Met Met Thr Pro Phe Gln Tyr Ala Lys Met Thr Val
325                 330                 335
Asn Glu Leu Ala Pro Ala Val Val Asp Asp Cys Leu
                340                 345
Ser Leu Val Gly Gly Leu Ala Tyr Thr Ala Gly His
        350                 355                 360
Pro Leu Ser Arg Leu Tyr Arg Asp Val Arg Ala Gly
                365                 370
Gly Phe Met Gln Pro Tyr Ser Tyr Val Asp Ala Val
        375                 380
Asp Tyr Leu Ser Gly Gln Ala Leu Gly Leu Asp Arg
385                 390                 395
Asp Asn Asp Tyr Met Ser Val Arg Ala Leu Arg Ser
            400                 405
Arg Thr Ser Ala.
410
```

7. A method for making an antibody that specifically binds to the polypeptide of claim 1 comprising immunizing a host animal with said polypeptide.

8. The method of claim 7 wherein the host animal is a rabbit, mouse, rat, sheep or goat.

9. The method of claim 7 wherein the polypeptide is conjugated to an immunogenic carrier.

10. The method of claim 7 further comprising generating a hybridoma from cells of the host animal.

\* \* \* \* \*